United States Patent
Kim et al.

(10) Patent No.: US 9,761,809 B2
(45) Date of Patent: Sep. 12, 2017

(54) COMPOUND AND ORGANIC LIGHT-EMITTING DEVICE COMPRISING SAME

(71) Applicant: SAMSUNG DISPLAY CO., LTD., Yongin, Gyeonggi-Do (KR)

(72) Inventors: Jongwoo Kim, Yongin (KR); Youngkook Kim, Yongin (KR); Seunggak Yang, Yongin (KR); Jino Lim, Yongin (KR); Hyungseok Jang, Yongin (KR); Seokhwan Hwang, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 320 days.

(21) Appl. No.: 14/683,744

(22) Filed: Apr. 10, 2015

(65) Prior Publication Data
US 2016/0126465 A1   May 5, 2016

(30) Foreign Application Priority Data
Nov. 3, 2014 (KR) ........................ 10-2014-0151583

(51) Int. Cl.
| H01L 51/00 | (2006.01) |
| C07D 209/86 | (2006.01) |
| C09K 11/06 | (2006.01) |
| C07D 405/14 | (2006.01) |
| C07D 401/14 | (2006.01) |
| C07D 403/14 | (2006.01) |
| H01L 51/50 | (2006.01) |

(52) U.S. Cl.
CPC ........ H01L 51/0061 (2013.01); C07D 209/86 (2013.01); C07D 401/14 (2013.01); C07D 403/14 (2013.01); C07D 405/14 (2013.01); C09K 11/06 (2013.01); *H01L 51/006* (2013.01); *C09K 2211/1029* (2013.01); *H01L 51/0052* (2013.01); *H01L 51/0058* (2013.01); *H01L 51/0067* (2013.01); *H01L 51/0071* (2013.01); *H01L 51/0072* (2013.01); *H01L 51/5056* (2013.01); *H01L 51/5072* (2013.01); *H01L 2251/301* (2013.01); *H01L 2251/308* (2013.01)

(58) Field of Classification Search
CPC .................................................. H01L 51/0061
USPC ........................................................ 428/690
See application file for complete search history.

(56) References Cited

U.S. PATENT DOCUMENTS

| 6,465,115 | B2 | 10/2002 | Shi et al. | |
| 6,596,415 | B2 | 7/2003 | Shi et al. | |
| 2010/0145067 | A1* | 6/2010 | Yokota | C07D 209/86 548/442 |
| 2011/0260138 | A1* | 10/2011 | Xia | C07D 405/14 257/40 |
| 2012/0223295 | A1 | 9/2012 | Inoue et al. | |

FOREIGN PATENT DOCUMENTS

| KR | 10-2009-0089332 A | 8/2009 |
| KR | 10-1072817 B1 | 10/2011 |
| KR | 10-2013-0100236 A | 9/2013 |
| KR | 10-2013-0134451 A | 12/2013 |
| KR | 10-2014-0000259 A | 1/2014 |

* cited by examiner

*Primary Examiner* — Doris Lee
(74) *Attorney, Agent, or Firm* — Lee & Morse, P.C.

(57) ABSTRACT

A compound represented by Formula 1 below, and an organic light-emitting device including the compound:

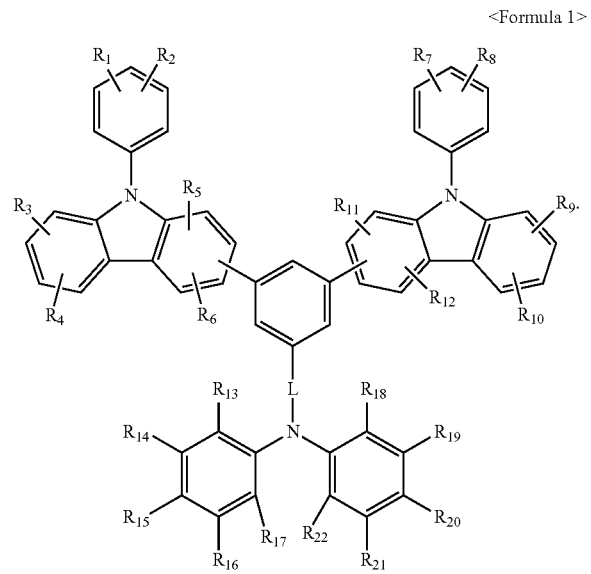

<Formula 1>

20 Claims, 1 Drawing Sheet

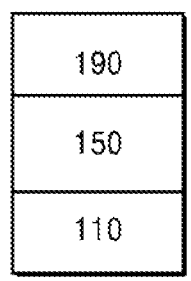

COMPOUND AND ORGANIC LIGHT-EMITTING DEVICE COMPRISING SAME

CROSS-REFERENCE TO RELATED APPLICATION

Korean Patent Application No. 10-2014-0151583, filed on Nov. 3, 2014, in the Korean Intellectual Property Office, and entitled: "Compound and Organic Light-Emitting Device Comprising Same," is incorporated by reference herein in its entirety.

BACKGROUND

1. Field

Embodiments relate to a compound and an organic light-emitting device comprising same.

2. Description of the Related Art

Organic light-emitting devices are self-emission devices that have wide viewing angles, high contrast ratios, short response times, and excellent brightness, driving voltage, and response speed characteristics, and produce full-color images.

The organic light-emitting device may have an anode, a hole transport layer, an emission layer, an electron transport layer, and a cathode on a substrate in this stated order. Here, the hole transport layer, the emission layer and the electron transport layer are organic thin films including an organic compound.

The organic light-emitting device having a structure described above is driven as follows.

As a voltage is applied between the anode and the cathode, holes provided from the anode move toward the emission layer through the hole transport layer and electrons provided from the cathode move toward the emission layer through the electron transport layer. Carriers such as the holes and the electrons recombine in the emission layer to generate excitons. These excitons change from an excited state to a ground state, thereby generating light.

SUMMARY

Embodiments are directed to a compound and an organic light-emitting device comprising same.

According to an embodiment, a compound represented by Formula 1 below is provided:

<Formula 1>

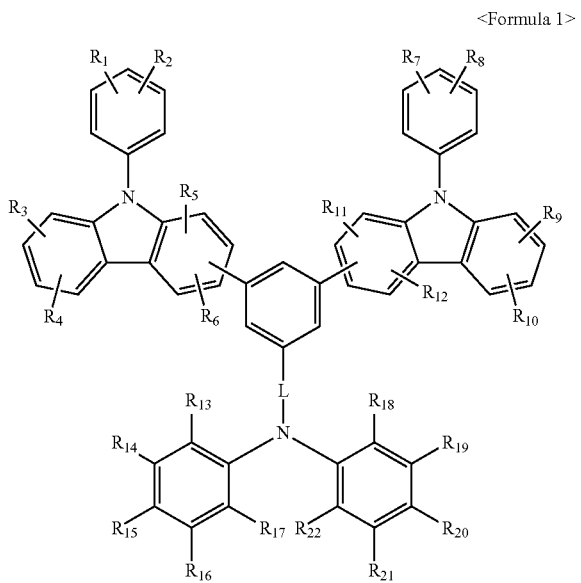

wherein in Formula 1, $R_1$ to $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$) and —B($Q_6$)($Q_7$);

L is selected from a substituted or unsubstituted $C_3$-$C_{10}$ cycloalkylene group; a substituted or unsubstituted $C_2$-$C_{10}$ heterocycloalkylene group; a substituted or unsubstituted $C_3$-$C_{10}$ cycloalkenylene group; a substituted or unsubstituted $C_2$-$C_{10}$ heterocycloalkenylene group; a substituted or unsubstituted $C_6$-$C_{60}$ arylene group; a substituted or unsubstituted $C_2$-$C_{60}$ heteroarylene group; a substituted or unsubstituted divalent non-aromatic condensed polycyclic group; a substituted or unsubstituted divalent non-aromatic condensed heteropolycyclic group; and a substituent including two or more groups selected from the $C_3$-$C_{10}$ cycloalkylene group, the $C_2$-$C_{10}$ heterocycloalkylene group, the $C_3$-$C_{10}$ cycloalkenylene group, the $C_2$-$C_{10}$ heterocycloalkenylene group, the $C_6$-$C_{60}$ arylene group, the $C_2$-$C_{60}$ heteroarylene group, the divalent non-aromatic condensed polycyclic group, and the divalent non-aromatic condensed heteropolycyclic group;

optionally, adjacent substituents from among $R_1$ to $R_{22}$ are connected to form a ring;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, substituted monovalent non-aromatic condensed heteropolycyclic group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted a divalent non-aromatic condensed polycyclic group and substituted a divalent non-aromatic condensed heteropolycyclic group, is selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each independently substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_3$-$C_{10}$ cycloalkyl group, $C_2$-$C_{10}$ heterocycloalkyl group, $C_3$-$C_{10}$ cycloalkenyl group, $C_2$-$C_{10}$ heterocycloalkenyl group, $C_6$-$C_{60}$ aryl group, $C_6$-$C_{60}$ aryloxy group (aryloxy), $C_6$-$C_{60}$ arylthio group (arylthio), $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$) and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each independently substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$) and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

According to another embodiment, provided is an organic light-emitting device including a first electrode; a second electrode; and an organic layer disposed between the first electrode and the second electrode wherein the organic layer includes the compound described above.

According to another embodiment, provided is a flat display apparatus including the organic light-emitting device wherein a first electrode of the organic light-emitting device is electrically connected to a source electrode or a drain electrode of a thin film transistor.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

Expressions such as "at least one of" when preceding a list of elements, modify the entire list of elements and do not modify the individual elements of the list.

A compound according to an embodiment may be represented by Formula 1 below.

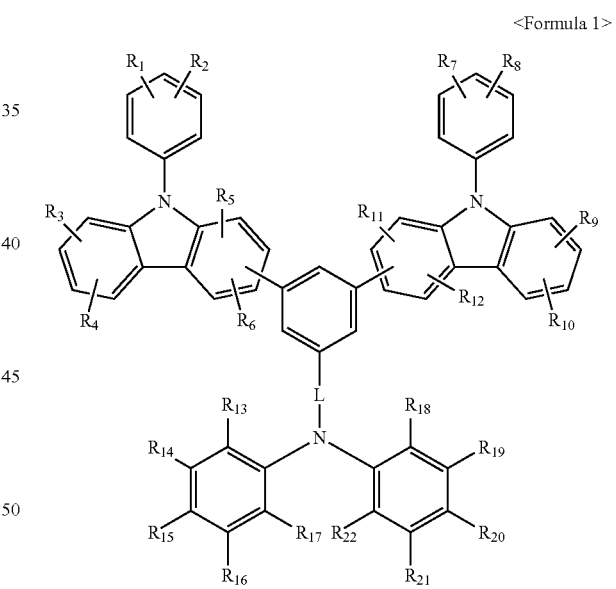

<Formula 1>

In Formula 1, $R_1$ to $R_{22}$ may be each independently selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$ and —$B(Q_6)(Q_7)$; and L may be selected from or include, e.g., a substituted or unsubstituted $C_3$-$C_{10}$ cycloalkylene group; a substituted or unsubstituted $C_2$-$C_{10}$ heterocycloalkylene group; a substituted or unsubstituted $C_3$-$C_{10}$ cycloalkenylene group; a substituted or unsubstituted $C_2$-$C_{10}$ heterocycloalkenylene group; a substituted or unsubstituted $C_6$-$C_{60}$ arylene group; a substituted or unsubstituted $C_2$-$C_{60}$ heteroarylene group; a substituted or unsubstituted divalent non-aromatic condensed polycyclic group; a substituted or unsubstituted divalent non-aromatic condensed heteropolycyclic group; and a substituent including two or more groups selected from the $C_3$-$C_{10}$ cycloalkylene group, the $C_2$-$C_{10}$ heterocycloalkylene group, the $C_3$-$C_{10}$ cycloalkenylene group, the $C_2$-$C_{10}$ heterocycloalkenylene group, the $C_6$-$C_{60}$ arylene group, the $C_2$-$C_{60}$ heteroarylene group, the divalent non-aromatic condensed polycyclic group, and the divalent non-aromatic condensed heteropolycyclic group In an implementation, adjacent substituents from among $R_1$ to $R_{22}$ may be connected to form a ring. For example, adjacent substituents from among $R_1$ to $R_{22}$ may be connected to form a ring or may be separate from one another.

At least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, substituted monovalent non-aromatic condensed heteropolycyclic group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted a divalent non-aromatic condensed polycyclic group and substituted a divalent non-aromatic condensed heteropolycyclic group, may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each independently substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group (aryloxy), a $C_6$-$C_{60}$ arylthio group (arylthio), a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$ and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$ and —$B(Q_{26})(Q_{27})$; and —$N(Q_{31})(Q_{32})$, —$Si(Q_{33})(Q_{34})(Q_{35})$, and —$B(Q_{36})(Q_{37})$.

$Q_1$ to $Q_7$, $Q_{11}$ to $Q_{17}$, $Q_{21}$ to $Q_{27}$, and $Q_{31}$ to $Q_{37}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

By using various linkers L, a HOMO level and a LUMO level may be adjusted to control a band gap between the HOMO and the LUMO. For example, a linker L may be introduced to a structure to lower the HOMO level so that the flow of holes may be good and thus efficiency of devices may be increased.

The substituents in Formula 1 will be explained in more detail.

In an implementation, in Formula 1, $R_1$ to $R_{22}$ may be each independently selected from or include, e.g., a hydrogen, a deuterium, —F, —Cl, —Br, —I, a substituted or unsubstituted $C_2$-$C_{60}$ alkenyl group, and a substituted or unsubstituted $C_6$-$C_{60}$ aryl group.

In an implementation, L may be selected from or include, e.g., a substituted or unsubstituted $C_6$-$C_{60}$ arylene group; a substituted or unsubstituted $C_2$-$C_{60}$ heteroarylene group; or a substituent including two or more groups selected from the $C_6$-$C_{60}$ arylene group and the $C_2$-$C_{60}$ heteroarylene group.

In an implementation, in Formula 1, $R_1$ to $R_{12}$ may be each independently or may include, e.g., a hydrogen, a deuterium, —F, —Cl, —Br, —I, a substituted or unsubstituted $C_2$-$C_{10}$ alkenyl group, or a group represented by Formula 2a below.

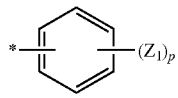

2a

In Formula 2a, $Z_1$ may independently be or include, e.g., a hydrogen, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, or a carboxyl group.

p may be an integer selected from 1 to 5; and * denotes a binding site to a neighboring atom.

When $Z_1$ is two or more, a plurality of $Z_1$ may be identical or different (the same applies hereinafter).

In an implementation, in Formula 1, $R_1$ to $R_{12}$ may be each independently a hydrogen or a deuterium.

In an implementation, in Formula 1, $R_{13}$ to $R_{22}$ may be each independently or may include, e.g., a hydrogen, a deuterium, —F, —Cl, —Br, —I, a substituted or unsubstituted $C_2$-$C_{10}$ alkenyl group, or a group represented by one of Formulae 3a to 3c below.

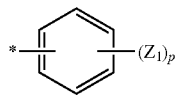

3a

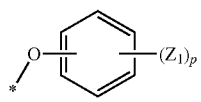

3b

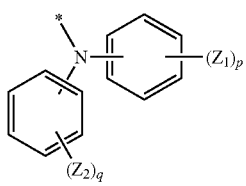

3c

In Formulae 3a to 3c, $Z_1$ and $Z_2$ may be each independently or may include, e.g., a hydrogen, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, or a carboxyl group.

p and q may each independently be integers selected from 1 to 5; and * denotes a bonding site to a neighboring atom.

In an implementation, in Formula 1, L may be a group represented by one of Formulae 4a to 4f below.

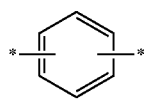

4a

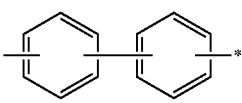

4b

4c

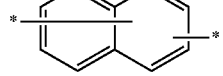

4d

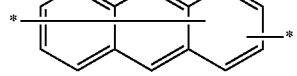

4e

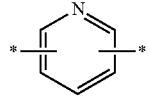

4f

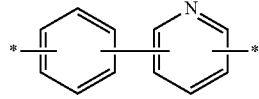

In Formulae 4a to 4f, * denotes a bonding site to a neighboring atom.

In an implementation, the compound represented by Formula 1 may be represented by one of Formula 2 or Formula 3 below.

<Formula 2>

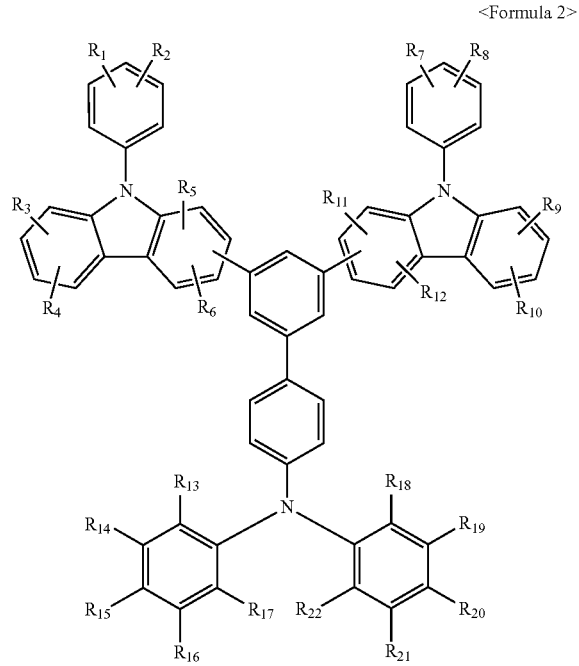

<Formula 3>
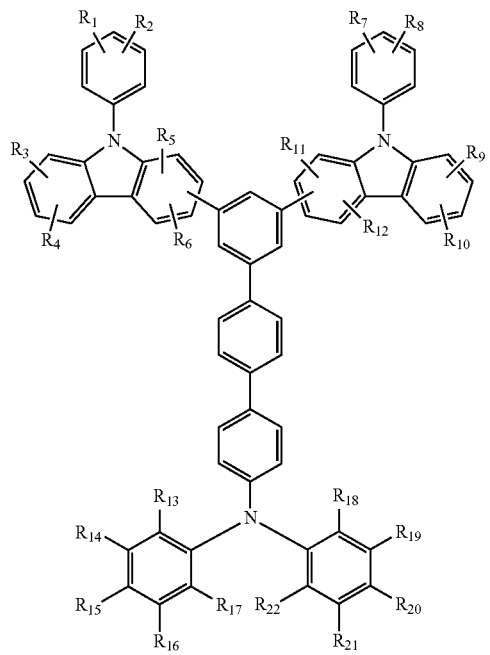
In Formulae 2 and 3, $R_1$ to $R_{22}$ may be the same as those defined with respect to Formula 1.
In an implementation, the compound represented by Formula 1 may be any one of the following compounds.
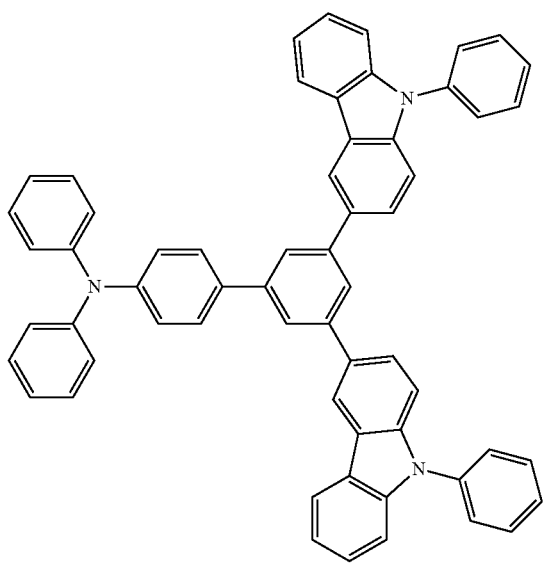
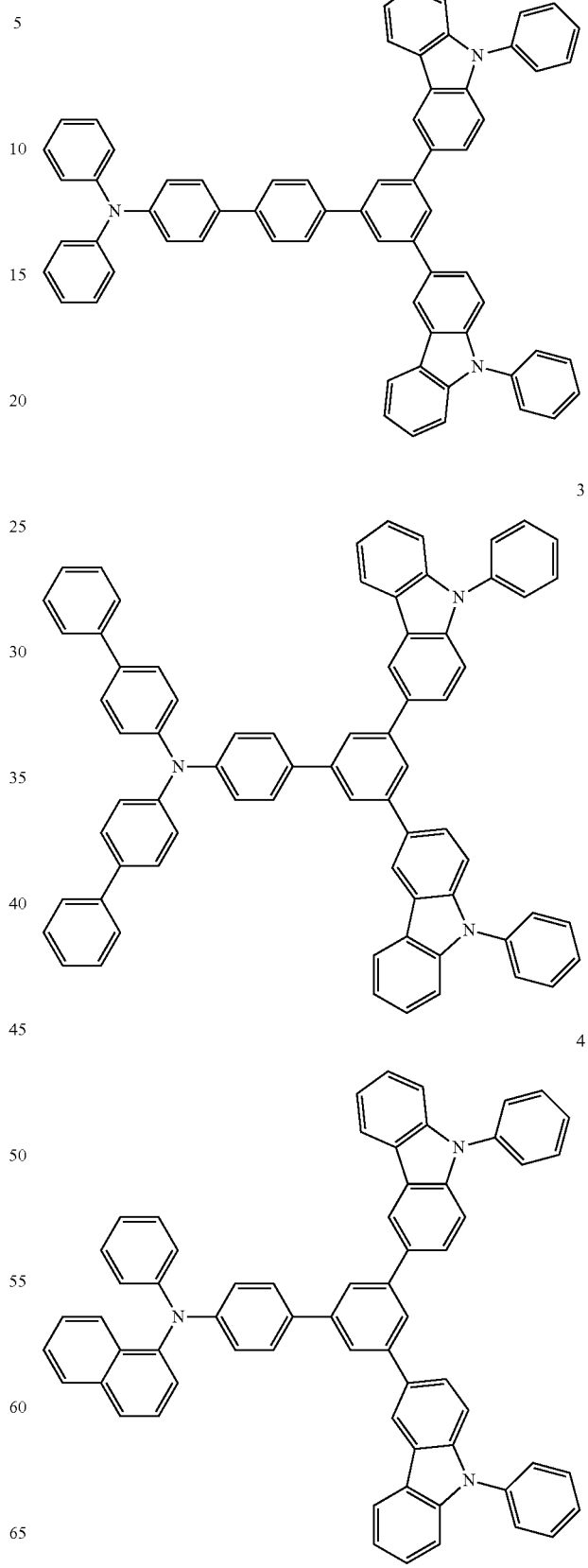

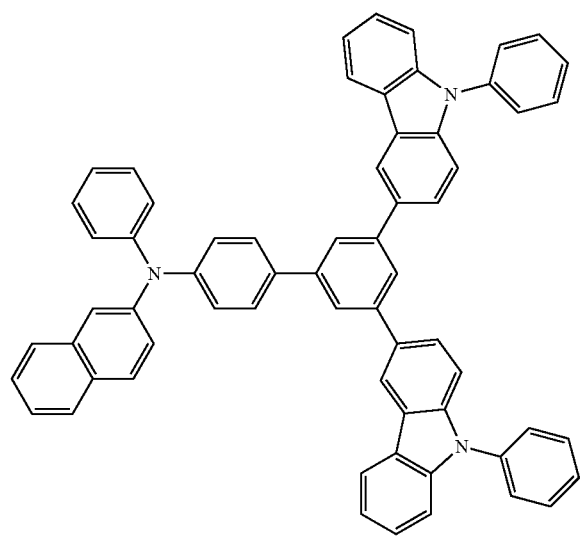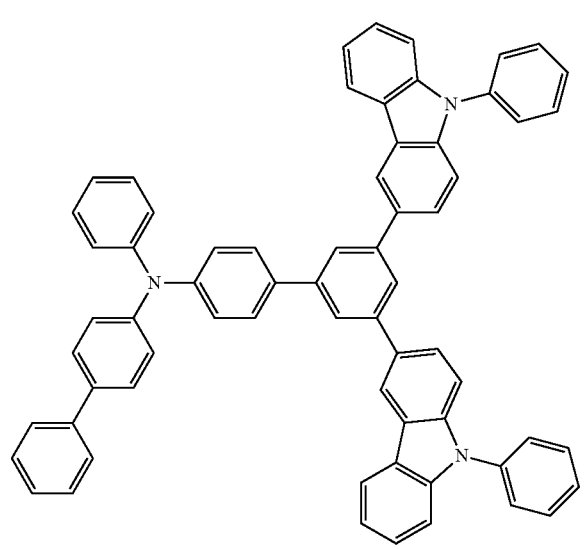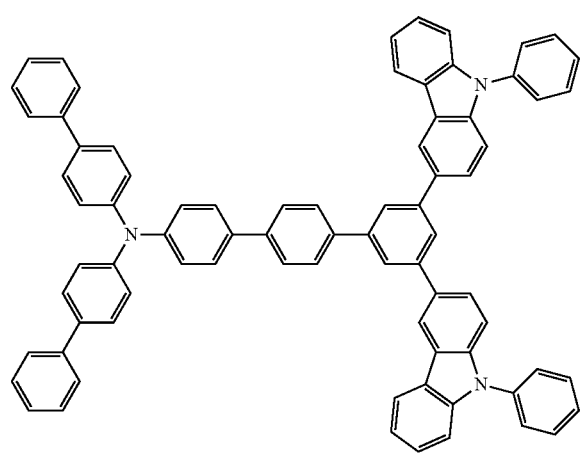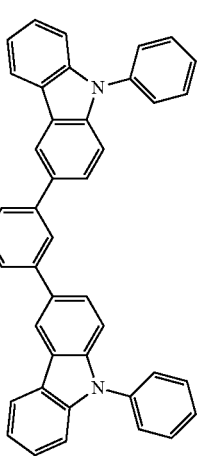

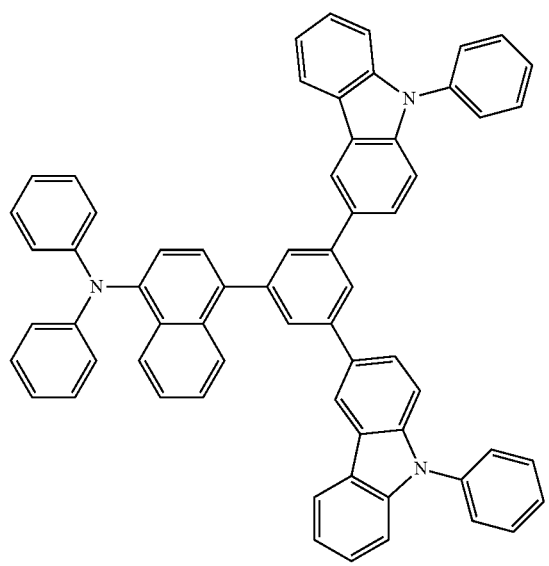
11
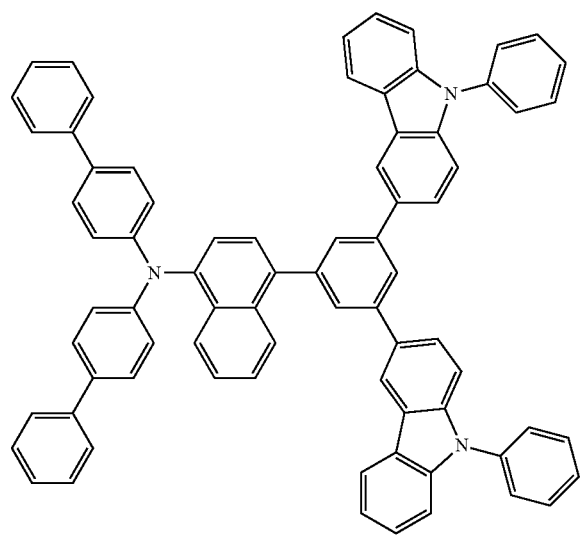
12
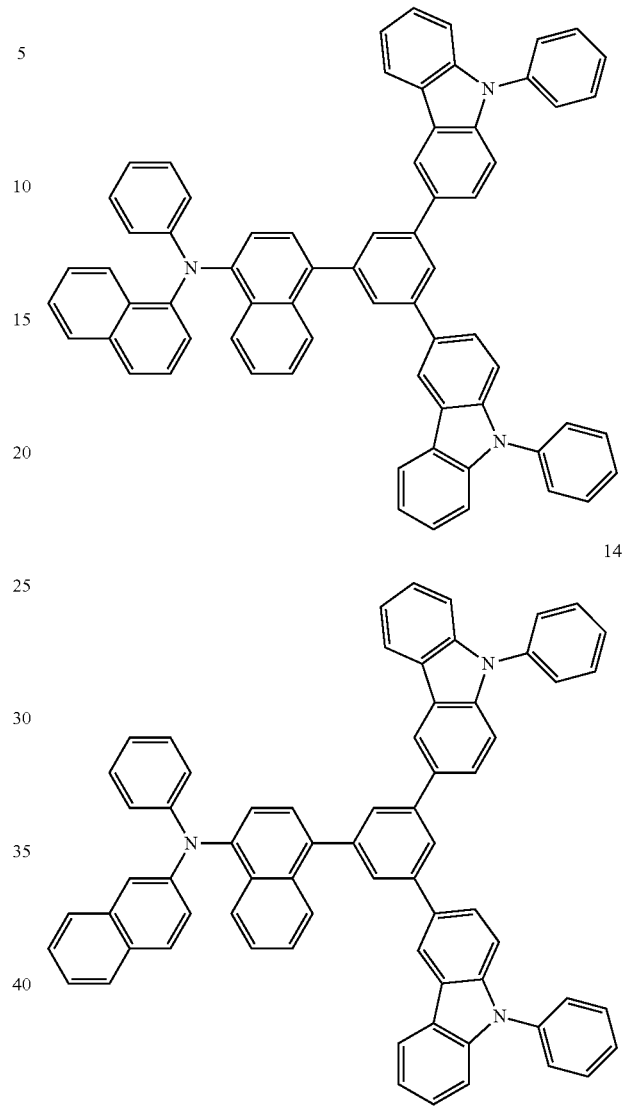
13
14
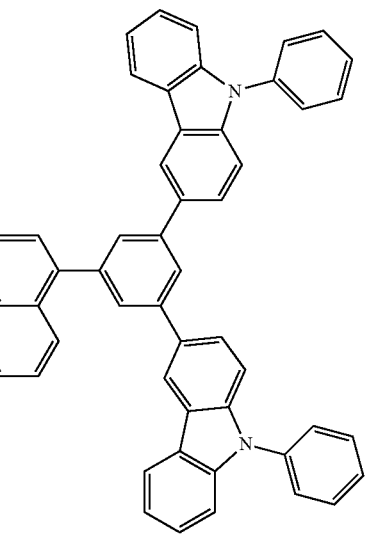
15

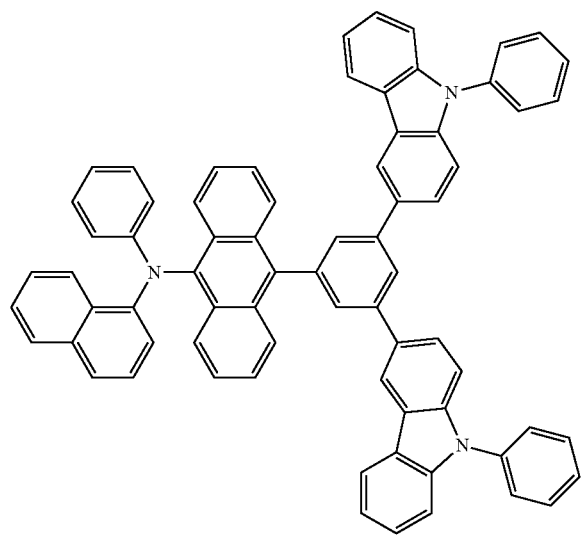
16
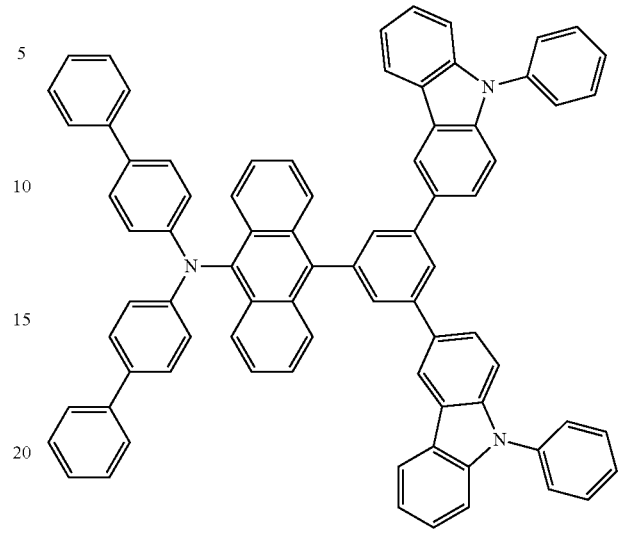
18
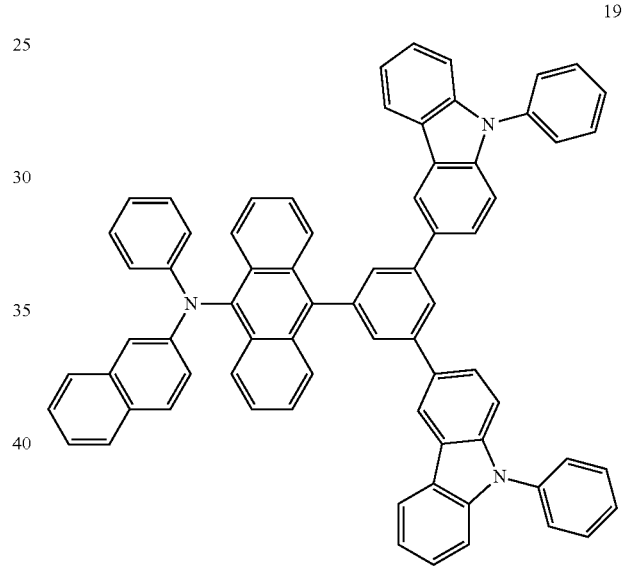
19
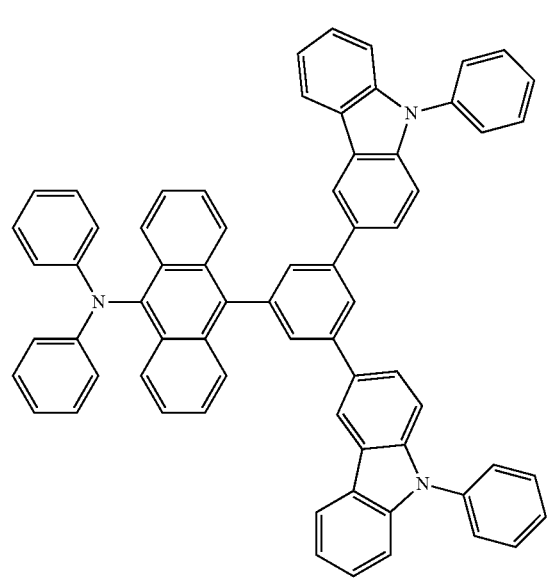
17
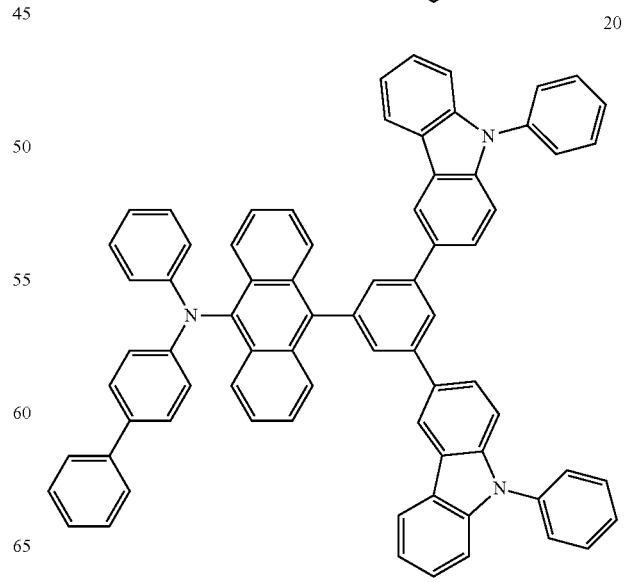
20

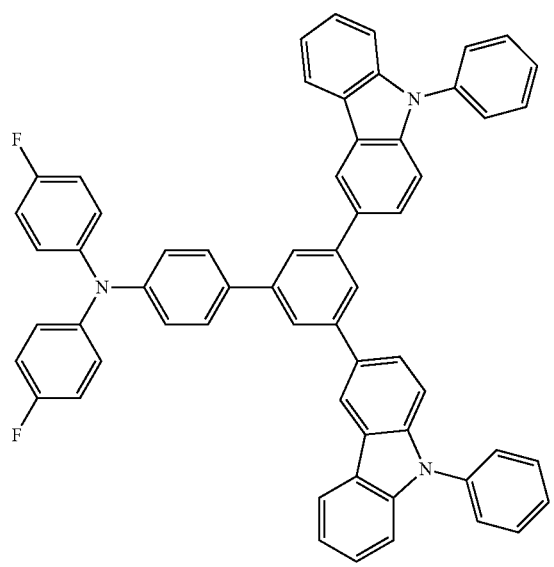
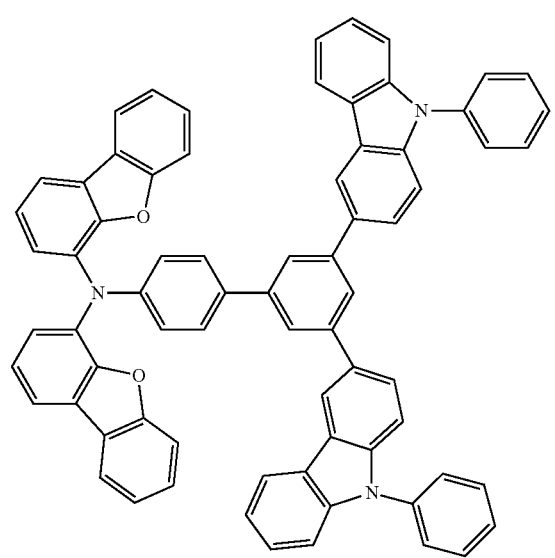
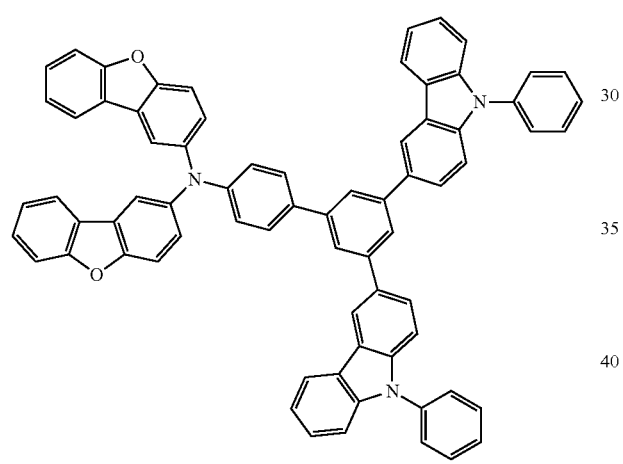
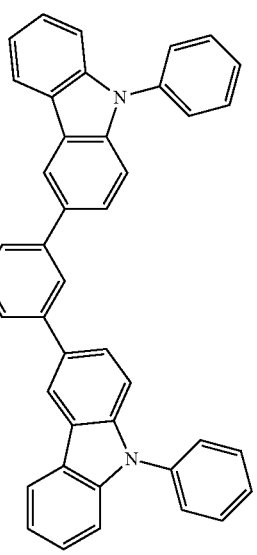
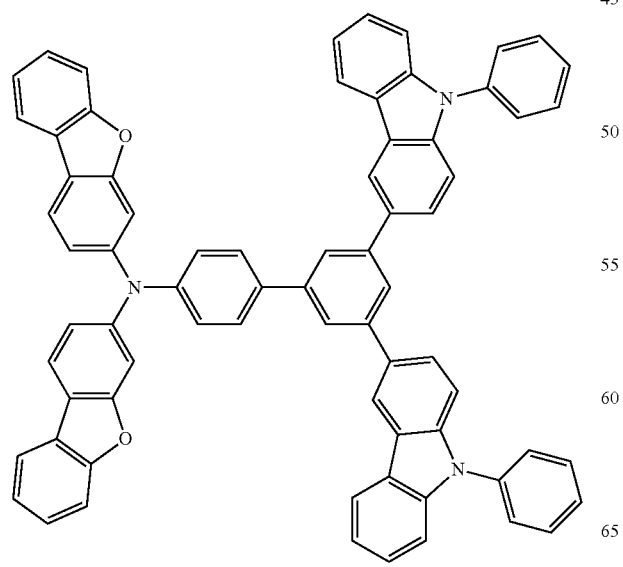
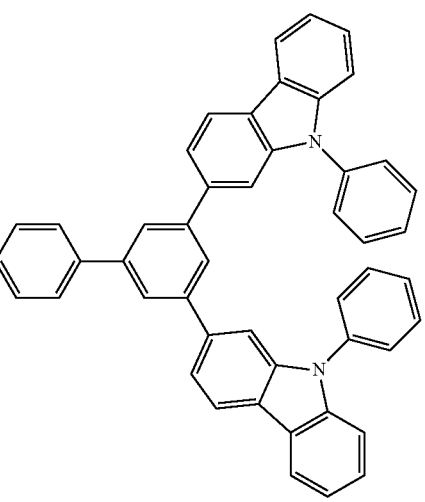

27
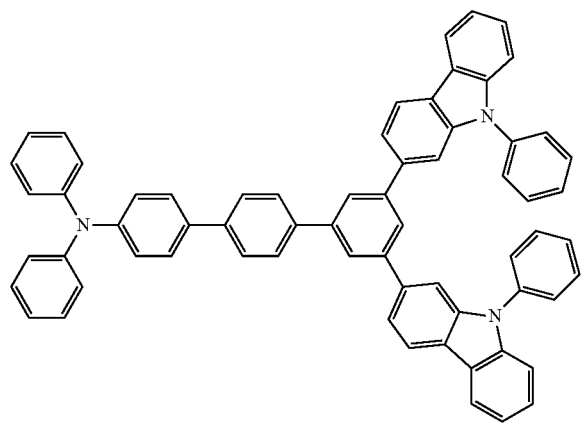
28
31
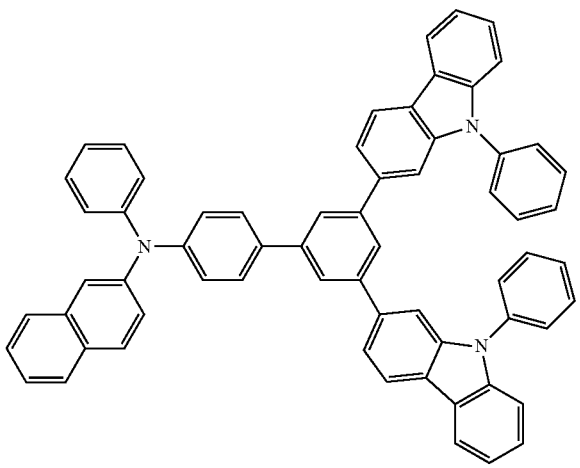
29
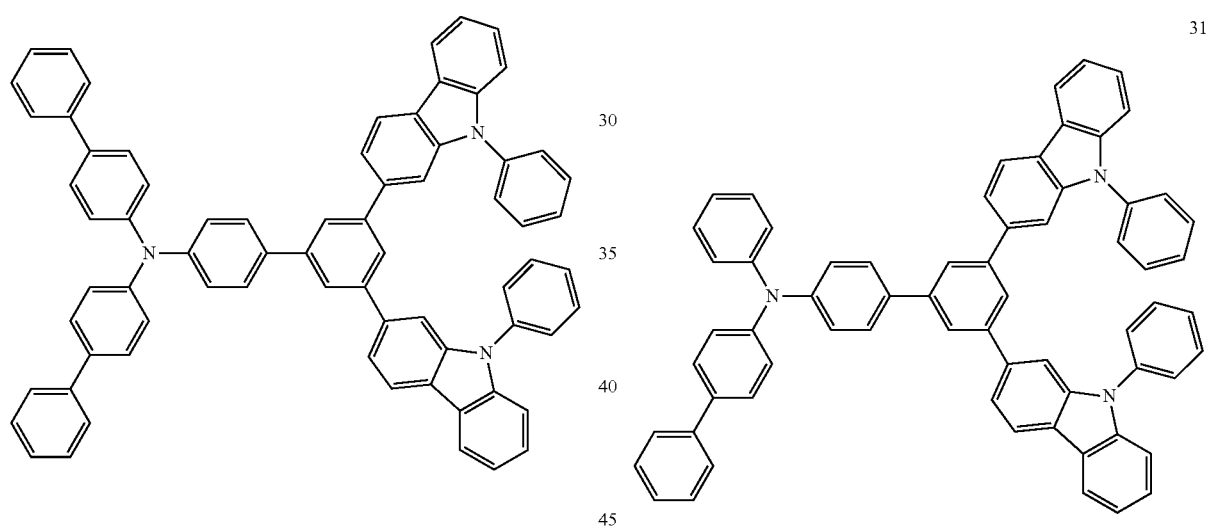
31
32
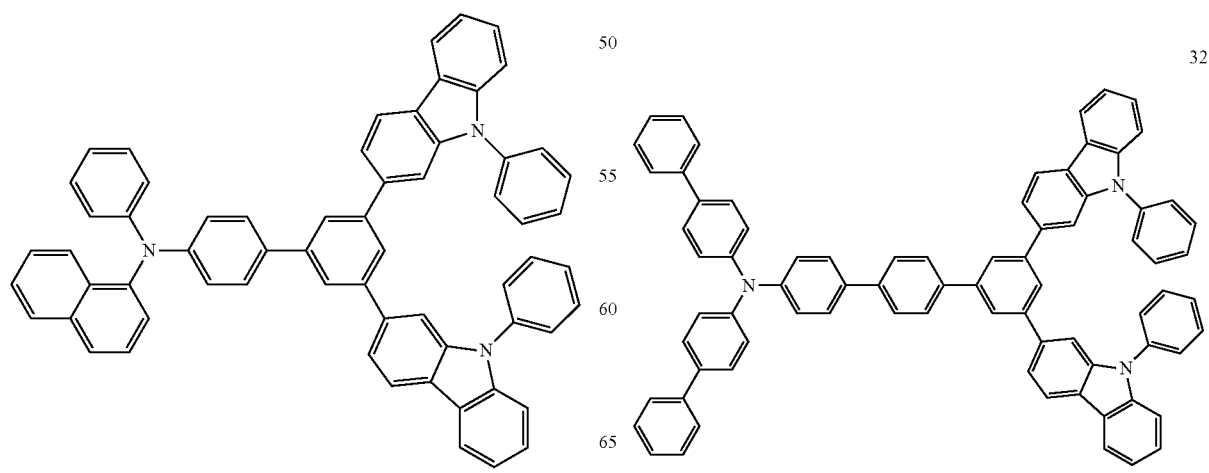

33
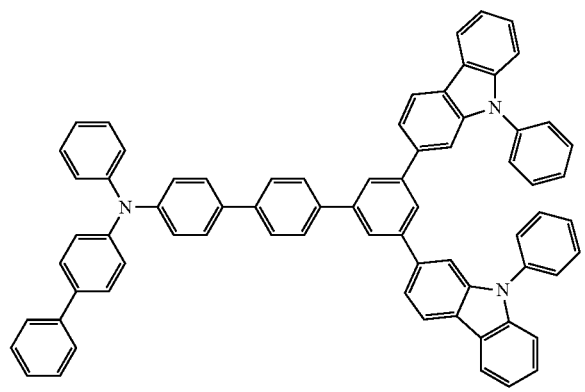
34
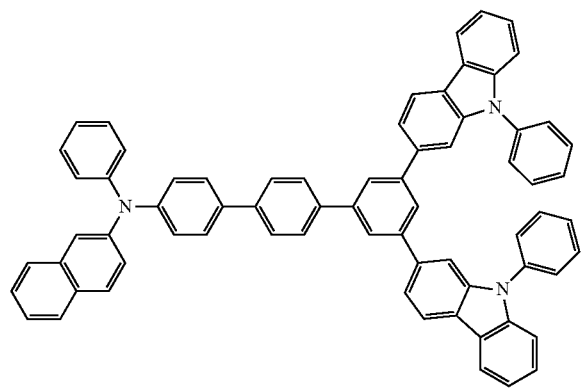
35
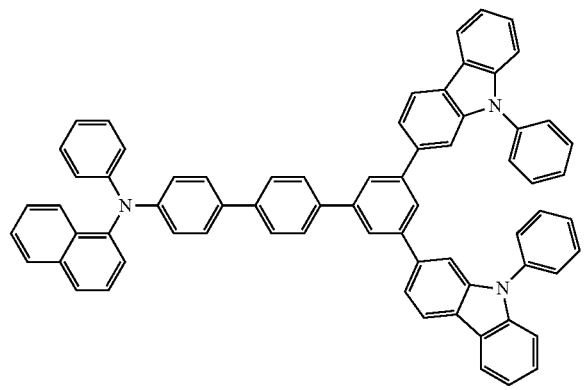
36
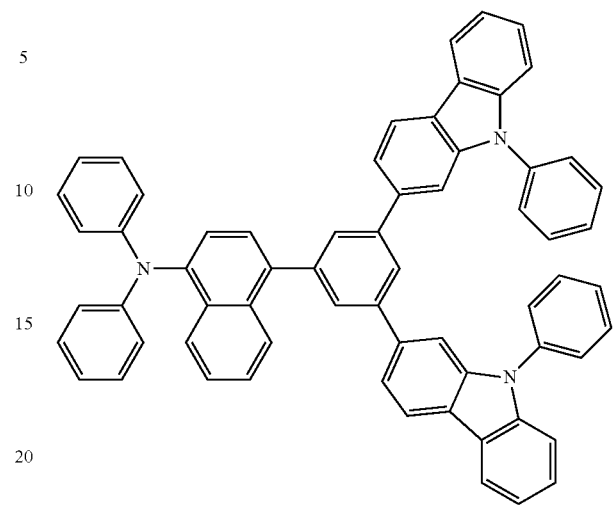
37
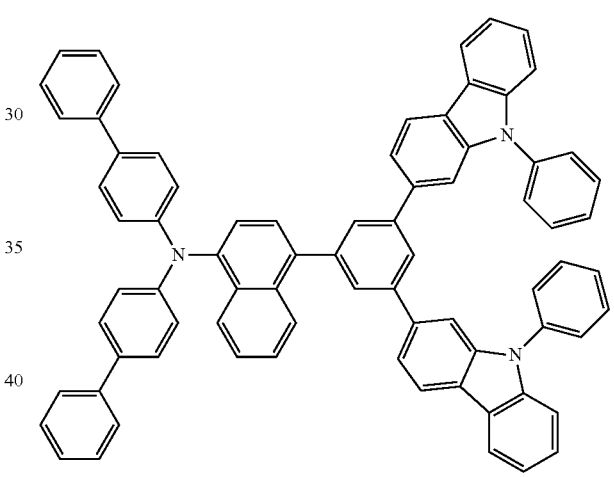
38
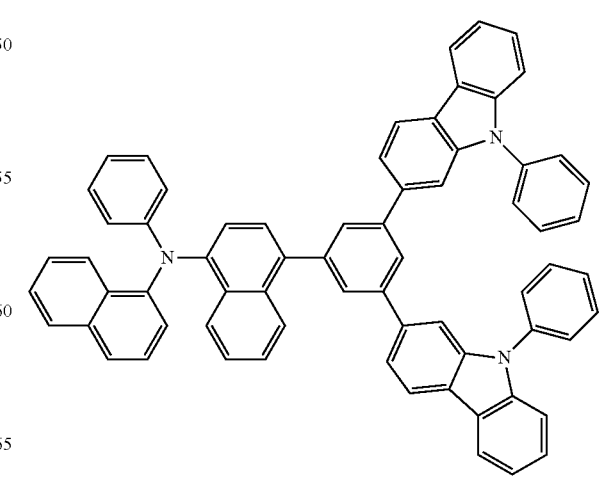

39
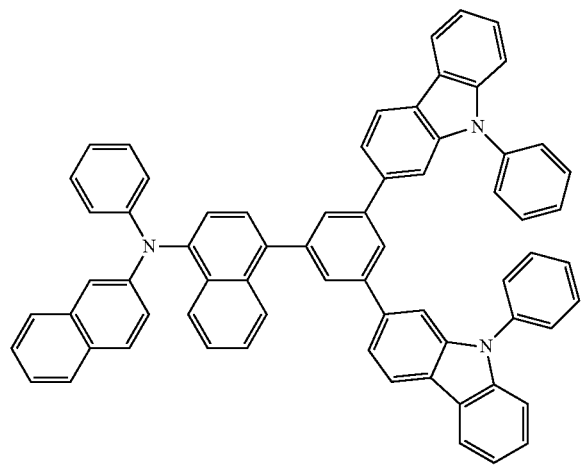
40
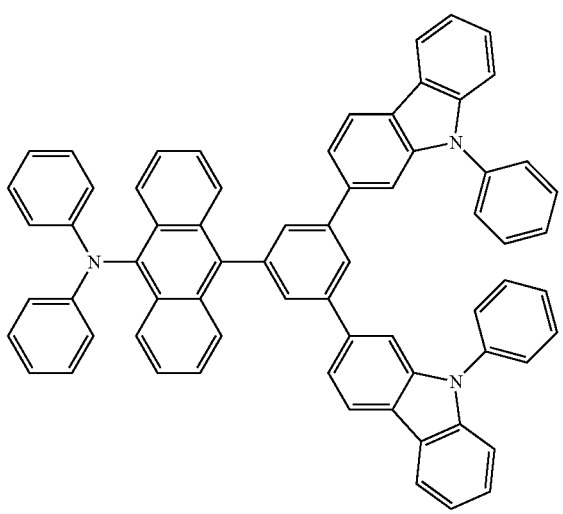
41
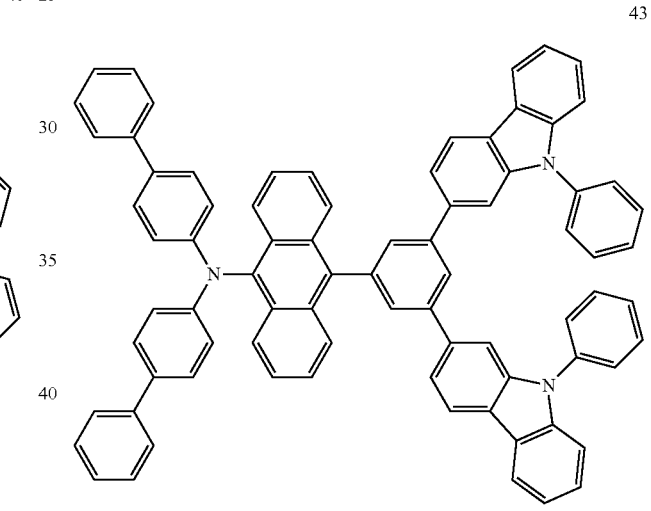
42
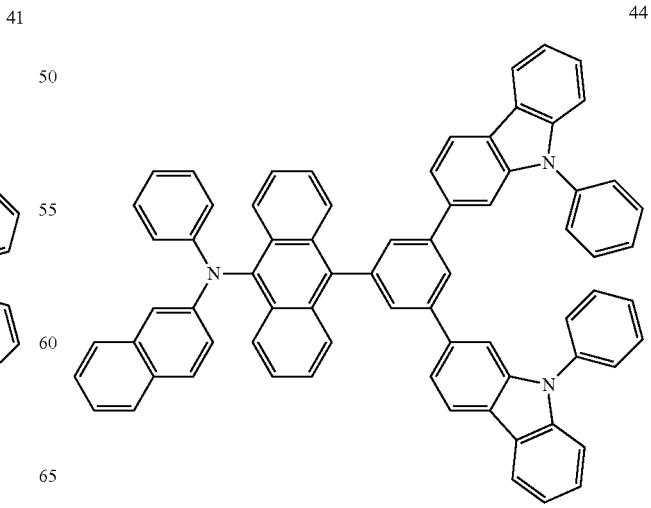

45
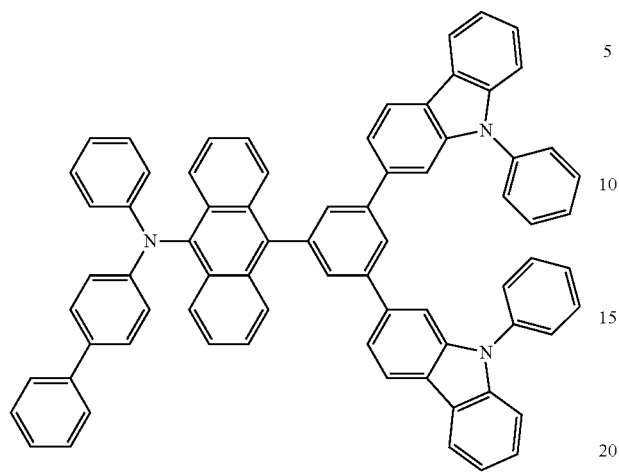
46
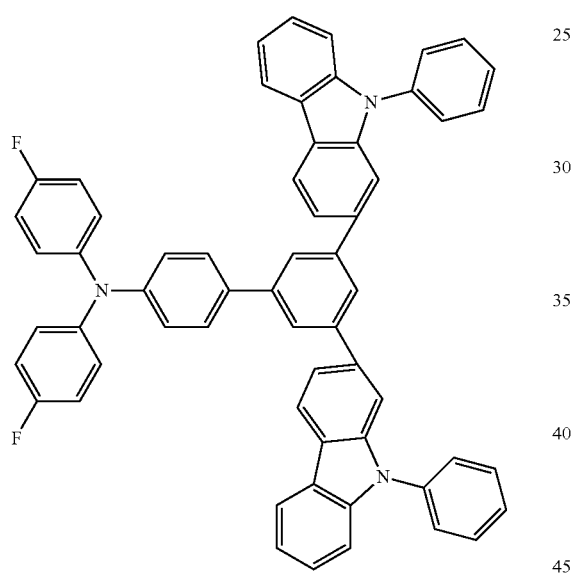
47
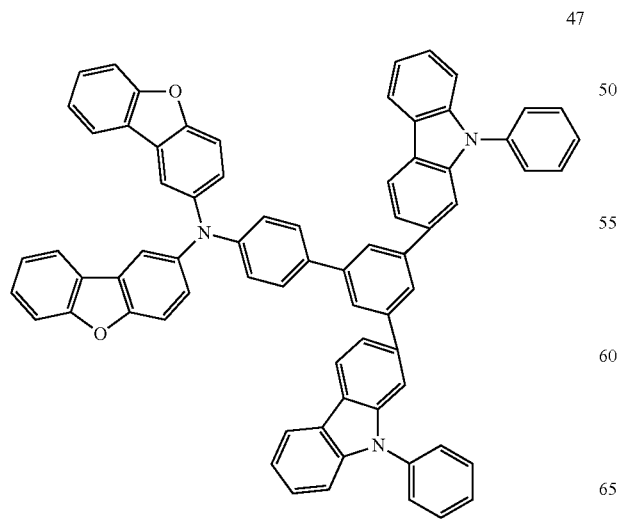
48
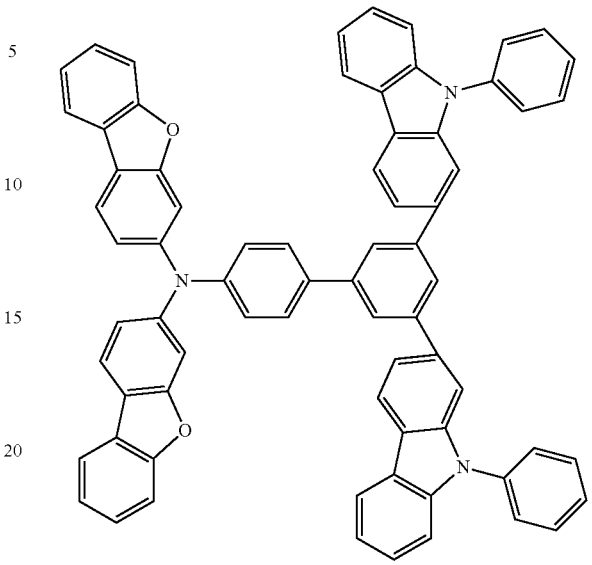
49
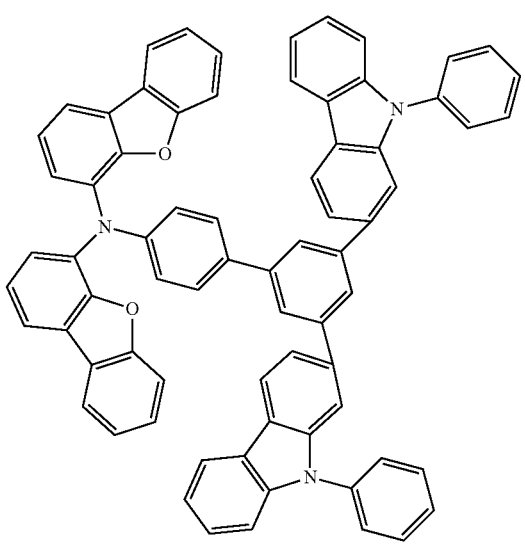

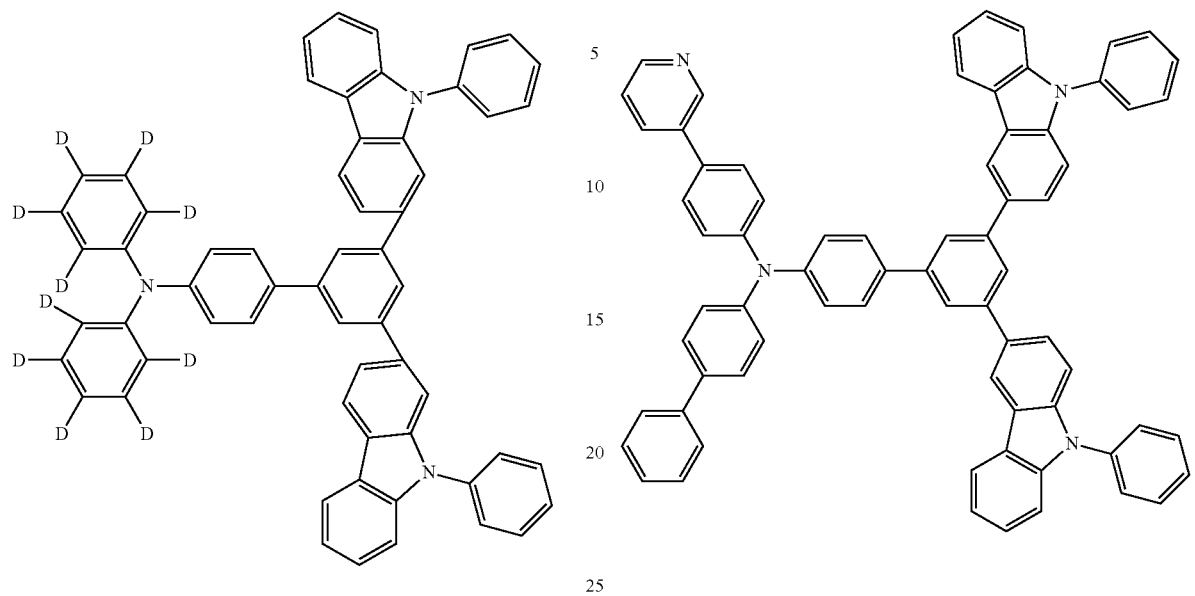
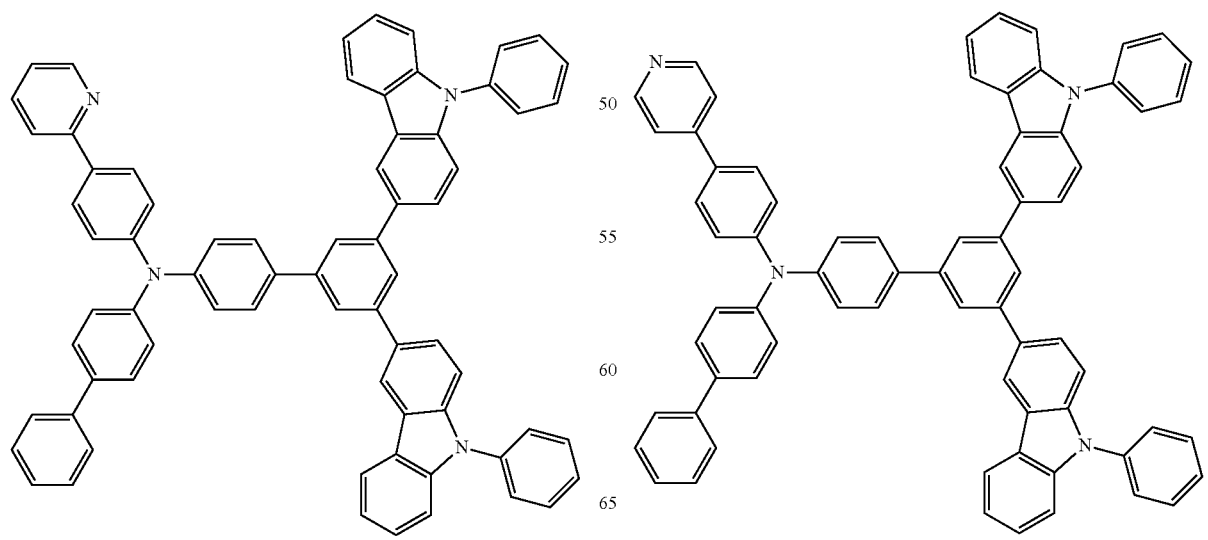

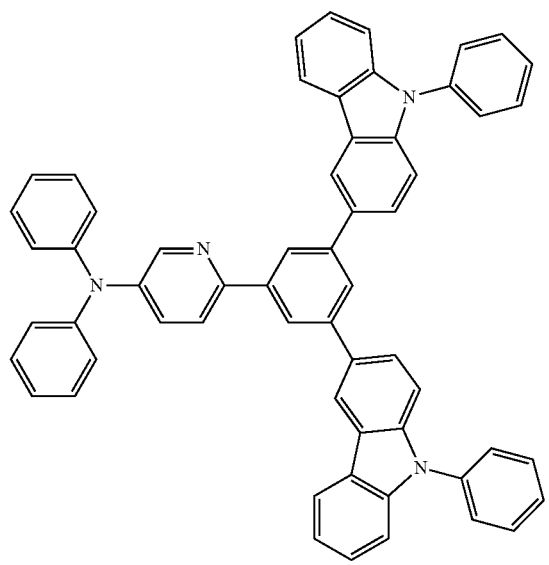
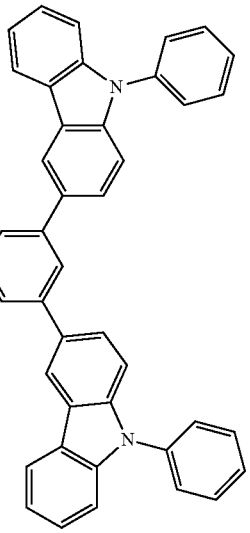
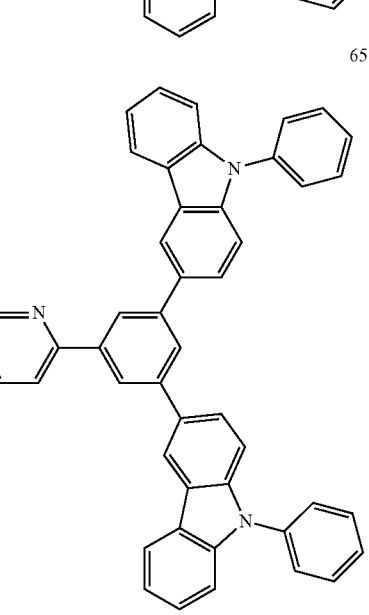

66
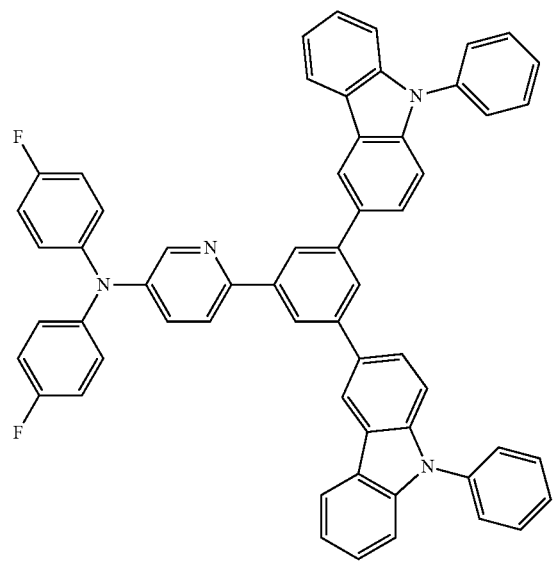
67
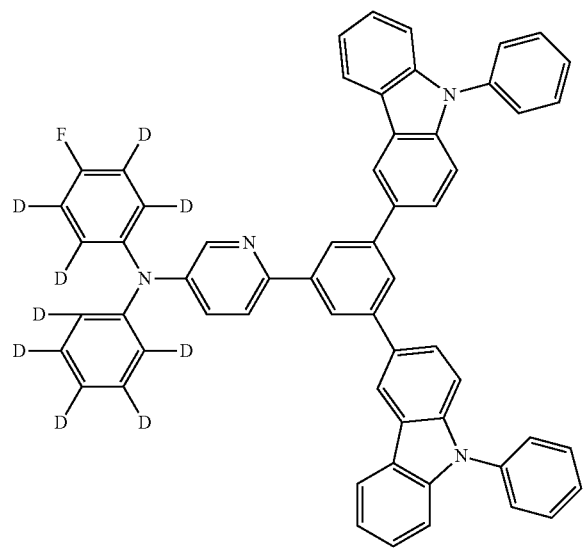
68
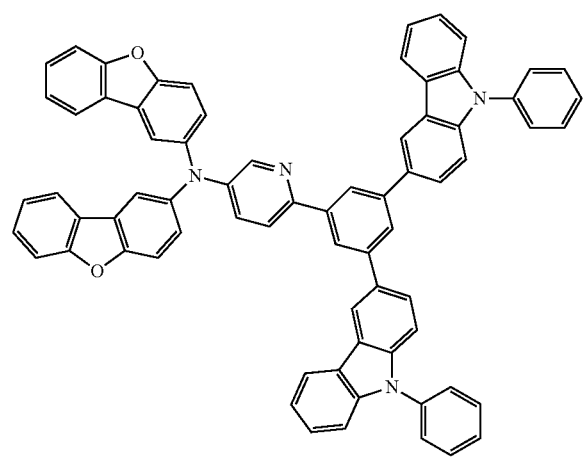
69
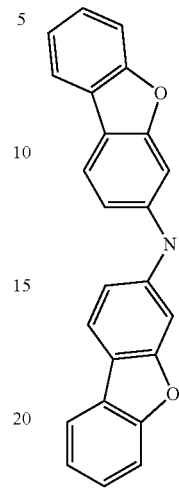
70
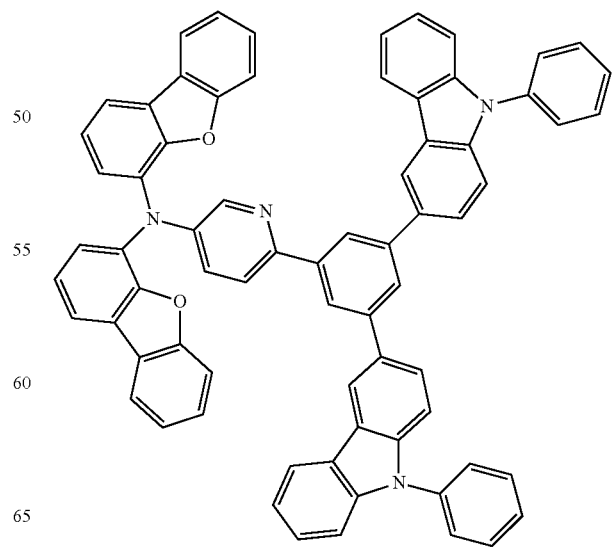

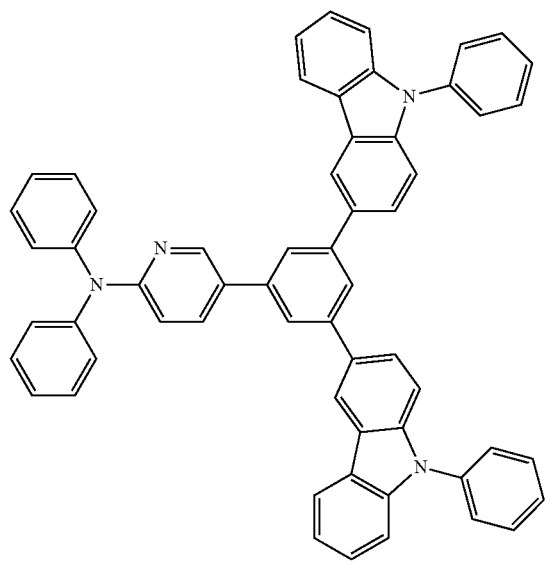
71
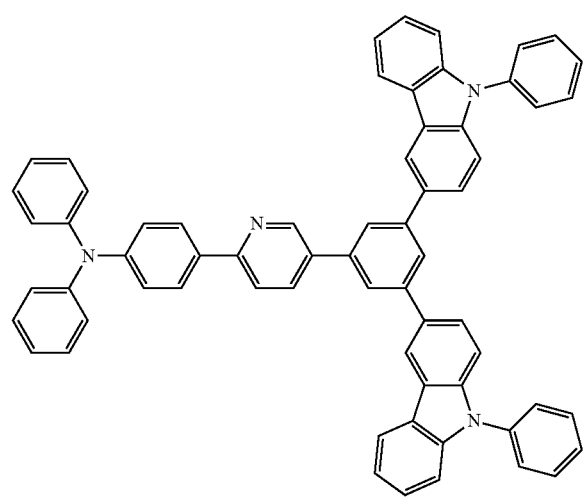
72
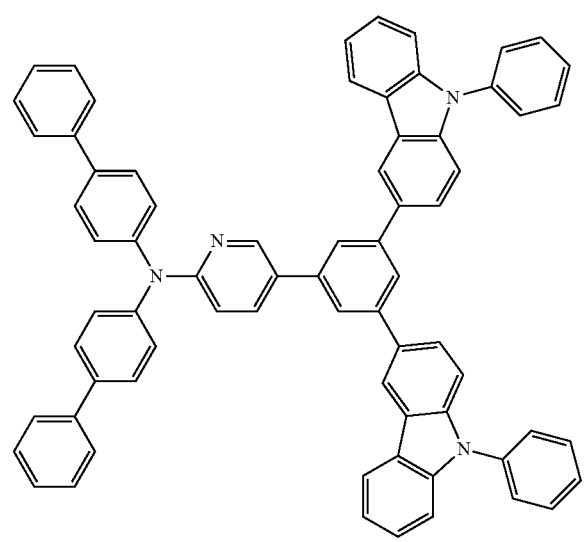
73
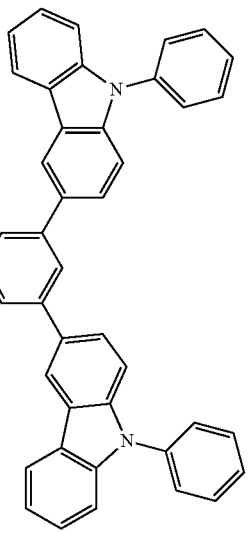
74
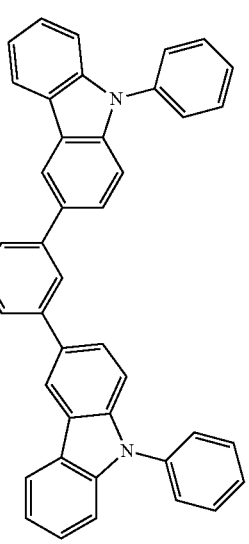
75
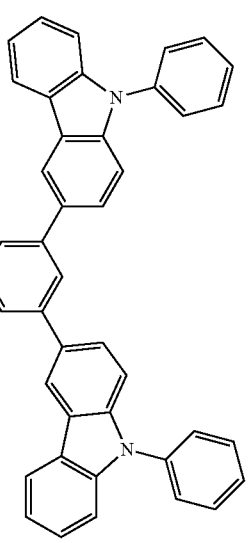
76

77
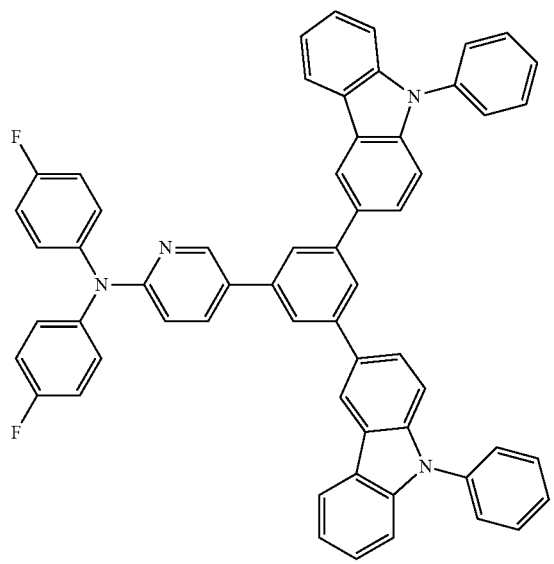
78
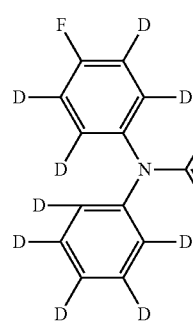
79
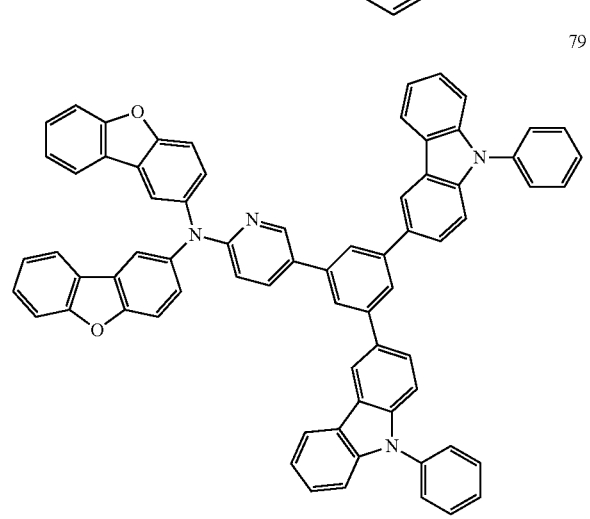
80
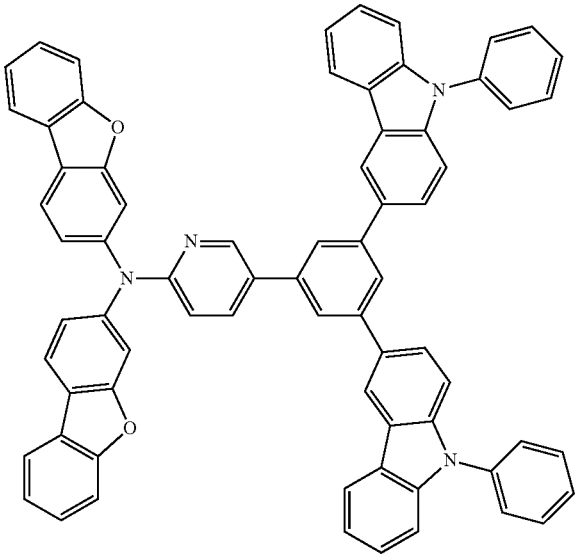
81
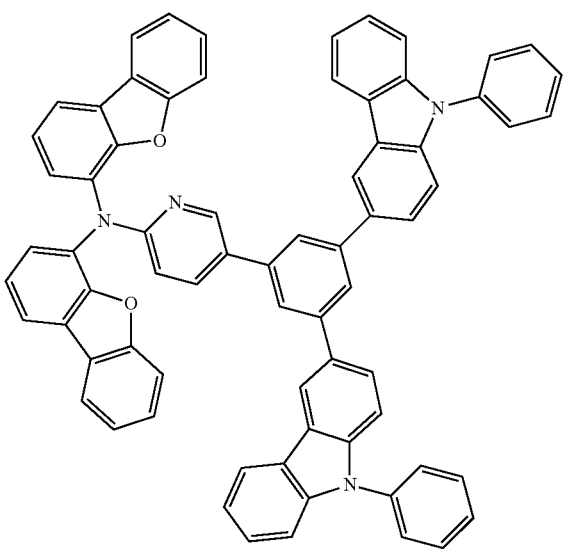

83
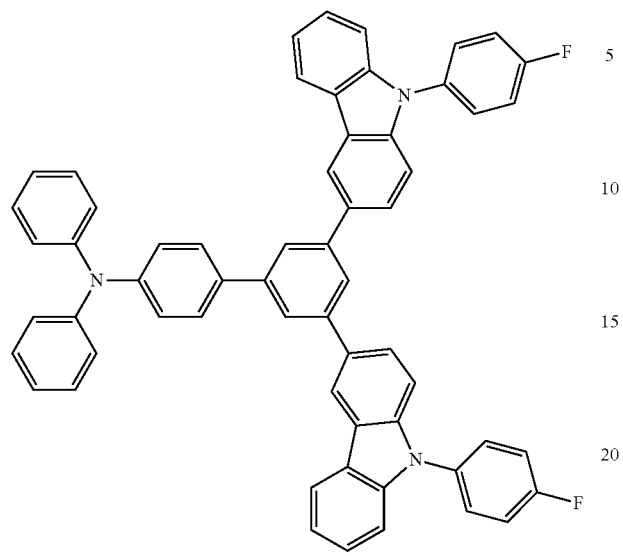
84
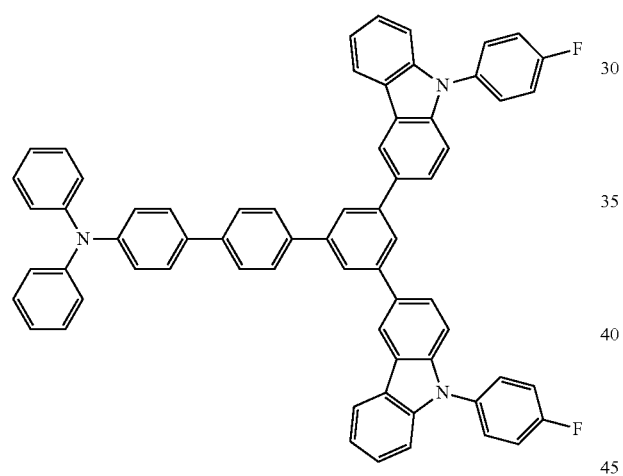
85
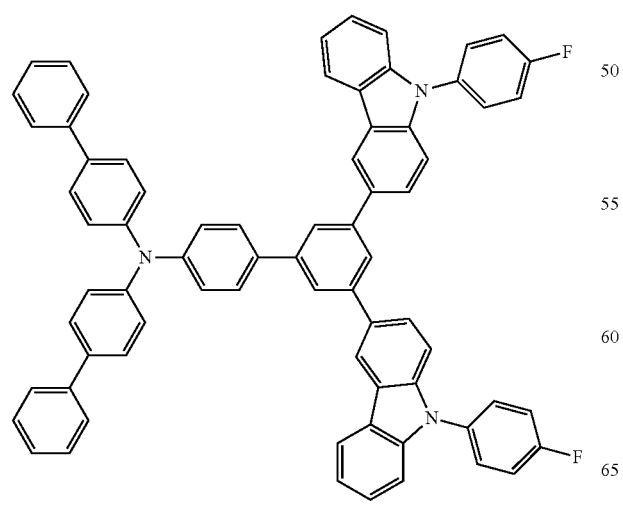
86
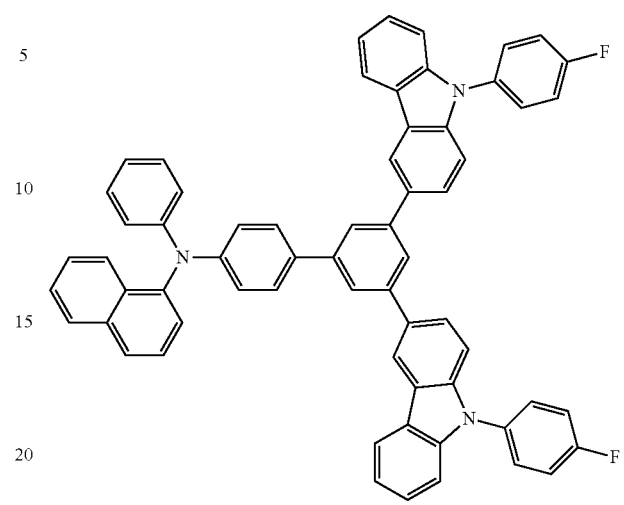
87
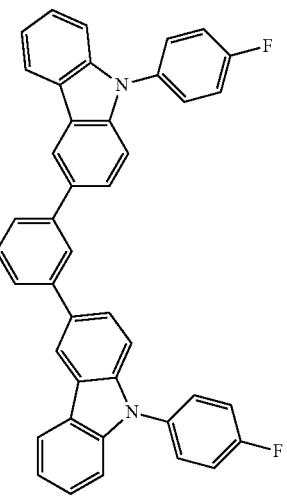
88
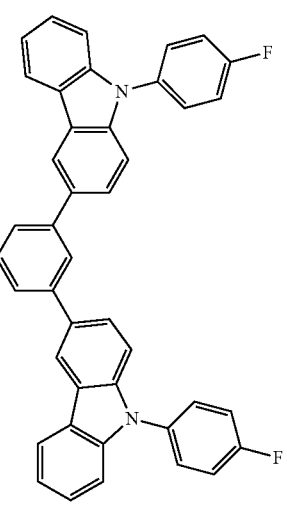

89
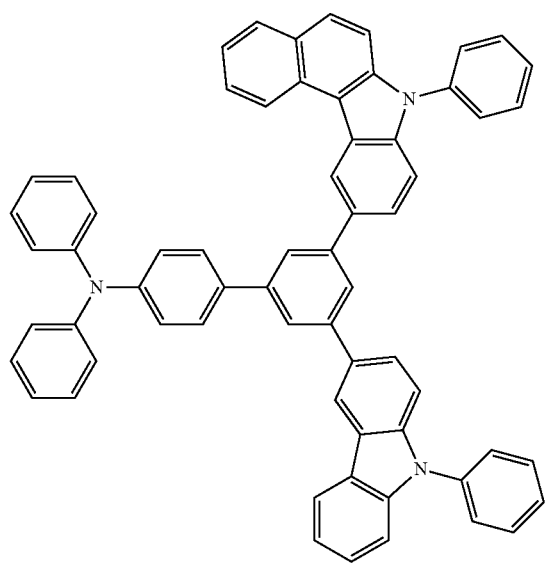
90
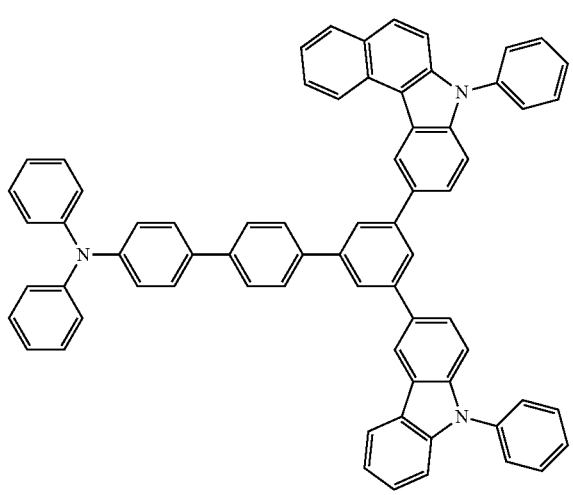
91
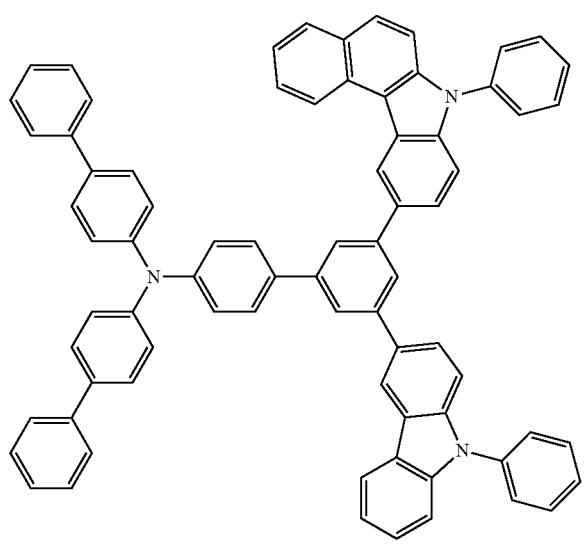
92
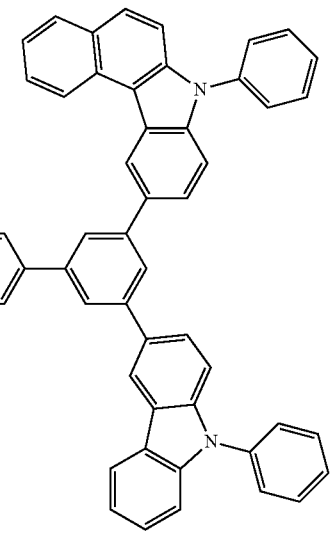
93
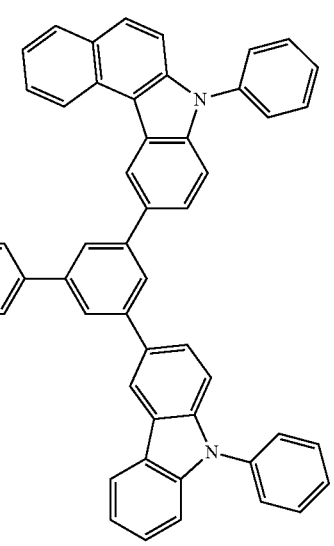
94
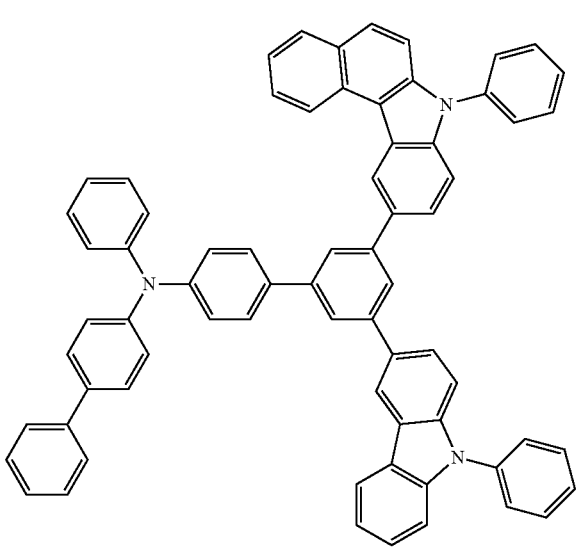

-continued
95
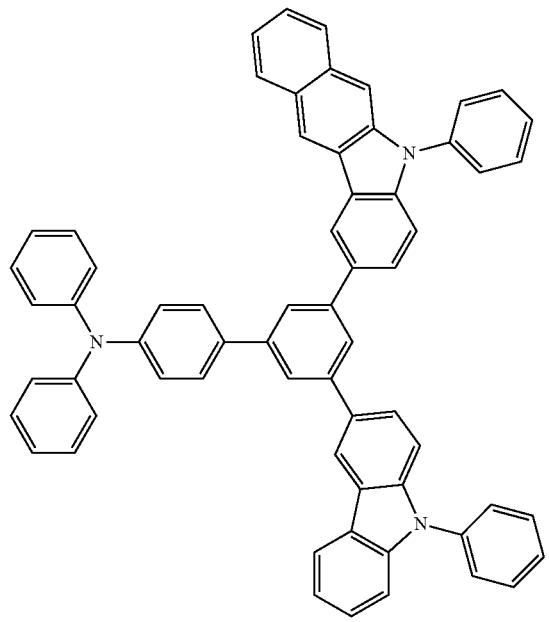
96
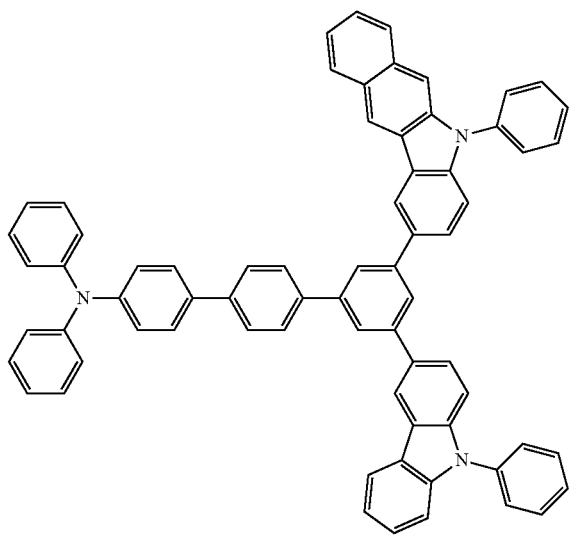
97
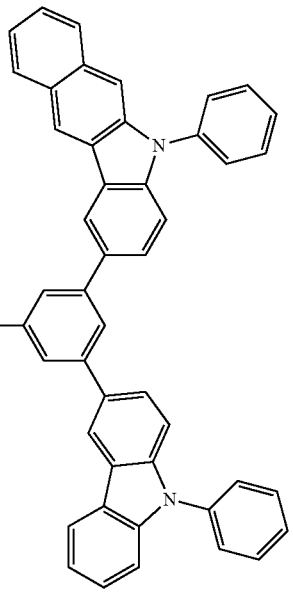
98
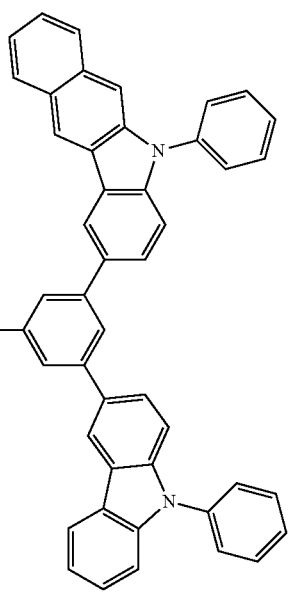

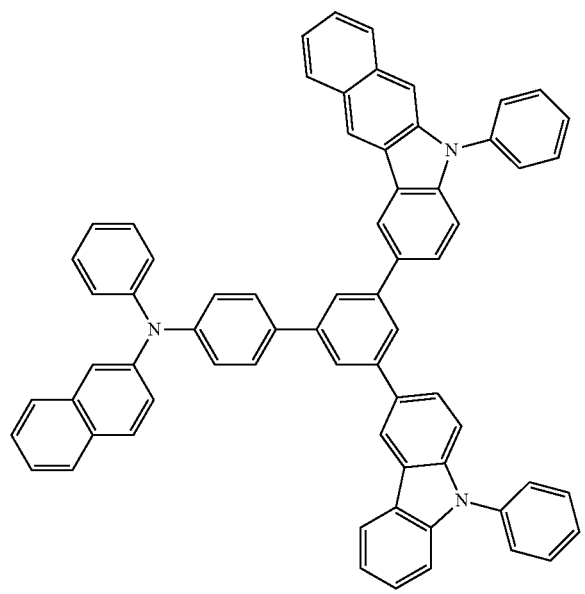
99
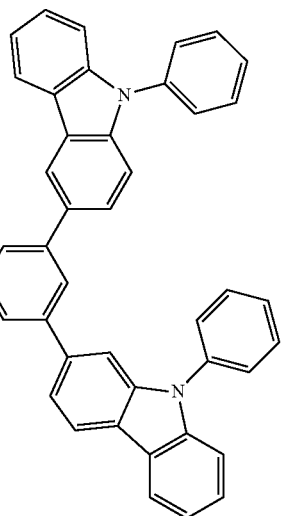
101
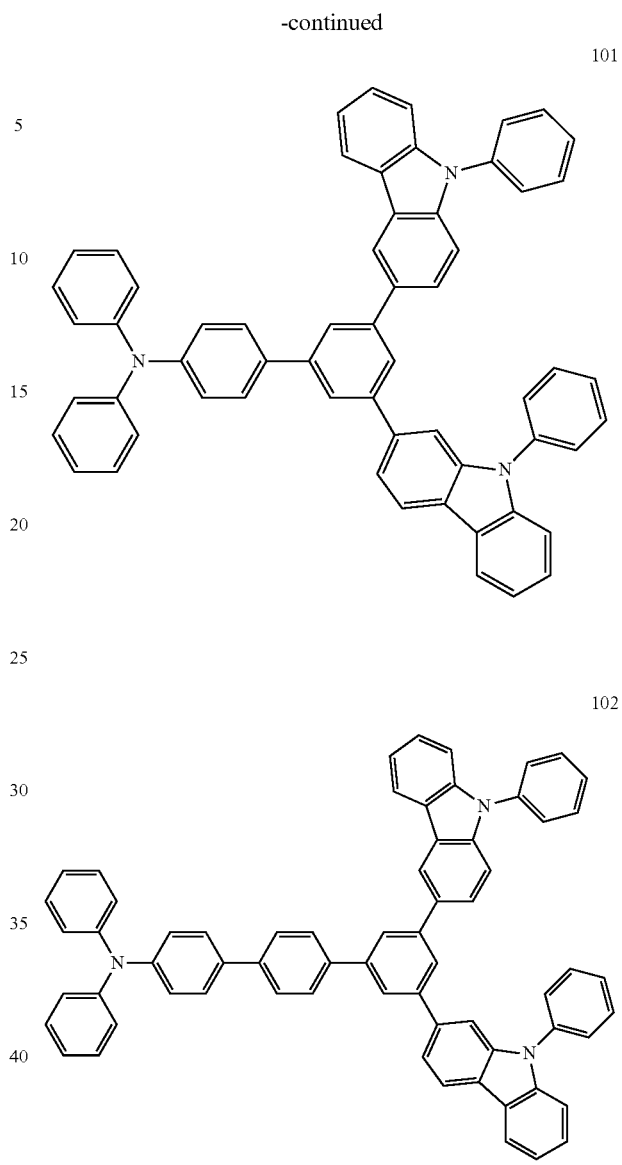
102
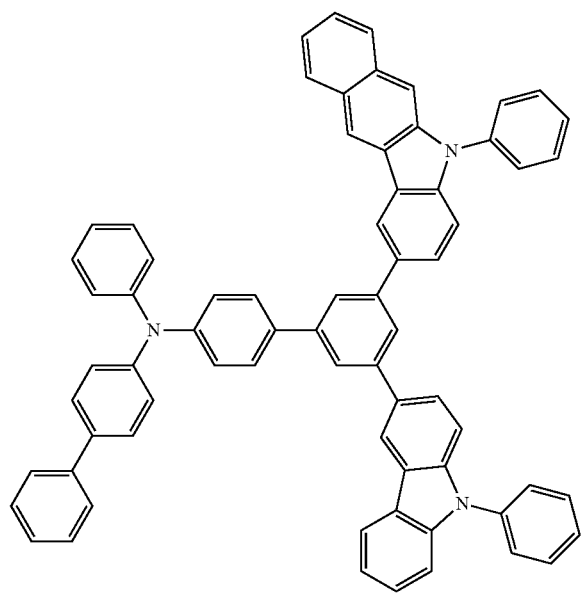
100
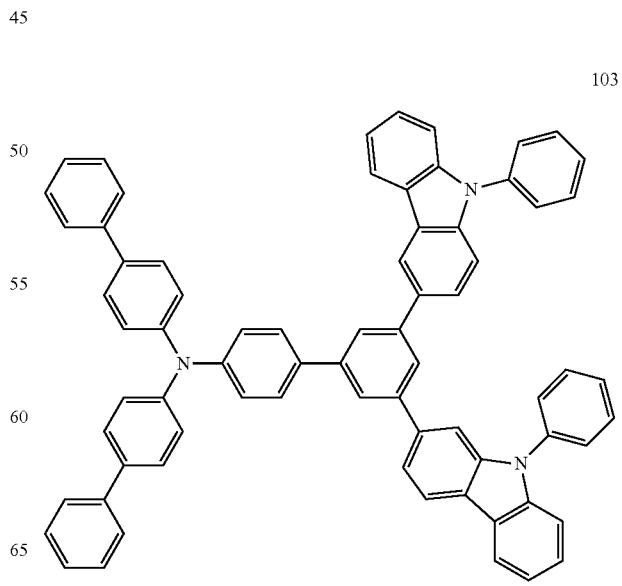
103

104
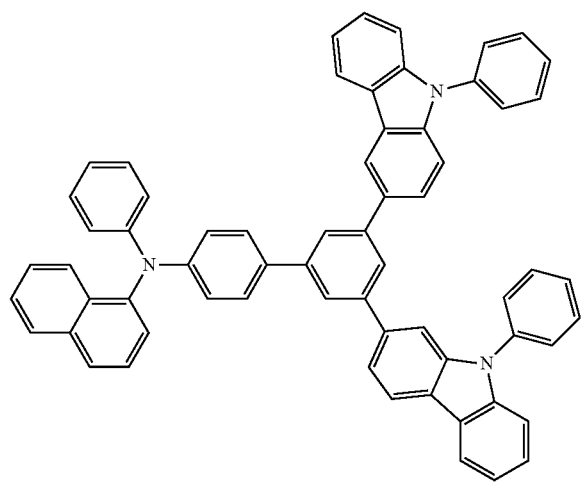
105
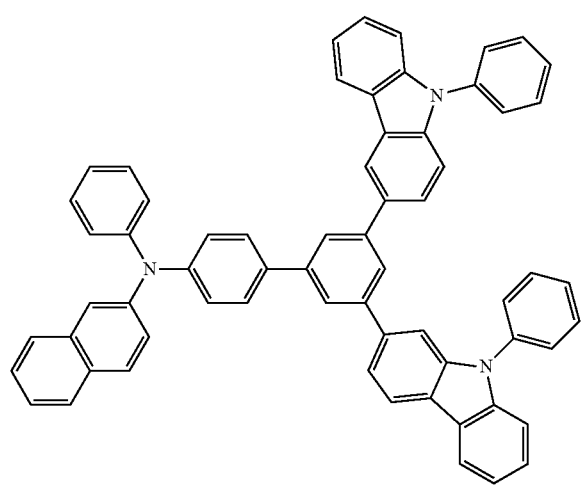
106
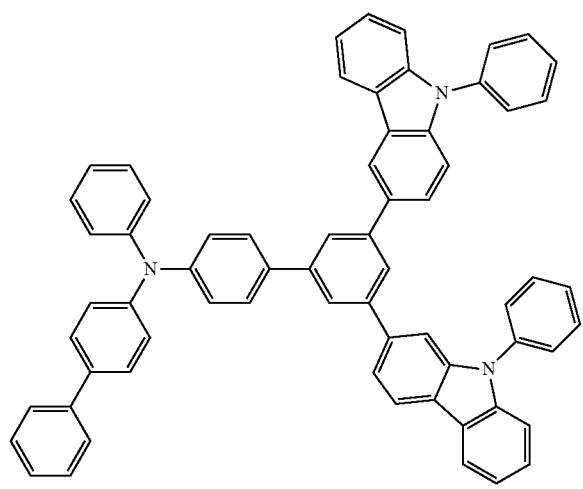
107
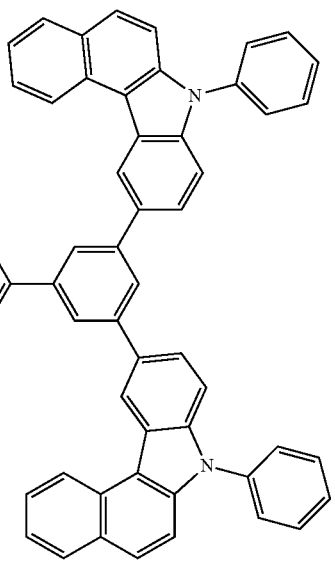
108
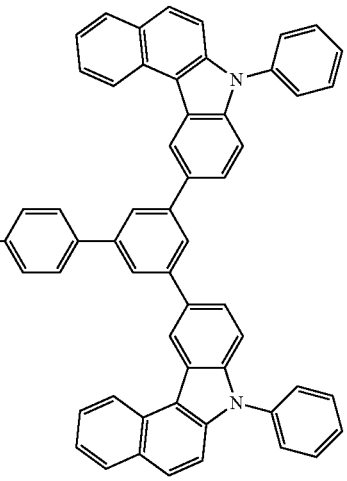
109
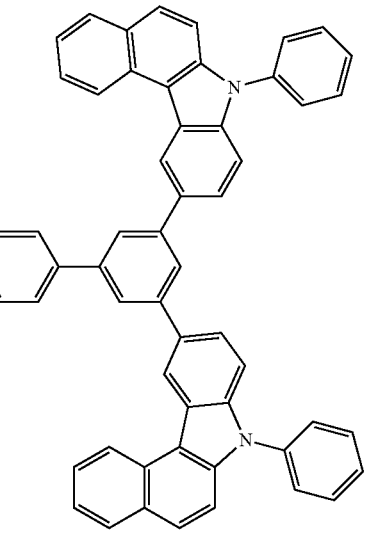

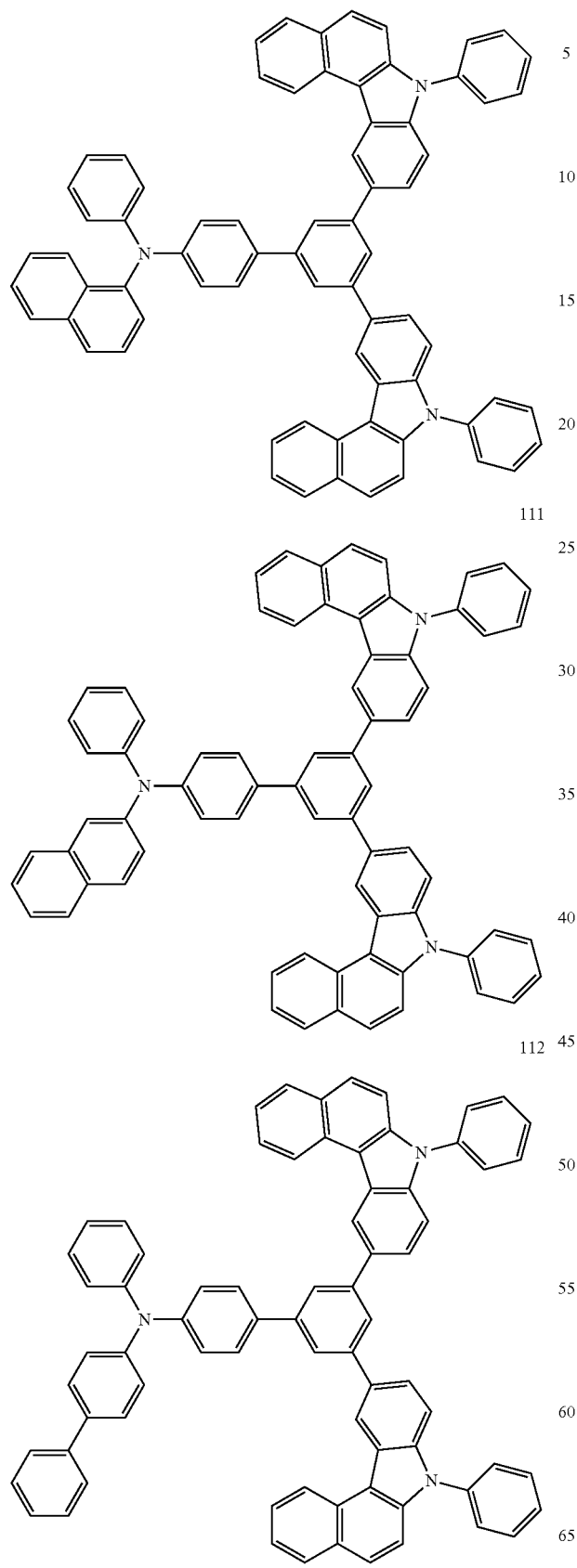
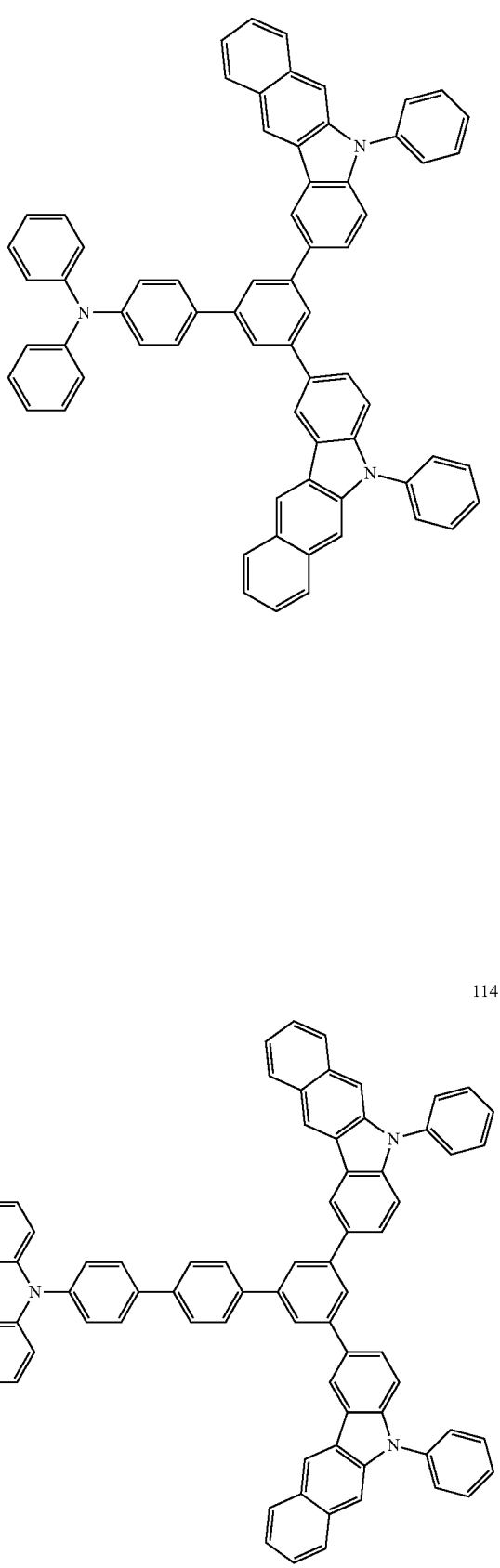

115
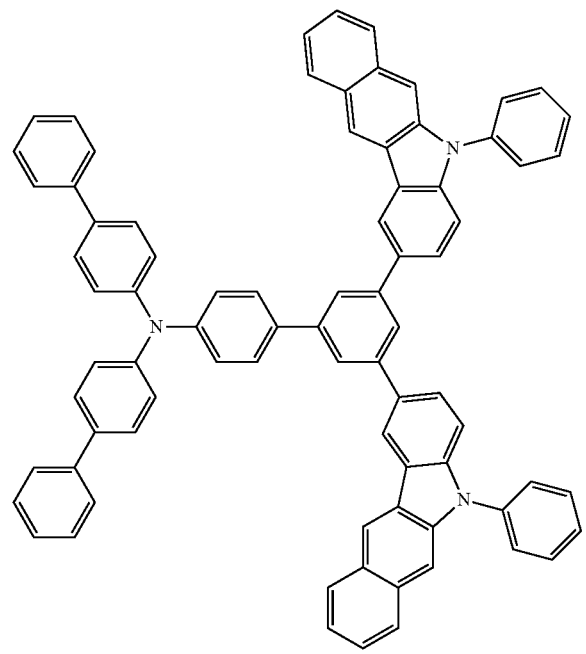
117
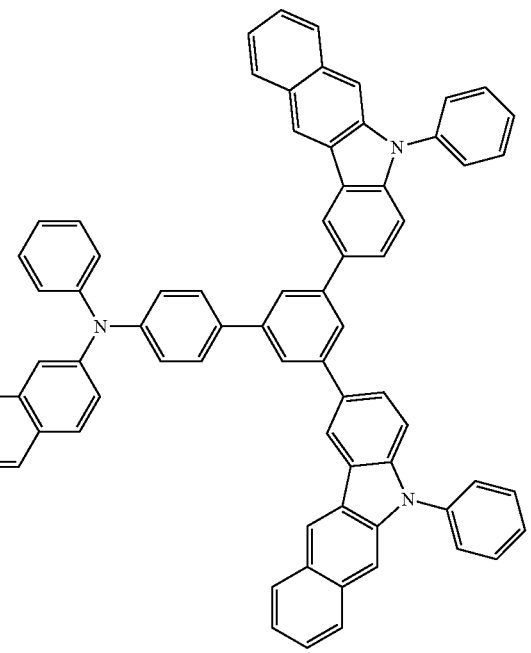
116
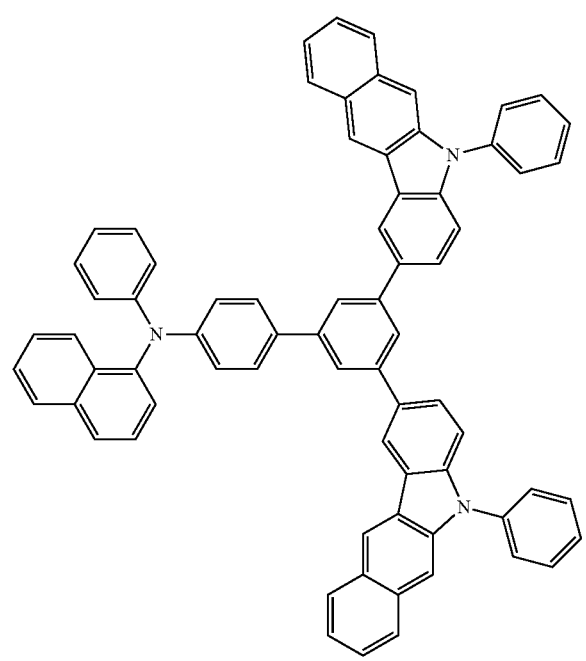
118
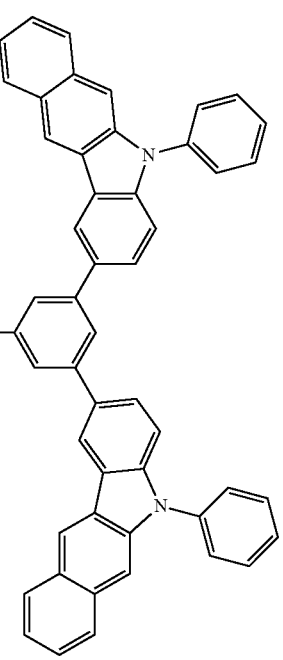

119
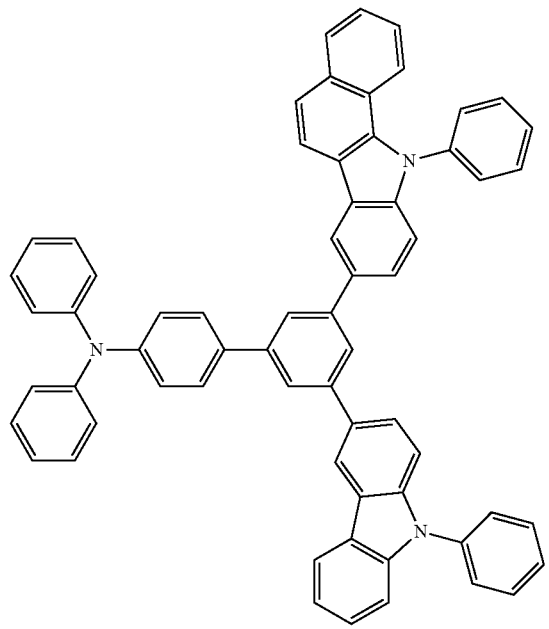
120
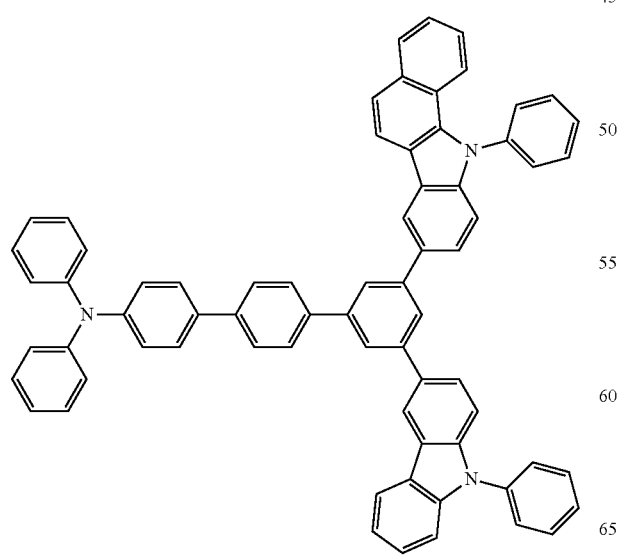
121
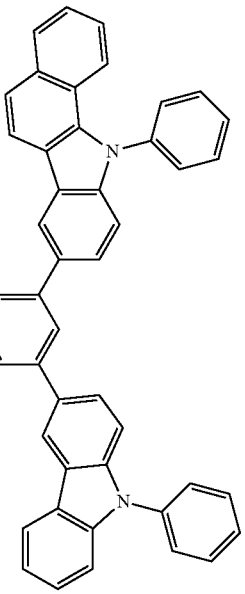
122
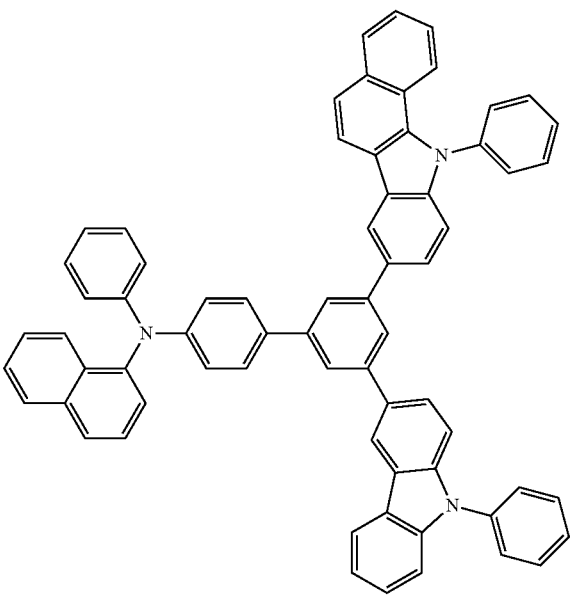

123
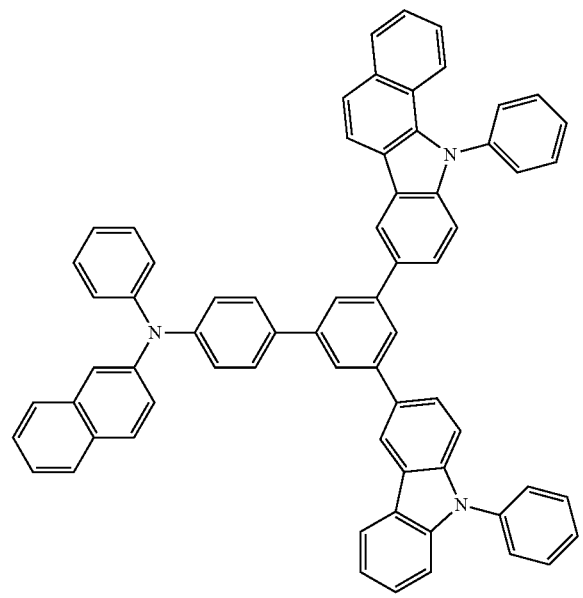
125
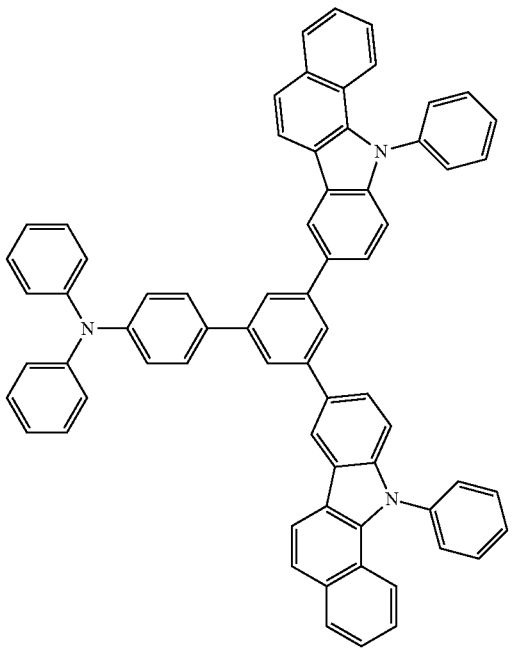
124
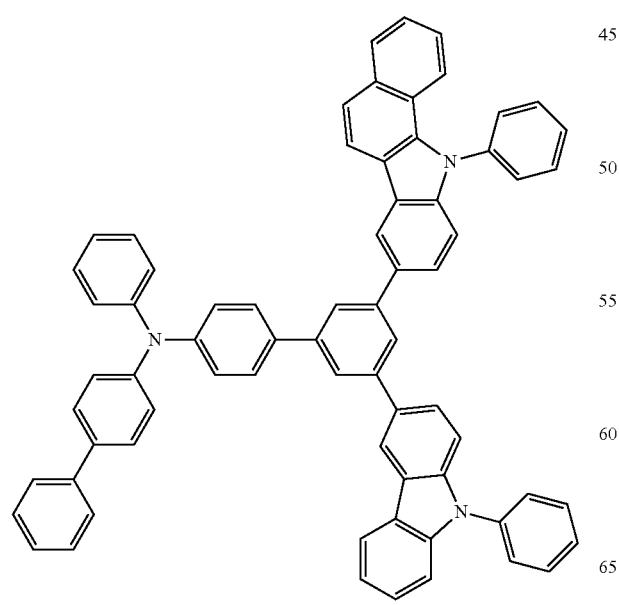
126
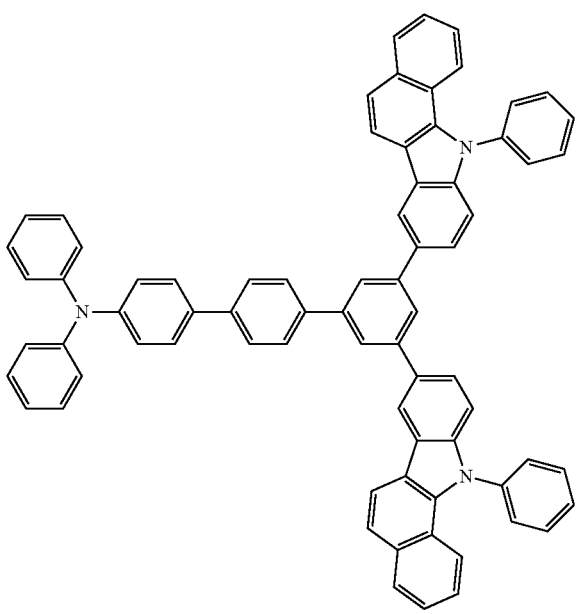

127
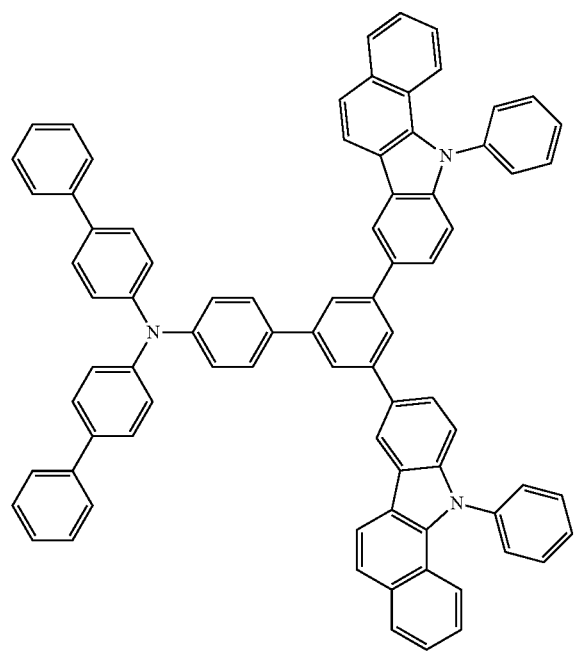
129
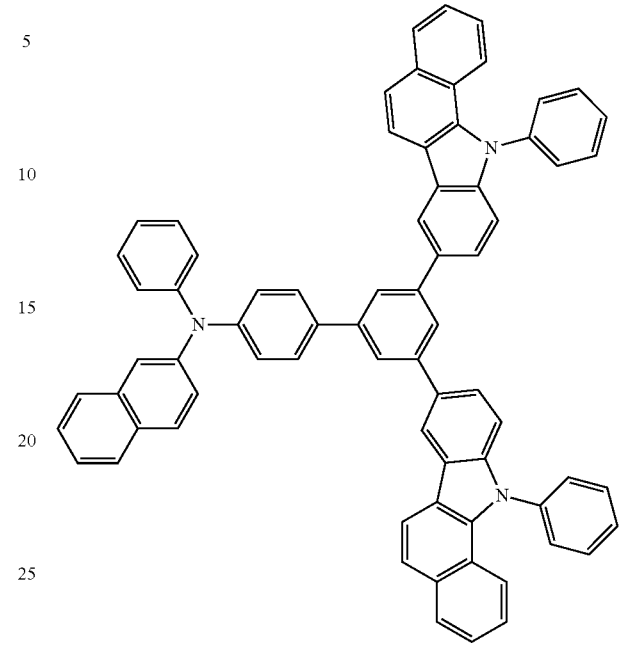
128
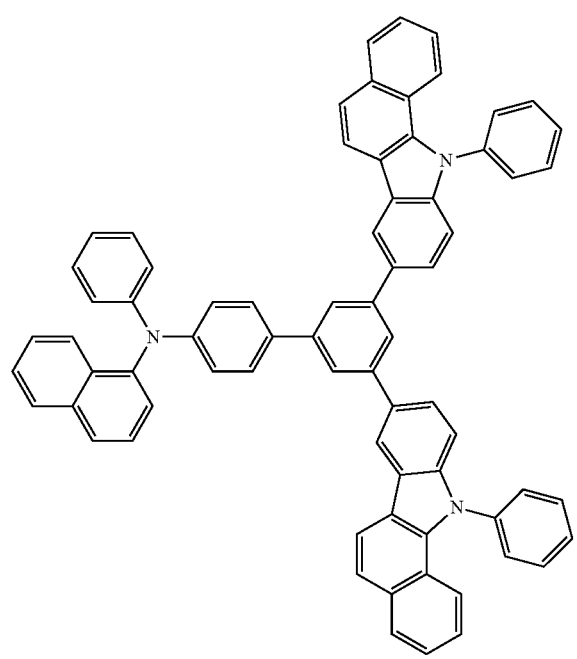
130
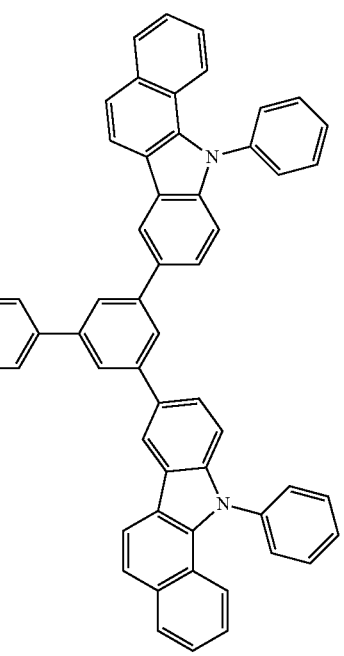

131
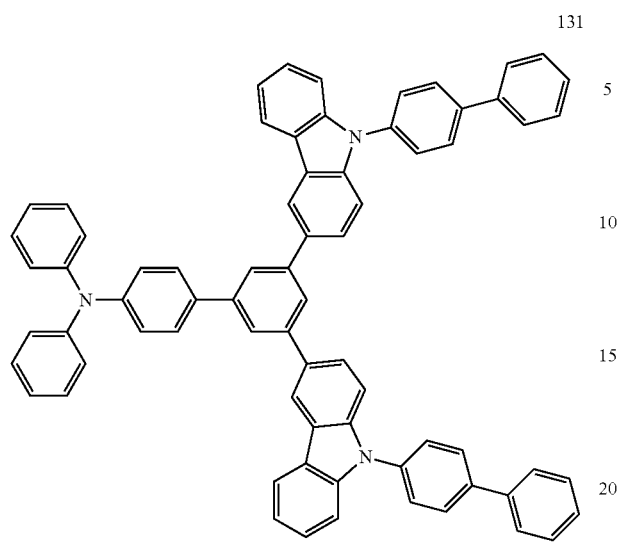
132
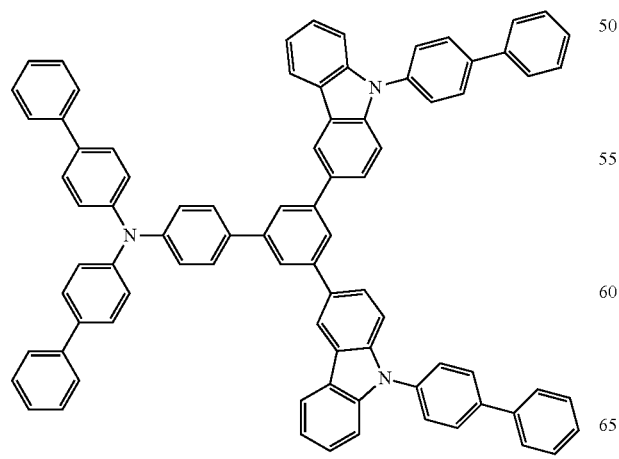
133
134
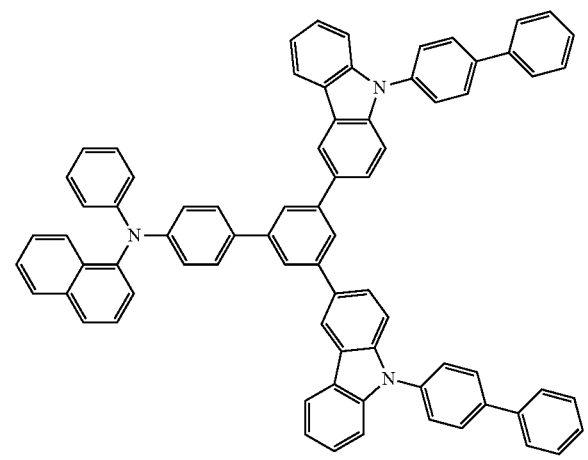
135
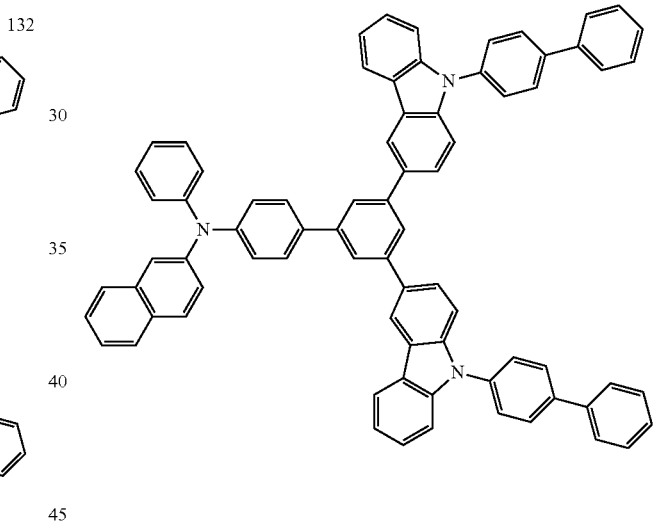
136
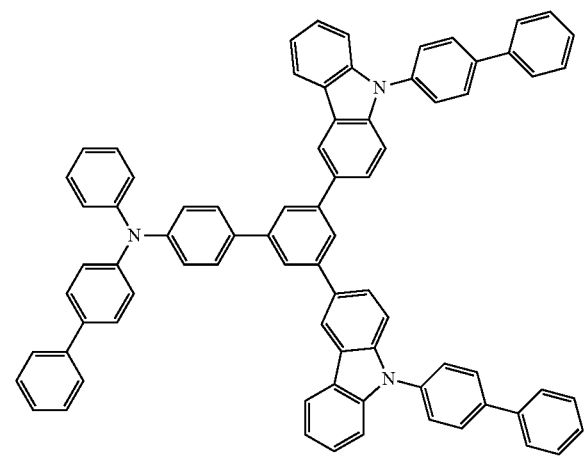

-continued
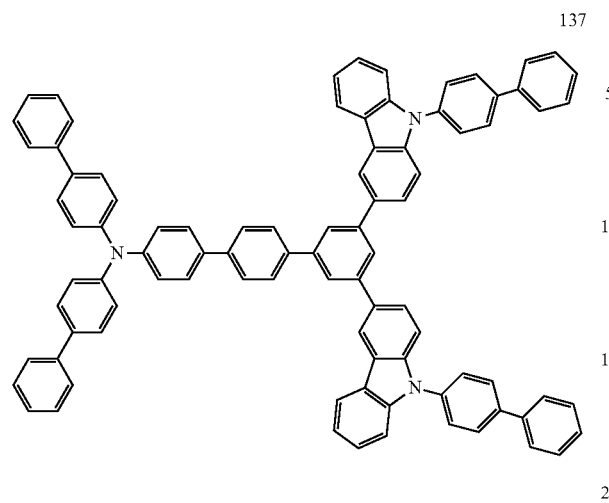
137
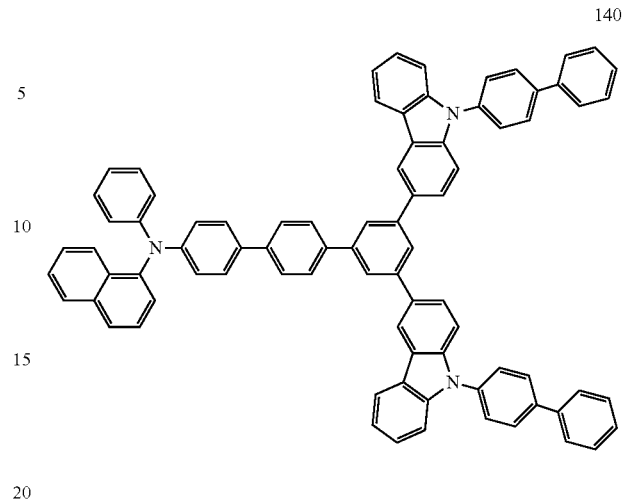
140
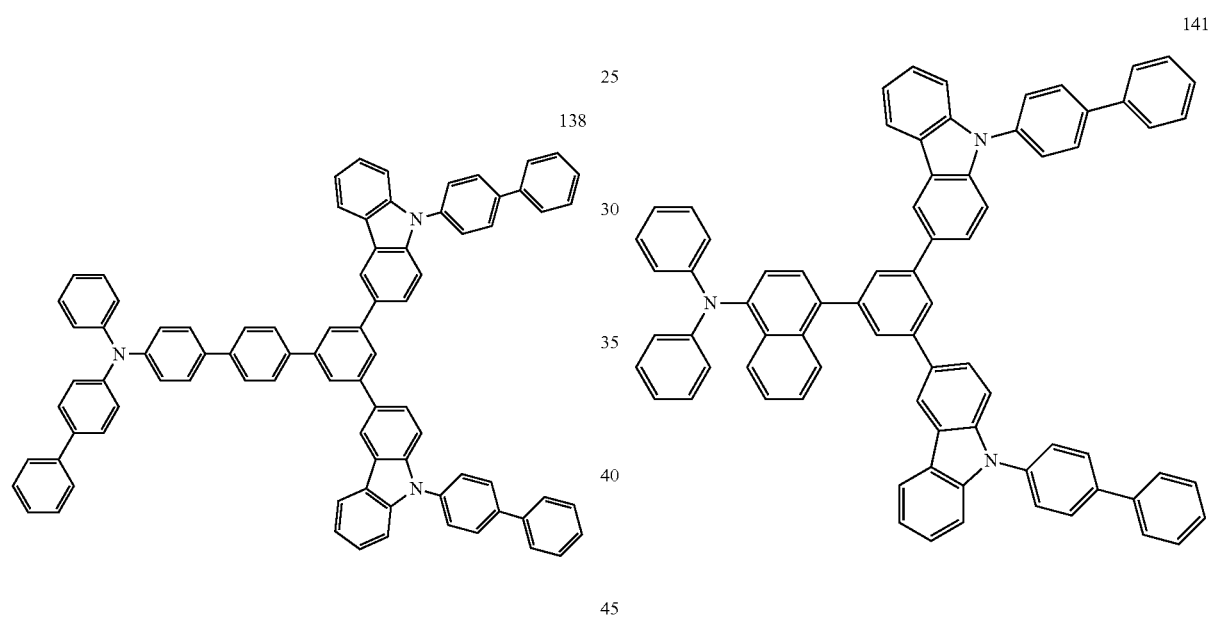
138
141
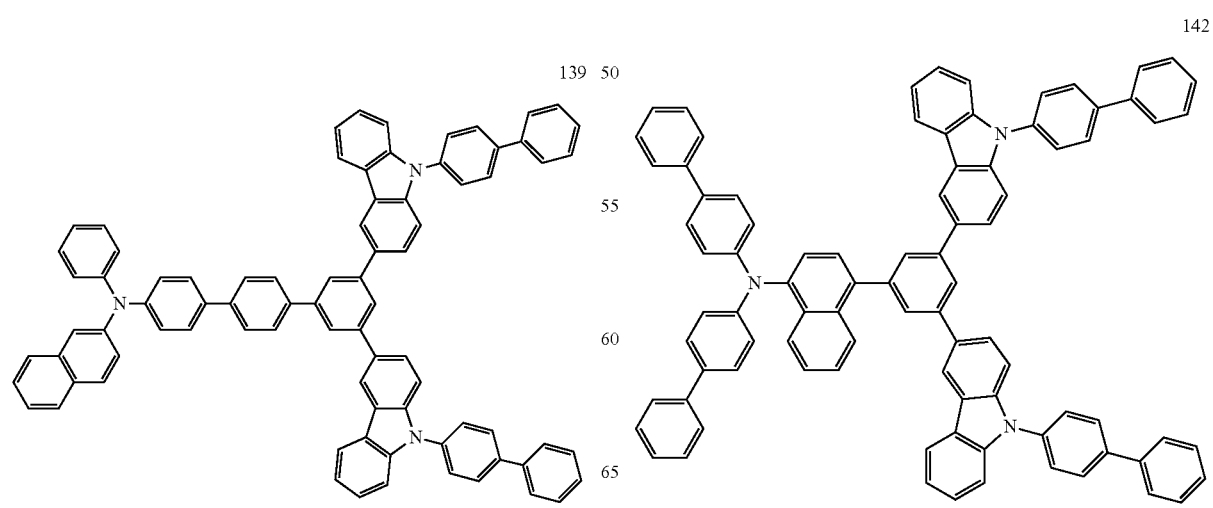
139
142

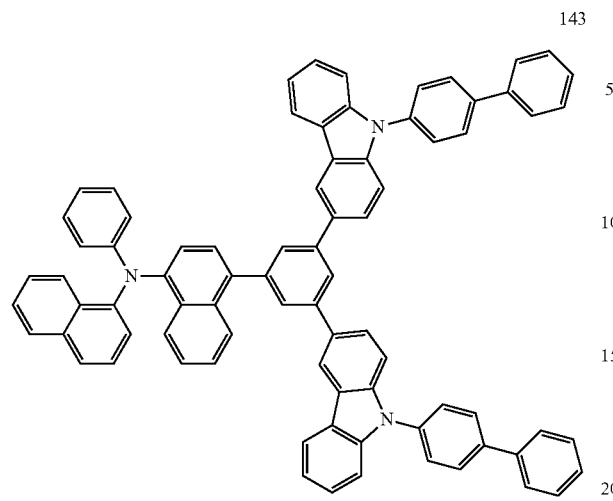
143
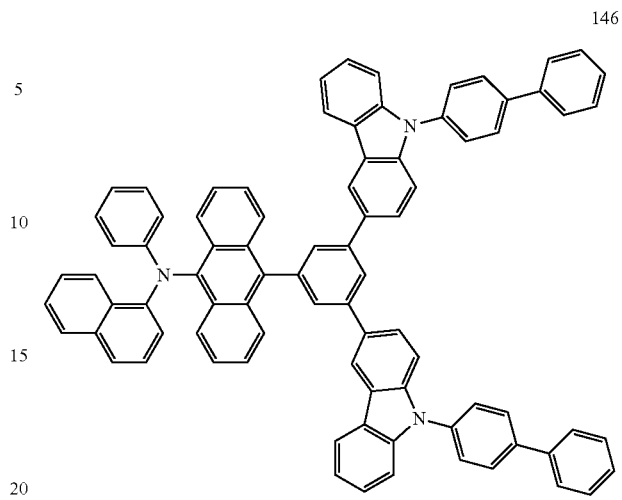
146
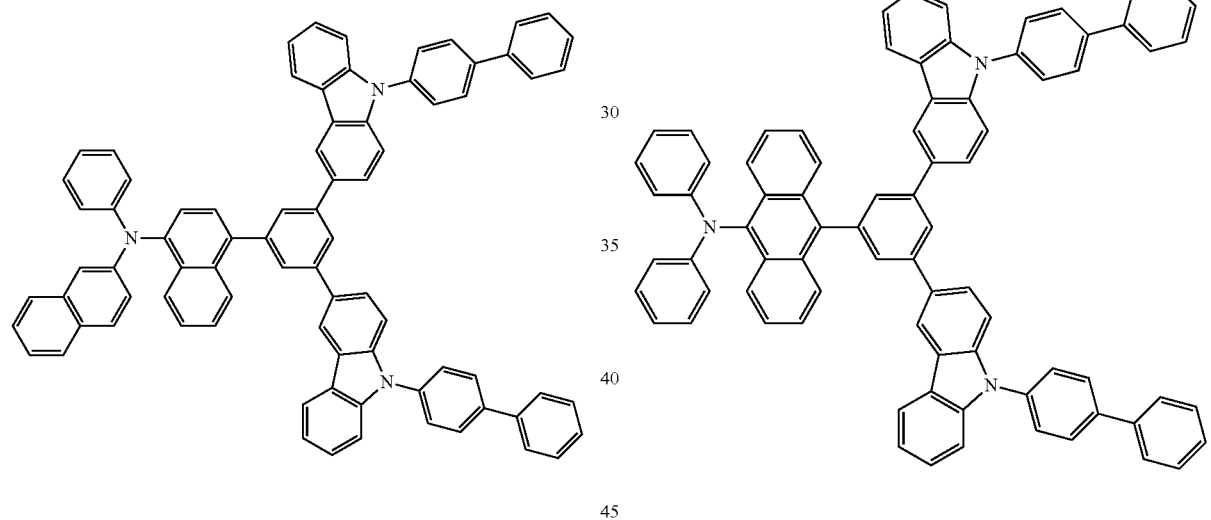
144
147
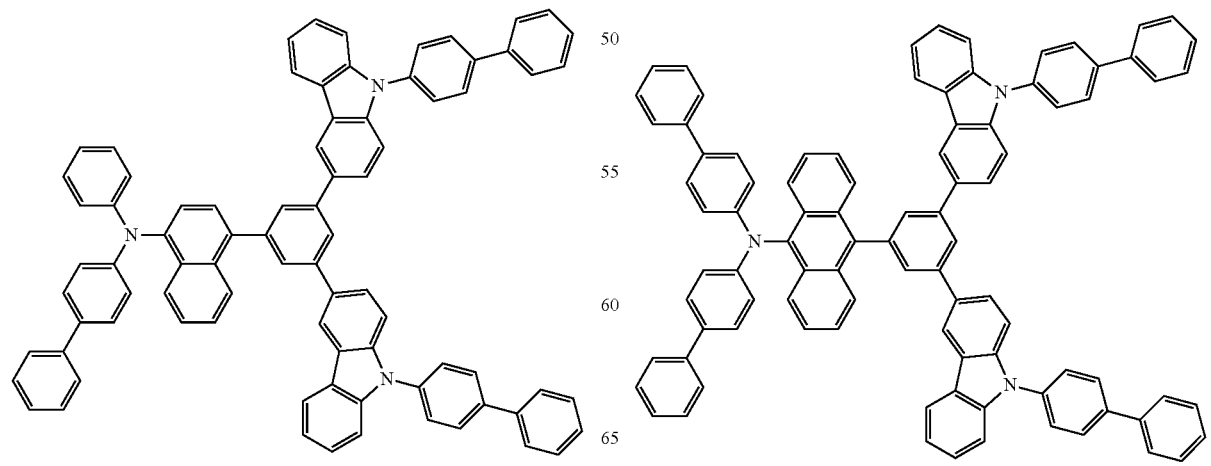
145
148

-continued
149
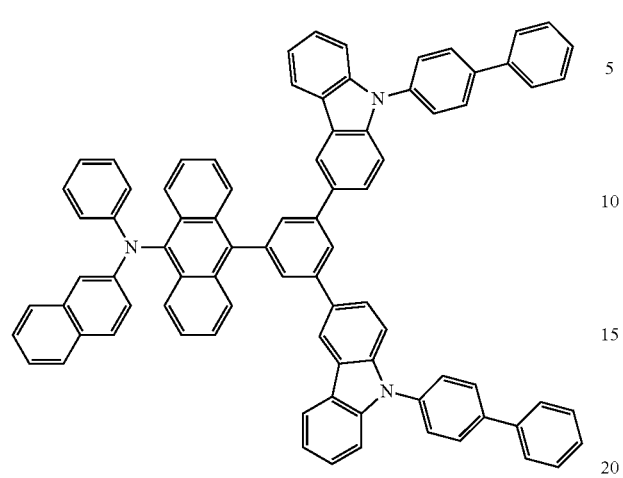
150
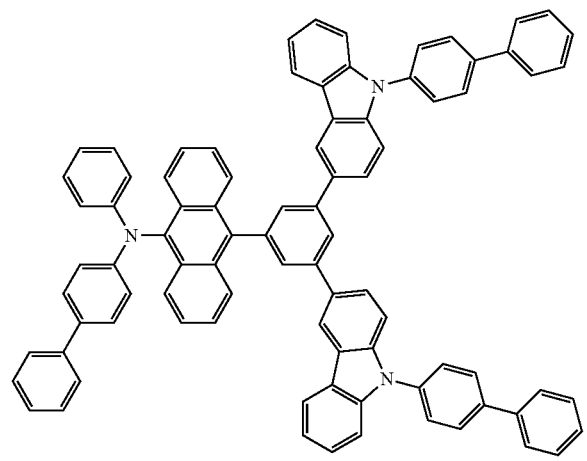
151
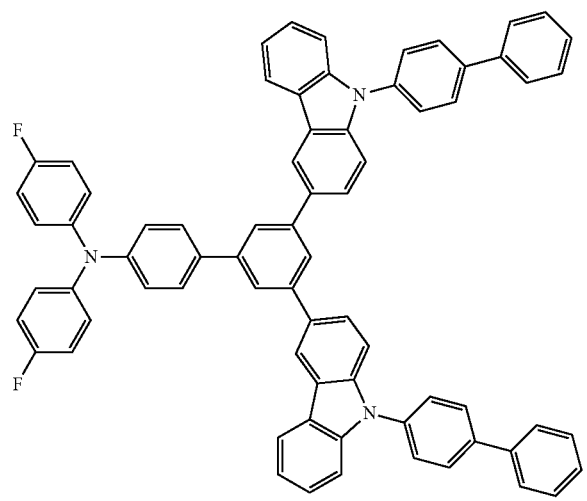
152
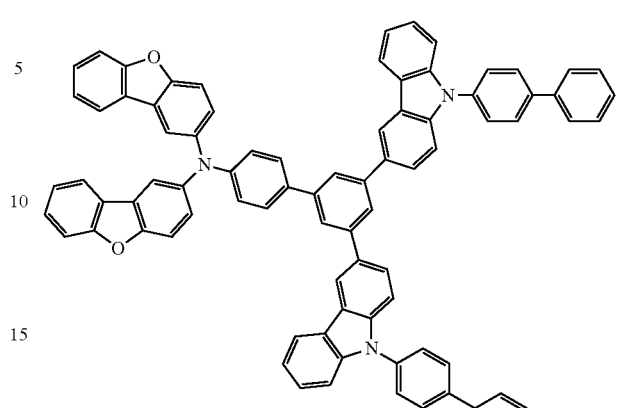
153
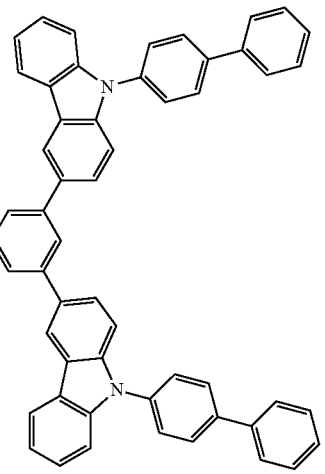
154
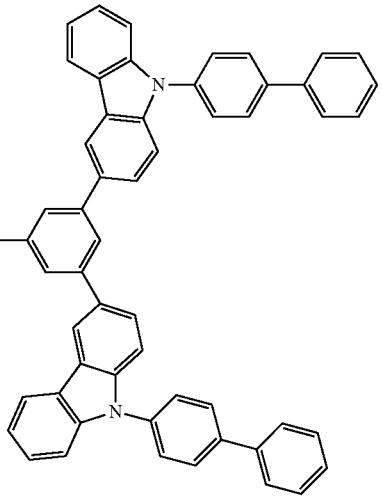

155
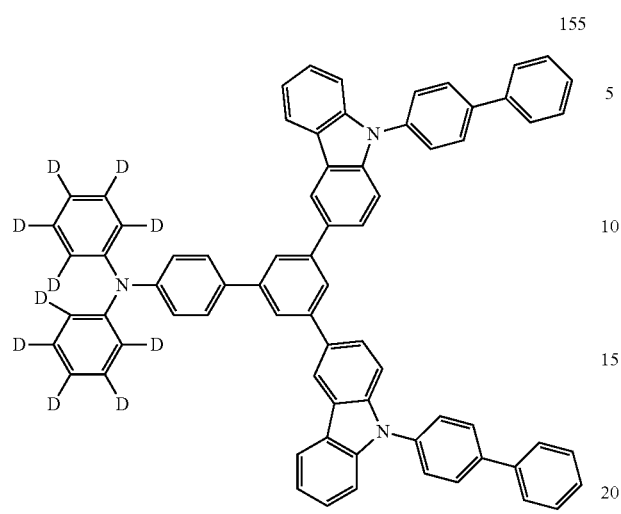
156
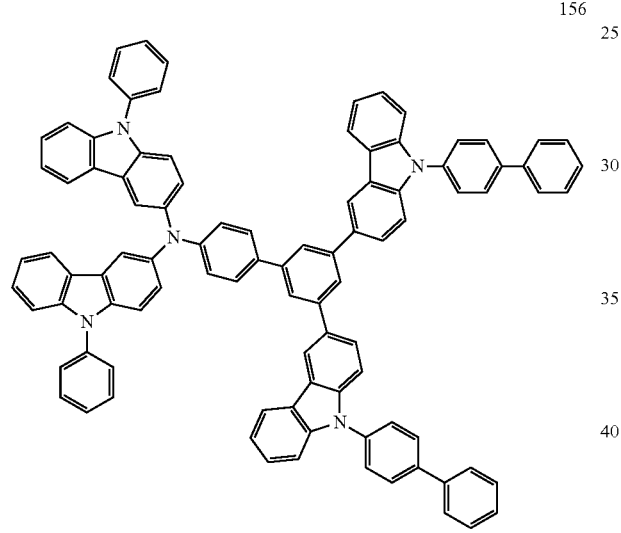
158
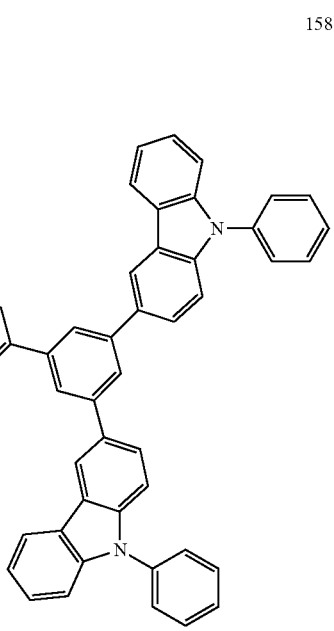
157 159
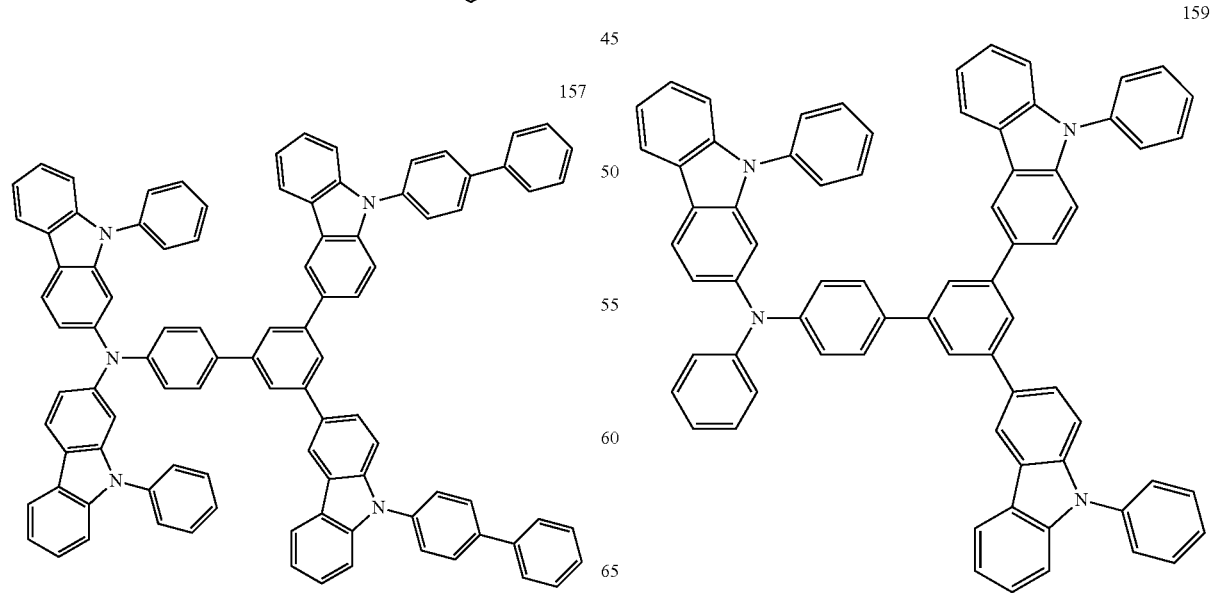

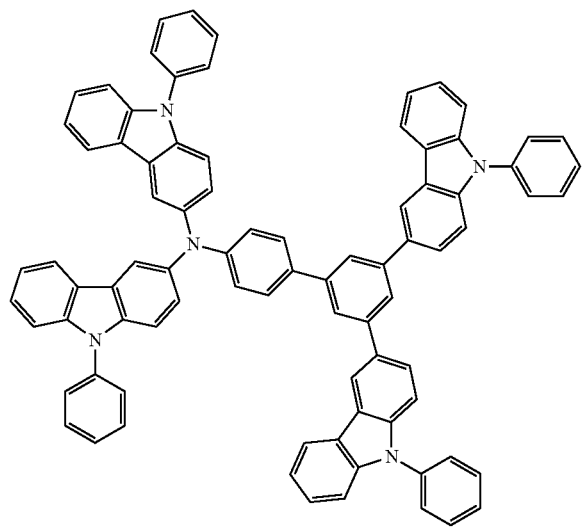
160
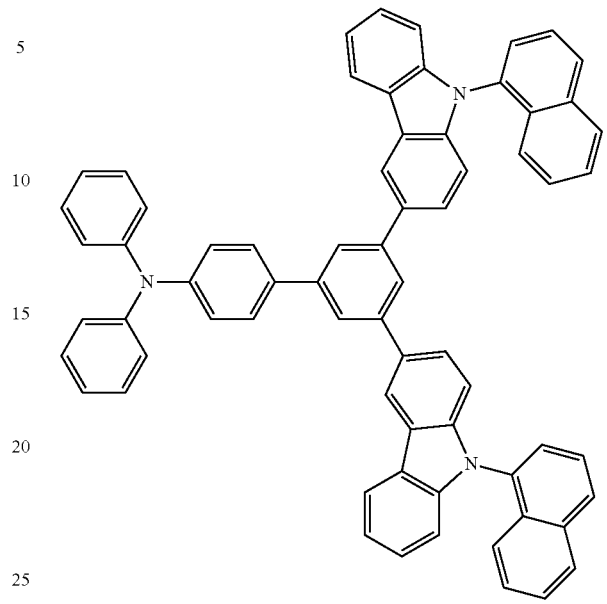
162
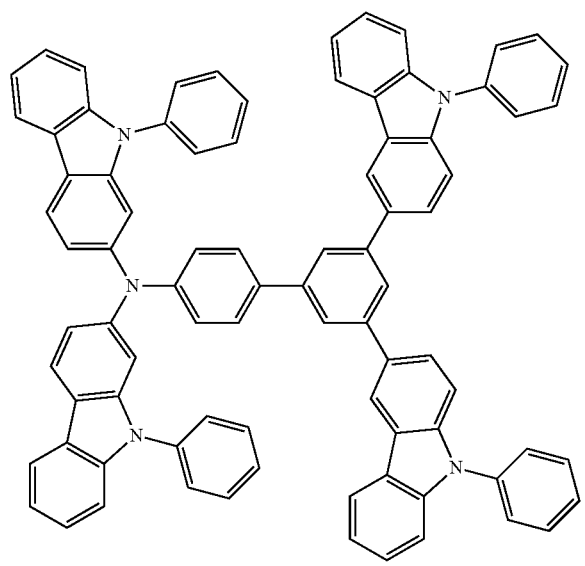
161
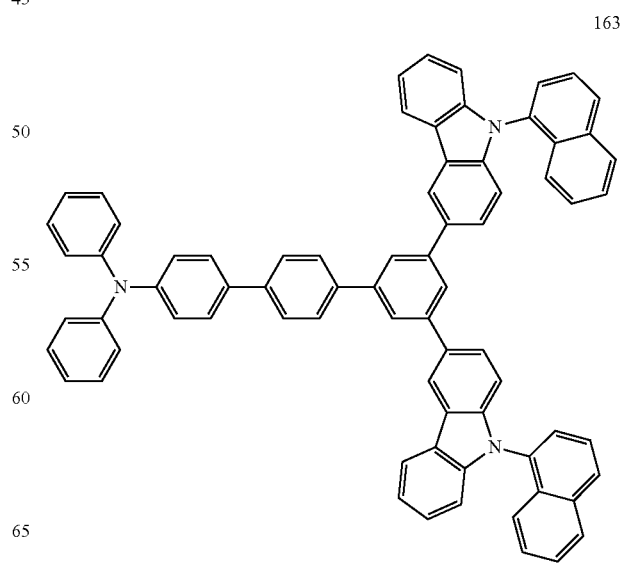
163

164
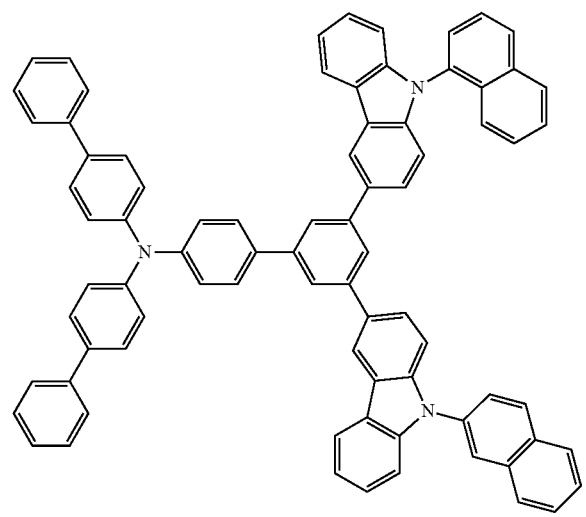
166
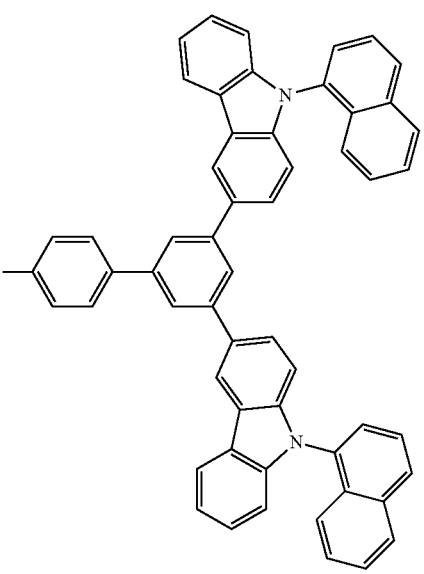
167
165
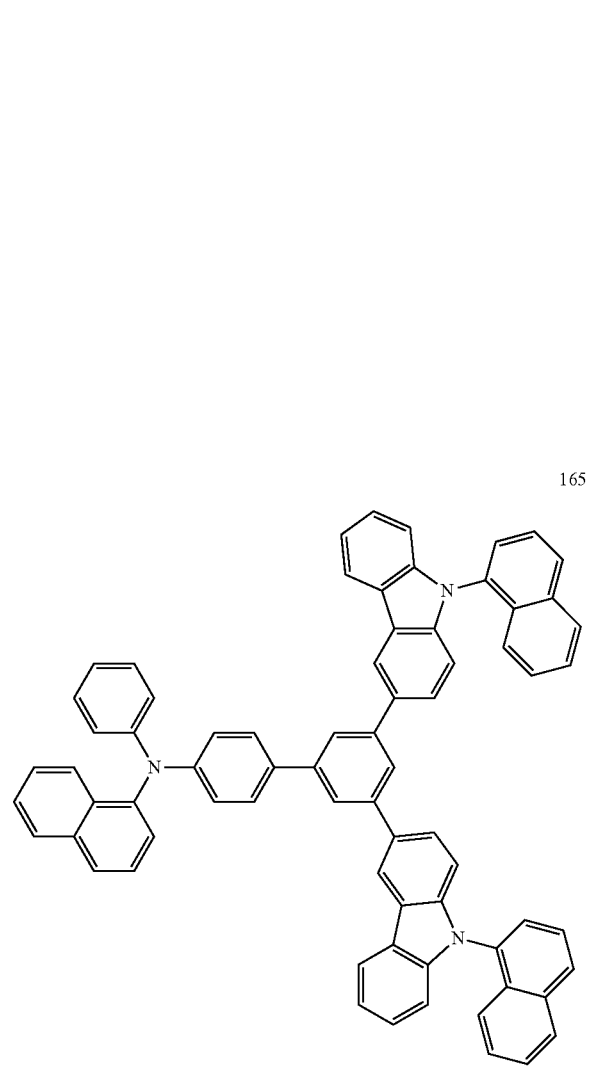
168
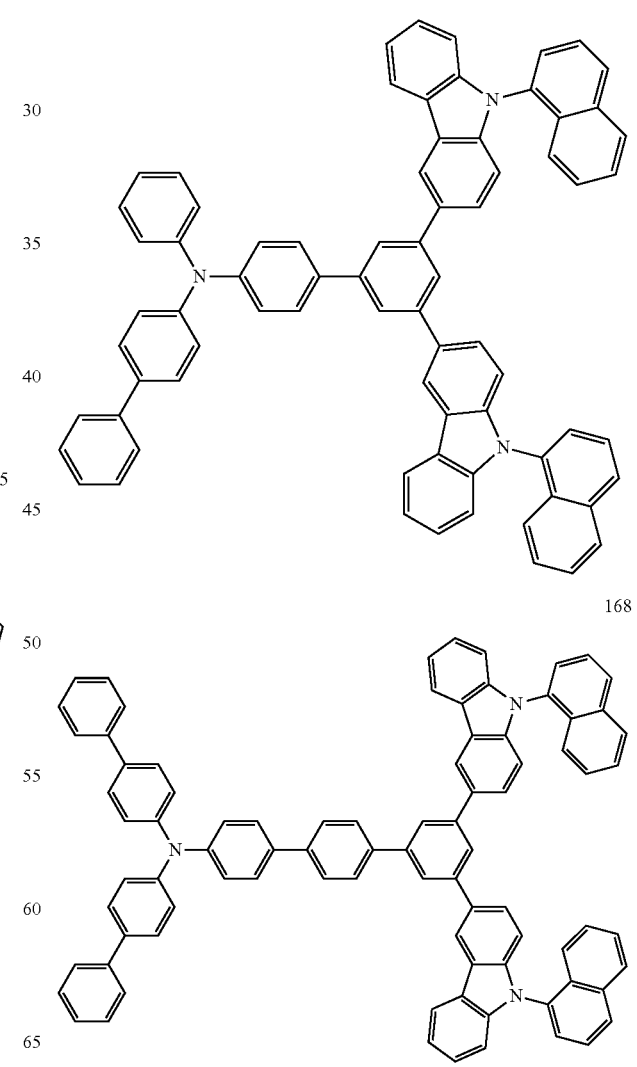

-continued
169
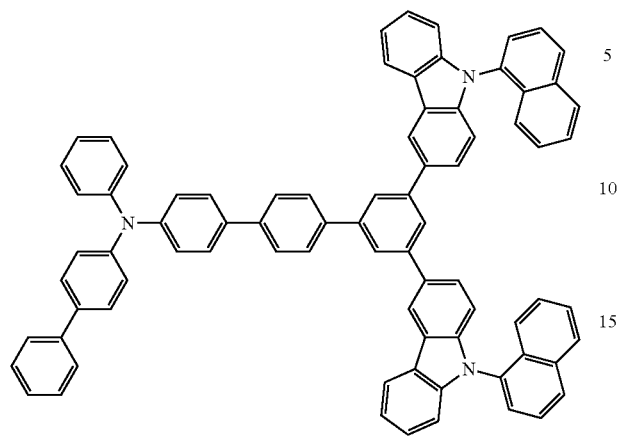
170
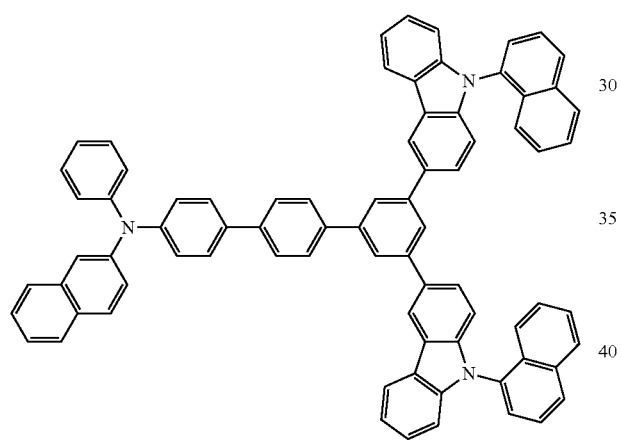
171
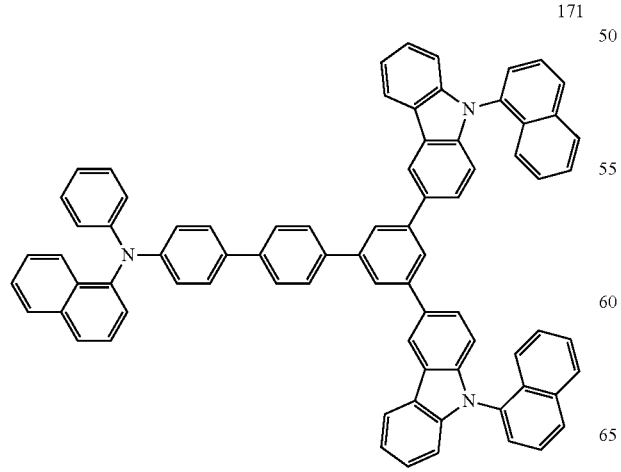
-continued
172
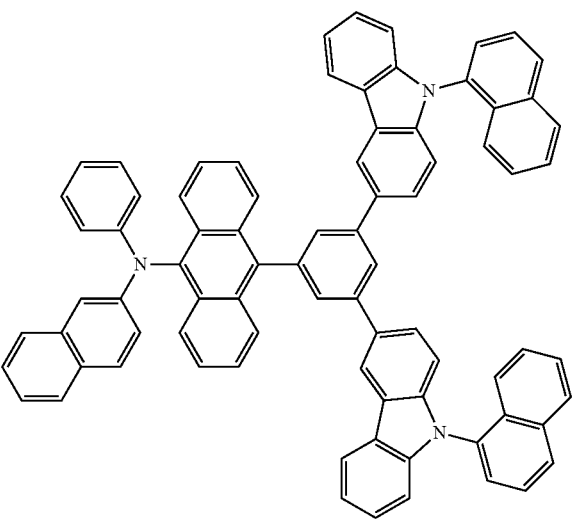
173
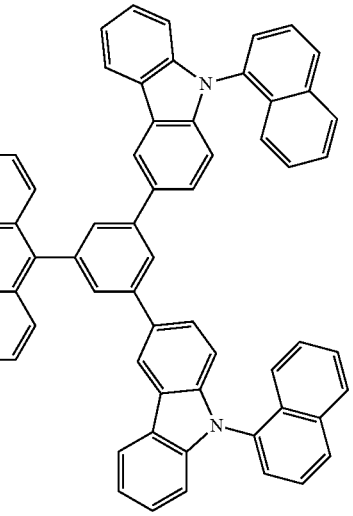
174
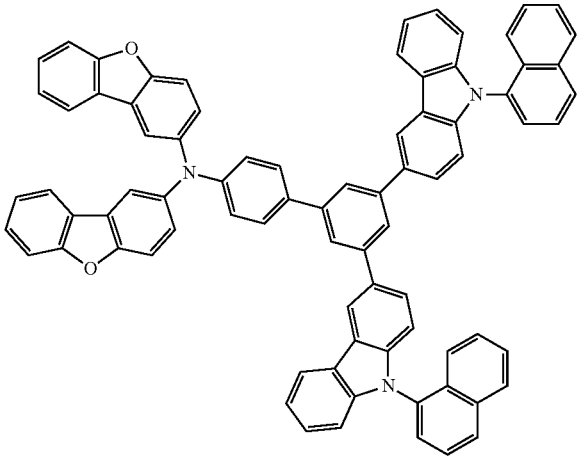

175
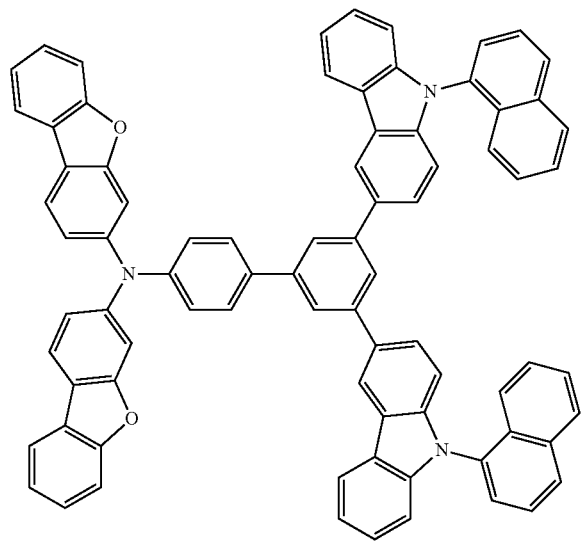
176
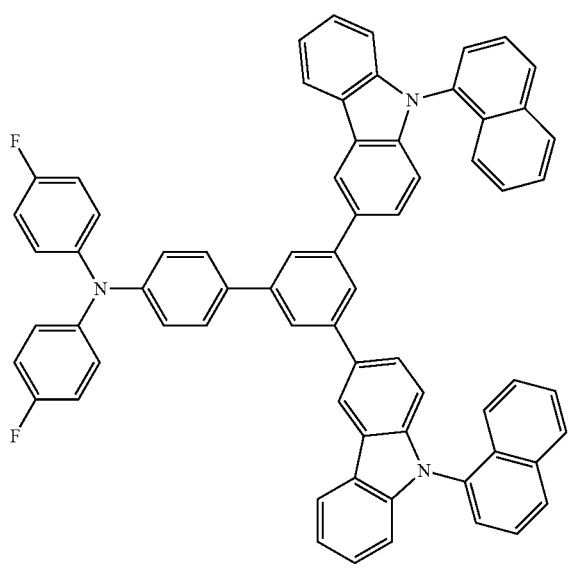
177
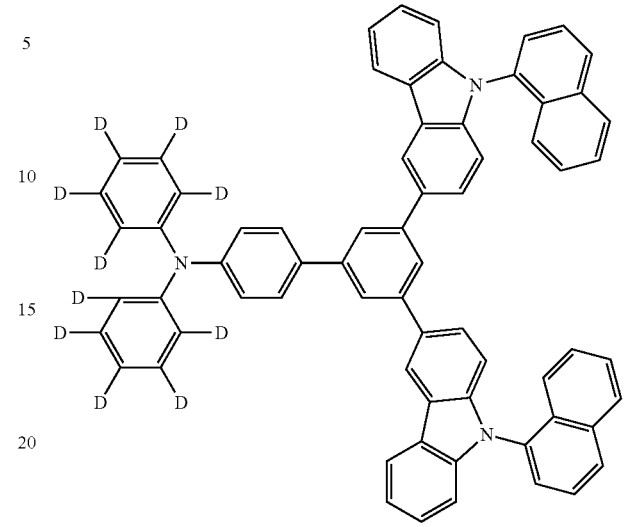
178
179

180
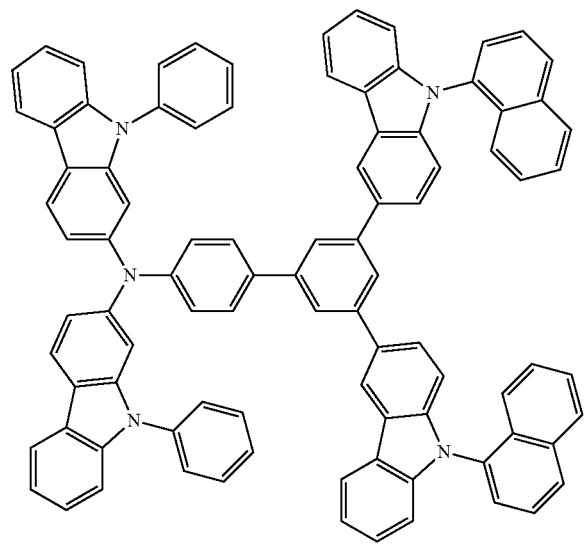
181
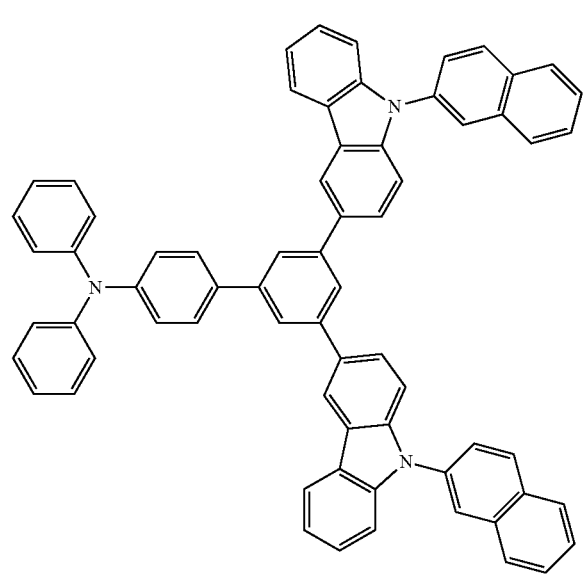
182
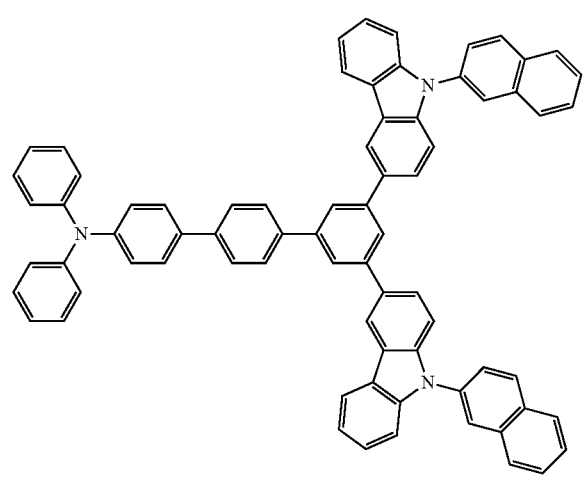
183
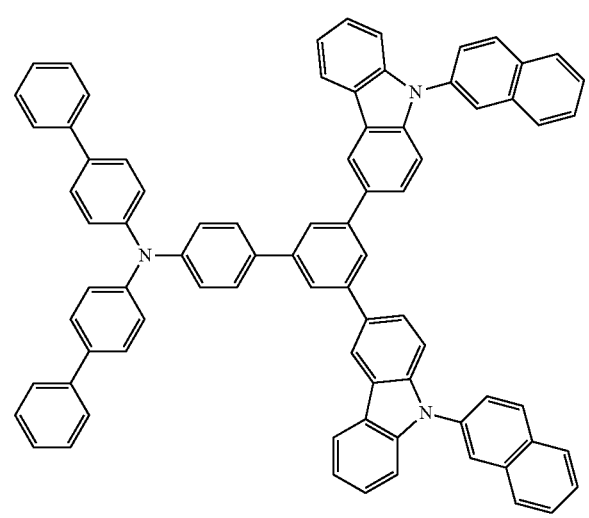
184
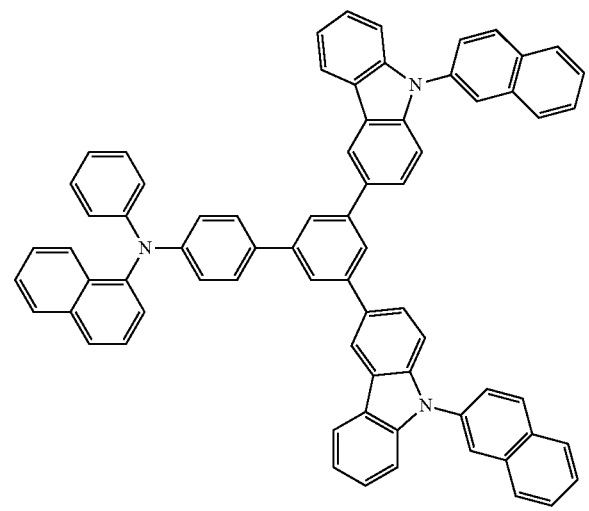
185
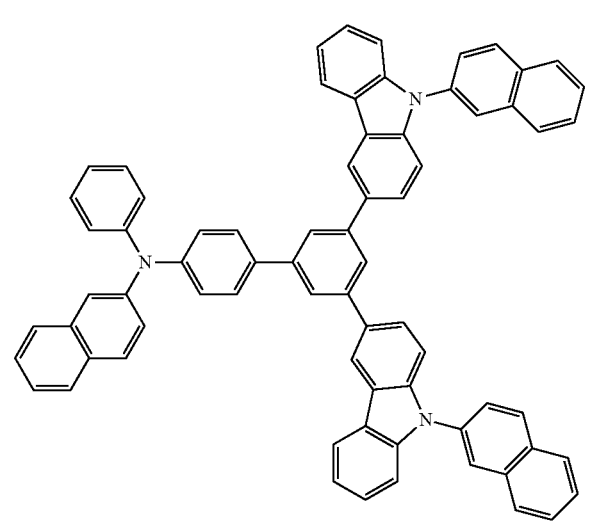

-continued
186
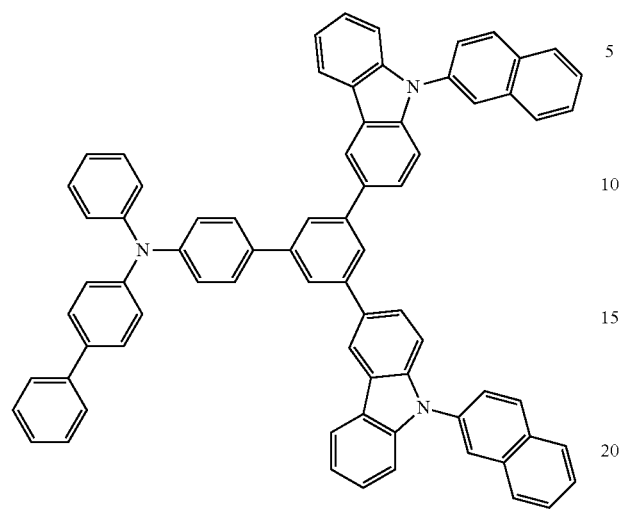
187
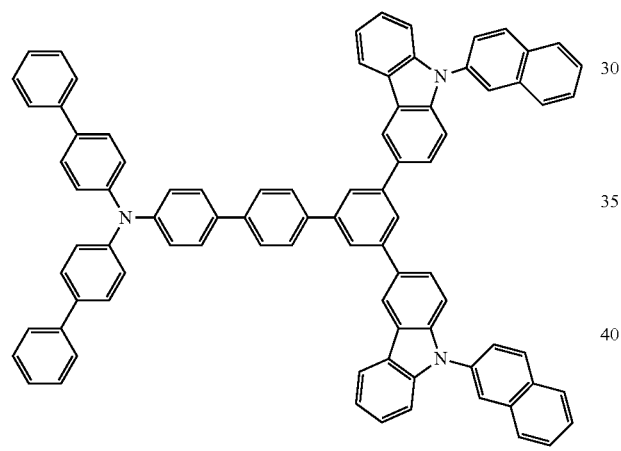
188
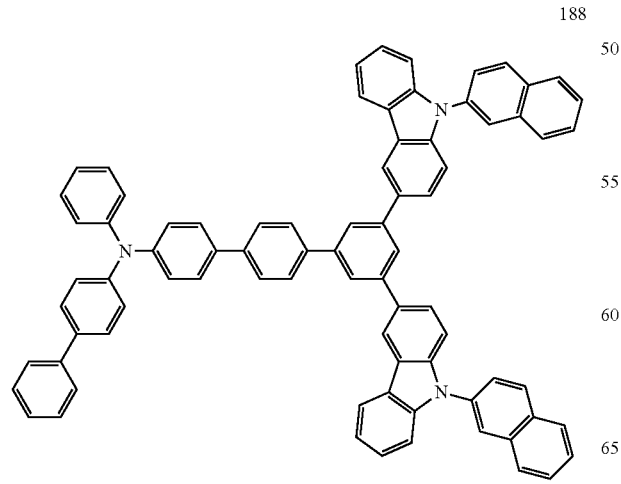
-continued
189
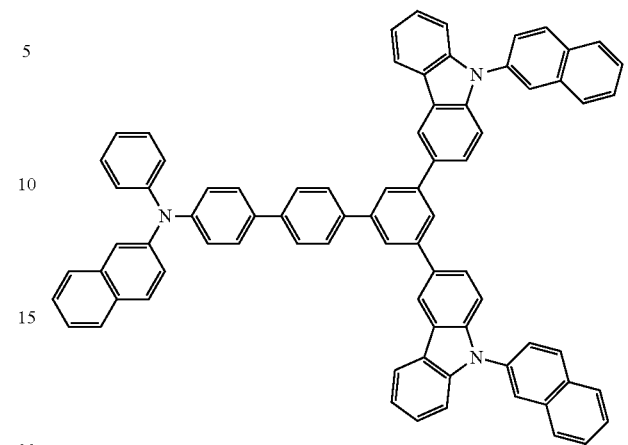
190
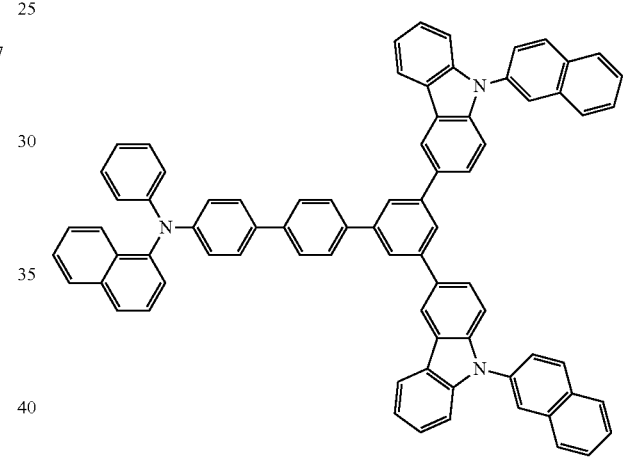
191
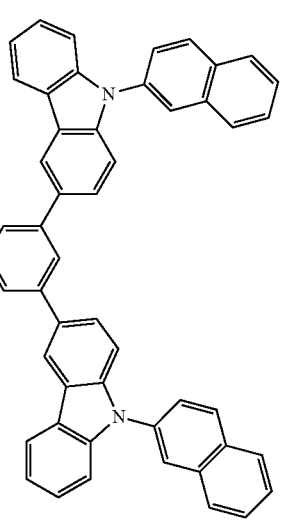

192
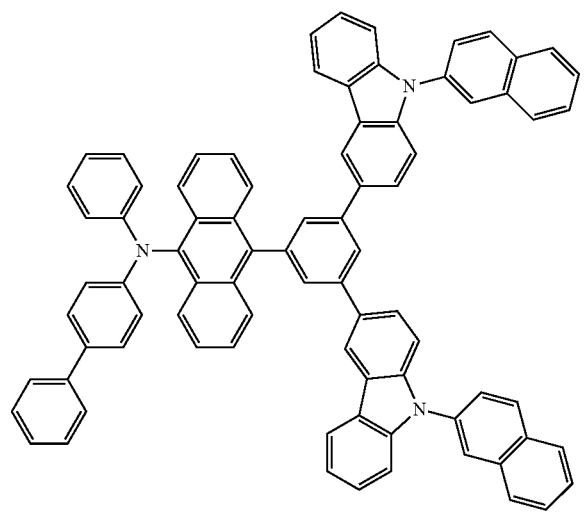
193
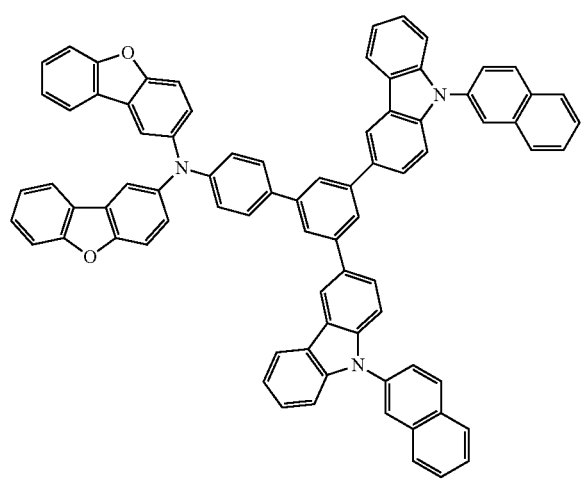
194
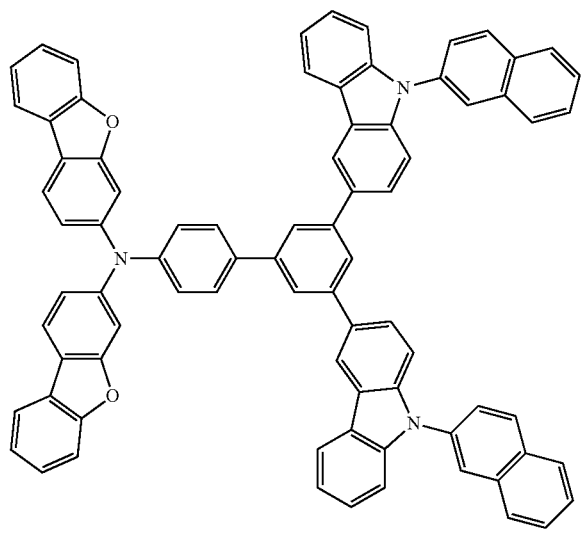
195
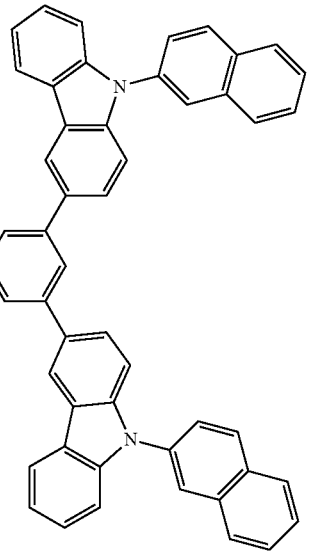
196
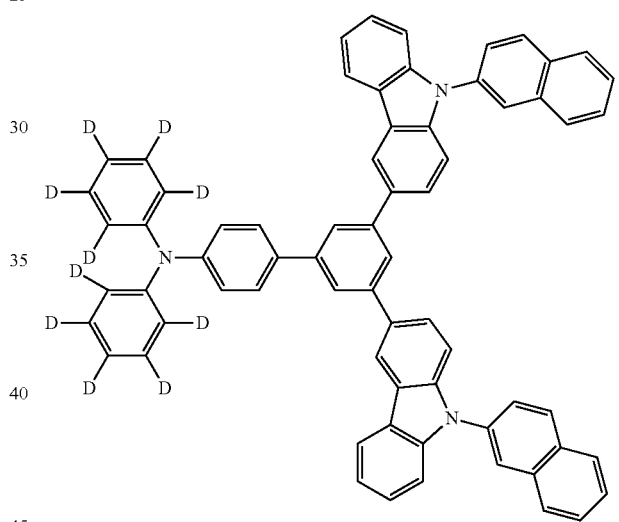
197

-continued

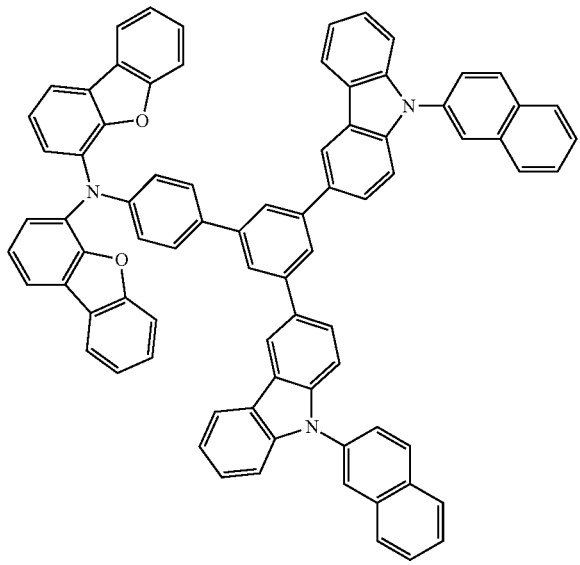
198

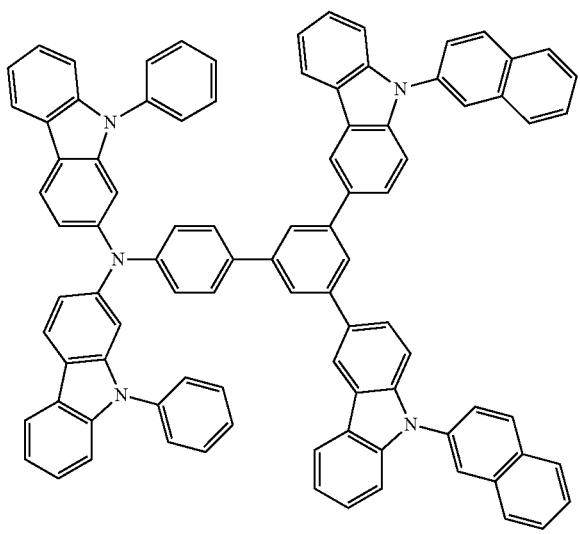
199

Hereinafter, definitions of substituents used herein will be presented (the number of carbon numbers used to restrict a substituent is not limited, and does not limit properties of the substituent, and unless defined otherwise, the definition of the substituent is consistent with a general definition thereof).

A $C_1$-$C_{60}$ alkyl group used herein refers to a linear or branched aliphatic hydrocarbon monovalent group including 1 to 60 carbon atoms, and detailed examples thereof are a methyl group, an ethyl group, a propyl group, an isobutyl group, a sec-butyl group, a tert-butyl group, a pentyl group, an iso-amyl group, or a hexyl group. A $C_1$-$C_{60}$ alkylene group used herein refers to a divalent group having the same structure as a $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group, and detailed examples thereof are an ethenyl group, a propenyl group and a butenyl group. A $C_2$-$C_{60}$ alkenylene group used herein refers to a divalent group having the same structure as a $C_2$-$C_{60}$ alkenyl group.

A $C_2$-$C_{60}$ alkynyl group used herein refers to a hydrocarbon group formed by substituting at least one carbon triple bond in the middle or at the terminal of the $C_2$-$C_{60}$ alkyl group, and detailed examples thereof are an ethynyl group and a propynyl group. A $C_2$-$C_{60}$ alkynylene group used herein refers to a divalent group having the same structure as a $C_2$-$C_{60}$ alkynyl group.

A $C_3$-$C_{10}$ cycloalkyl group used herein refers to a monovalent monocyclic saturated hydrocarbon group including 3 to 10 carbon atoms, and detailed examples thereof are a cyclopropyl group, a cyclobutyl group, a cyclopentyl group, a cyclohexyl group and a cycloheptyl group. A $C_3$-$C_{10}$ cycloalkylene group used herein refers to a divalent group having the same structure as a $C_3$-$C_{10}$ cycloalkyl group.

A $C_2$-$C_{10}$ heterocycloalkyl group used herein refers to a monovalent monocyclic group including at least one hetero atom selected from N, O, P, and S as a ring-forming atom and 2 to 10 carbon atoms, and detailed examples thereof are a tetrahydrofuranyl group and a tetrahydrothiophenyl group. A $C_2$-$C_{10}$ heterocycloalkylene group used herein refers to a divalent group having the same structure as a $C_2$-$C_{10}$ heterocycloalkyl group.

A $C_3$-$C_{10}$ cycloalkenyl group used herein refers to a monovalent monocyclic group including 3 to 10 carbon atoms and at least one double bond in the ring thereof and does not have aromaticity, and detailed examples thereof are a cyclopentenyl group, a cyclohexenyl group and a cycloheptenyl group. A $C_3$-$C_{10}$ cycloalkenylene group used herein refers to a divalent group having the same structure as a $C_3$-$C_{10}$ cycloalkenyl group.

A $C_2$-$C_{10}$ heterocycloalkenyl group used herein refers to a monovalent monocyclic group including at least one hetero atom selected from N, O, P, and S as a ring-forming atom, 2 to 10 carbon atoms, and at least one double bond in its ring. Detailed examples of the $C_2$-$C_{10}$ heterocycloalkenyl group are a 2,3-hydrofuranyl group and a 2,3-hydrothiophenyl group. A $C_2$-$C_{10}$ heterocycloalkenylene group used herein refers to a divalent group having the same structure as a $C_2$-$C_{10}$ heterocycloalkenyl group.

A $C_6$-$C_{60}$ aryl group used herein refers to a monovalent group including a carbocyclic aromatic system having 6 to 60 carbon atoms, and a $C_6$-$C_{60}$ arylene group used herein refers to a divalent group including a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group including a carbocyclic aromatic system having at least one hetero atom selected from N, O, P, and S as a ring-forming atom and 2 to 60 carbon atoms. A $C_2$-$C_{60}$ heteroarylene group used herein refers to a divalent group including a carbocyclic aromatic system having at least one hetero atom selected from N, O, P, and S as a ring-forming atom and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as ring forming atoms, wherein the molecular structure as a whole is non-aromatic in the entire molecular structure. A detailed example of the monovalent non-aromatic condensed polycyclic group is a fluorenyl group. A divalent non-aromatic condensed polycyclic group used herein refers to a divalent group including the same structure as the monovalent non-aromatic condensed polycyclic group.

A monovalent non-aromatic condensed heteropolycyclic group used herein refers to a momovalent group (for example, having 2 to 60 carbon atoms) that includes two or more rings condensed to each other, has a hetero atom selected from N, O, P, and S, other than carbon atoms as ring forming atoms, wherein the molecular structure as a whole is non-aromatic in the entire molecular structure. A detailed example of the monovalent non-aromatic condensed heteropolycyclic group is a carbazolyl group. A divalent non-aromatic condensed hetero-polycyclic group used herein refers to a divalent group including the same structure as the monovalent non-aromatic condensed hetero-polycyclic group.

At least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group and substituted monovalent non-aromatic condensed heteropolycyclic group, may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group (aryloxy), a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$ and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$ and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group and a monovalent non-aromatic condensed heteropolycyclic group.

For example, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group and substituted monovalent non-aromatic condensed heteropolycyclic group, may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$) and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a (uranyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$) and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group.

"Ph" used herein refers to a phenyl group, "Me" refers to a methyl group, "Et" refers to an ethyl group, and "ter-Bu" or "Bu$^t$" refers to a tert-butyl group.

Hereinafter, an organic light-emitting device according to an embodiment will be described in detail with reference to Synthesis Examples and Examples. The expression "B was used instead of A" as used in Synthesis Example refers that a molar weight of A and a molar weight of B are identical.

A compound (e.g., condensed cyclic compound) represented by Formula 1 may be synthesized by using a suitable organic synthetic method. A synthetic method of the compound may be understood by referring to Examples that will be explained later.

A compound represented by Formula 1 may be used or included between a pair of electrodes in an organic light-emitting device. In an implementation, the compound may be included in a hole transport region, e.g., a hole transport layer. Accordingly, provided is an organic light-emitting device including a first electrode, a second electrode facing the first electrode, and an organic layer disposed between the first electrode and the second electrode and including an emission layer, wherein the organic layer includes at least one compound represented by Formula 1 described above.

The expression "(an organic layer) includes at least one compound" as used herein may include a case in which "(an organic layer) includes identical compound represented by Formula 1, or a case in which (an organic layer) includes two or more different compounds represented by Formula 1".

For example, the organic layer may include only Compound 1 as the compound. Here, Compound 1 may be situated in an electron transport layer of the organic light-emitting device. Alternatively, the organic layer may include Compound 1 and Compound 2 as the compound. Here, Compound 1 and Compound 2 may be situated in either an identical layer (for example, Compound 1 and Compound 2 all may be situated in an electron transport layer), or different layers (for example, Compound 1 may be situated in an emission layer and Compound 2 may be situated in an electron transport layer). The organic layer includes i) a hole transport region that is disposed between the first electrode (anode) and the emission layer and includes at least one selected from a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. The hole transport region may include a compound represented by Formula 1. For example, the hole transport region may include the hole transport layer, and the hole transport layer may include a compound represented by Formula 1.

The term "organic layer" as used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, a structure and a method of manufacturing the organic light-emitting device according to an embodiment will be described with reference to FIG. 1.

Referring to FIG. 1, a substrate may be additionally disposed under the first electrode 110 or on the second electrode 190. The substrate may be a glass substrate or transparent plastic substrate, each with excellent mechanical strength, thermal stability, transparency, surface smoothness, ease of handling, and water resistance.

The first electrode 110 may be formed by depositing or sputtering a material for forming the first electrode on the substrate. When the first electrode 110 is an anode, the material for the first electrode may be selected from materials with a high work function to facilitate hole injection. The first electrode 110 may be a reflective electrode, a semi-transmissive electrode, or a transmissive electrode. The material for the first electrode may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including a plurality of layers. For example, the first electrode 110 may have a triple-layer structure of ITO/Ag/ITO, but it is not limited thereto.

The organic layer 150 may be disposed on the first electrode 110. The organic layer 150 may include an emission layer.

The organic layer 150 may further include a hole transport region between the first electrode and the emission layer, and an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL).

The hole transport region may have a single-layer structure formed of a single material, a single-layer structure formed of a plurality of different materials, or a multi-layer structure having a plurality of layers formed of a plurality of different materials.

For example, the hole transport region may have a single-layer structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, e.g., vacuum deposition, spin coating, casting, Langmuir-Blodgett (LB) method, ink-jet printing, laser-printing, or laser-induced thermal imaging (LITI).

When a hole injection layer is formed by vacuum deposition, e.g., the vacuum deposition may be performed at a deposition temperature of about 100° C. to about 500° C., at a vacuum degree of about $10^{-8}$ torr to about $10^{-3}$ torr, and/or at a deposition rate of about 0.01 Å/sec to about 100 Å/sec, in consideration of a compound to be deposited for forming a hole injection layer, and the structure of a hole injection layer to be formed.

When a hole injection layer is formed by spin coating, e.g., the spin coating may be performed at a rate of about 2,000 revolutions per minute (rpm) to about 5,000 rpm, and/or at a temperature of about 80° C. to 200° C. in consideration of a compound to be deposited for forming a hole injection layer, and the structure of a hole injection layer to be formed.

When the hole transport region includes a hole transport layer, the hole transport layer may be formed on the first electrode 110 or the hole injection layer by using various methods, e.g., vacuum deposition, spin coating, casting, LB method, ink-jet printing, laser-printing, or LITI. When the hole transport layer is formed by vacuum deposition or spin coating, conditions for vacuum deposition and coating may be similar to the above-described vacuum deposition and coating conditions for forming the hole injection layer.

The hole transport region may include at least one selected from, (except for or in addition to a compound represented by Formula 1), m-MTDATA, TDATA, 2-TNATA, NPB, β-NPB, TPD, Spiro-TPD, Spiro-NPB, α-NPB, TAPC, HMTPD, TCTA (4,4',4''-tris(N-carbazolyl)triphenylamine(4,4',4''-tris(N-carbazolyl)triphenylamine)), Pani/DBSA (polyaniline/dodecylbenzene sulfonic acid: polyaniline/dodecylbenzene sulfonic acid), PEDOT/PSS (poly(3,4-ethylenedioxythiophene)/poly(4-styrenesulfonate):poly(3,4-ethylenedioxythiophene)/poly(4-styrenesulfonate)), Pani/CSA (polyaniline/camphor sulfonic acid: polyaniline/camphor sulfonic acid), PANI/PSS (polyaniline/poly(4-styrenesulfonate):polyaniline/poly(4-styrene sulfonate)), a compound represented by Formula 201 below, and a compound represented by Formula 202 below.

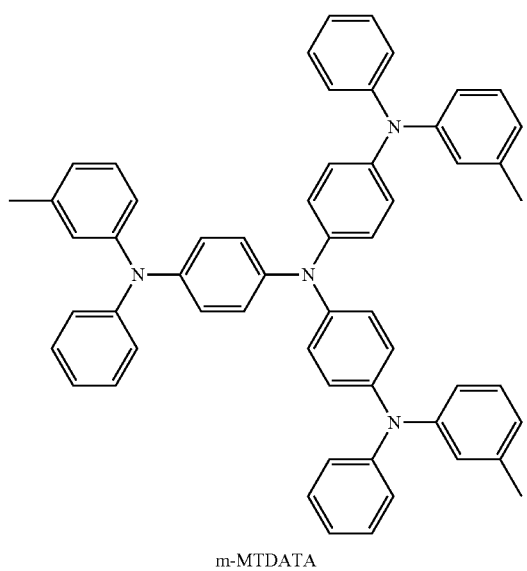

m-MTDATA

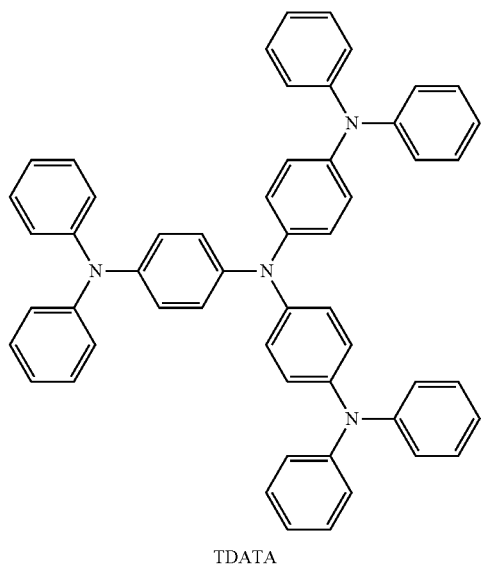

TDATA

-continued
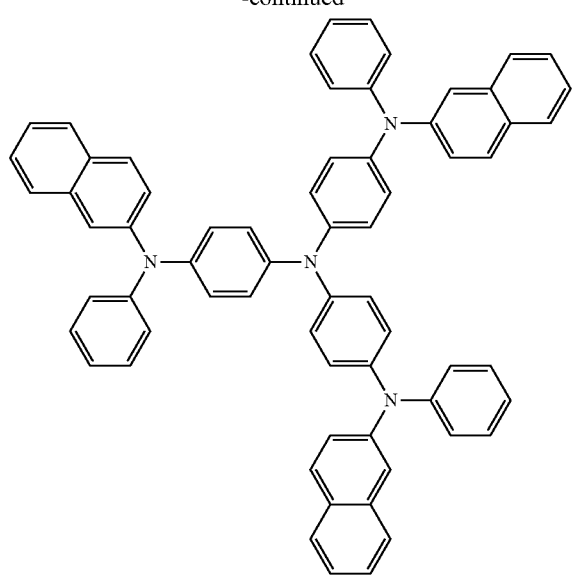
2-TNATA
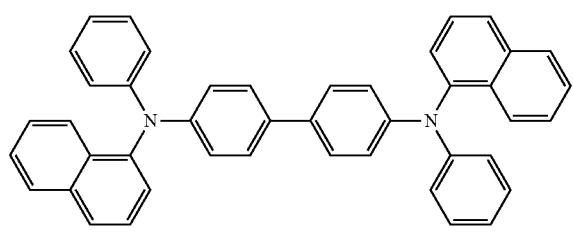
NPB
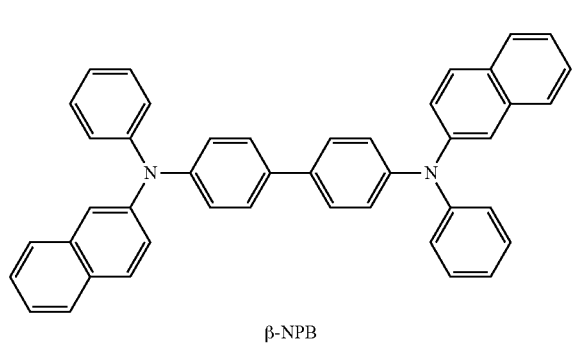
β-NPB
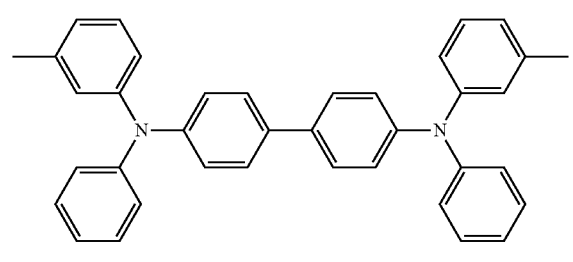
TPD
-continued
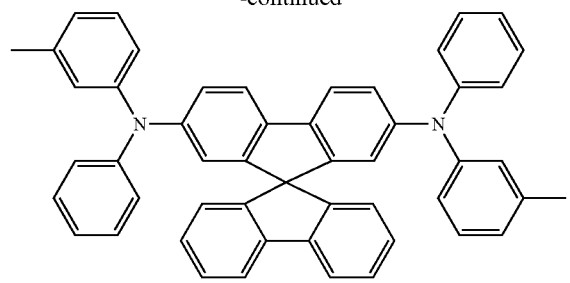
Spiro-TPD
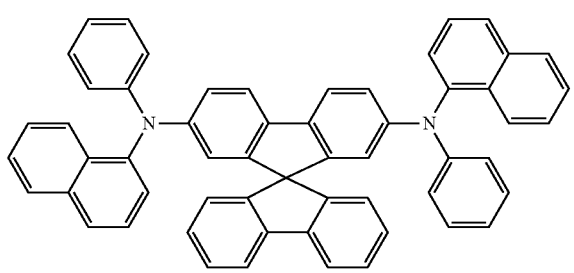
Spiro-NPB
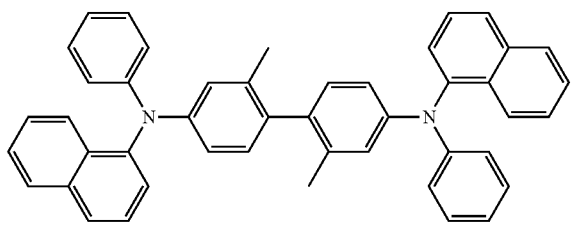
α-NPB
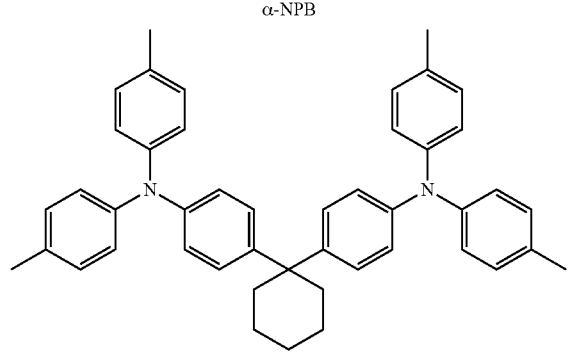
TAPC
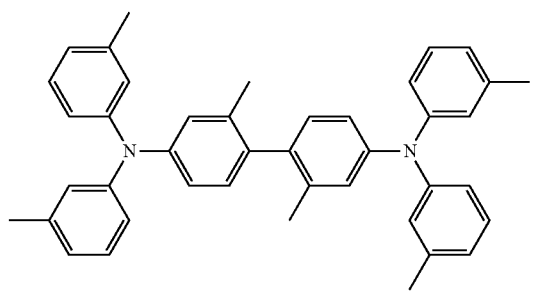
HMTPD

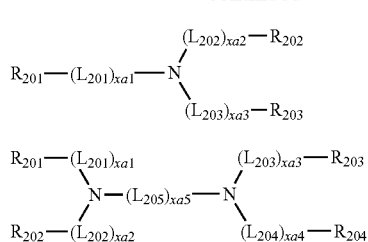

<Formula 201>

<Formula 202>

In Formulae 201 to 202,

The descriptions for $L_{201}$ to $L_{205}$ are the same as the description for L provided herein;

xa1 to xa3 may be each independently selected from 0, 1, 2, and 3; and xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group and a substituted or unsubstituted monovalent non-aromatic condensed heteropolycyclic group.

For example, in Formulae 201 and 202, $L_{201}$ to $L_{205}$ may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group and a triazinyl group;

xa1 to xa4 may be each independently selected from 0, 1, and 2;

xc1 may be selected from 1, 2, and 3;

$R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_1$-$C_{20}$ alkyl group, $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group.

In an implementation, the hole transport layer may include a compound represented by Formula 1 according to an embodiment.

A thickness of the hole transport region may be in a range of about 100 Å to about 10,000 Å, e.g., about 100 Å to about 1,000 Å. When the hole transport region includes a hole injection layer and a hole transport layer, the thickness of the hole injection layer may be in a range of about 100 Å to about 10,000 Å, e.g., about 100 Å to about 1,000 Å, and the thickness of the hole transport layer may be in a range of about 50 Å to about 2,000 Å, e.g., about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, e.g., a p-dopant. The p-dopant may be one selected from a quinone derivative, a metal oxide, and a cyano group-containing compound, but is not limited thereto. Non-limiting examples of the p-dopant may include a quinine derivative such as tetracyanoquinonedimethane (TCNQ) or 2,3,5,6-tetra-fluoro-tetracyano-1,4-benzoquinonedimethane (F4-TCNQ); a metal oxide such as a tungsten oxide or a molybdenum oxide; and Compound HT-D1 below.

<Compound HT-D1>

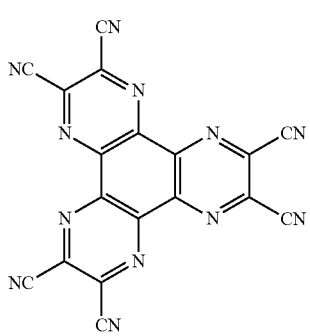

<F4-TCNQ>

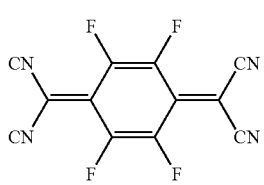

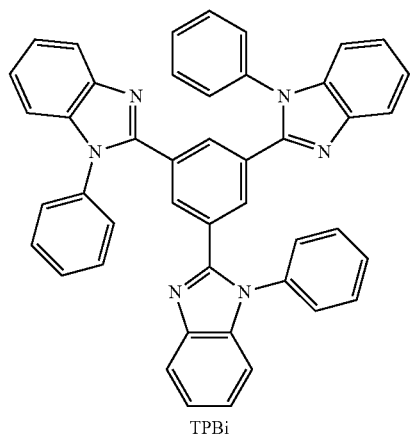

TPBi

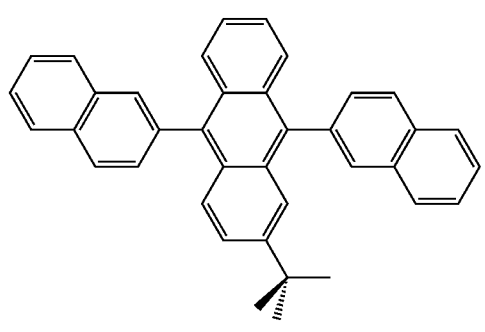

TBADN

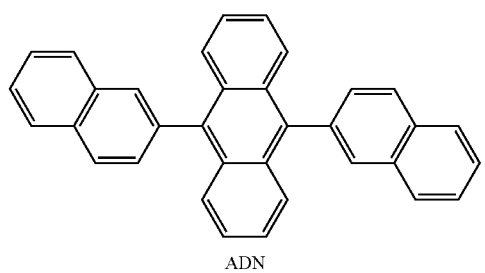

ADN

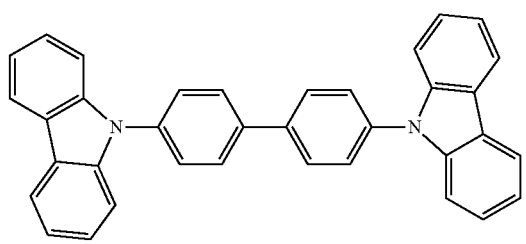

CBP

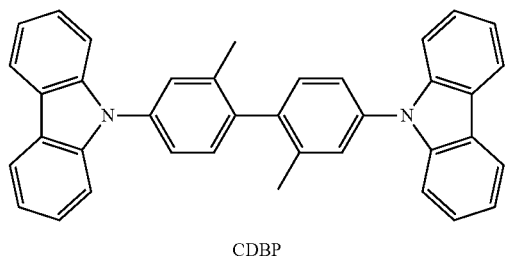

CDBP

The hole transport region may further include, in addition to the hole injection layer and the hole transport layer, at least one selected from a buffer layer and an electron blocking layer. The buffer layer may compensate for an optical resonance distance according to a wavelength of light emitted from the emission layer, and light-emission efficiency of a formed organic light-emitting device may be improved. For use as a material included in the buffer layer, materials that are included in the hole transport region may be used. The electron blocking layer prevents injection of electrons from the electron transport region.

An emission layer may be formed on the first electrode 110 or the hole transport region by using various methods, e.g., vacuum deposition, spin coating, casting, LB method, ink-jet printing, laser-printing, or LITI. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In an implementation, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from TPBi, TBADN, ADN(also referred to as "DNA"), CBP, CDBP and TCP below.

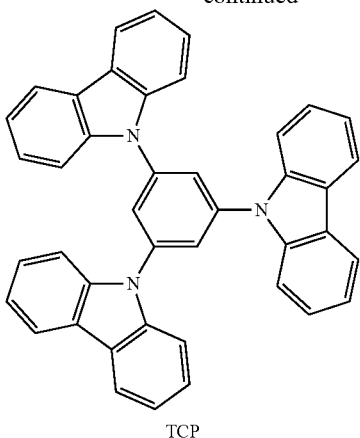

TCP

In an implementation, the host may further include a compound represented by Formula 301.

Ar$_{301}$-[(L$_{301}$)$_{xb1}$-R$_{301}$]$_{xb2}$  <Formula 301>

In Formula 301,

Ar$_{301}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$) (Q$_{301}$ to Q$_{303}$ may be each independently selected from a hydrogen, a C$_1$-C$_{60}$ alkyl group, a C$_2$-C$_{60}$ alkenyl group, a C$_6$-C$_{60}$ aryl group, and a C$_2$-C$_{60}$ heteroaryl group);

The descriptions for L$_{301}$ may be the same as defined in connection with L$_{201}$ herein;

R$_{301}$ may be selected from a C$_1$-C$_{20}$ alkyl group and a C$_1$-C$_{20}$ alkoxy group;

a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4;

In some embodiments, in Formula 301,

L$_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

R$_{301}$ may be selected from a C$_1$-C$_{20}$ alkyl group and a C$_1$-C$_{20}$ alkoxy group;

a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

In an implementation, the host may include a compound represented by Formula 301A.

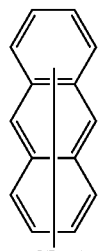

<Formula 301A>

$[(L_{301})_{xb1}$—$R_{301}]_{xb2}$

The descriptions for Formula 301A may be understood by referring to the descriptions provided herein.

In an implementation, the compound represented by Formula 301 may include at least one compound selected from Compounds H1 to H42 below.

H1

H2

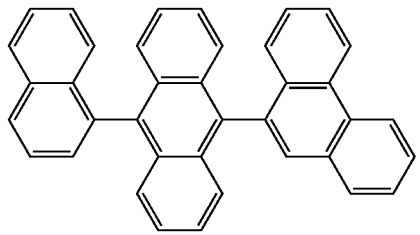

H3

H4

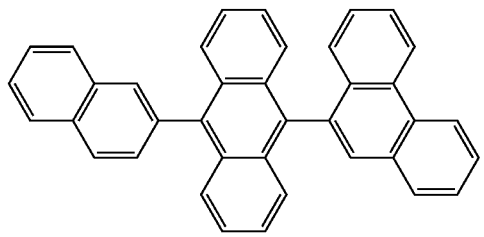

H5

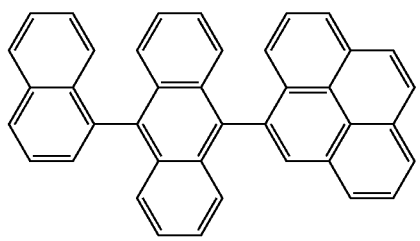

H6

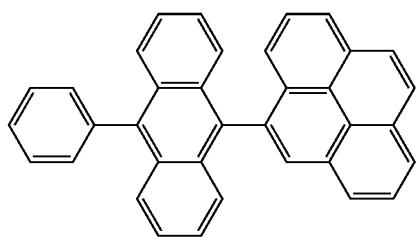

H7

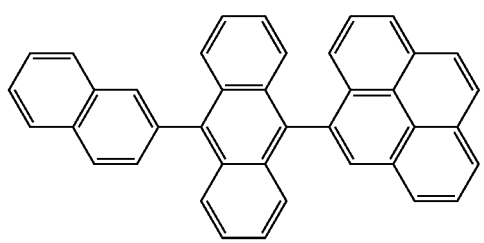

H8

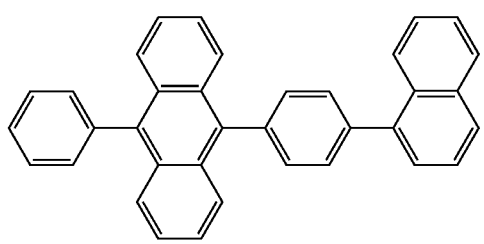

| 101 | 102 |
|---|---|
| -continued | -continued |
H9
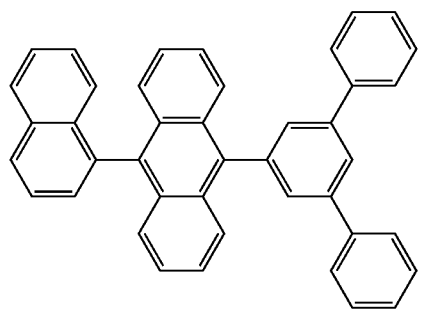
H10
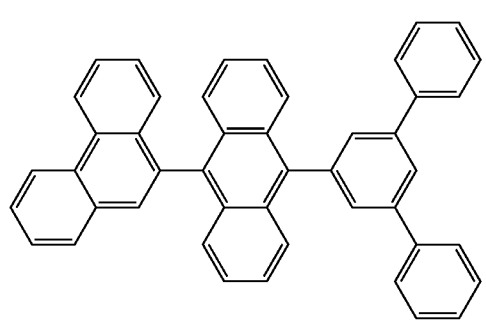
H11
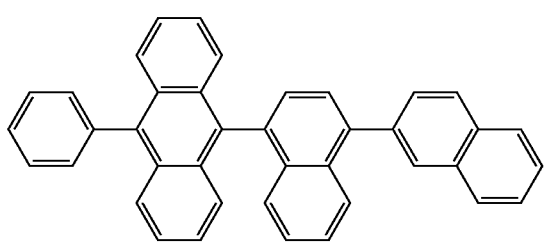
H12
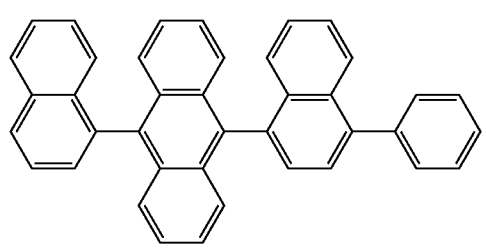
H13
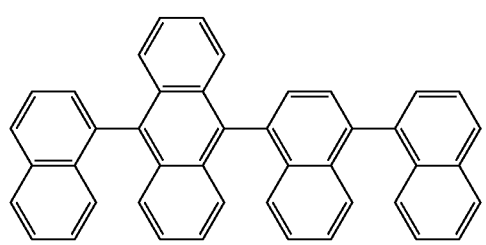
H14
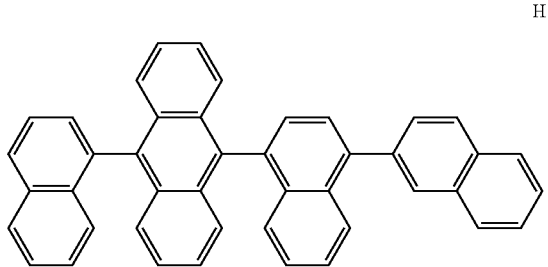
H15
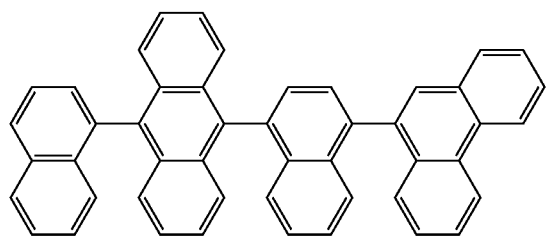
H16
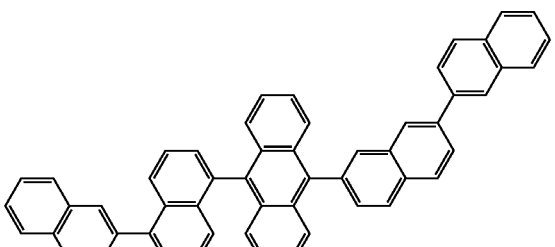
H17
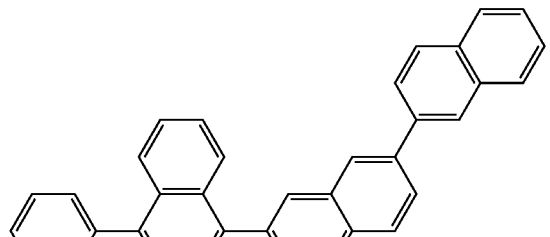
H18
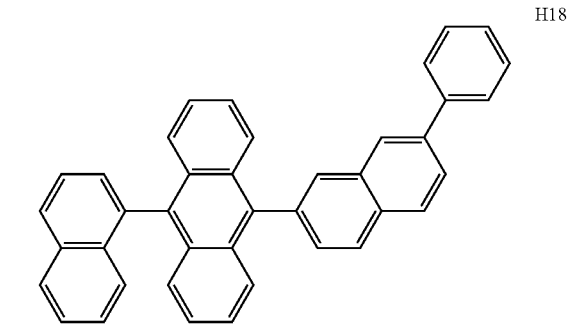
H19
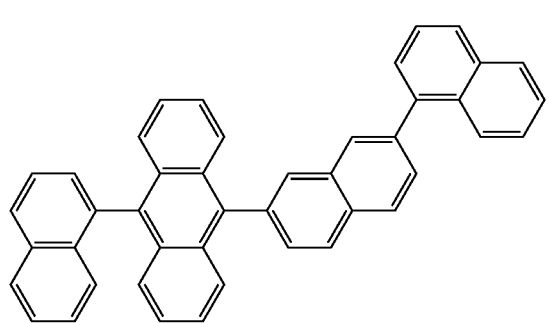

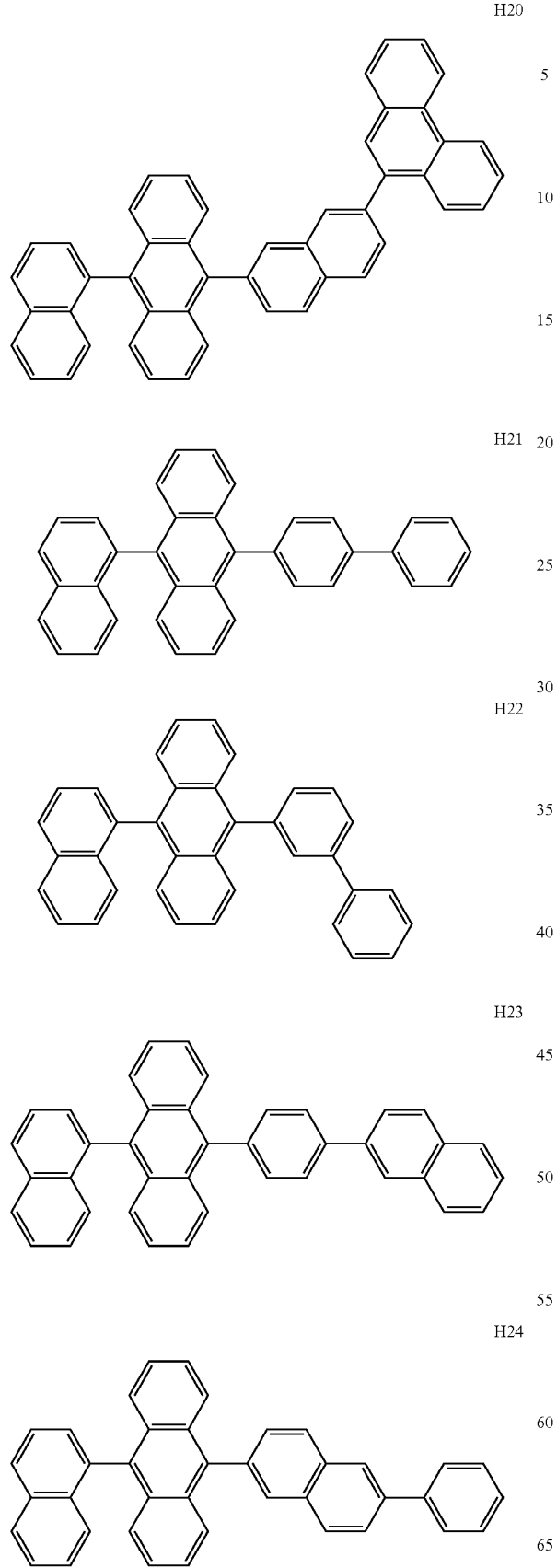
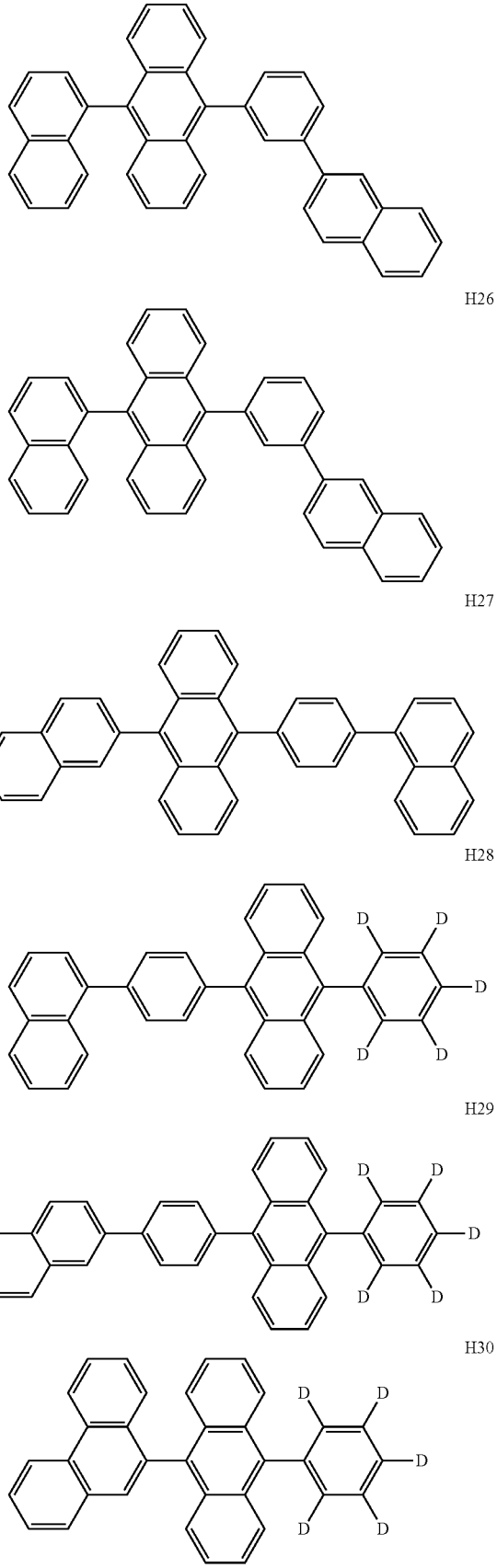

105
-continued
H31
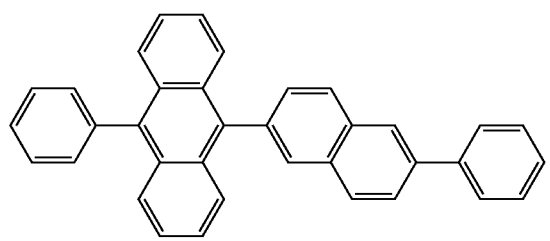
H32
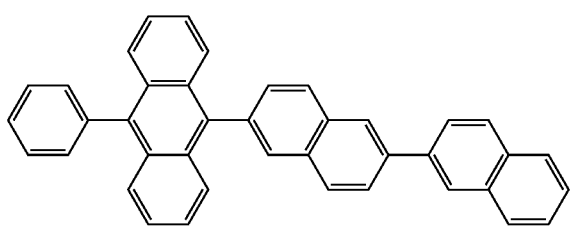
H33
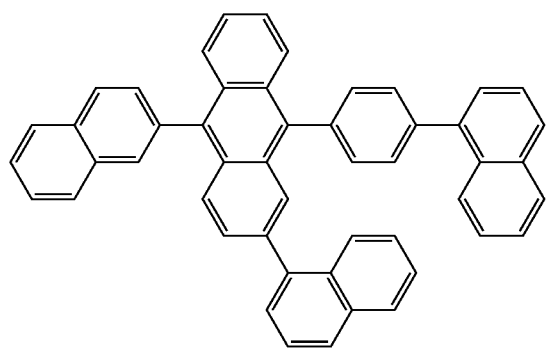
H34
106
-continued
H35
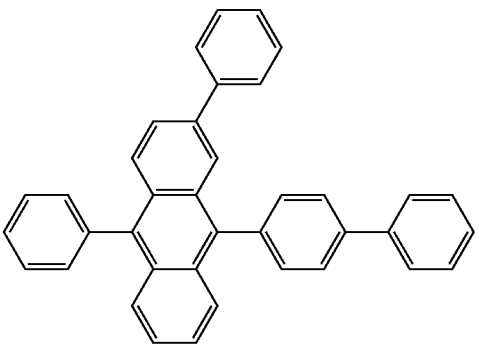
H36
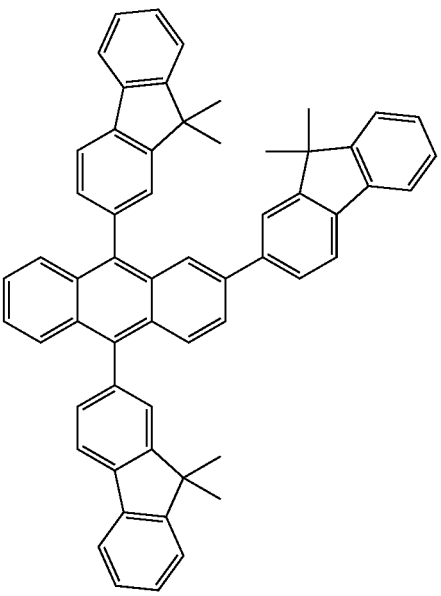
H37
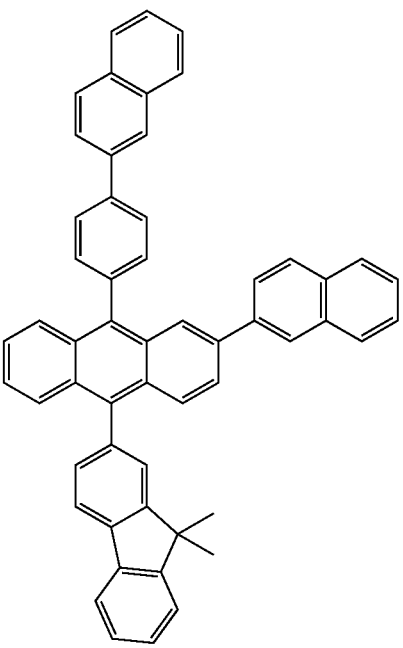

H38
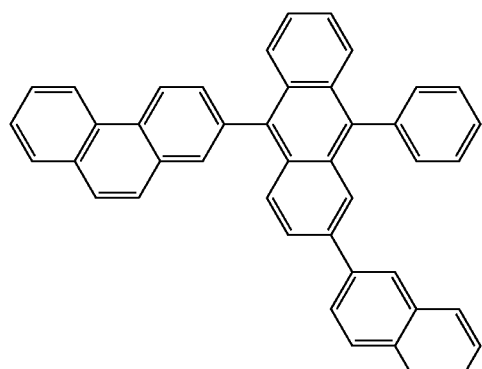
H39
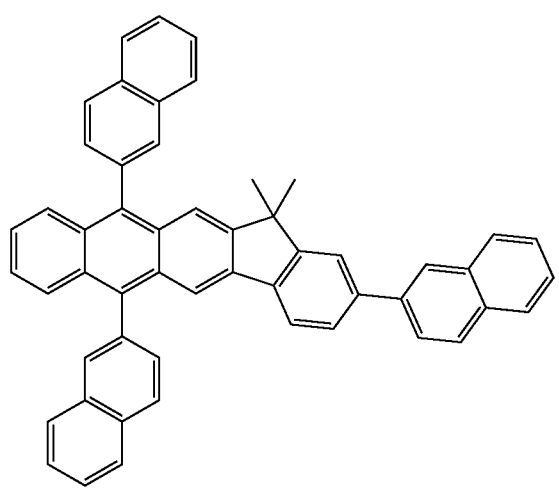
H40
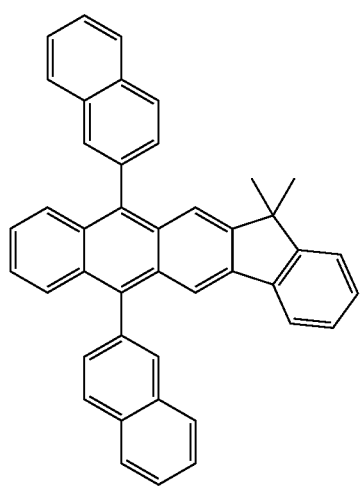
H41
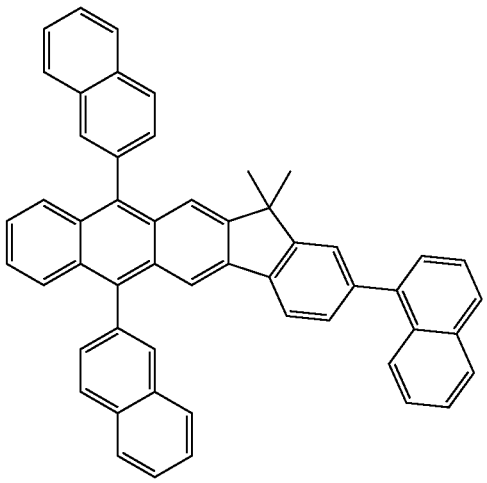
H42
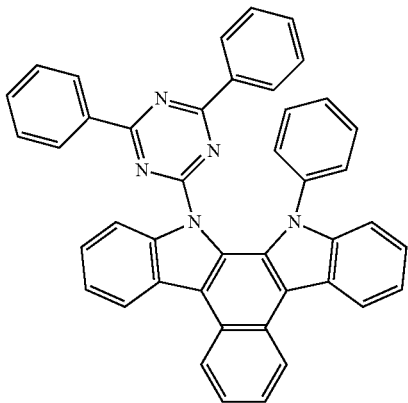
In an implementation, the host may include at least one selected from Compounds H43 to H49 below.
H43

H44 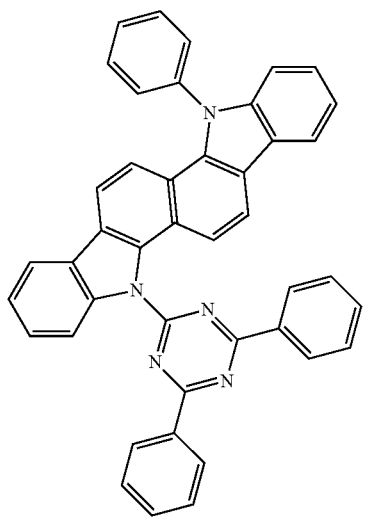

H45 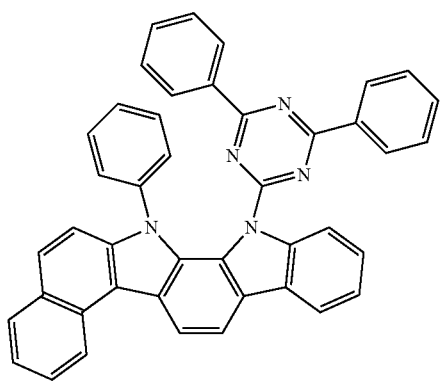

H46 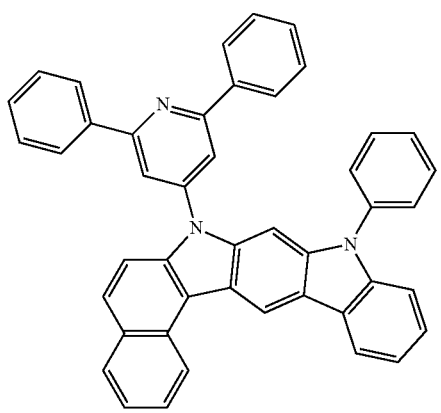

H47 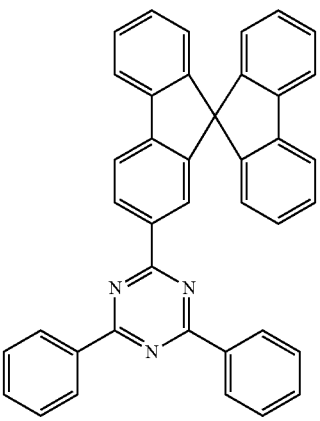

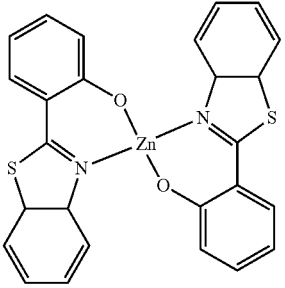

H48 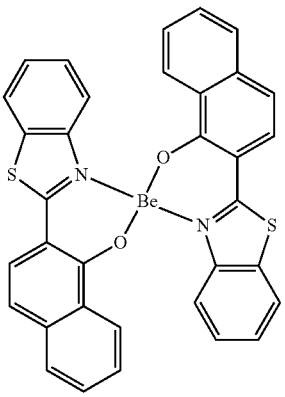

H49 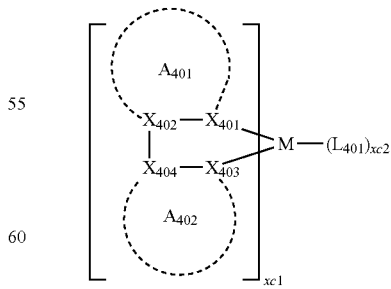

The dopant may include at least one selected from a fluorescent dopant and a phosphorescent dopant.

The phosphorescent dopant may include an organometallic complex represented by Formula 401 below.

<Formula 401>

$$\left[ \begin{array}{c} A_{401} \\ X_{402}-X_{401} \\ X_{404}-X_{403} \\ A_{402} \end{array} M-(L_{401})_{xc2} \right]_{xc1}$$

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran and a substituted or unsubstituted dibenzothiophene;

at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3; and xc2 may be 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, or phosphaite).

When $A_{401}$ in Formula 401 has two or more substituents, the two or more substituents of $A_{401}$ may be bonded together to form a saturated or an unsaturated ring.

When $A_{402}$ in Formula 401 has two or more substituents, the two or more substituents of $A_{402}$ may be bonded together to form a saturated or an unsaturated ring.

When xc1 in Formula 401 is two or more, a plurality of ligands

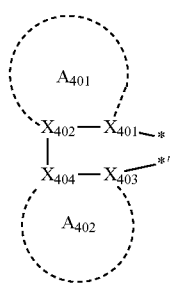

in Formula 401 may be identical or different. When xc1 in Formula 401 is two or more, $A_{401}$ and $A_{402}$ may be respectively linked to another $A_{401}$ and $A_{402}$ of a neighboring ligand directly or via a linking group (for example, a $C_1$-$C_5$ alkylene group, —N(R')— (wherein R' is a $C_1$-$C_{10}$ alkyl group or a $C_6$-$C_{20}$ aryl group) or —C(=O)—).

The phosphorescent dopant may include at least one selected from Compounds PD1 to PD74 below.

PD1
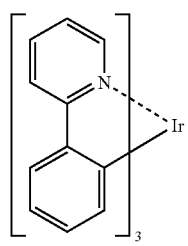

PD2
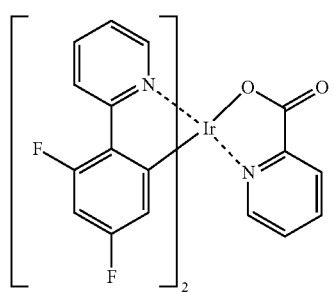

PD3
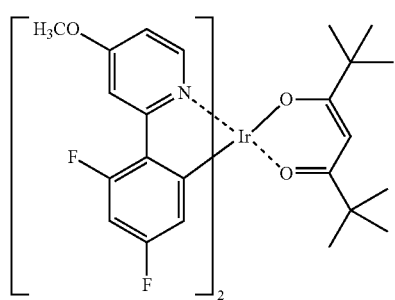

PD4
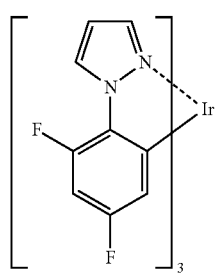

PD5
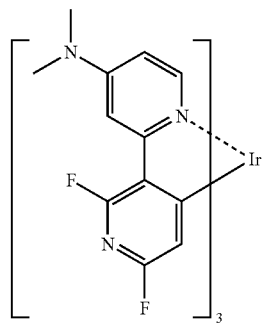

PD6
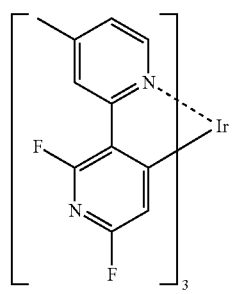

PD7
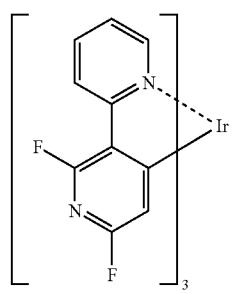

PD8
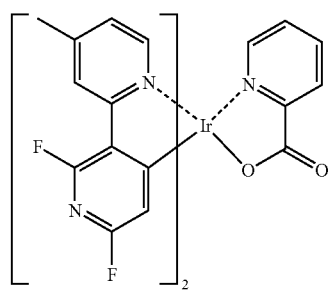

PD9
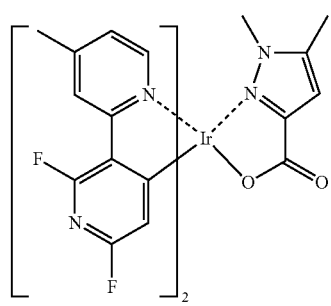

PD10 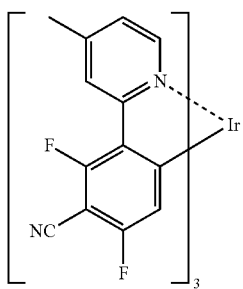
PD15 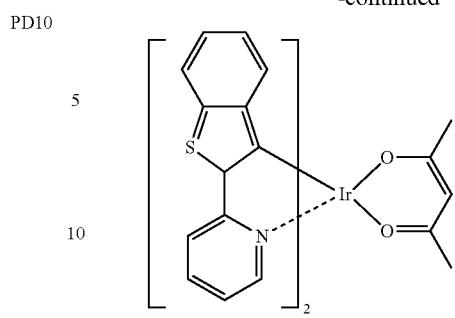
PD11 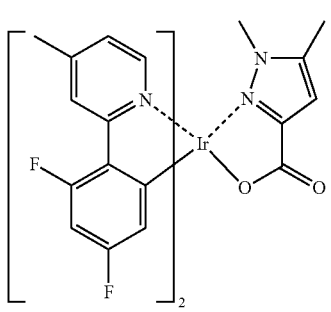
PD16 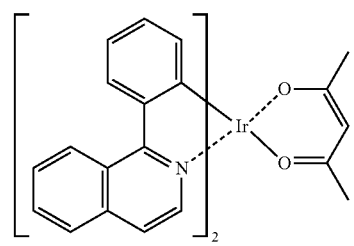
PD12 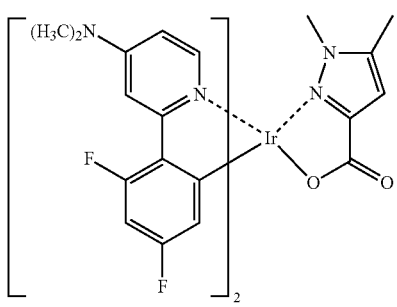
PD17 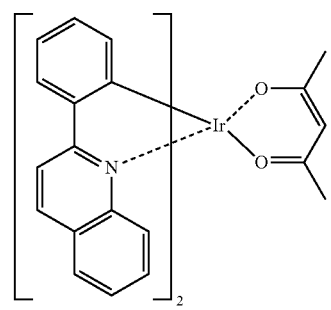
PD13 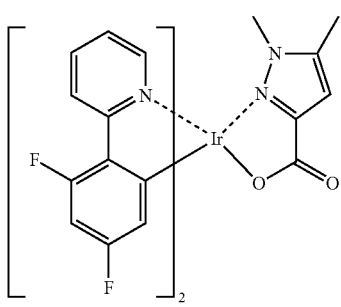
PD18 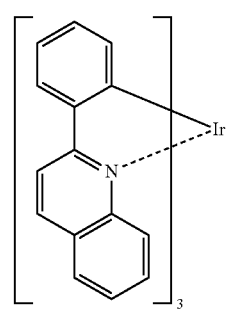
PD14 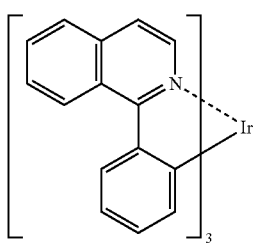
PD19 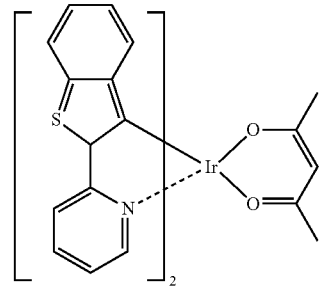

-continued
PD20 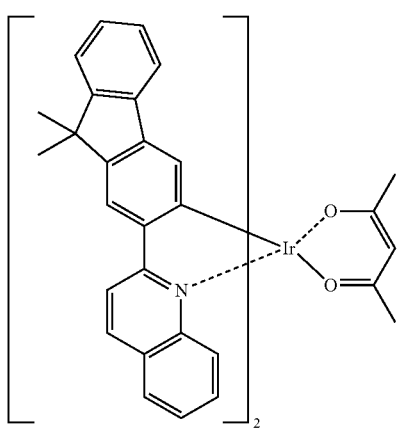
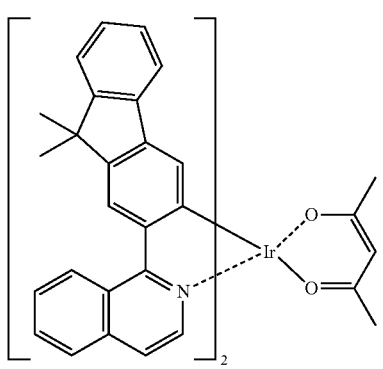
PD22 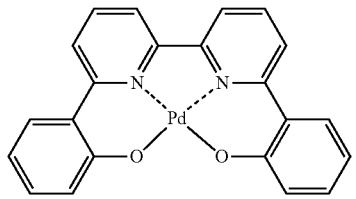
PD23 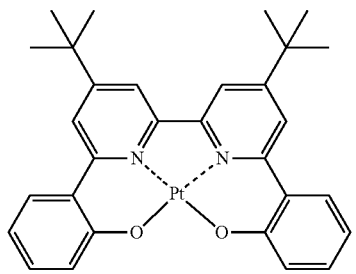
PD24 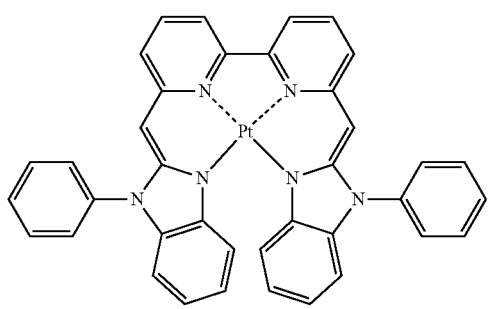
-continued
PD25 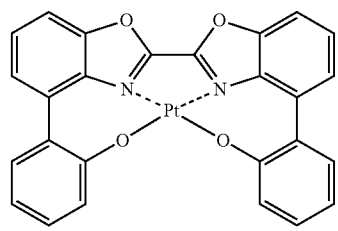
PD26 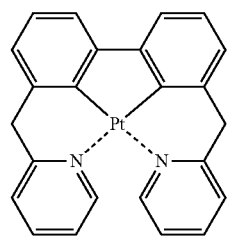
PD27 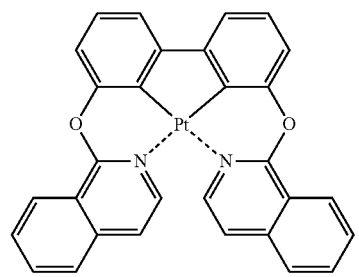
PD28 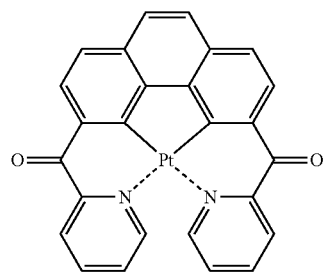
PD29 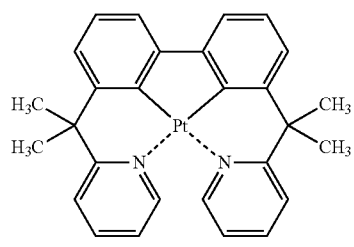
PD30 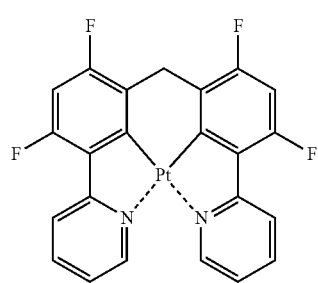

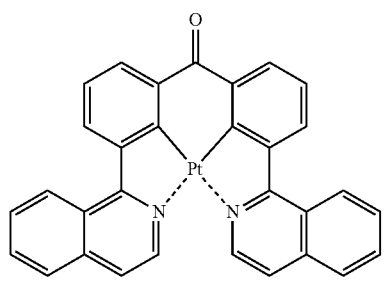 PD31
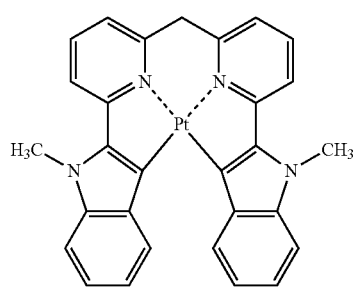 PD32
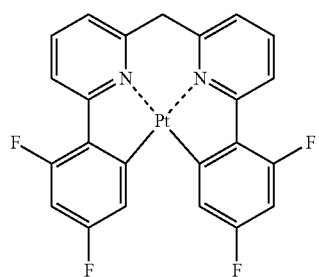 PD33
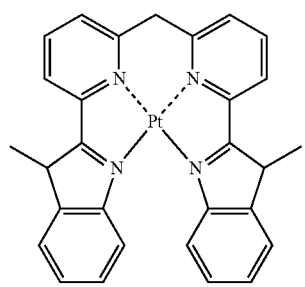 PD34
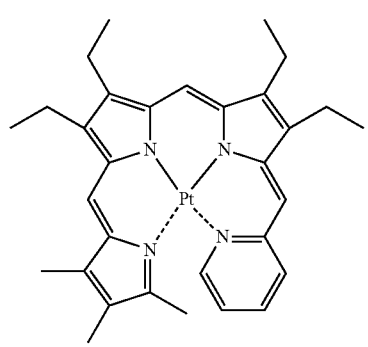 PD35
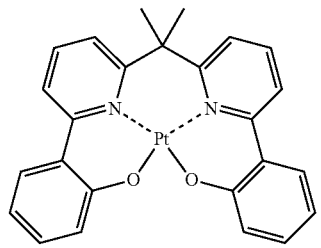 PD36
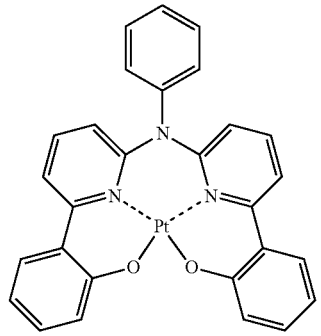 PD37
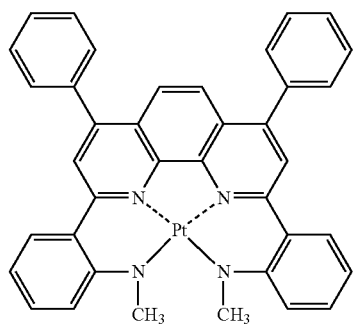 PD38
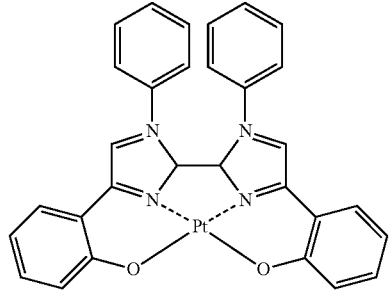 PD39
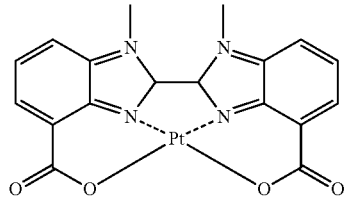 PD40
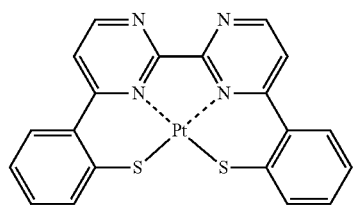 PD41

-continued
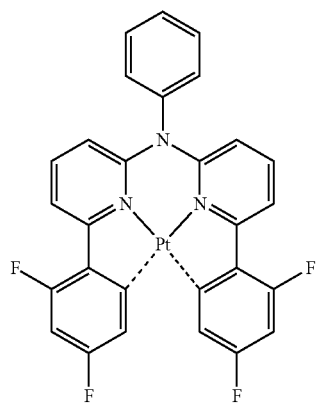
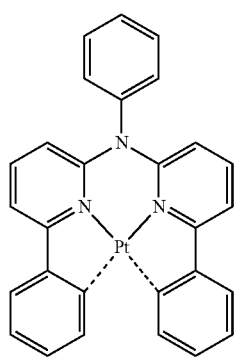
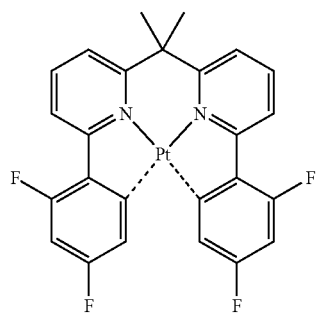
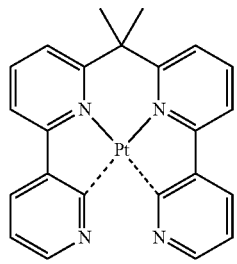
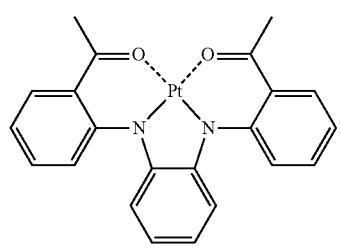
-continued
PD42
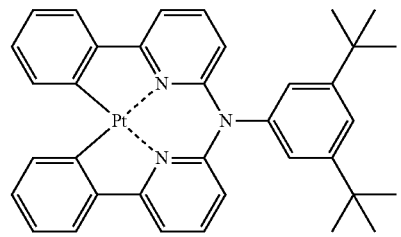
PD43
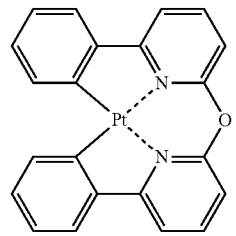
PD44
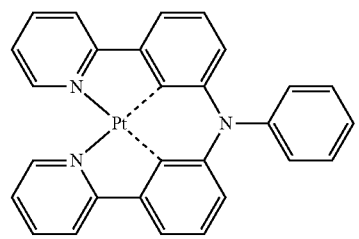
PD45
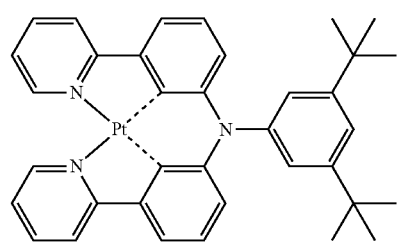
PD46
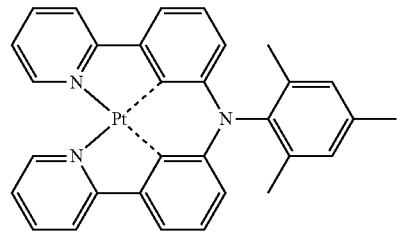
PD47
PD48
PD49
PD50
PD51
PD52
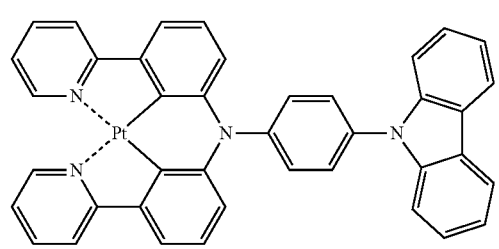

PD53
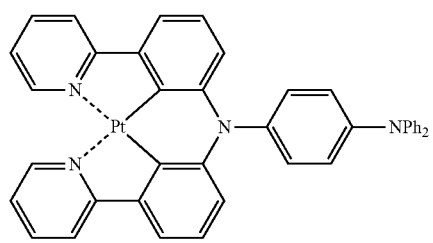
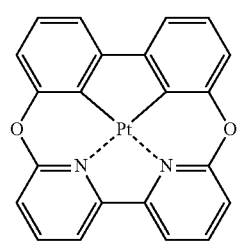
PD54
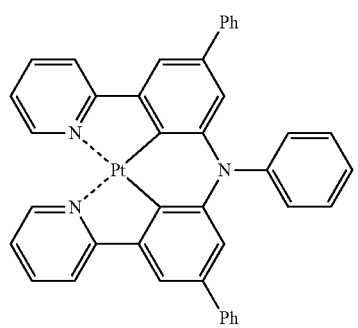
PD55
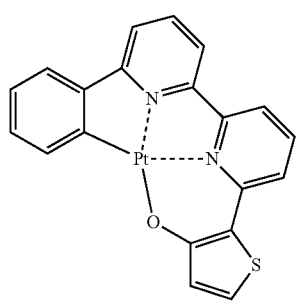
PD56
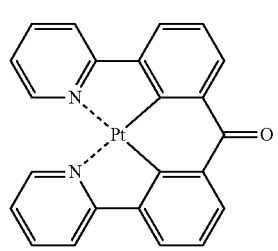
PD57
PD58
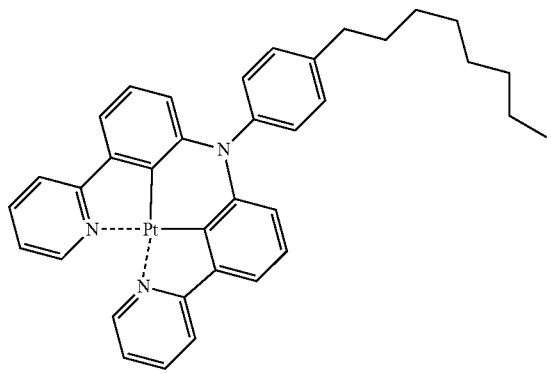
PD59
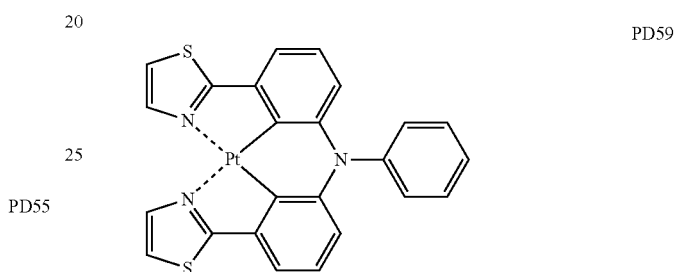
PD60
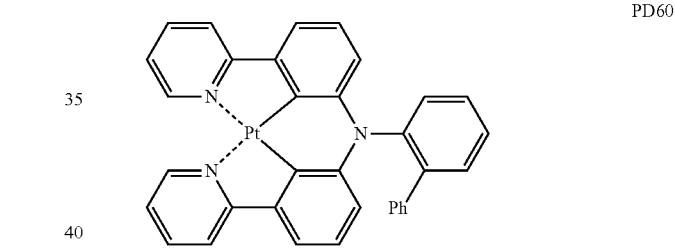
PD61
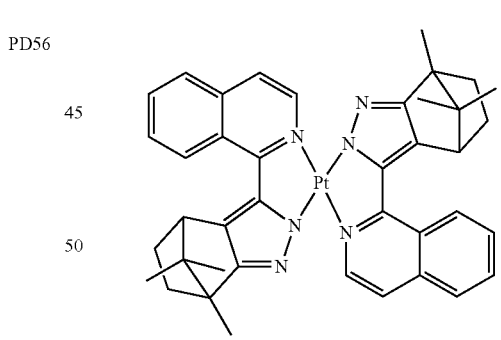
PD62
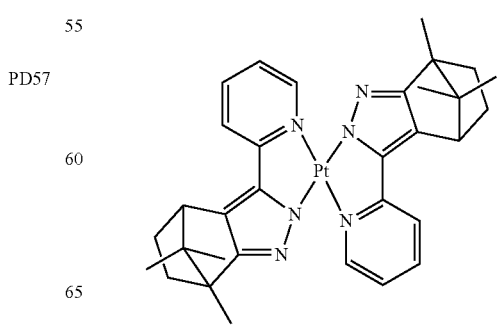

PD63 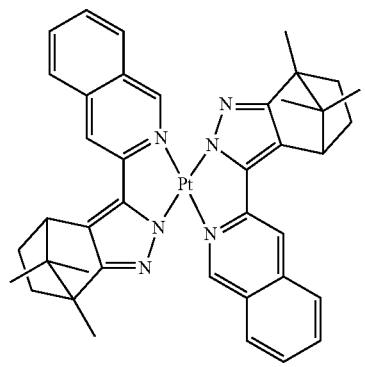
PD64 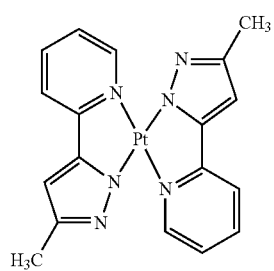
PD65 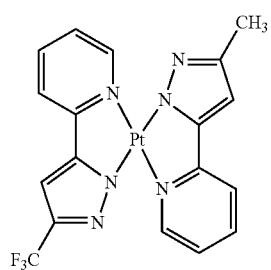
PD66 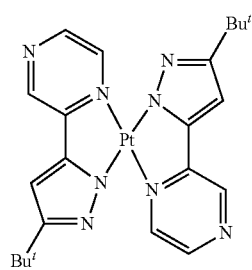
PD67 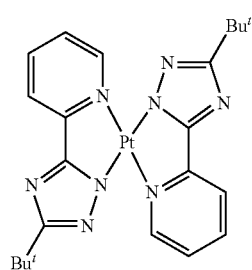
PD68 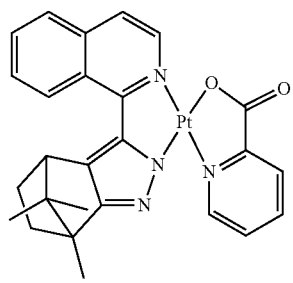
PD69 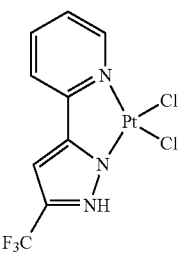
PD70 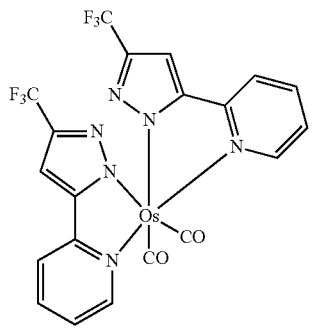
PD71 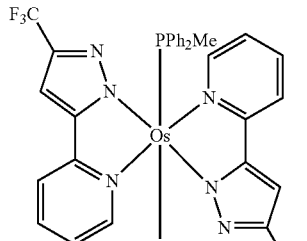
PD72 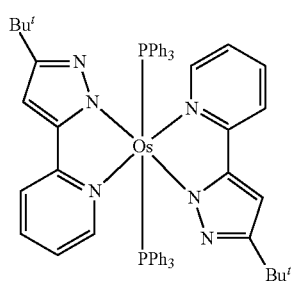

-continued
PD73
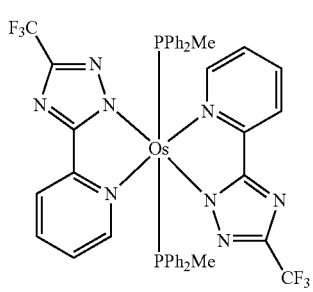
PD74
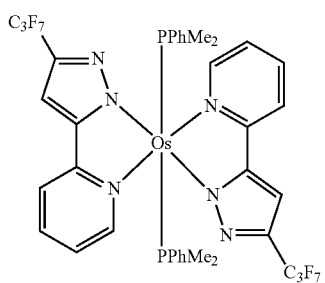
In an implementation, the phosphorescent dopant may include PtOEP below.
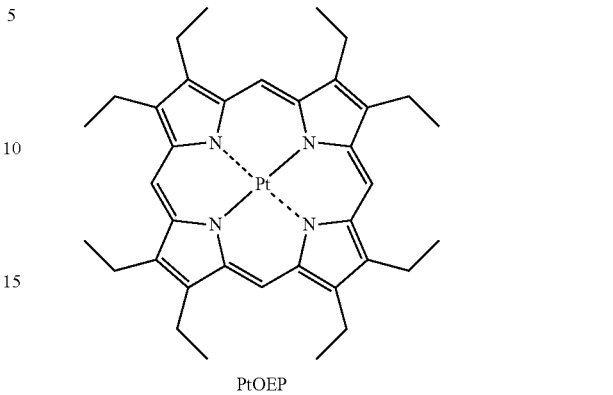
PtOEP
The fluorescent dopant may include at least one selected from DPAVBi, BDAVBi, TBPe, DCM, DCJTB, Coumarin 6, and C545T.
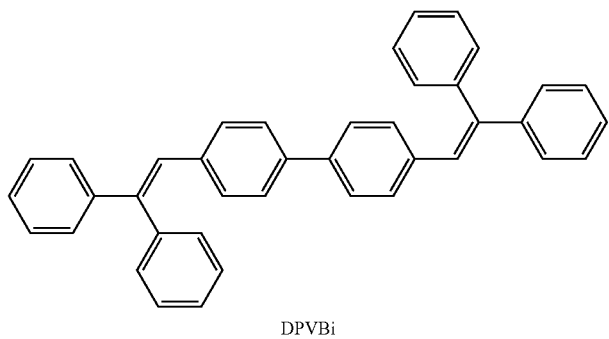
DPVBi
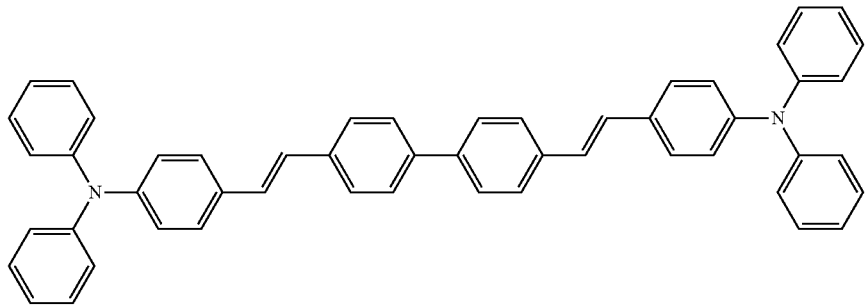
DPAVBi
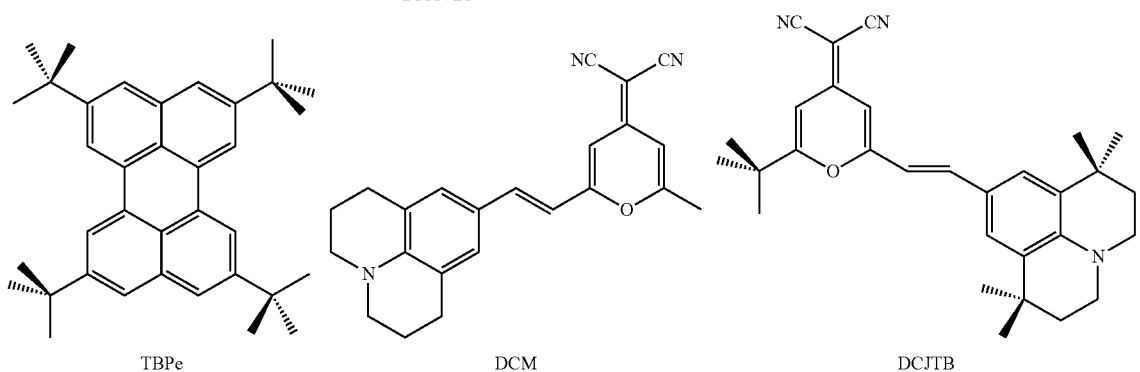
TBPe     DCM     DCJTB

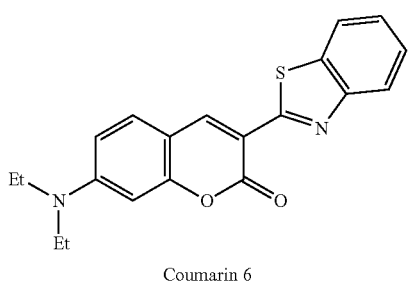
Coumarin 6

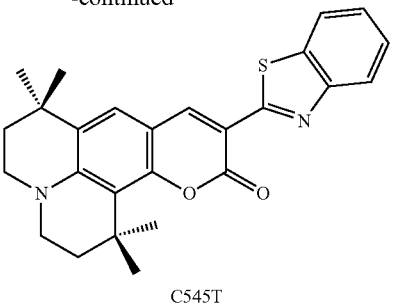
C545T

In an implementation, the fluorescent dopant may include a compound represented by Formula 501.

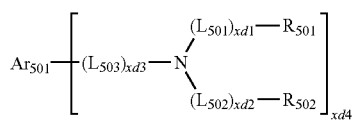
<Formula 501>

In Formula 501,

Ar$_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) ($Q_{501}$ to $Q_{503}$ may be each independently selected from a hydrogen, a $C_1$-$C_{60}$) alkyl group, a $C_2$-$C_{60}$ alkenyl group, a $C_6$-$C_{60}$ aryl group, and a $C_2$-$C_{60}$ heteroaryl group);

$L_{501}$ to $L_{503}$ may be the same as defined in connection with $L_{201}$ provided herein;

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and a dibenzofuranyl group and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group and dibenzothiophenyl group;

xd1 to xd3 may be each independently selected from 0, 1, 2, and 3; and xd4 may be selected from 1, 2, 3, and 4.

The fluorescent host may include at least one selected from compounds FD1 to FD8 below.

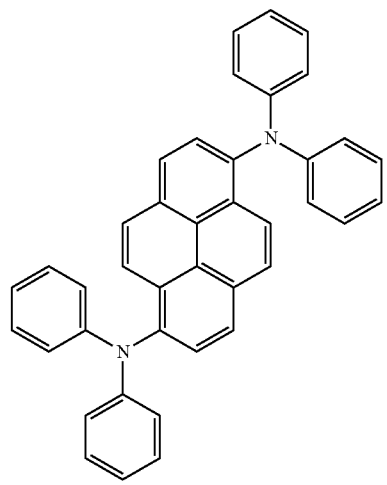
FD1

-continued
FD2
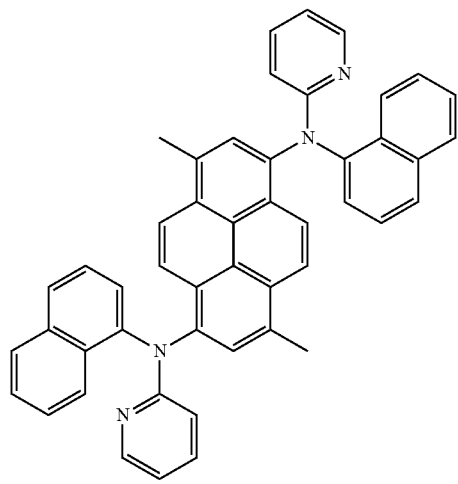
FD3
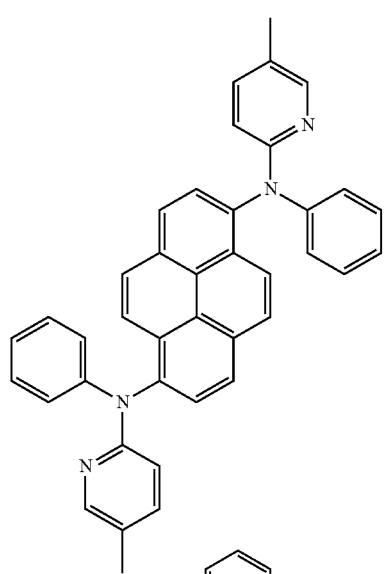
FD4
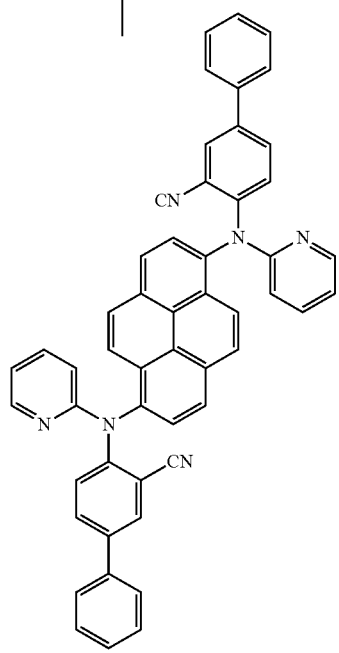
-continued
FD5
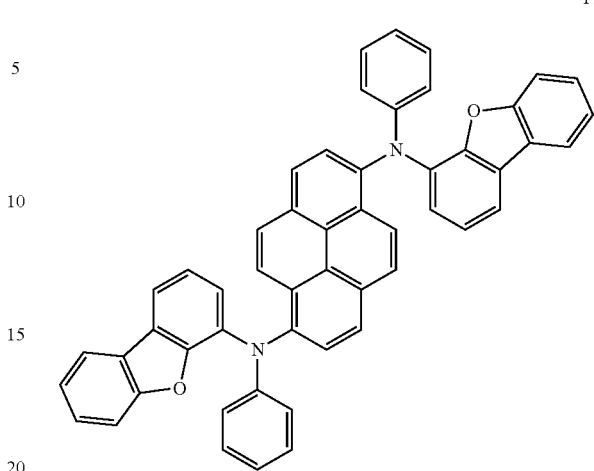
FD6
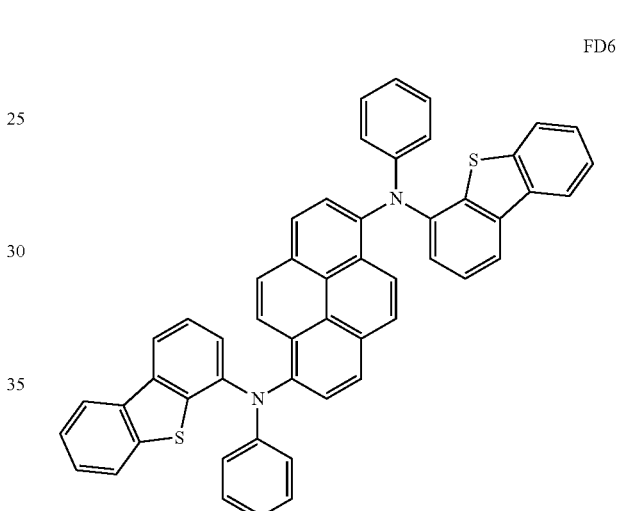
FD7
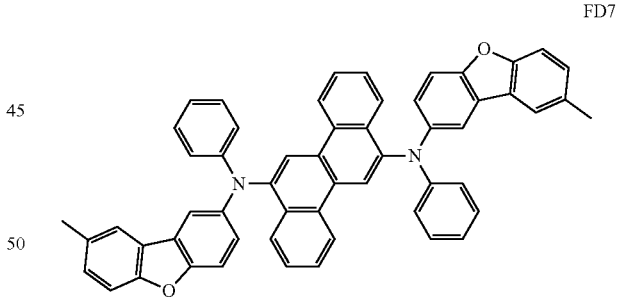
FD8
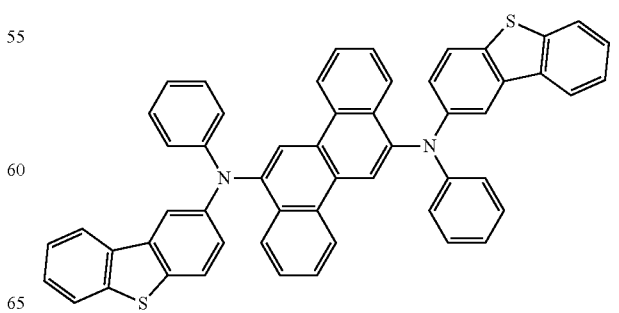

An amount of the dopant in the emission layer may be, e.g., in a range of about 0.01 part by weight to about 15 parts by weight, based on 100 parts by weight of the host, but is not limited thereto.

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

In an implementation, the organic layer 150 of the organic light-emitting device may include an electron transport region between the emission layer and the second electrode 190.

The electron transport region may include a hole blocking layer. The hole blocking layer may be formed, when the emission layer includes a phosphorescent dopant, to help prevent diffusion of excitons or holes into an electron transport layer.

When the electron transport region includes a hole blocking layer, the hole blocking layer may be formed on the emission layer by using various methods, e.g., vacuum deposition, spin coating, casting, LB method, ink-jet printing, laser-printing, or LITI. When the hole blocking layer is formed by vacuum deposition or spin coating, deposition and coating conditions for the hole blocking layer may be determined by referring to the deposition and coating conditions for the hole injection layer.

The hole blocking layer may include, e.g., at least one selected from BCP and Bphen.

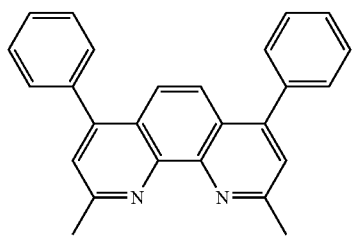

BCP

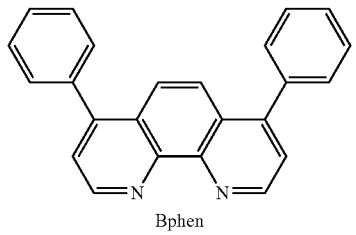

Bphen

A thickness of the hole blocking layer may be in a range of about 20 Å to about 1,000 Å, e.g., about 30 Å to about 300 Å. When the thickness of the hole blocking layer is within this range, excellent hole blocking characteristics may be obtained without a substantial increase in driving voltage.

The electron transport region may include an electron transport layer. The electron transport layer may be formed on the emission layer or the hole blocking layer by using various methods, e.g., vacuum deposition, spin coating, casting, LB method, ink-jet printing, laser-printing, or LITI. When the electron transport layer is formed by using vacuum deposition or spin coating, vacuum deposition and coating conditions for the electron transport layer may be determined by referring to the vacuum deposition and coating conditions for the hole injection layer.

In an implementation, the organic layer 150 of the organic light-emitting device may include the electron transport region between the emission layer and the second electrode 190, and the electron transport region may include the electron transport layer.

The electron transport layer may further include at least one selected from BCP, Bphen and Alq$_3$, Balq, TAZ and NTAZ below.

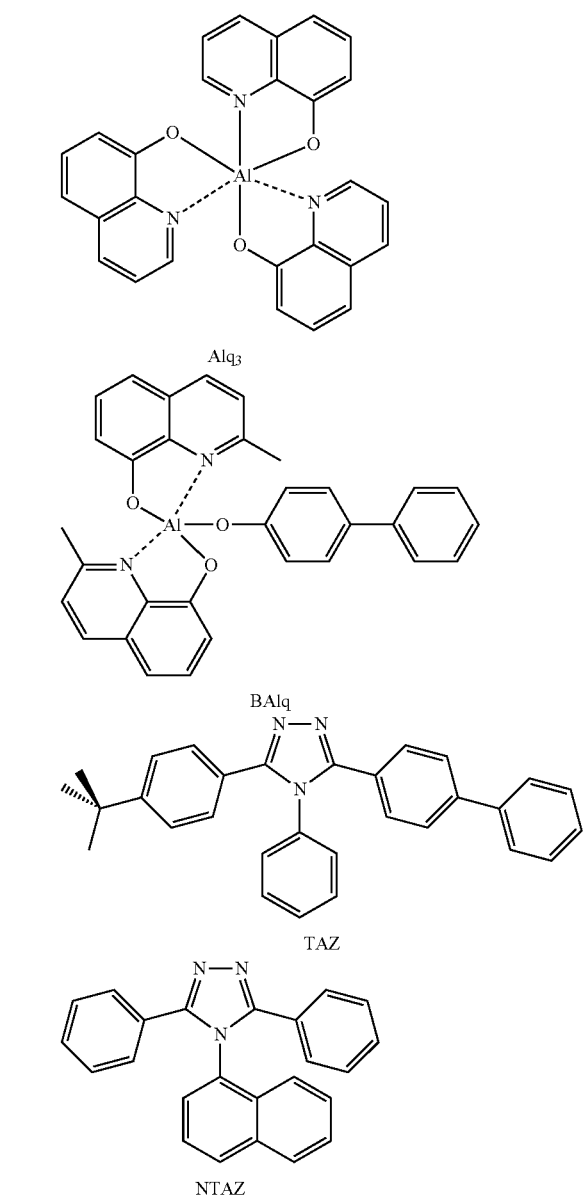

A thickness of the electron transport layer may be in a range of about 100 Å to about 1,000 Å, e.g., about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, e.g., Compound ET-D1 (lithium quinolate, LiQ) or ET-D2.

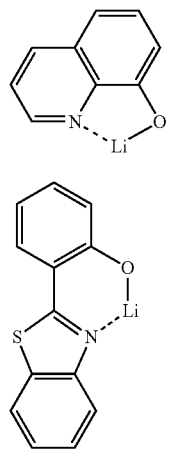

ET-D1

ET-D2

The electron transport region may include an electron injection layer that facilitates electron injection from the second electrode 190.

The electron injection layer may be formed on the electron transport layer by using various methods, e.g., vacuum deposition, spin coating, casting, LB method, ink-jet printing, laser-printing, or LITI. When the electron injection layer is formed by vacuum deposition or spin coating, vacuum deposition and coating conditions for the electron injection layer may be determined by referring to the vacuum deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, e.g., about 3 Å to about 90 Å. When the thickness of the electron injection layer is within this range, excellent electron injection characteristics may be obtained without a substantial increase in driving voltage.

The second electrode 190 may be disposed on the organic layer 150. The second electrode 190 may be a cathode that is an electron injection electrode, and in this regard, a material for forming the second electrode 190 may be a material with a low work function, and such a material may be metal, alloy, an electrically conductive compound, or a mixture thereof. Examples of materials for the second electrode 190 may include lithium (Li), magnesium (Mg), aluminum (Al), aluminum-lithium (Al—Li), calcium (Ca), magnesium-indium (Mg—In), and magnesium-silver (Mg—Ag). In an implementation, the material for forming the second electrode 190 may be ITO or IZO. The second electrode 190 may be a reflective electrode, a semi-transmissive electrode, or a transmissive electrode.

Hereinbefore, the organic light-emitting device has been described with reference to FIG. 1.

Hereinafter, an organic light-emitting device according to an embodiment will be explained in detail with reference to Synthesis Examples and Examples. However, the organic light-emitting device is not limited thereto.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example

Synthesis of Compound 1

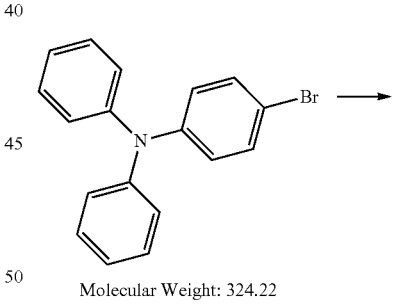

Molecular Weight: 324.22

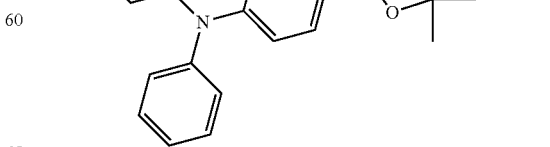

1-1

-continued

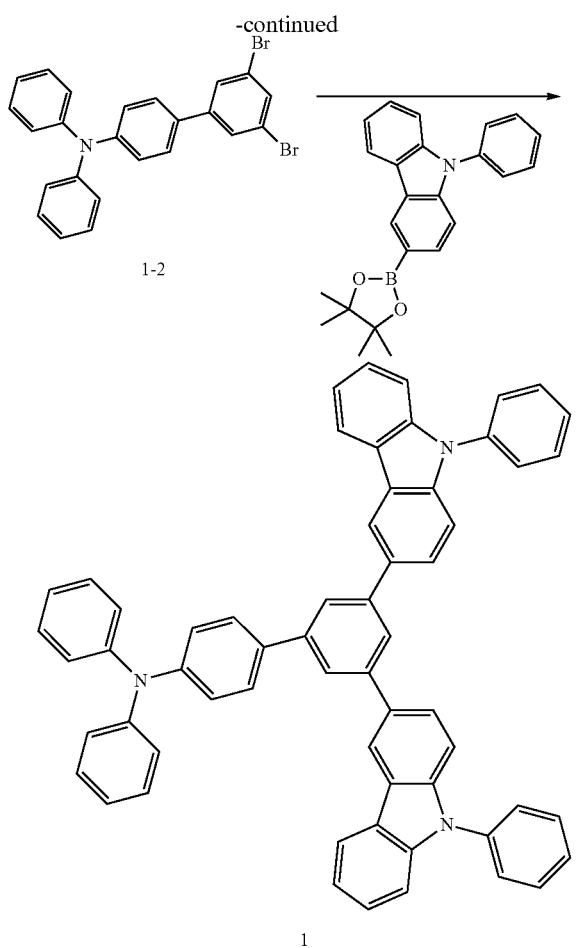

1-2

1

(1) Synthesis of Intermediate 1-1

10 g of bromotriphenylamine was dissolved in 150 ml of tetrahydrofuran, and then the resultant was cooled to −78° C. n-BuLi (2.5 M, 14.7 ml) was slowly added dropwise thereto at −78° C. After an hour, 3 g of 2-isopropoxy-4,4,5,5-tetramethyl-1,3,2-dioxaborolane was slowly added thereto. After 30 minutes, the resultant was slowly heated to ambient temperature and then stirred for 6 hours. Saturated ammonium chloride aqueous solution was added thereto to quench the reaction and obtain an organic layer. The organic layer obtained therefrom was dried by using anhydrous magnesium sulfate and concentrated at a reduced pressure. The residual was separation-purified by silica gel column chromatography to obtain Intermediate 1-1 (9.9 g, yield of 78%).

LC/MS cal'd: 371.21. found: 371.22.

(2) Synthesis of Intermediate 1-2

9.9 g of Intermediate 1-1 and 8.4 g of 1,3,5-tribromobenzene were dissolved in 120 ml of tetrahydrofuran, and then 1.5 g of Pd(PPh3)4 and 1.1 g of potassium carbonate were added thereto and the resultant was stirred at 60° C. After 12 hours, the temperature thereof was decreased to ambient temperature and an extraction process using ethyl acetate was performed three times. The extracted organic layer therefrom was dried by using anhydrous magnesium sulfate and evaporated at a reduced pressure. The residual was separation-purified by silica gel column chromatography to obtain Intermediate 1-2 (8.7 g, yield of 68%).

LC/MS cal'd: 476.97. found: 476.99.

(3) Synthesis of Compound 1

Compound 1 (3.6 g, yield of 72%) was obtained in the same manner as in the synthesis of Intermediate 1-2 except for using 3 g of Intermediate 1-2 and 4.8 g of 9-phenyl-3-(4,4,5,5-tetramethyl-1,3,2-dioxaborolane-2-yl)-9H-carbazole.

$^1$H NMR (400 MHz, CDCl$_3$) δ 8.23(m, 2H), 8.11(m, 2H), 7.94(t, 1H), 7.82(d, 2H), 7.73-7.71(m, 4H), 7.50-7.46(m, 8H), 7.37-7.25(m, 8H), 7.20(m, 2H), 7.06-7.02(m, 4H), 6.87-6.84(m, 2H), 6.66-6.63(m, 2H), 6.15-6.12(m, 4H). LC/MS cal'd: 803.33. found: 803.34.

Synthesis of Compound 2

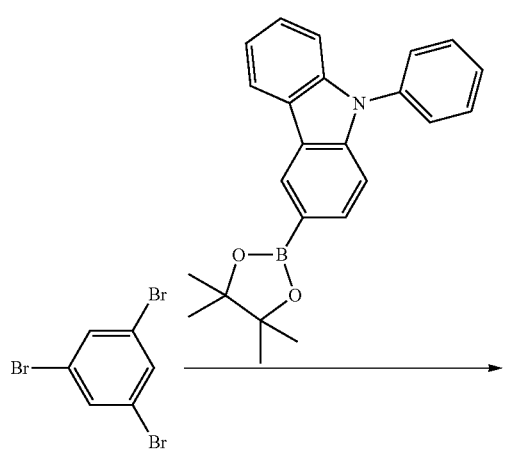

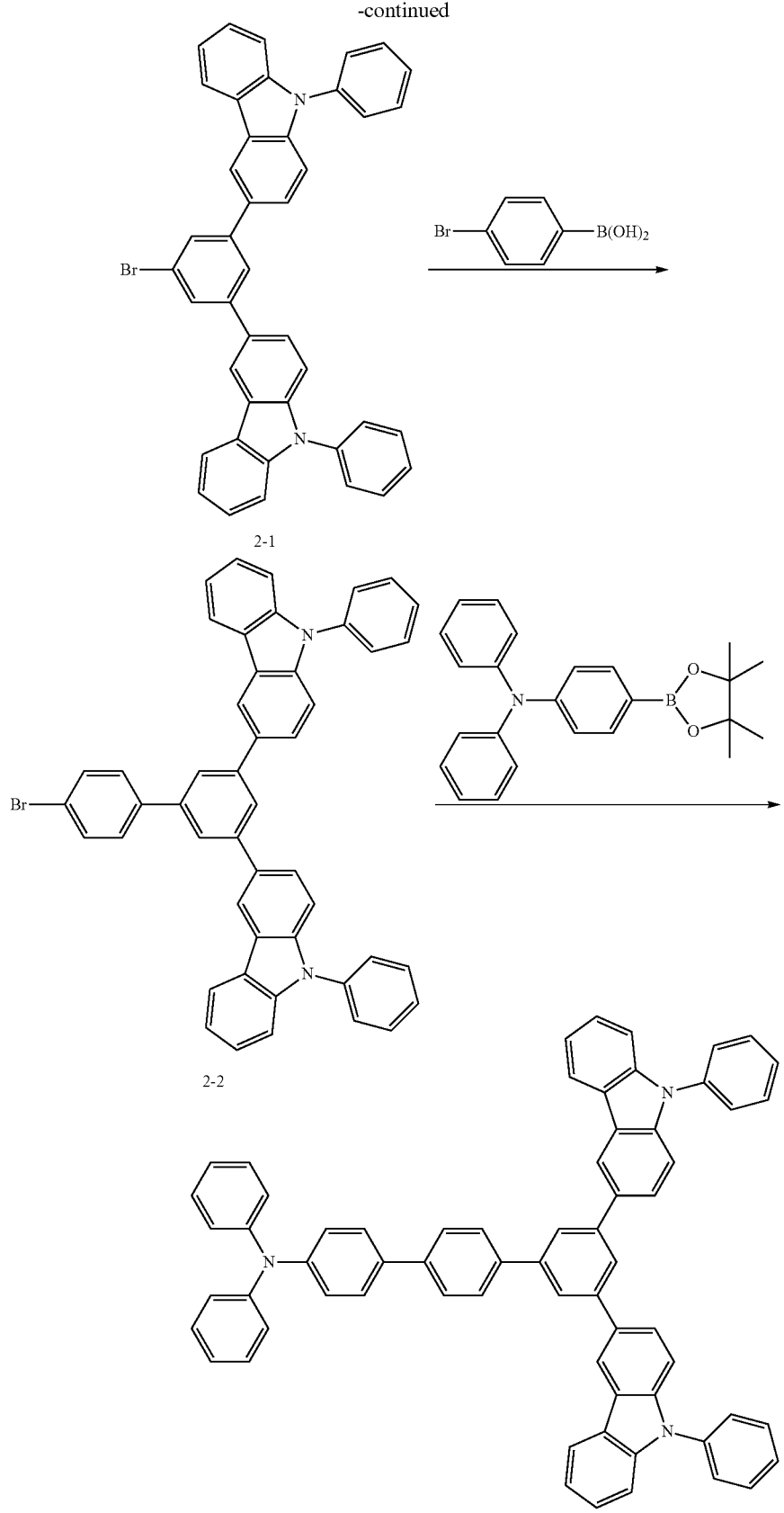

(1) Synthesis of Intermediate 2-1

Compound 2-1 (4.1 g, yield of 68%) was obtained in the same manner as in the synthesis of Intermediate 1-2 except for using 3 g of 1,3,5-tribromobenzene and 7 g of 9-phenyl-3-(4,4,5,5-tetramethyl-1,3,2-dioxaborolane-2-yl)-9H-a carbazole.

LC/MS cal'd: 638.14. found: 638.12.

(2) Synthesis of Intermediate 2-2

Intermediate 2-2 (3.3 g, yield of 73%) was obtained in the same manner as in the synthesis of Intermediate 1-2 except for using 4 g of Intermediate 2-1 and 1.3 g of 4-bromobenzene boronic acid.

LC/MS cal'd: 714.17. found: 714.18.

(3) Synthesis of Compound 2

Compound 2 (3.4 g, yield of 83%) was obtained in the same manner as in the synthesis of Intermediate 1-1 except for using Intermediate 1-2 and 3.3 g of Intermediate 2-2.

$^1$H NMR (400 MHz, CDCl$_3$) δ 8.23(m, 2H), 8.11(m, 2H), 7.94-7.86(m, 3H), 7.79-7.71(m, 8H), 7.50-7.42(m, 10H), 7.36-7.34(m, 2H), 7.30-7.26(m, 4H), 7.20(m, 2H), 7.07-7.05(m, 4H), 6.83(2H), 6.61(m, 2H), 6.16-6.13(m, 4H). LC/MS cal'd: 879.36. found: 879.37.

Synthesis of Compound 3

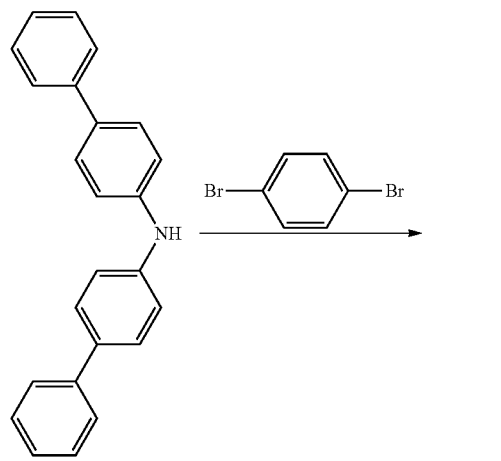

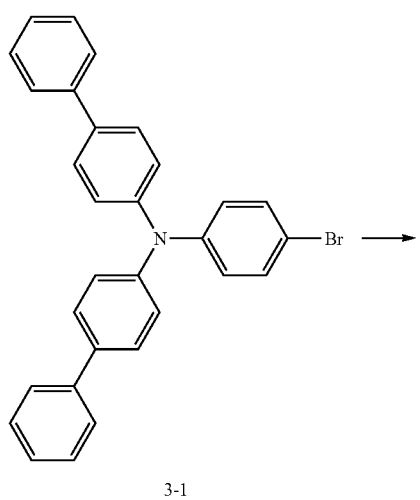

3-1

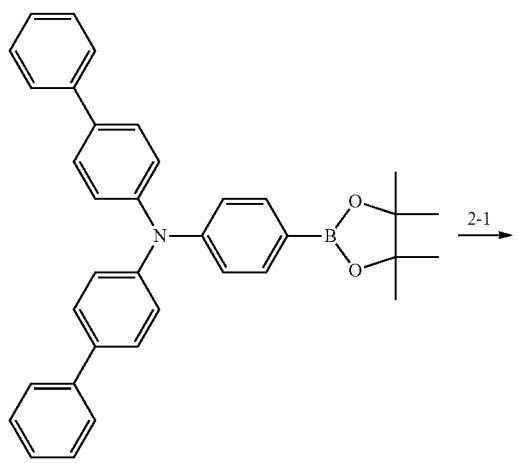

3-2

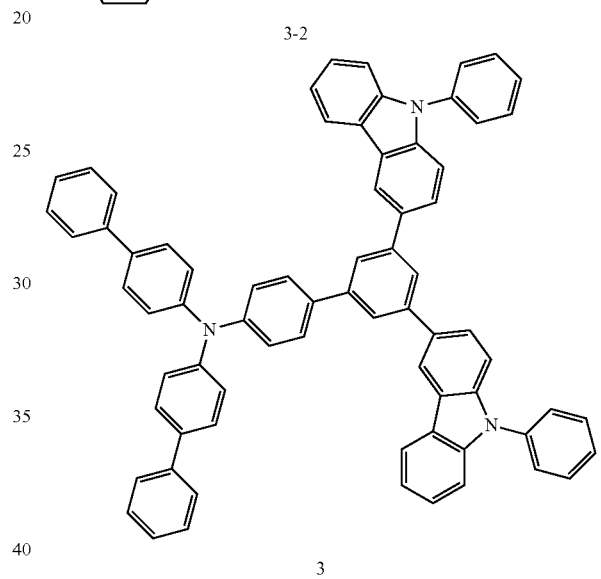

3

(1) Synthesis of Intermediate 3-1

5 g of 1,4-dibromobenzene, 5 g of di([1,1'-biphenyl]-4-yl)amine, 0.34 g of Pd$_2$(dba)$_3$, PtBu$_3$ (0.1 ml) and 3.6 g of KOtBu were dissolved in 60 mL of toluene, and then the resultant was stirred for 2 hours at 85° C. Pure water was added to quench the reaction at ambient temperature, and then an extraction process using ethyl acetate was performed three times. The extracted organic layer was dried using anhydrous magnesium sulfate and then evaporated at a reduced pressure. The residual was separation-purified by silica gel column chromatography to obtain Intermediate 3-1 (6.4 g, yield of 87%). LC/MS cal'd: 475.09. found: 475.11.

(2) Synthesis of Intermediate 3-2

Intermediate 3-2 (5.3 g, yield of 76%) was obtained in the same manner as in the synthesis of Intermediate 1-1 except that 6.4 g of Intermediate 3-1 was used. LC/MS cal'd: 523.27. found: 523.29.

(3) Synthesis of Compound 3

Compound 3 (6.7 g, yield of 69%) was obtained in the same manner as in the synthesis of Intermediate 1-2 except that 5.3 g of Intermediate 3-2 and 6.5 g of Intermediate 2-1 were used. $^1$H NMR (400 MHz, CDCl$_3$) δ 8.23-8.20(m, 2H), 8.11(m, 2H), 7.94(t, 1H), 7.82(d, 1H), 7.73-7.71(m, 4H), 7.57-7.48(m, 23H), 7.37-7.29(m, 8H), 7.20-7.16(m, 2H), 6.83-6.80(m, 4H) 6.65-6.62(m, 2H). LC/MS cal'd: 955.39. found: 955.40.

Synthesis of Compound 7
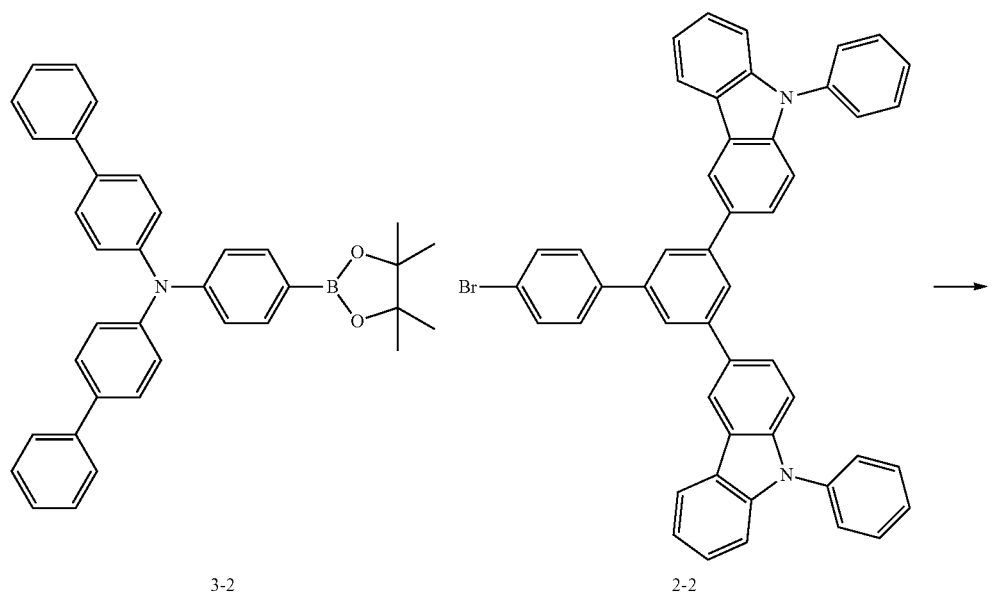
3-2     2-2
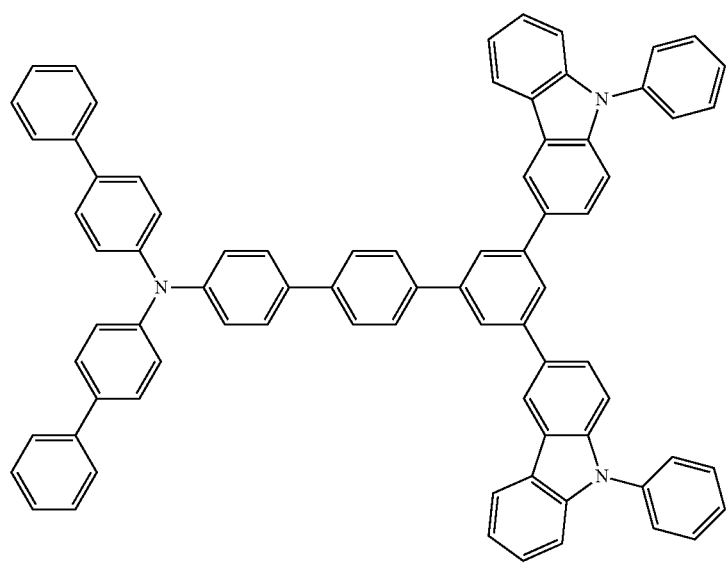
7
(1) Synthesis of Compound 7
Compound 7 (4.2 g, yield of 71%) was obtained in the same manner as in the synthesis of Compound 3, except that 3 g of Intermediate 3-2 and 4.1 g of Intermediate 2-2 were used. $^1$H NMR (400 MHz, CDCl$_3$) δ 8.23-8.21(m, 2H), 8.11(m, 2H), 7.94(t, 1H), 7.79-7.71(m, 6H), 7.66-7.64(m, 2H), 7.57-7.36(m, 26H), 7.30-7.26(m, 4H), 7.20 (m, 2H), 6.83(m, 4H), 6.60(m, 2H). LC/MS cal'd: 1031.42. found: 1031.41.

Synthesis of Compound 22

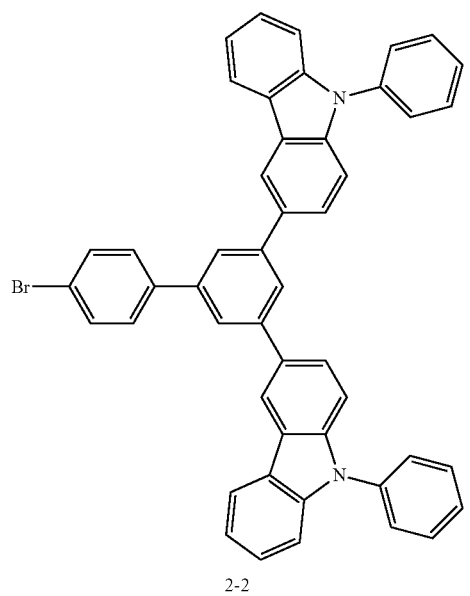

2-2

Synthesis of Compound 26

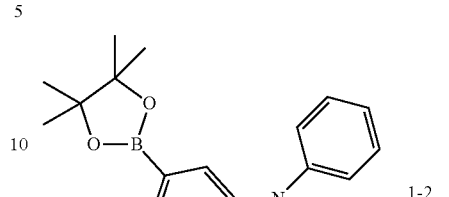

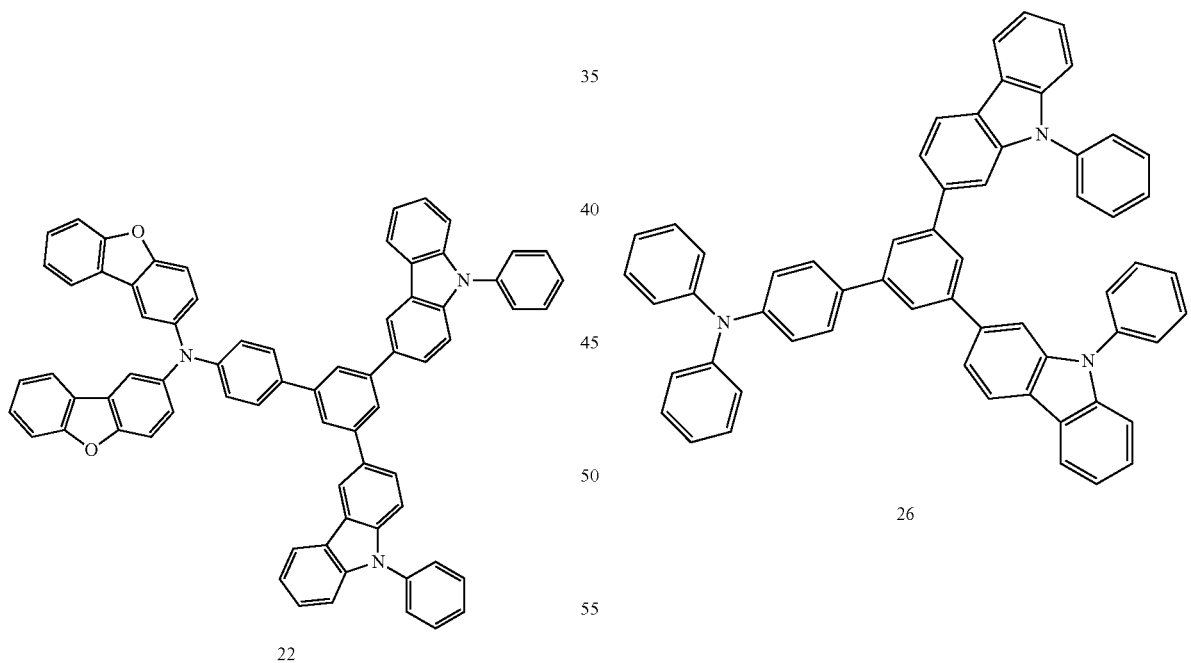

Compound 22 (3 g, yield of 73%) was obtained in the same manner as in the synthesis of Intermediate 1-2, except that 3 g of Intermediate 2-2 and 1.4 g of bis(dibenzo[b,d]furan-2-yl)amine were used. $^1$H NMR (400 MHz, CDCl$_3$) δ 8.23-8.20(m, 2H), 8.11(m, 2H), 7.94(t, 1H), 7.82-7.79(m, 3H), 7.73-7.71(m, 4H), 7.53-7.34(m, 23H), 7.30-7.26(m, 4H), 7.20(m, 2H), 6.97(dd, 2H), 6.78(m, 2H). LC/MS cal'd: 983.35. found: 983.34.

Compound 26 (4 g, yield of 81%) was obtained in the same manner as in the synthesis of Compound 1, except that 3 g of Intermediate 1-2 and 2.2 g of 9-phenyl-2-(4,4,5,5-tetramethyl-1,3,2-dioxaborolane-2-yl)-9H-carbazole were used.
$^1$H NMR (400 MHz, CDCl$_3$) δ 8.15-8.12(m, 3H), 8.04(m, 2H), 7.85(d, 2H), 7.75(m, 2H), 7.51-7.42(m, 12H), 7.37 (2H), 7.31-7.28(m, 4H), 7.20(m, 2H), 7.06(m, 4H), 6.87(m, 2H), 6.65(m, 2H), 6.15(m, 4H). LC/MS cal'd: 803.33. found: 803.35.

Synthesis of Compound 27
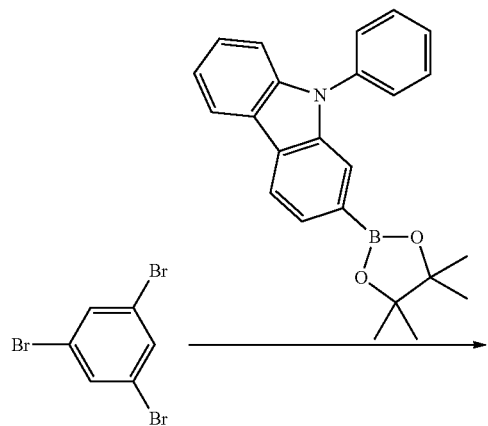
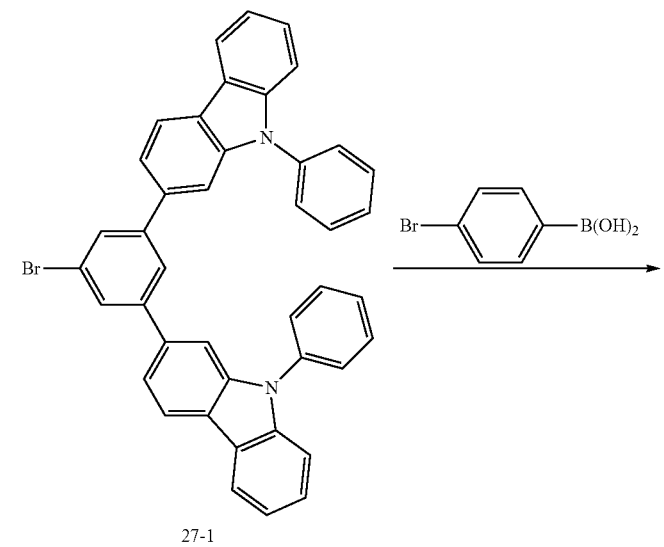
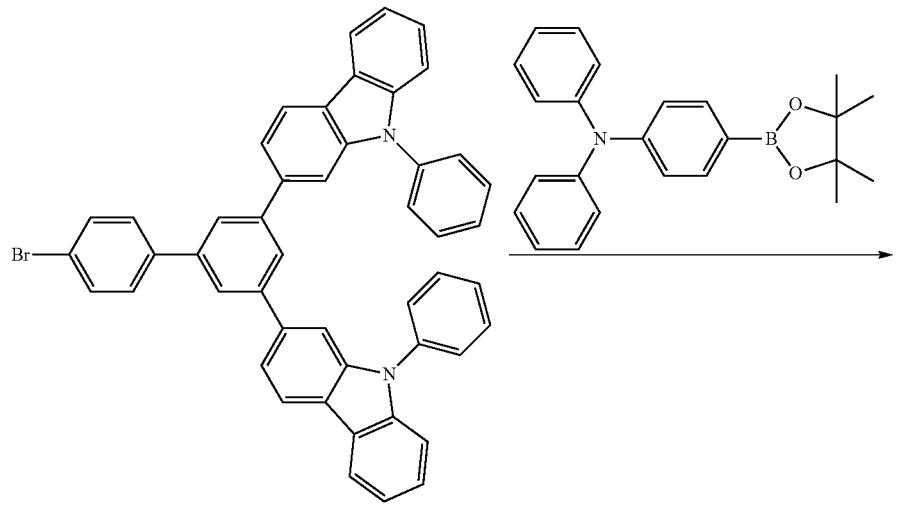

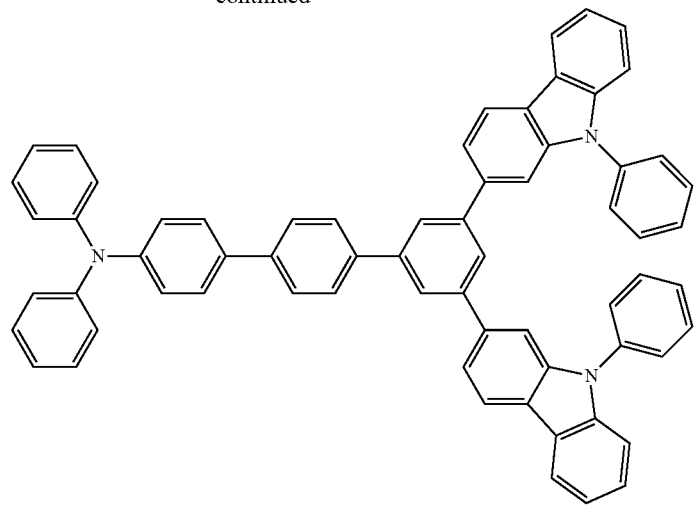

27

(1) Synthesis of Intermediate 27-1

Intermediate 27-1 (3.9 g, yield of 64%) was obtained in the same manner as in the synthesis of Intermediate 1-2, except that 3 g of 1,3,5-tribromobenzene and 7 g of 9-phenyl-2-(4,4,5,5-tetramethyl-1,3,2-dioxaborolane-2-yl)-9H-carbazole were used.

LC/MS cal'd: 638.14. found: 638.15.

(2) Synthesis of Intermediate 27-2

Intermediate 27-2 (3.4 g, yield of 74%) was obtained in the same manner as in the synthesis of Intermediate 1-2, except that 3.9 g of Intermediate 27-1 and 1.3 g of 4-bromobenzene boronic acid were used.

LC/MS cal'd: 714.17. found: 714.17.

(3) Synthesis of Compound 27.

Compound 27 (3.2 g, yield of 78%) was obtained in the same manner as in the synthesis of Intermediate 1-2, except that Intermediate 27-2 and 3.4 g of Intermediate 2-2 was used. $^1$H NMR (400 MHz, CDCl$_3$) δ 8.15-8.12(m, 3H), 7.94(m, 2H), 7.85(m, 2H), 7.79(m, 4H), 7.66-7.49(m, 10H), 7.45-7.36(m, 6H), 7.31-7.28(m, 4H), 7.20(m, 2H), 7.06(m, 4H), 6.83(m, 2H), 6.65(m, 2H), 6.15(m, 4H). LC/MS cal'd: 879.36. found: 879.37.

Synthesis of Compound 28

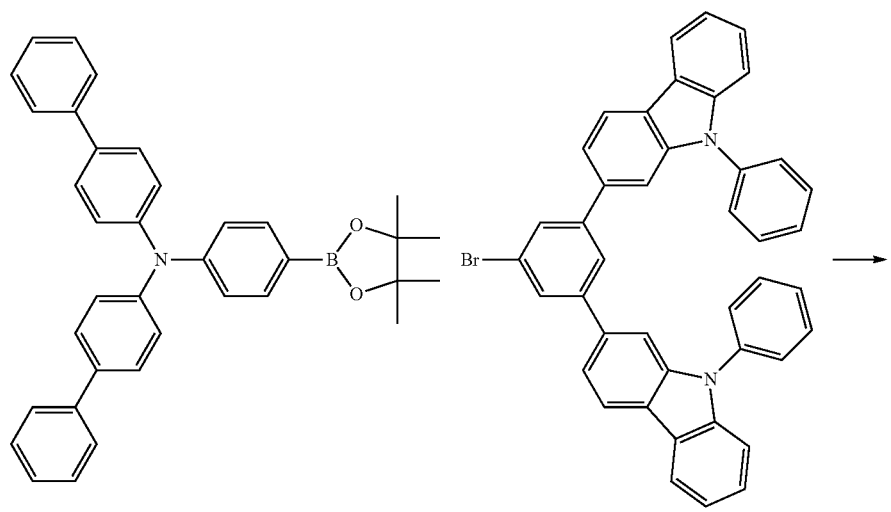

3-2    27-1

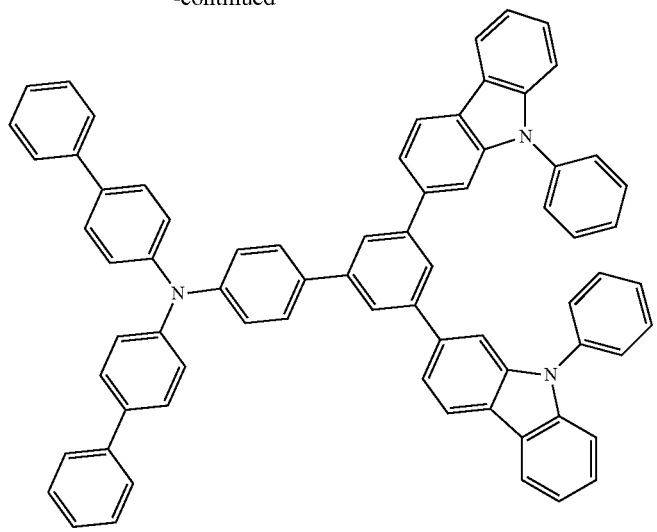
28
Compound 28 (4.7 g, yield of 86%) was obtained in the same manner as in the synthesis of Compound 3, except that 3 g of Intermediate 3-2 and 3.7 g of Intermediate 27-1 were used. $^1$H NMR (400 MHz, CDCl$_3$) δ 8.15-8.12(m, 3H), 7.94(m, 2H), 7.85(m, 2H), 7.75(d, 2H), 7.56-7.53(m, 4H), 7.51-7.40(m, 20H), 7.37(m, 4H), 7.31-7.28(m, 4H), 7.20(m, 2H), 6.83(m, 4H), 6.65(m, 2H). LC/MS cal'd: 955.39. found: 955.43.
Synthesis of Compound 47
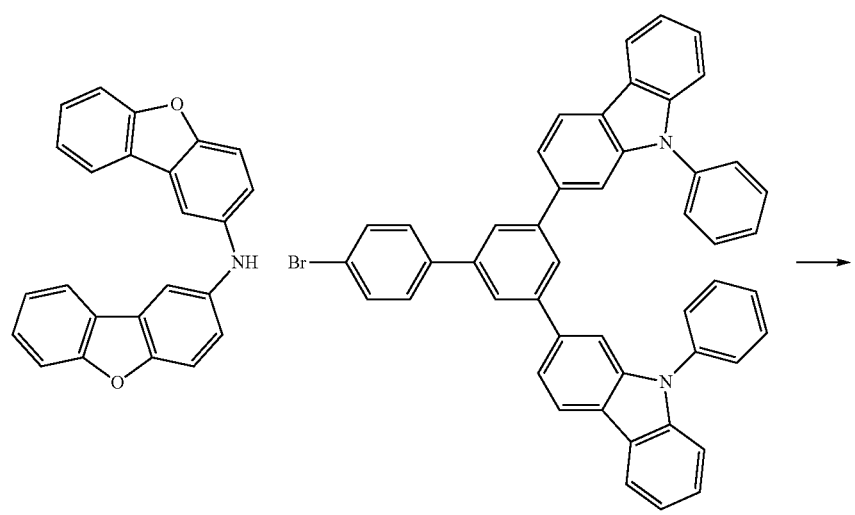
27-2

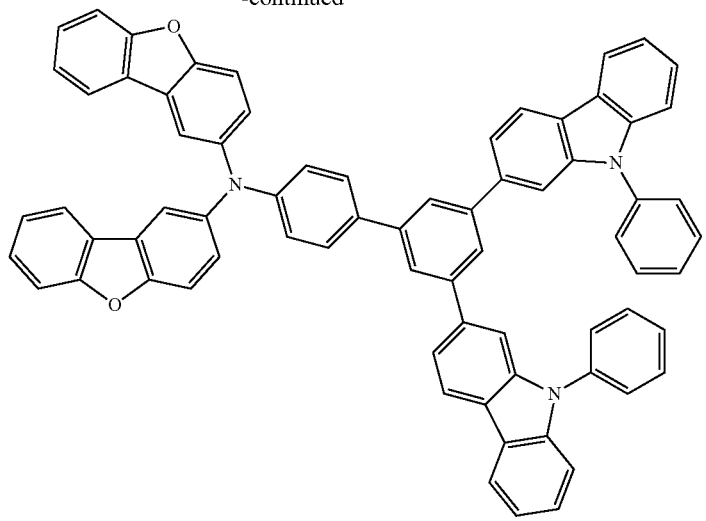
47
Compound 47 (3.3 g, yield of 81%) was obtained in the same manner as in the synthesis of Compound 22, except that 3 g of Intermediate 27-2 was used. $^1$H NMR (400 MHz, CDCl$_3$) δ 8.16-8.12(m, 3H), 7.94(m, 2H), 7.85(m, 2H), 7.82(m, 2H), 7.75(d, 2H), 7.53-7.47(m, 14H), 7.43-7.35(m, 10H), 7.32-7.29(m, 4H), 7.20(m, 2H), 6.97(dd, 2H), 6.78(m, 2H). LC/MS cal'd: 983.35. found: 983.36.
Synthesis of Compound 131
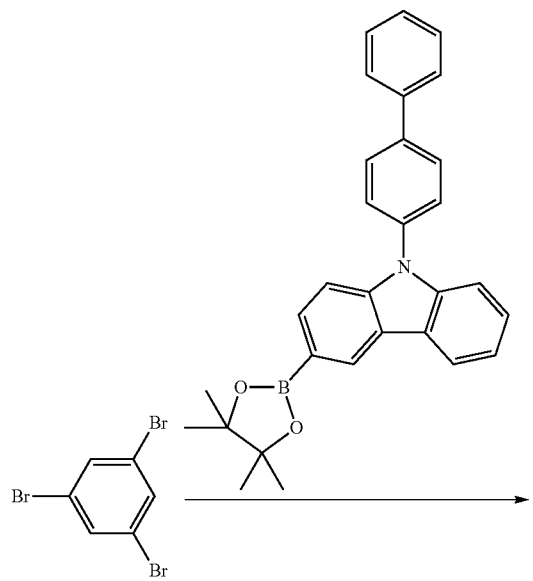

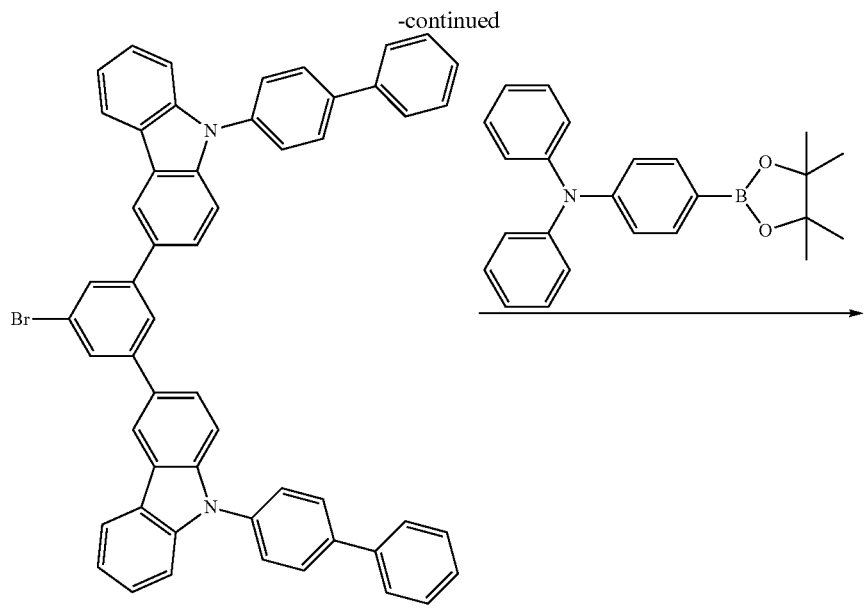

131-1

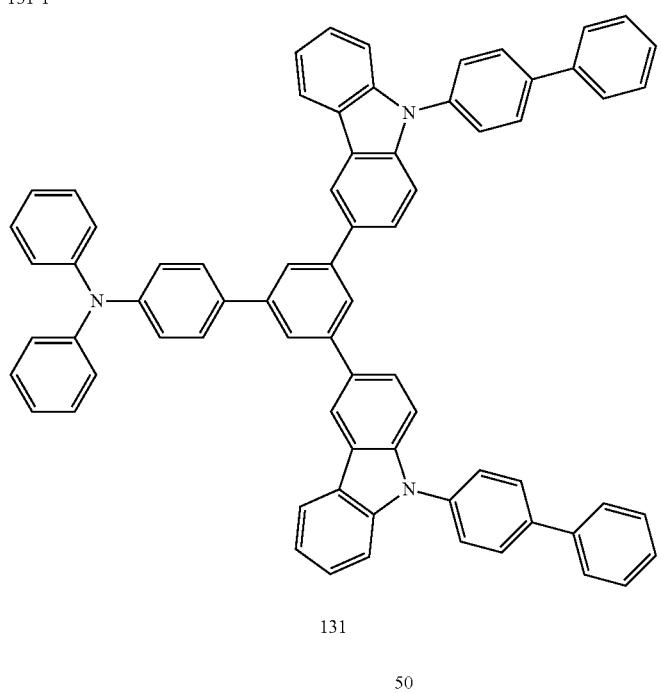

131

(1) Synthesis of Intermediate 131-1

Intermediate 131-1 (4.7 g, yield of 67%) was obtained in the same manner as in the synthesis of Intermediate 2-1, except that 4 g of 9-([1,1'-biphenyl]-4-yl)-3-(4,4,5,5-tetramethyl-1,3,2-dioxaborolane-2-yl)-9H-carbazole was used.

LC/MS cal'd: 790.20. found: 790.21.

(2) Synthesis of Compound 131

Compound 131 (4.7 g, yield of 83%) was obtained in the same manned as in the synthesis of Compound 2, except that 4.7 g of Intermediate 131-1 was used. $^1$H NMR (400 MHz, CDCl$_3$) δ 8.23(m, 2H), 8.11(m, 2H), 7.94(t, 1H), 7.82(d, 2H), 7.74-7.70(m, 4H), 7.57-7.53(m, 4H), 7.48-7.40(m, 14H), 7.37-7.35(m, 4H), 7.29(m, 2H), 7.19(m, 2H), 7.06(m, 4H), 6.87(m, 2H), 6.65(m, 2H), 6.15(m, 4H). LC/MS cal'd: 955.39. found: 955.42.

Comparative Example 1

A glass substrate (produce of Corning Incorporated) with ITO anode (15 Ω/cm$^2$ 1,200 Å) was cut to a size of 50 mm×50 mm×0.7 mm, and then, ultrasonically cleaned with isopropyl alcohol, and pure water for 5 minutes each, and then exposed to ultraviolet (UV) light for 30 minutes and then ozone. Then, the glass substrate was loaded into a vacuum deposition apparatus.

2-TNATA was deposited on the glass substrate to form a hole injection layer having a thickness of 600 Å, and then 4,4'-bis[N-(1-naphthyl)-N-phenylamino group]biphenyl (hereinafter, referred to as NPB), which is a hole transport material, was deposited on the hole injection layer to form a hole transport layer having a thickness of 300 Å.

9,10-di(naphthalen-2-yl)anthracene (hereinafter, referred to as DNA) as a blue fluorescent host and 4,4'-bis[2-(4-(N, N-diphenylamino)phenyl)vinyl]biphenyl (hereinafter, referred to as DPAVBi) as a blue fluorescent dopant, were co-deposited on the hole transport layer at a weight ratio of 98:2 to form an emission layer having a thickness of 300 Å.

Subsequently, Alq3 was deposited on the emission layer to form an electron transport layer having a thickness of 300 Å, and then alkali metal halide LiF was deposited on the electron transport layer to form an electron injection layer

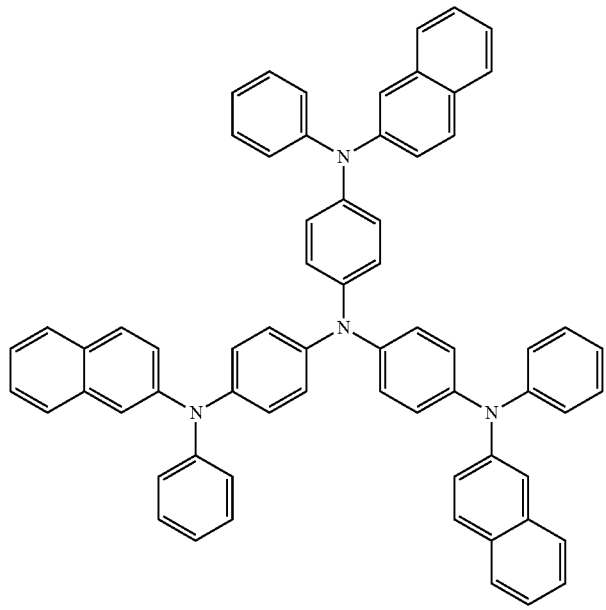
2-TNATA

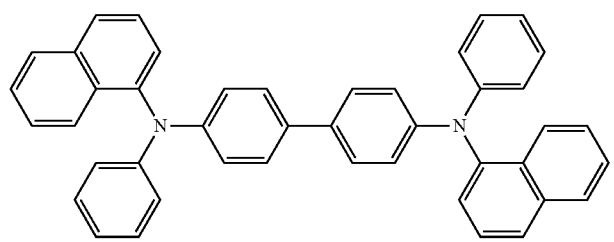
NPB

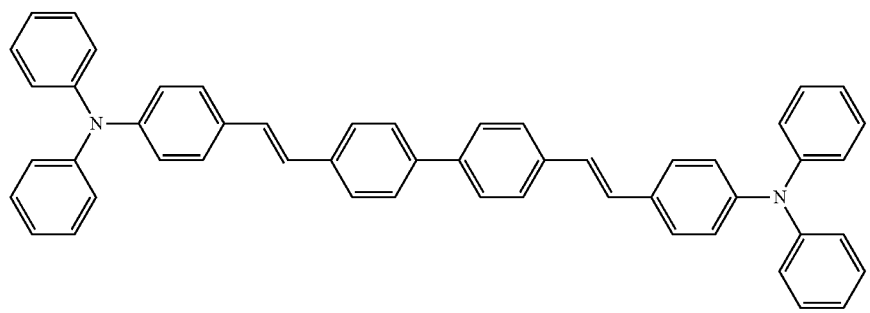
DPAVBi

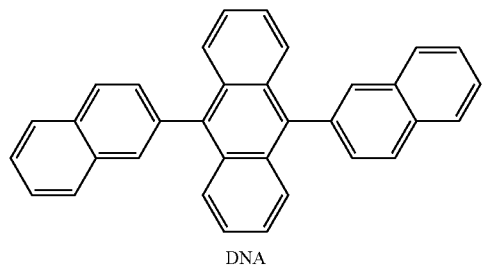
DNA having a thickness of 10 Å. Al (cathode electrode) was vacuum deposited to have a thickness of 3000 Å so that LiF/Al electrode was formed to manufacture an an organic electroluminescence device (hereinafter, referred to as organic EL device).

Comparative Example 2

An organic EL device was manufactured in the same manner as in Comparative Example 1, except that in forming the hole transport layer, Compound A was used instead of NPB.

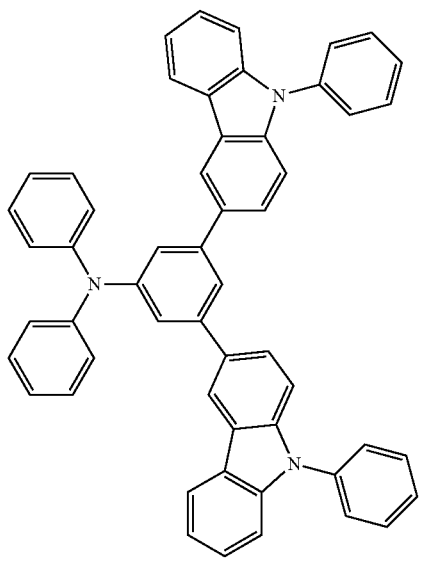

A

Example 1

An organic EL device was manufactured in the same manner as in Comparative Example 1, except that in forming the hole transport layer, Compound 1 was used instead of NPB.

Example 2

An organic EL device was manufactured in the same manner as in Comparative Example 1, except that in forming the hole transport layer, Compound 2 was used instead of NPB.

Example 3

An organic EL device was manufactured in the same manner as in Comparative Example 1, except that in forming the hole transport layer, Compound 3 was used instead of NPB.

Example 4

An organic EL device was manufactured in the same manner as in Comparative Example 1, except that in forming the hole transport layer, Compound 7 was used instead of NPB.

Example 5

An organic EL device was manufactured in the same manner as in Comparative Example 1, except that in forming the hole transport layer, Compound 22 was used instead of NPB.

Example 6

An organic EL device was manufactured in the same manner as in Comparative Example 1, except that in forming the hole transport layer, Compound 26 was used instead of NPB.

Example 7

An organic EL device was manufactured in the same manner as in Comparative Example 1, except that in forming the hole transport layer, Compound 27 was used instead of NPB.

Example 8

An organic EL device was manufactured in the same manner as in Comparative Example 1, except that in forming the hole transport layer, Compound 28 was used instead of NPB.

Example 9

An organic EL device was manufactured in the same manner as in Comparative Example 1, except that in forming the hole transport layer, Compound 47 was used instead of NPB.

Example 10

An organic EL device was manufactured in the same manner as in Comparative Example 1, except that in forming the hole transport layer, Compound 131 was used instead of NPB.

When compounds represented by Formula 1 were used as hole transport materials, an organic EL device had lower driving voltage, excellent I-V-L characteristics with better efficiency, and a longer lifetime than when a know material A and NBP were used as hole transport materials. Each result of the Examples and Comparative Examples, and a respective lifetime are shown in Table 1 below.

By selecting a suitable linker, a HOMO level of a compound represented by Formula 1 may be adjusted. Accordingly, an organic light-emitting device including the compound represented by Formula 1 may facilitate a flow of holes, and thus efficiency and a lifetime thereof may be increased.

TABLE 1

|  | hole transport material | Driving voltage (V) | Current Density (mA/cm$^2$) | brightness (cd/m$^2$) | efficiency (cd/A) | emission color | half lifetime (hr @100 mA/cm$^2$) |
| --- | --- | --- | --- | --- | --- | --- | --- |
| Comparative Example 1 | NPB | 7.01 | 50 | 2645 | 5.29 | blue | 258 |
| Comparative Example 2 | A | 6.16 | 50 | 3010 | 6.02 | blue | 317 |
| Example 1 | Compound 1 | 5.43 | 50 | 3460 | 6.92 | blue | 386 |
| Example 2 | Compound 2 | 5.34 | 50 | 3505 | 7.01 | blue | 368 |
| Example 3 | Compound 3 | 5.20 | 50 | 3435 | 6.87 | blue | 392 |
| Example 4 | Compound7 | 5.21 | 50 | 3440 | 6.88 | blue | 380 |
| Example 5 | Compound22 | 5.10 | 50 | 3385 | 6.76 | blue | 385 |
| Example 6 | Compound 26 | 5.40 | 50 | 3385 | 6.77 | blue | 388 |
| Example 7 | Compound 27 | 5.67 | 50 | 3375 | 6.75 | blue | 401 |
| Example 8 | Compound 28 | 5.68 | 50 | 3410 | 6.82 | blue | 392 |
| Example 9 | Compound47 | 5.57 | 50 | 3385 | 6.77 | blue | 368 |
| Example 10 | Compound131 | 5.42 | 50 | 3335 | 6.67 | blue | 382 |

As described above, according to the one or more of the above exemplary embodiments, a compound represented by Formula 1 may efficiently adjust a band gap by using a linker and may be effectively used as a hole transport material. In this regard, an organic light-emitting device with high efficiency, low driving voltage, high brightness, and long lifespan may be manufactured.

The embodiments may provide materials having excellent electric stability, electron transport ability, and/or light-emission ability; higher glass transition temperature than some organic small molecular materials; and that help reduce and/or prevent crystallization.

The embodiments may provide a compound having excellent electric characteristics, electron transport ability, and light-emission ability, and high glass transition temperature; preventing crystallization; and that is used as a hole transport material.

The embodiments may provide an organic light-emitting device including the compound and having high efficiency, low driving voltage, high brightness, and a long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A compound represented by Formula 1 below:

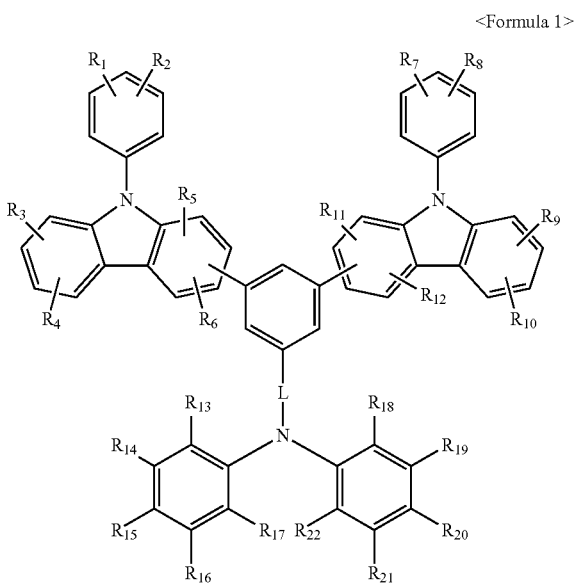

<Formula 1> wherein in Formula 1,
$R_1$ to $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

L is selected from a substituted or unsubstituted $C_3$-$C_{10}$ cycloalkylene group; a substituted or unsubstituted $C_2$-$C_{10}$ heterocycloalkylene group; a substituted or unsubstituted $C_3$-$C_{10}$ cycloalkenylene group; a substituted or unsubstituted $C_2$-$C_{10}$ heterocycloalkenylene group; a substituted or unsubstituted $C_6$-$C_{60}$ arylene group; a substituted or unsubstituted $C_2$-$C_{60}$ heteroarylene group; a substituted or unsubstituted divalent non-aromatic condensed polycyclic group; a substituted or unsubstituted divalent non-aromatic condensed heteropolycyclic group; a substituent comprising two or more groups selected from the $C_3$-$C_{10}$ cycloalkylene group, the $C_2$-$C_{10}$ heterocycloalkylene group, the $C_3$-$C_{10}$ cycloalkenylene group, the $C_2$-$C_{10}$ heterocycloalkenylene group, the $C_6$-$C_{60}$ arylene group, the $C_2$-$C_{60}$ heteroarylene group, the divalent non-aromatic condensed polycyclic group, and the divalent non-aromatic condensed heteropolycyclic group;

adjacent substituents from among $R_1$ to $R_{22}$ are separate or are connected to form a ring;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, substituted monovalent non-aromatic condensed heteropolycyclic group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted a divalent non-aromatic condensed polycyclic group and substituted a divalent non-aromatic condensed heteropolycyclic group, is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$) and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$) and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

2. The compound as claimed in claim 1, wherein in Formula 1, $R_1$ to $R_{22}$ are each independently selected from a hydrogen, a deuterium, —F, —Cl, —Br, —I, a substituted or unsubstituted $C_2$-$C_{60}$ alkenyl group, and a substituted or unsubstituted $C_6$-$C_{60}$ aryl group.

3. The compound as claimed in claim 1, wherein in Formula 1, L is selected from a substituted or unsubstituted $C_6$-$C_{60}$ arylene group; a substituted or unsubstituted $C_2$-$C_{60}$ heteroarylene group; or a substituent that includes two or more groups selected from the $C_6$-$C_{60}$ arylene group and the $C_2$-$C_{60}$ heteroarylene group.

4. The compound as claimed in claim 1, wherein
in Formula 1, $R_1$ to $R_{12}$ are each independently a hydrogen, a deuterium, —F, —Cl, —Br, —I, a substituted or unsubstituted $C_2$-$C_{10}$ alkenyl group, or a group represented Formula 2a below:

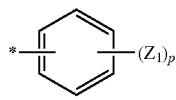

2a wherein, in Formula 2a, $Z_1$ is a hydrogen, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, halogen group, a cyano group, a nitro group, a hydroxyl group, or a carboxyl group;

p is an integer selected from 1 to 5; and

* denotes a bonding site to a neighboring atom.

5. The compound as claimed in claim 1, wherein in Formula 1, $R_1$ to $R_{12}$ are each independently a hydrogen or a deuterium.

6. The compound of claim 1, wherein in Formula 1, $R_{13}$ to $R_{22}$ are each independently a hydrogen, a deuterium, —F, —Cl, —Br, —I, a substituted or unsubstituted $C_2$-$C_{10}$ alkenyl group, or a group represented by one of Formulae 3a to 3c below:

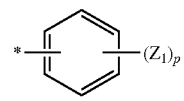

3a

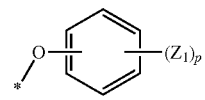

3b

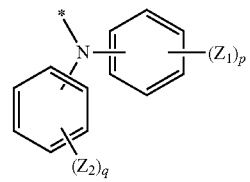

3c wherein in Formulae 3a to 3c, $Z_1$ and $Z_2$ are each independently a hydrogen, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, or a carboxyl group;

p and q are each independently an integer selected from 1 to 5; and

* denotes a bonding site to a neighboring atom.

7. The compound as claimed in claim 1, wherein, in Formula 1, L is a group represented by one of Formulae 4a to 4f below:

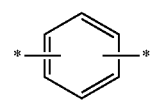

4a

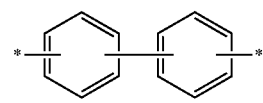

4b

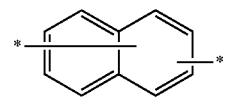

4c

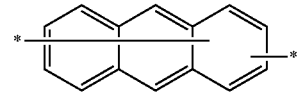

4d

-continued

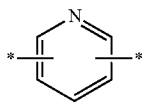
4e

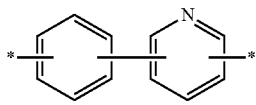
4f wherein, in Formulae 4a to 4f, * denotes a bonding site to a neighboring atom.

8. The compound as claimed in claim 1, wherein the compound represented by Formula 1 is represented by Formula 2 below:

<Formula 2>

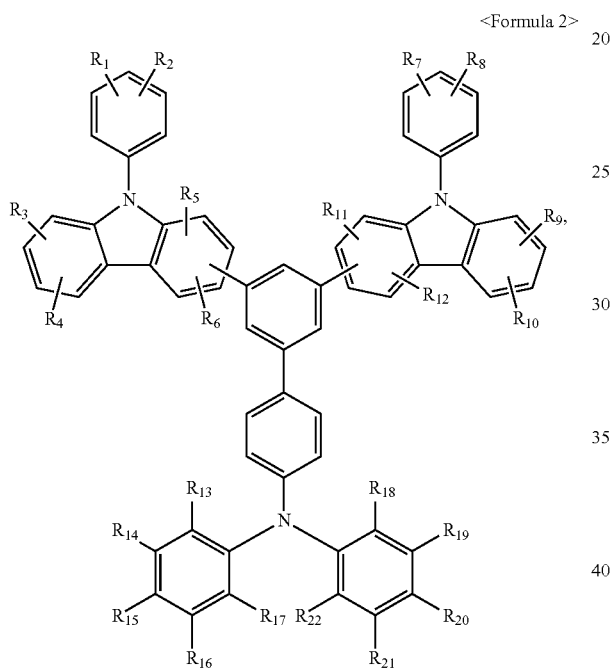

wherein, in Formula 2, $R_1$ to $R_{22}$ are the same as those defined with respect to Formula 1.

9. The compound as claimed in claim 1, wherein the compound represented by Formula 1 is represented by Formula 3 below:

<Formula 3>

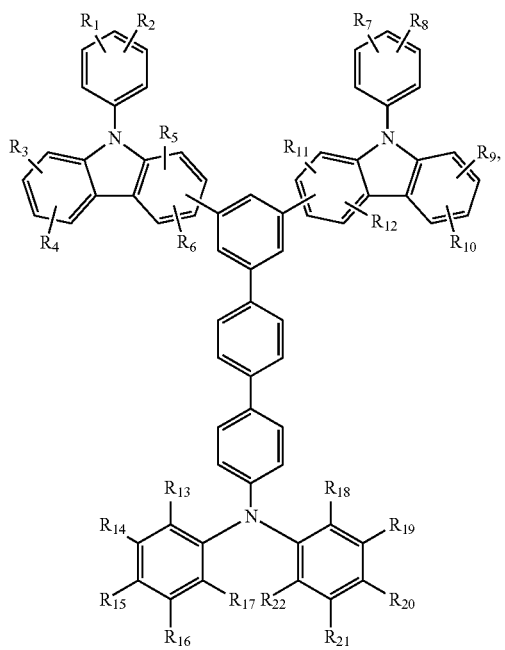

wherein, in Formula 3, $R_1$ to $R_{22}$ are the same as those defined with respect to Formula 1.

10. The compound as claimed in claim 1, wherein the compound represented by Formula 1 is one of the following compounds:

1

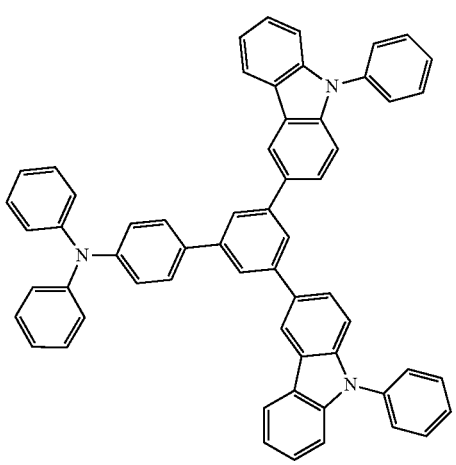

2

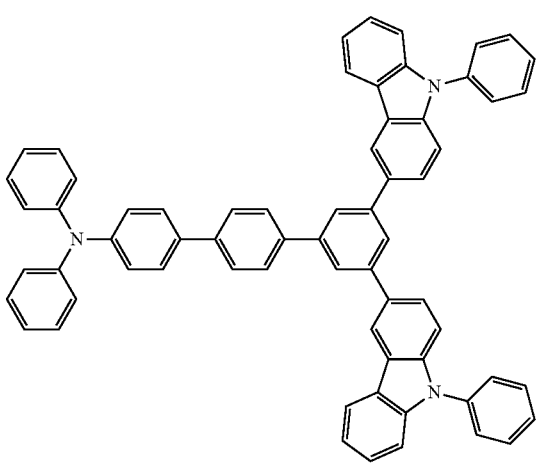

-continued
3
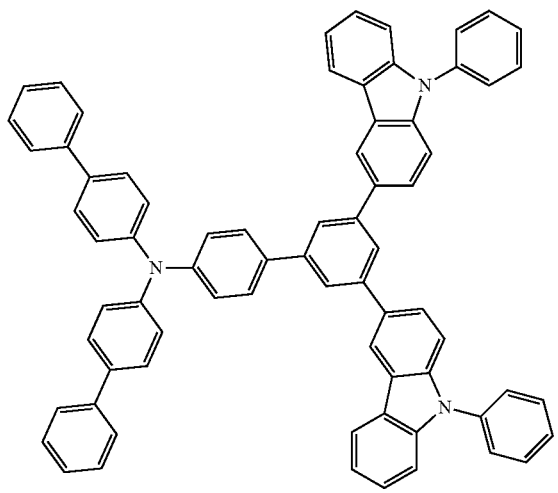
4
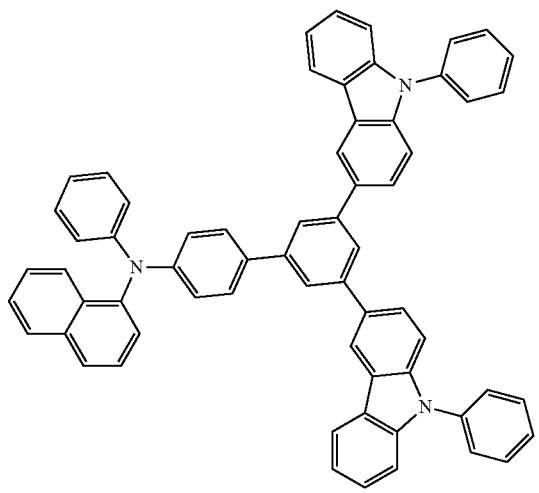
5
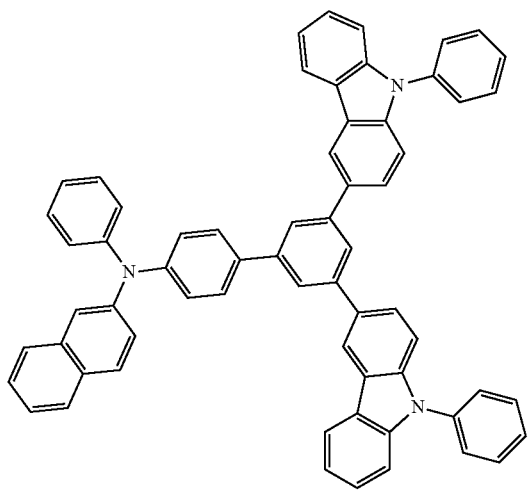
6
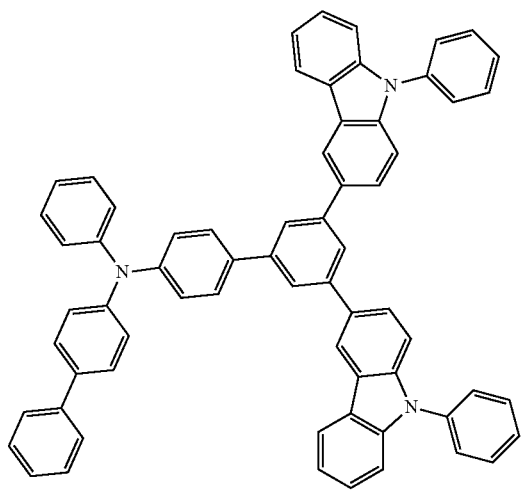
7
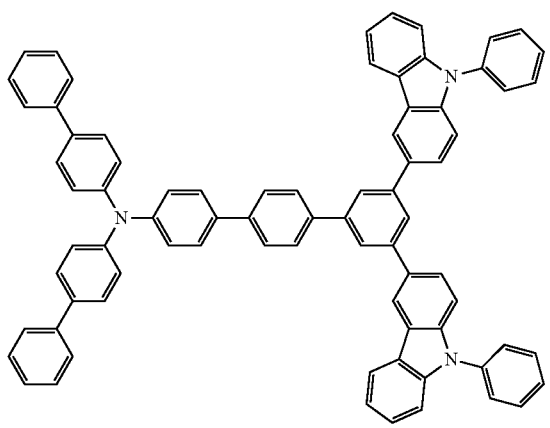
8
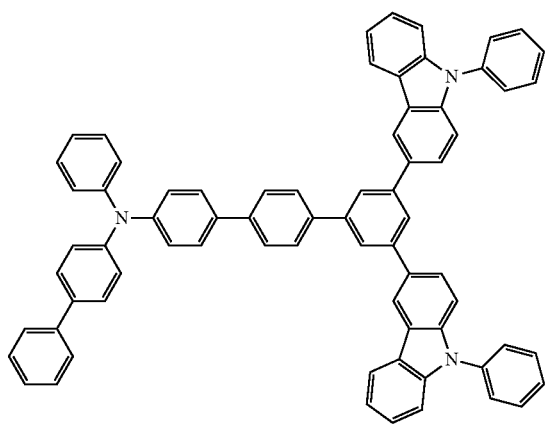

-continued
9
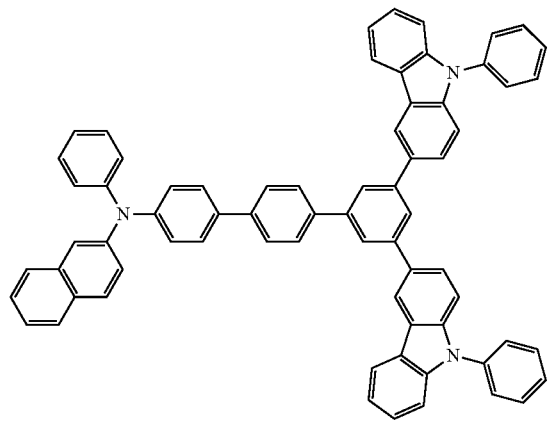
10
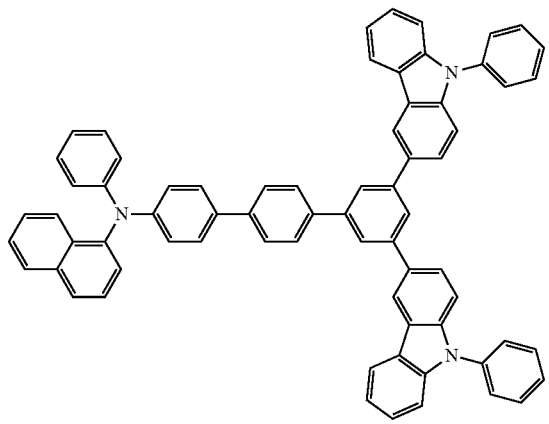
11
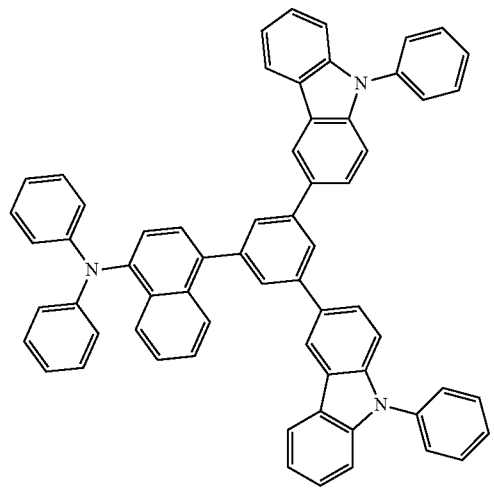
12
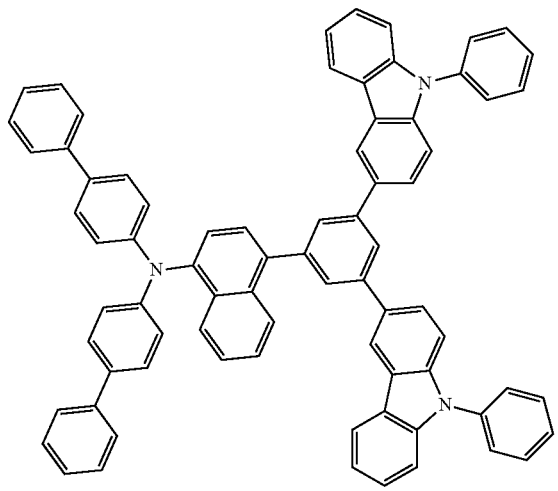
13
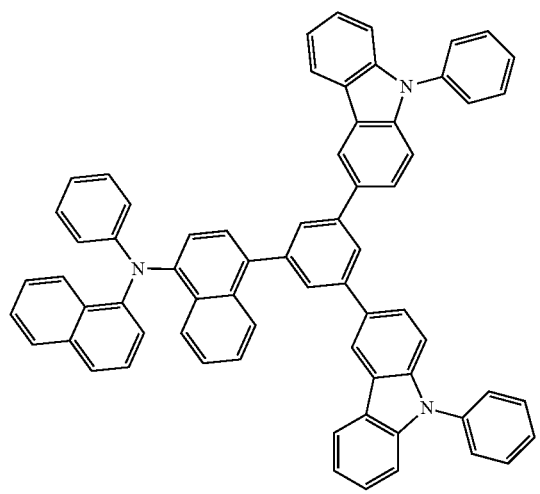
14
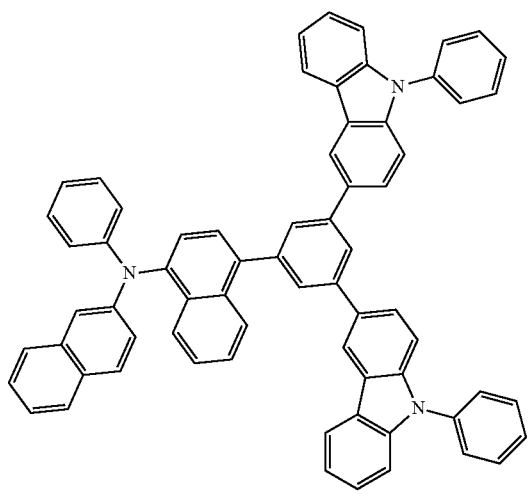

-continued
15
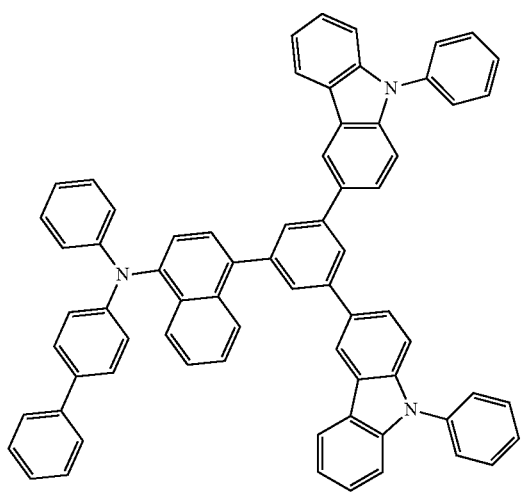
16
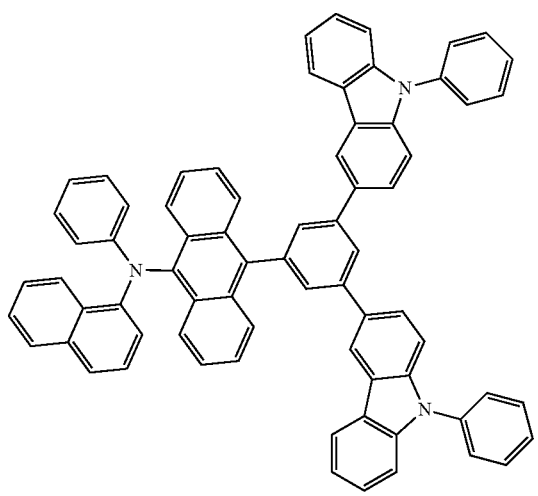
17
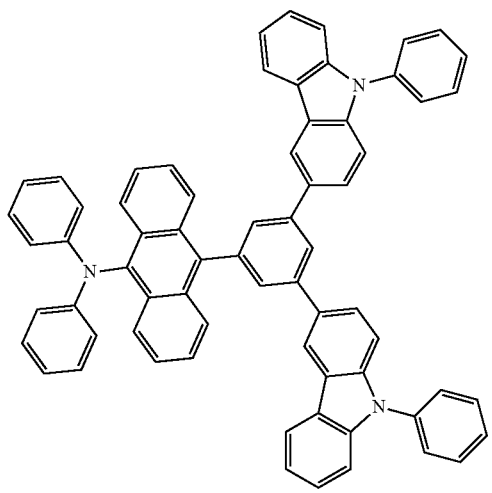
18
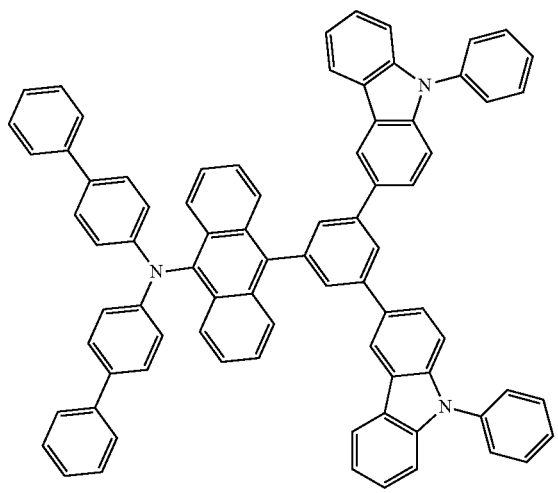
19
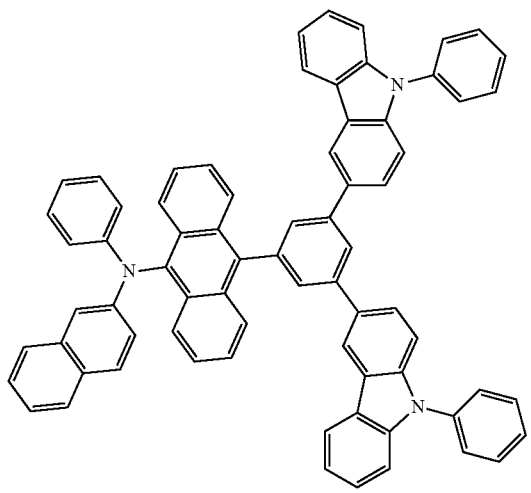
20
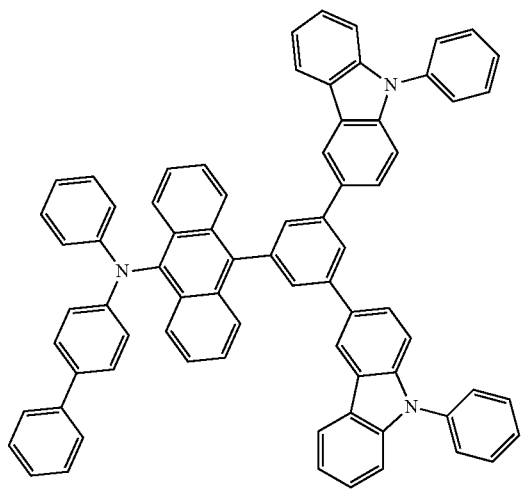

-continued
21
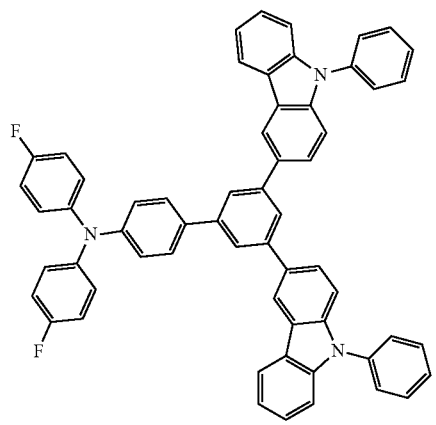
22
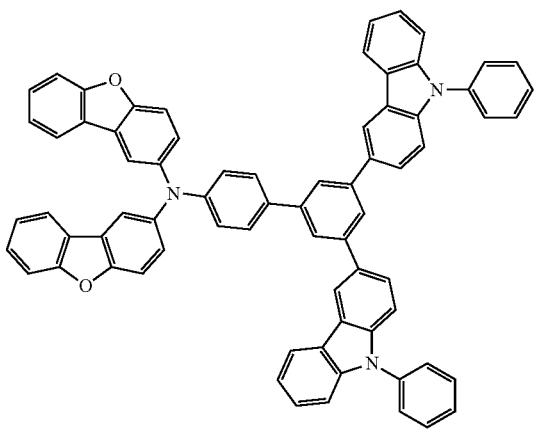
23
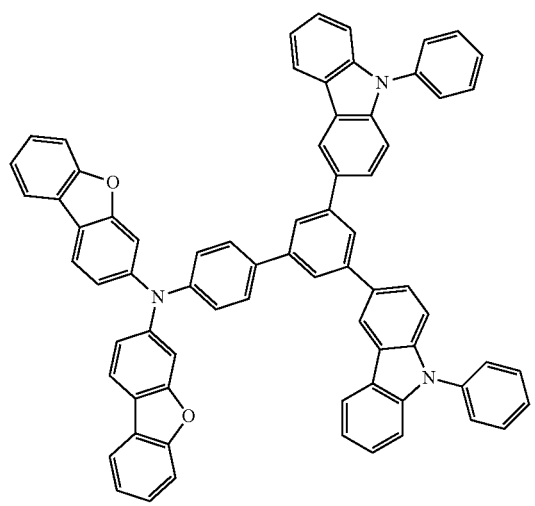
24
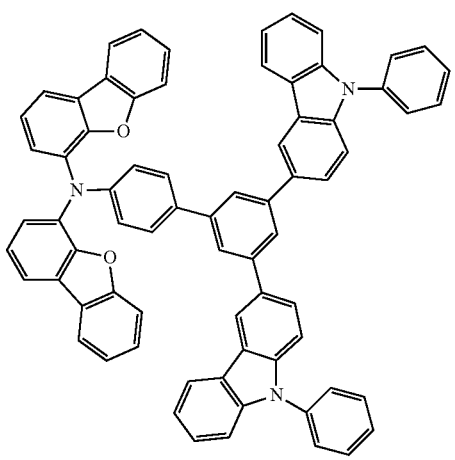
25
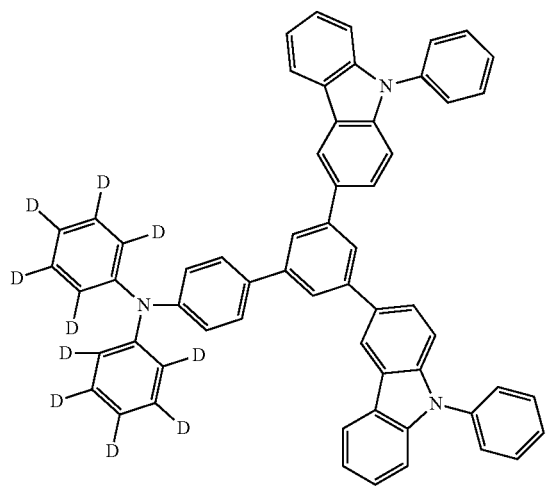
26
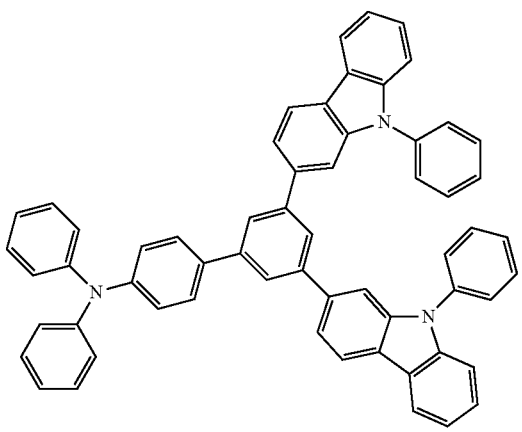

27 28
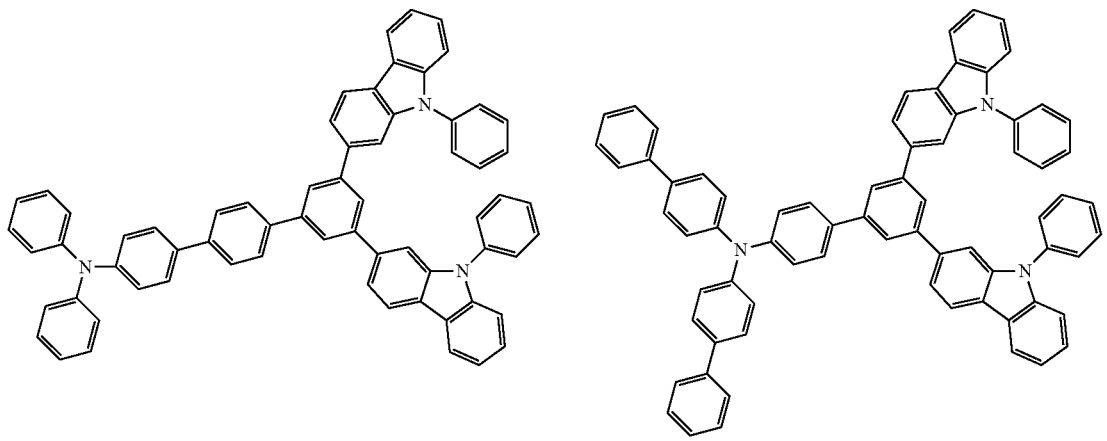
29 31
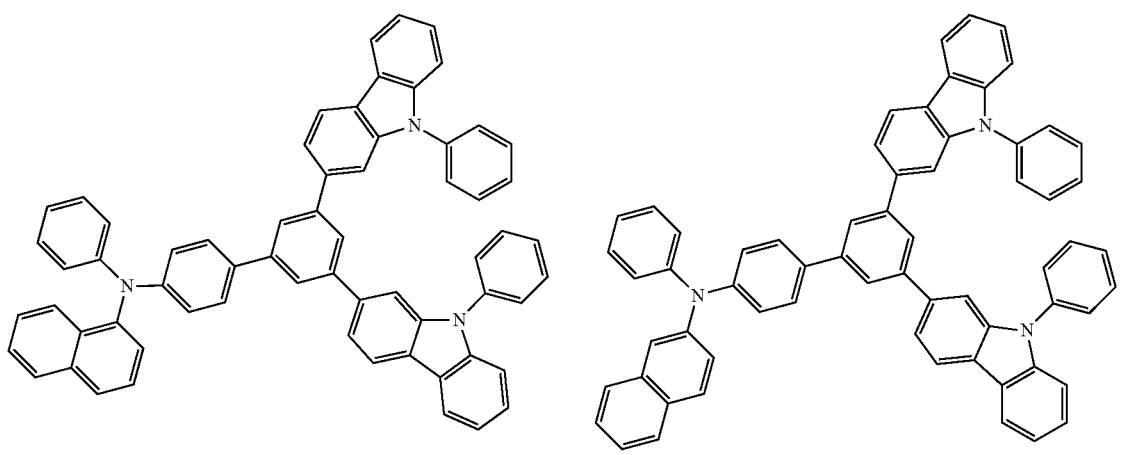
31
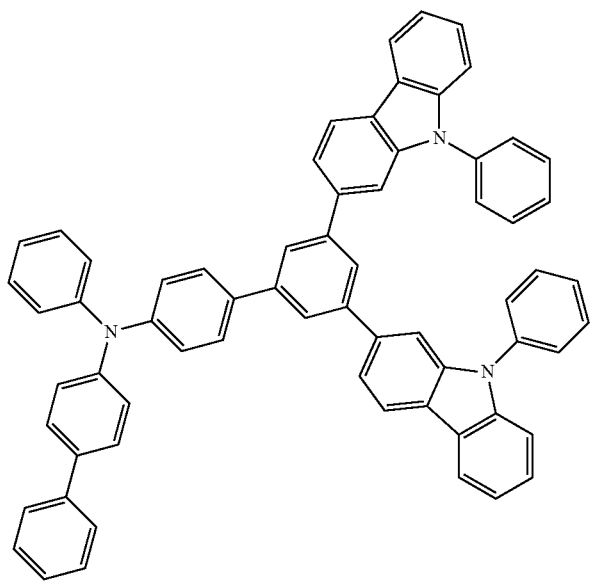

32
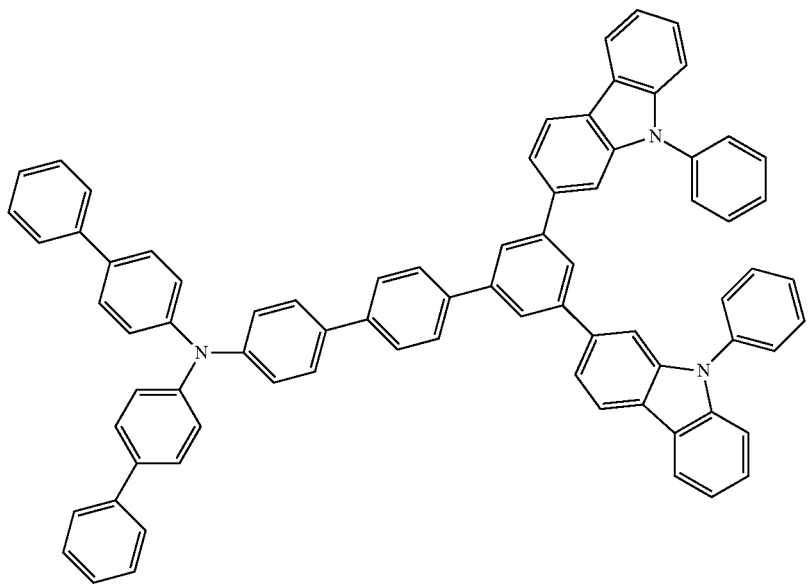
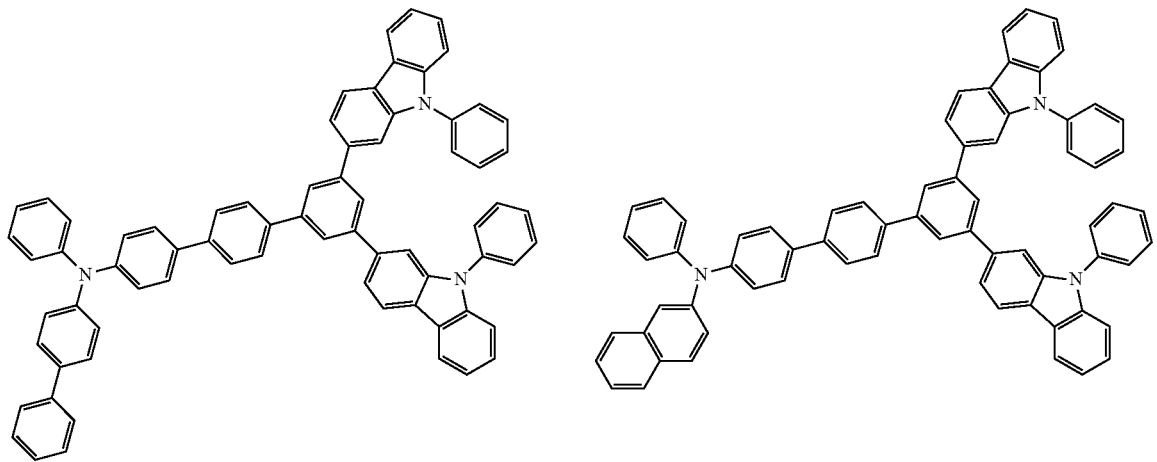

35
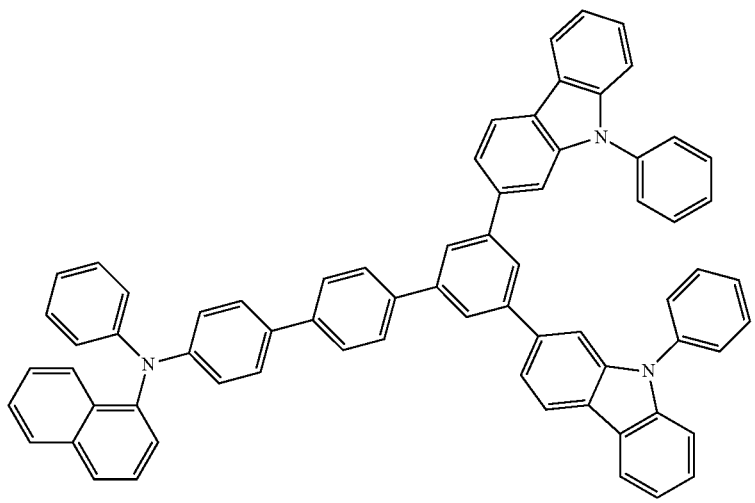
36
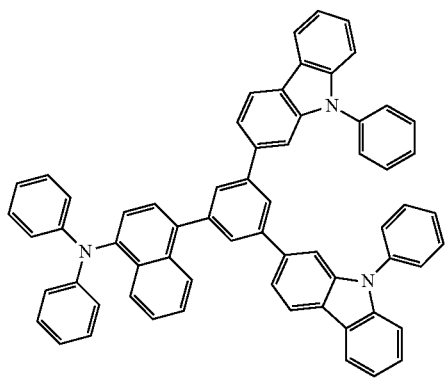
37
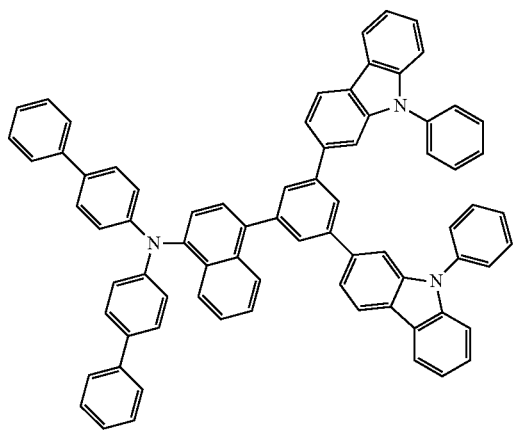
38
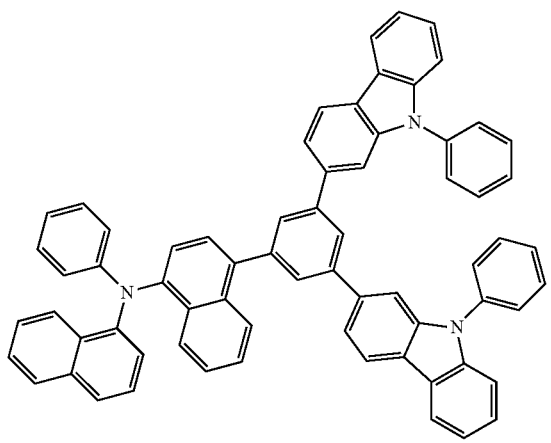
39
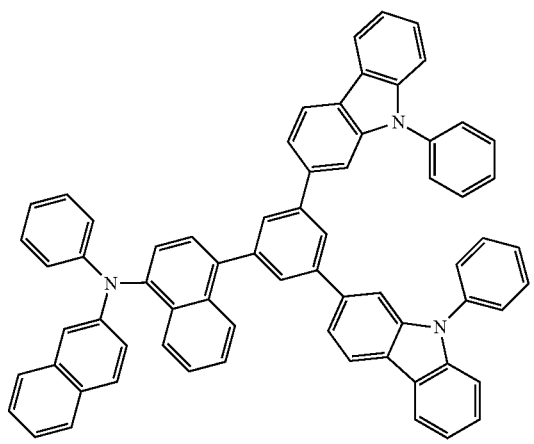

-continued
40
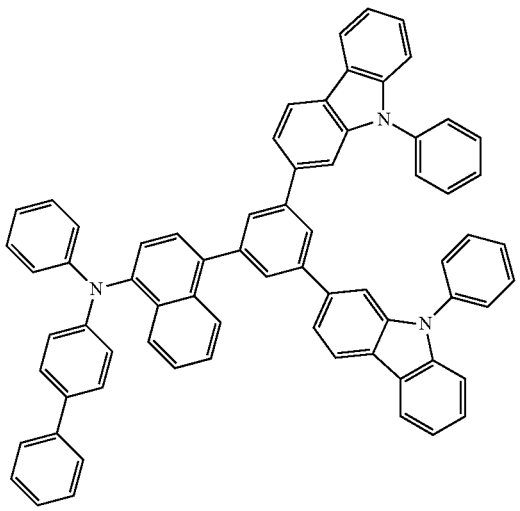
41
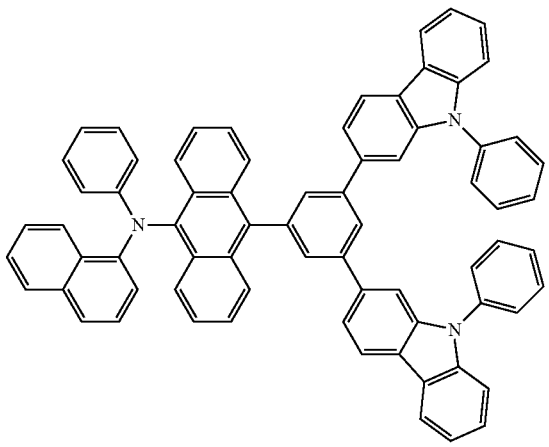
42
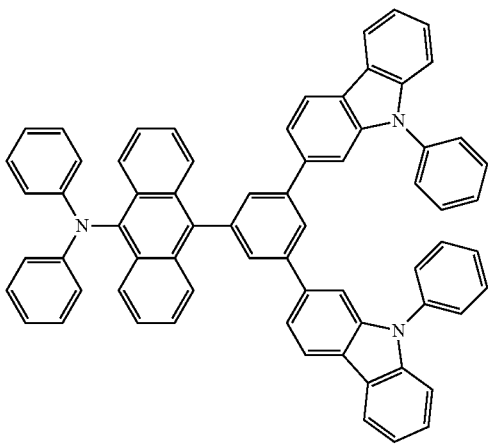
43
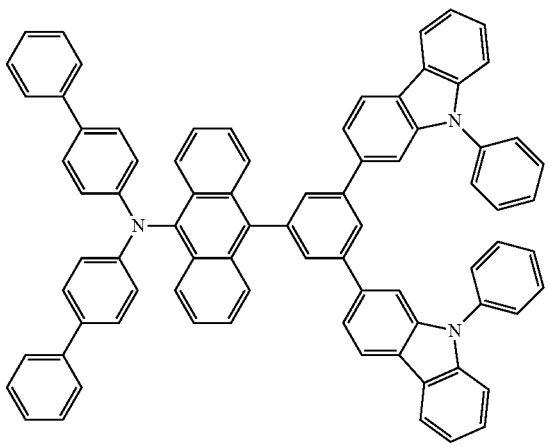
44
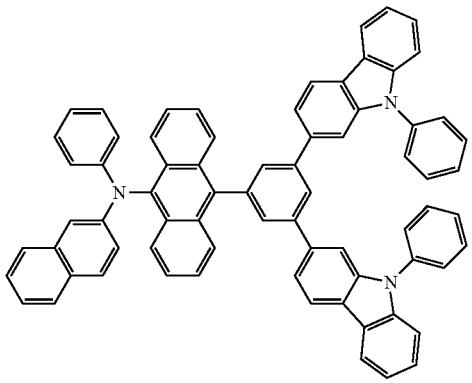
45
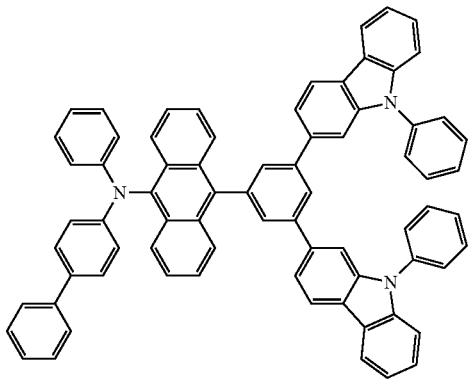

46
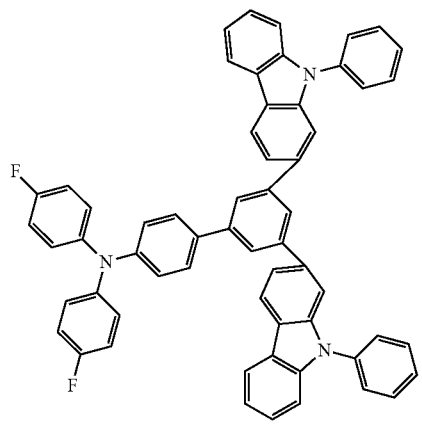
47
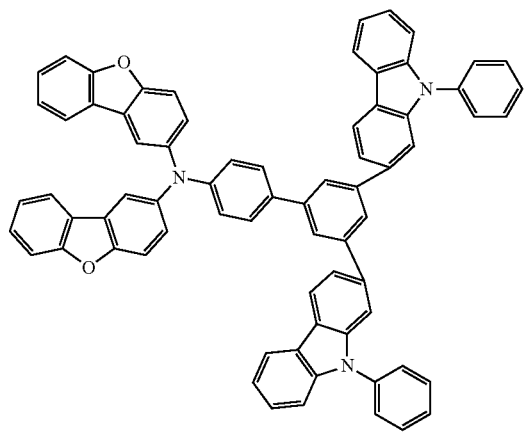
48
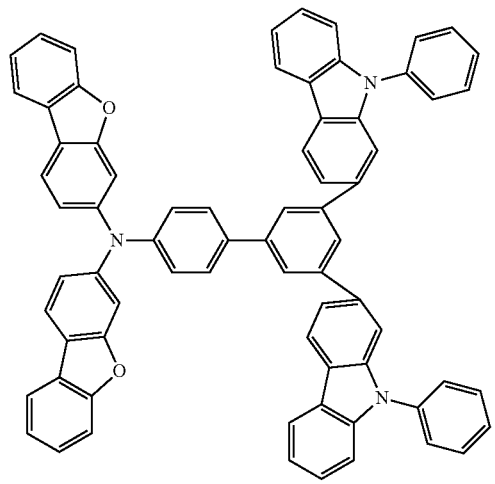
49
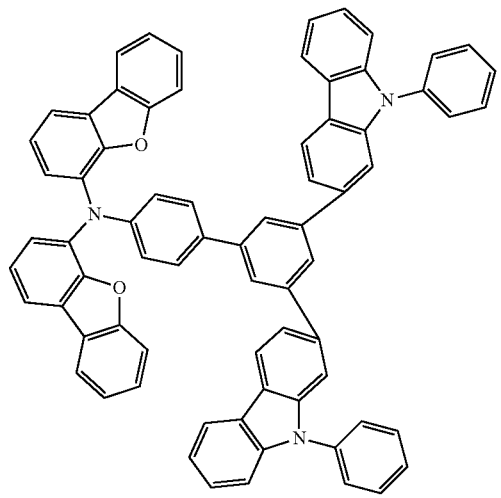
50
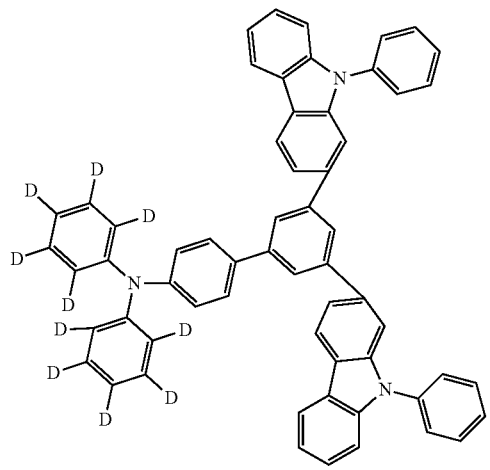
57
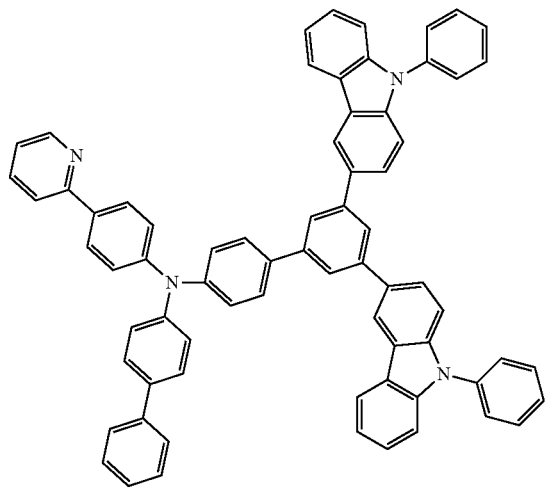

-continued
58
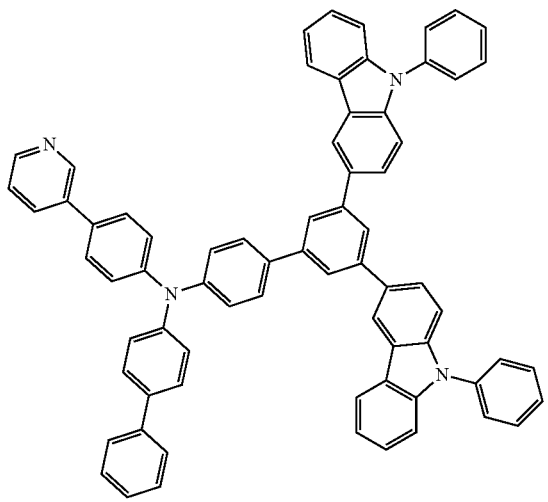
59
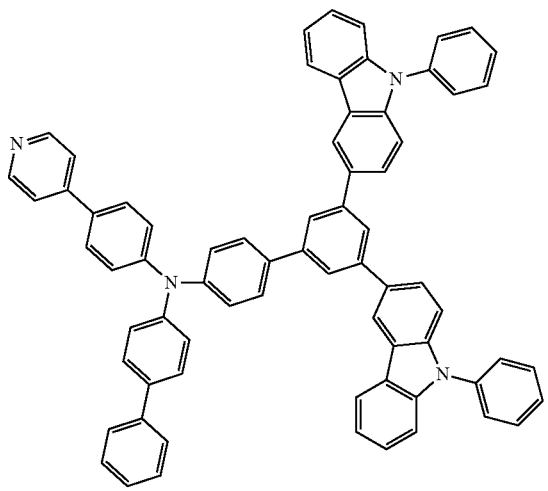
60
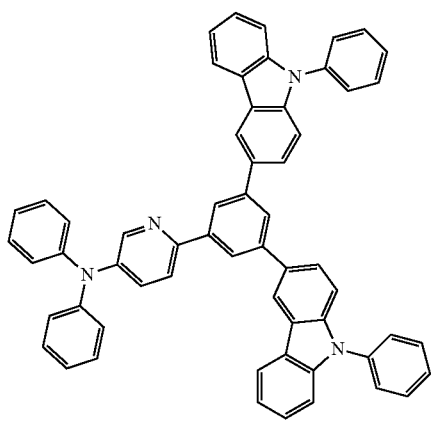
61
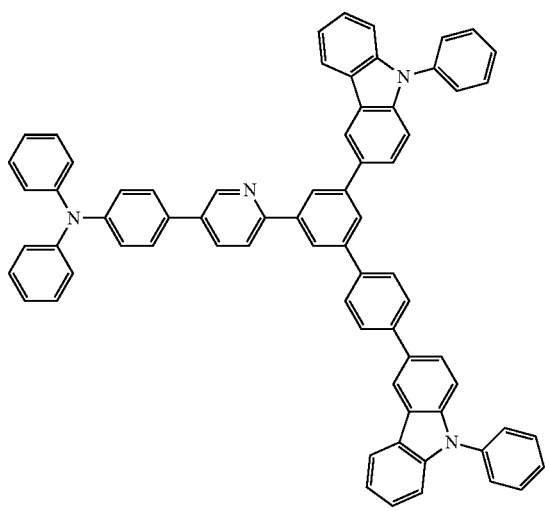
62
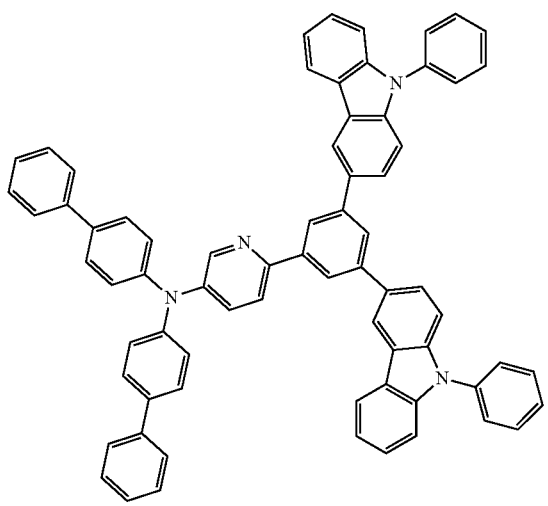
63
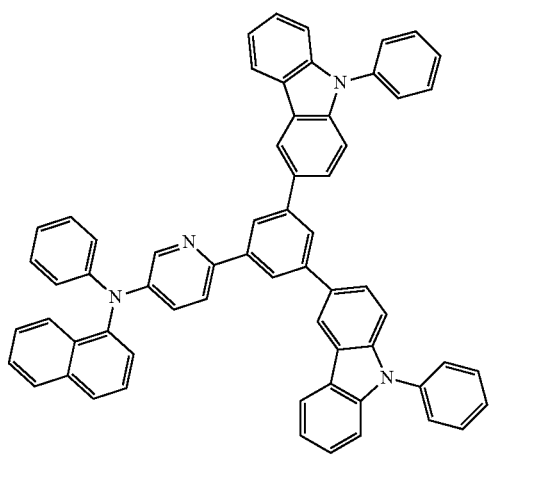

-continued
64
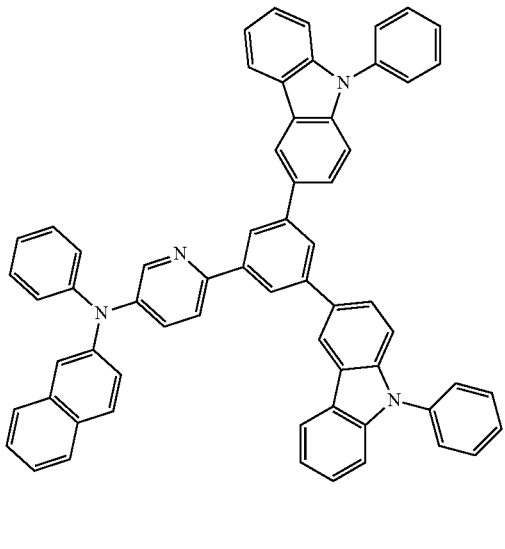
65
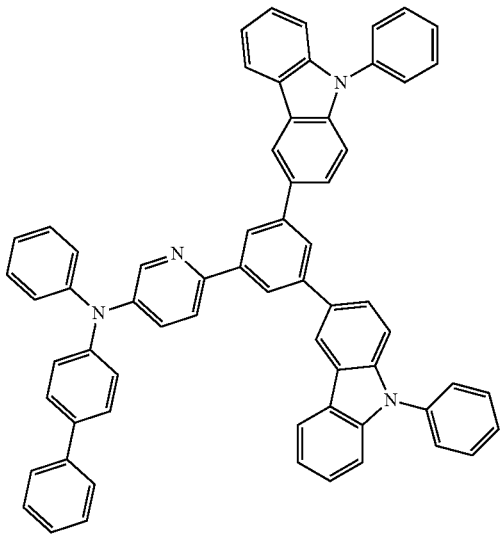
66
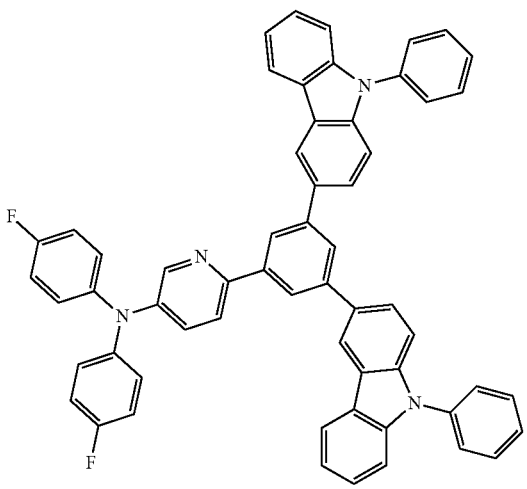
67
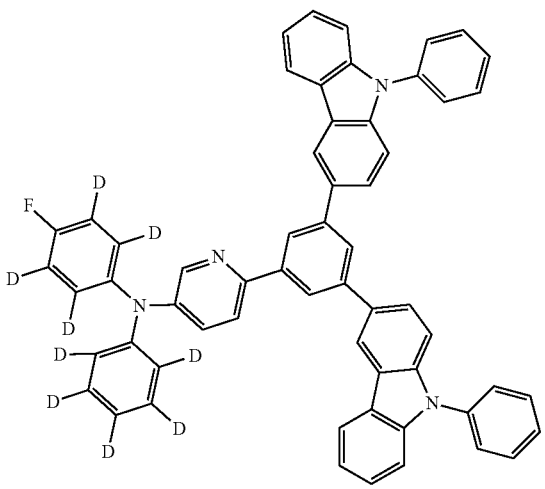
68
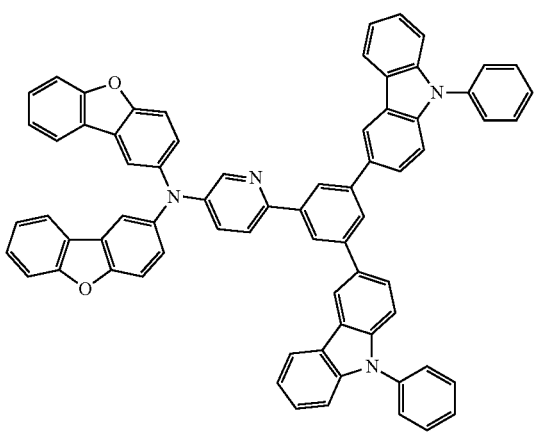
69
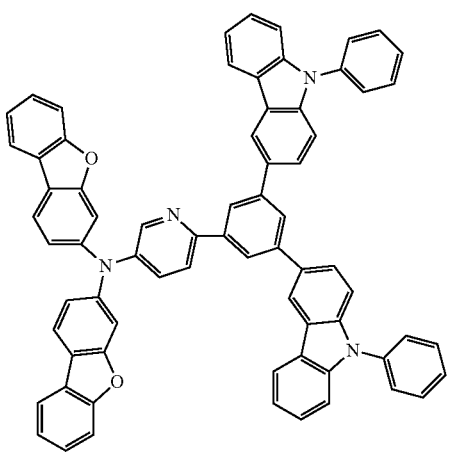

-continued
70
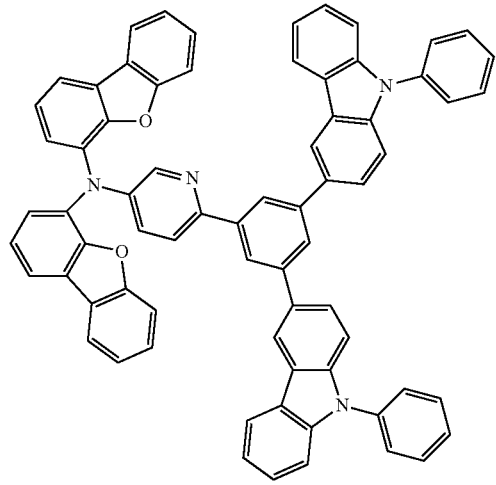
71
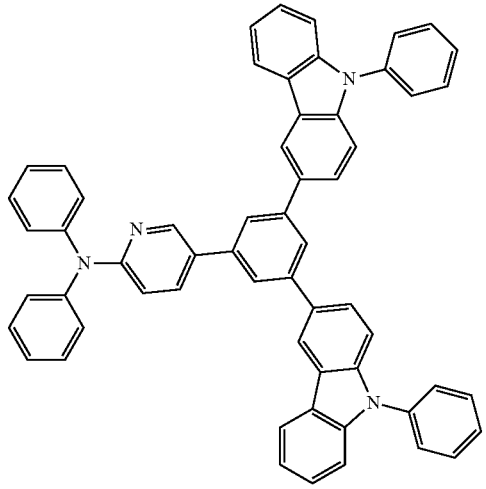
72
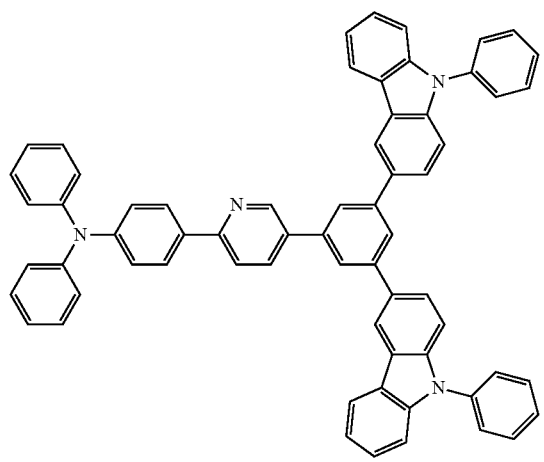
73
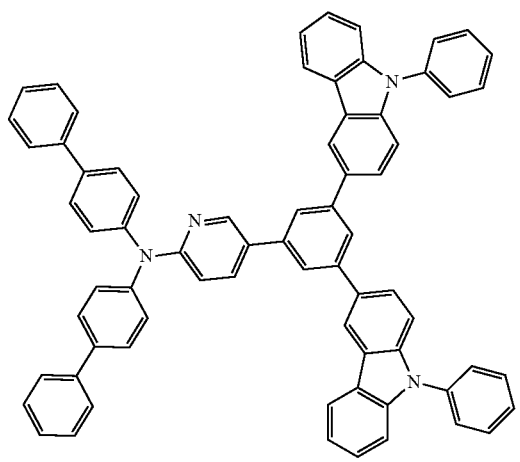
74
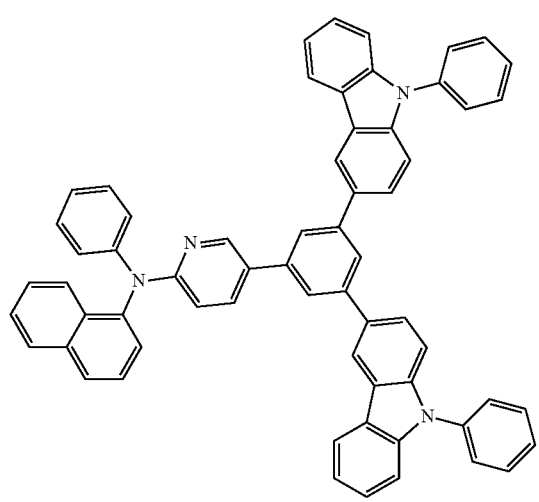
75
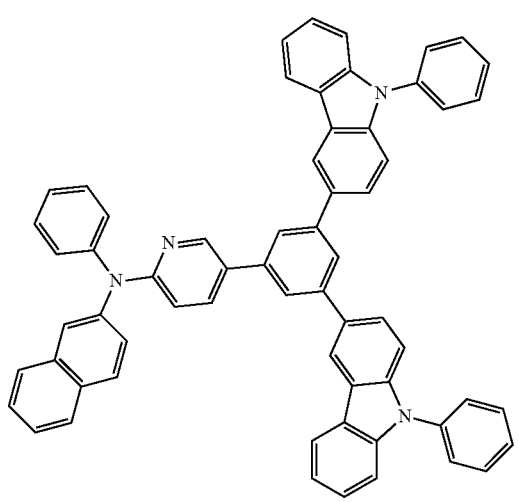

76
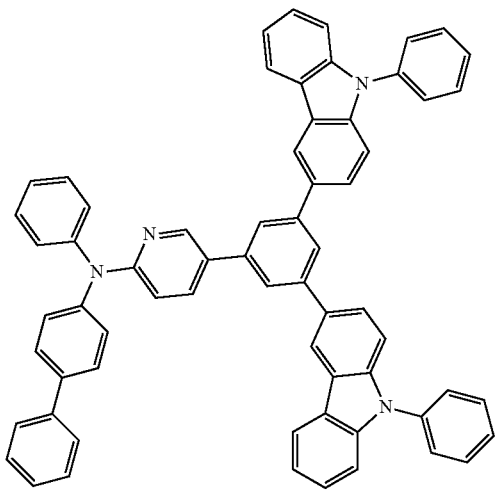
77
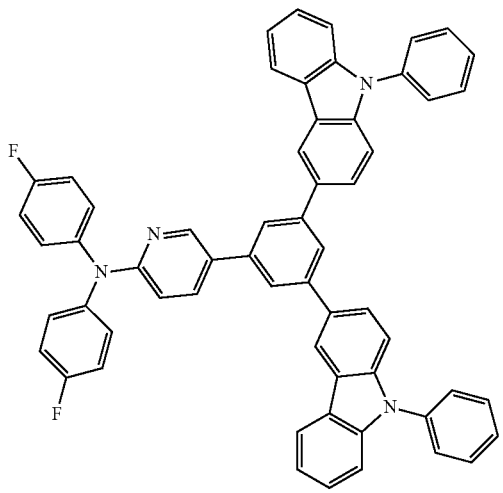
78
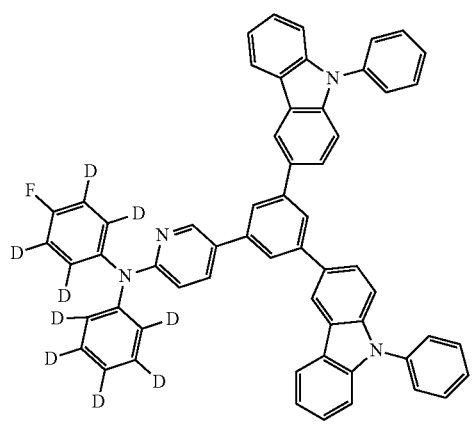
79
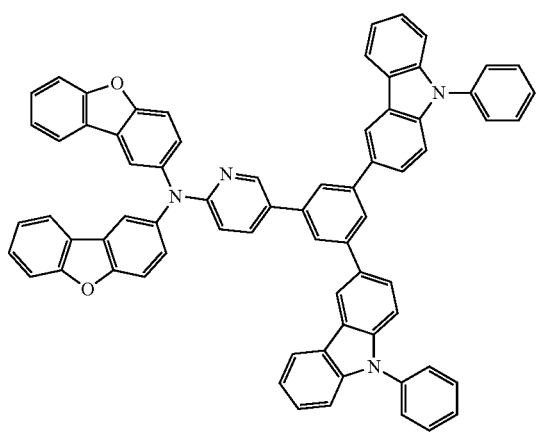
80
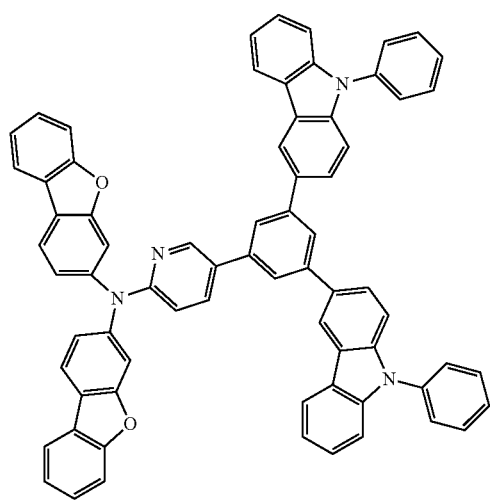
81
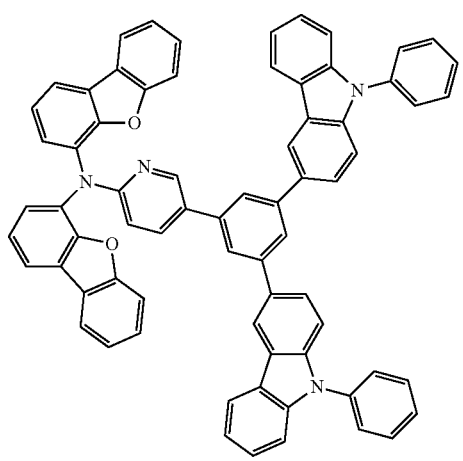

-continued
83
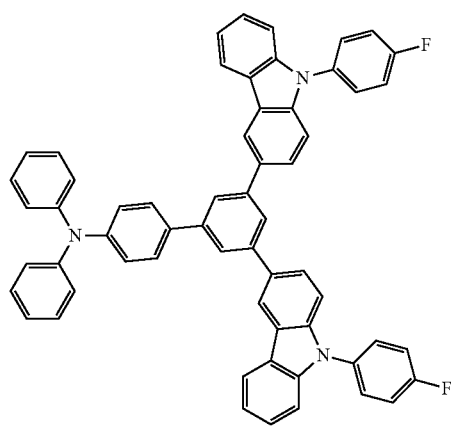
84
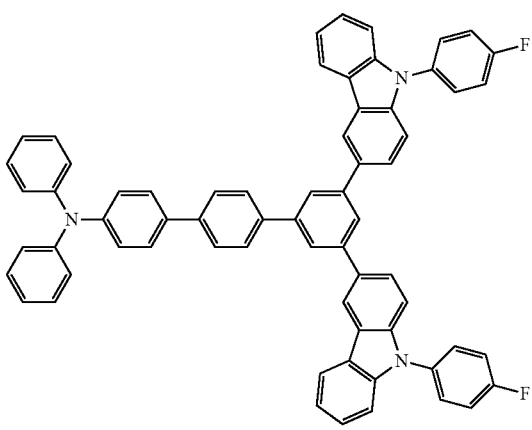
85
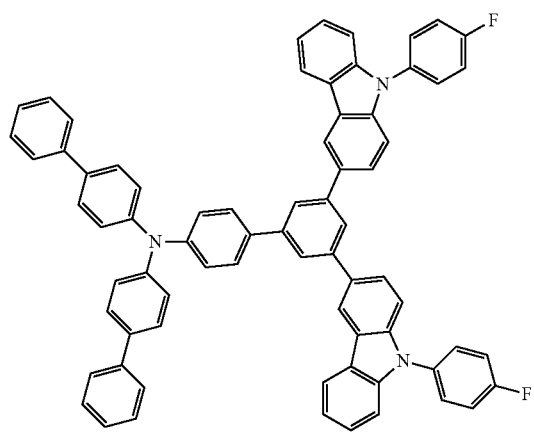
86
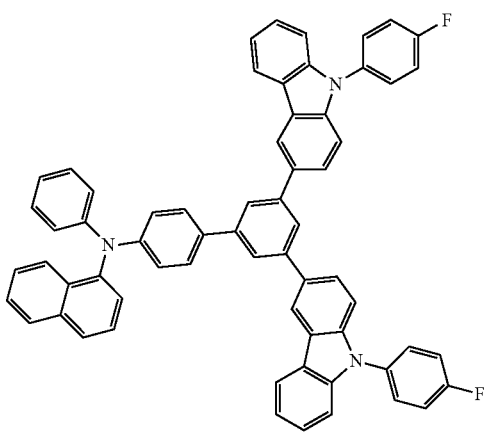
87
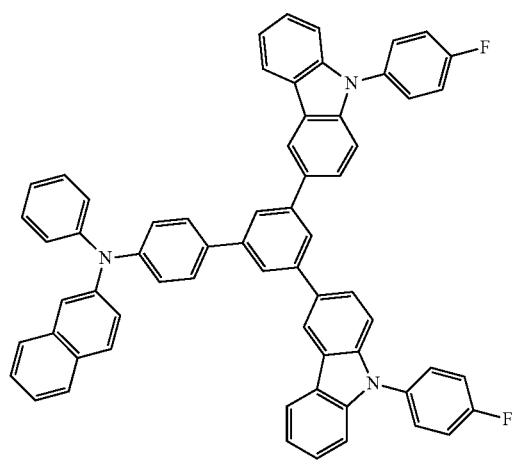
88
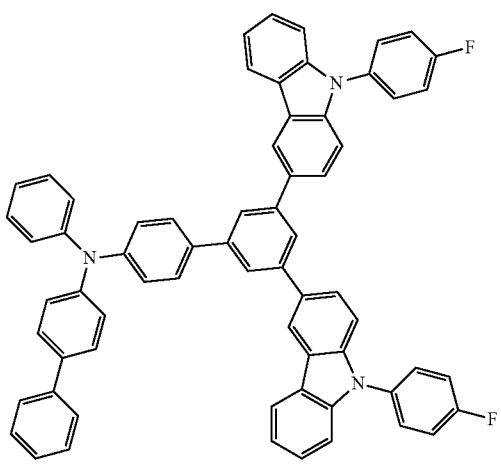

-continued
89
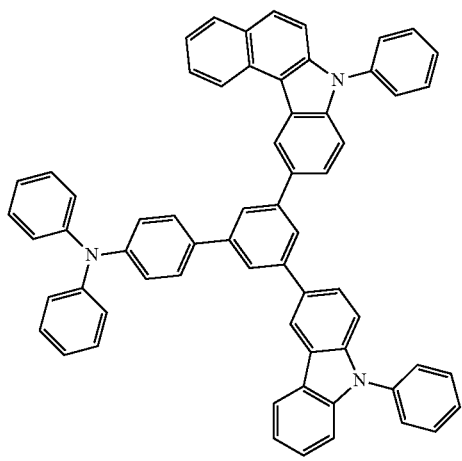
90
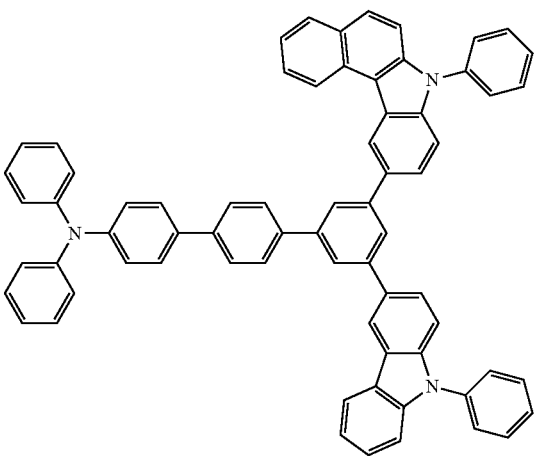
91
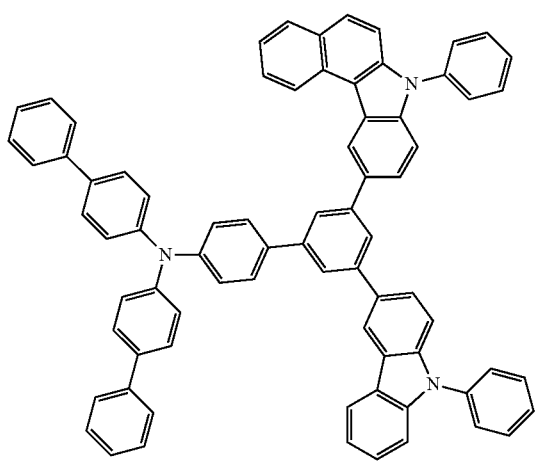
92
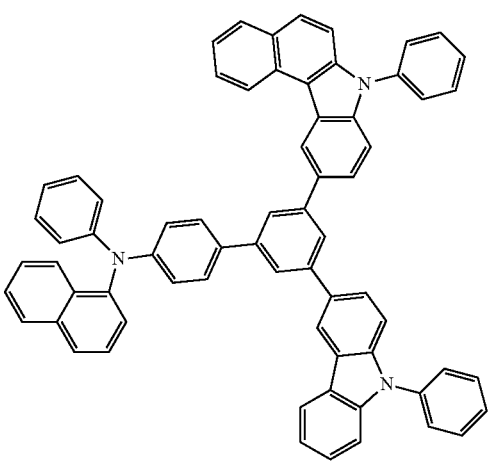
93
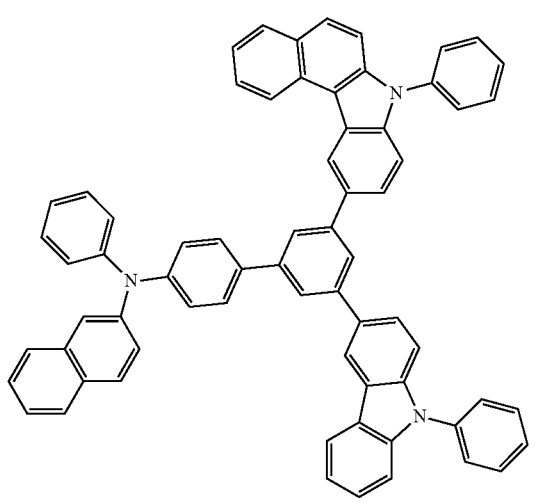
94
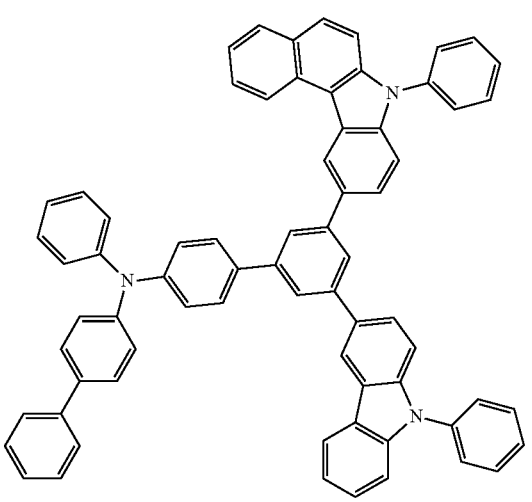

-continued
95
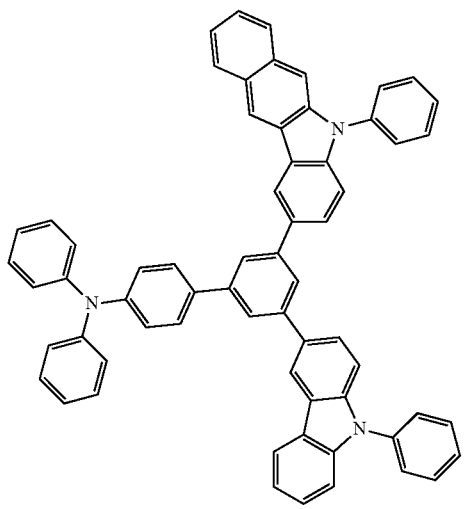
96
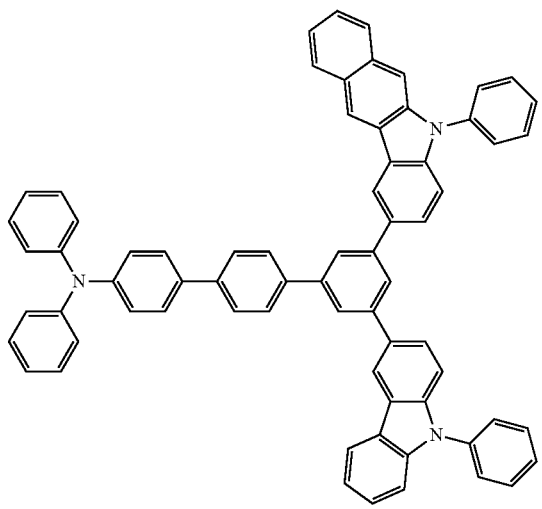
97
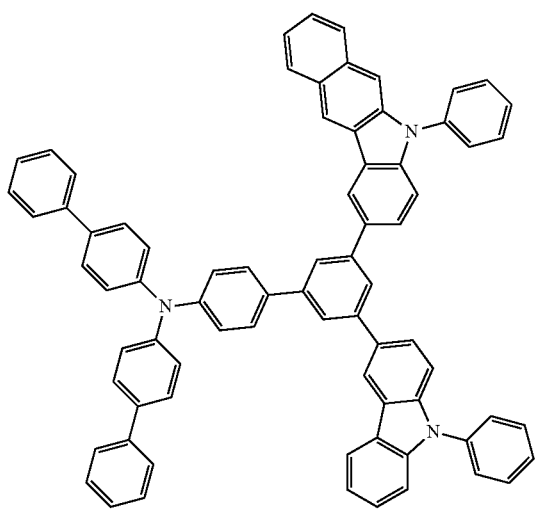
98
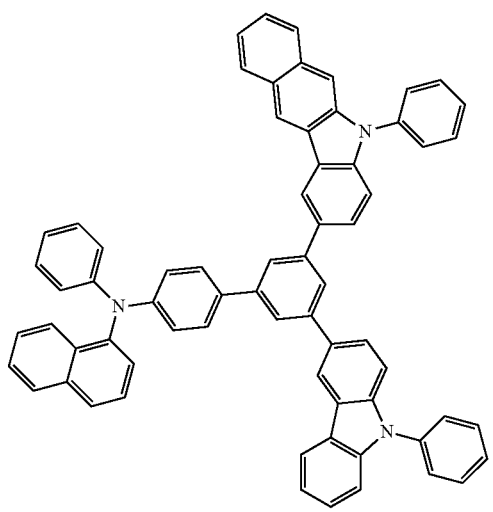
99
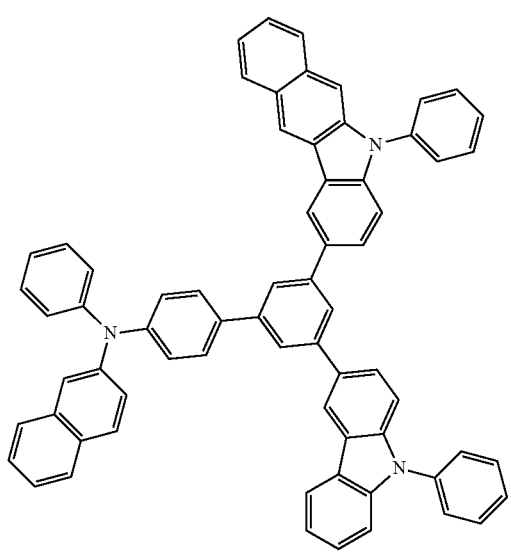
100
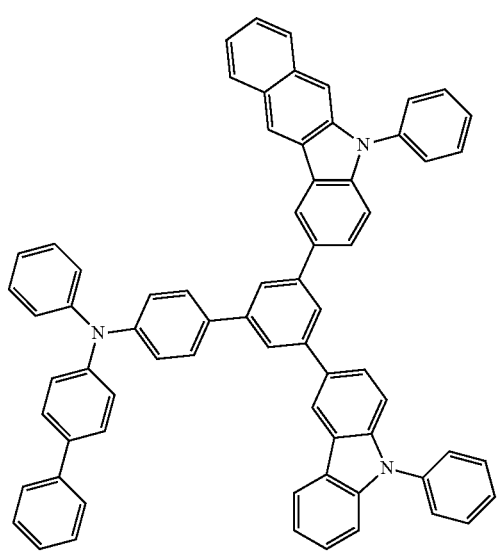

-continued
101
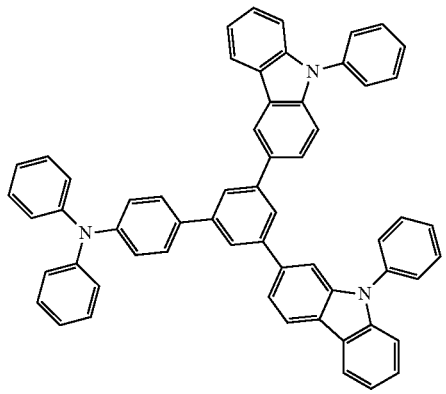
102
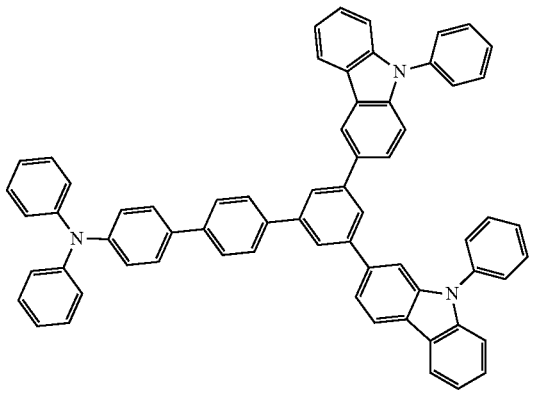
103
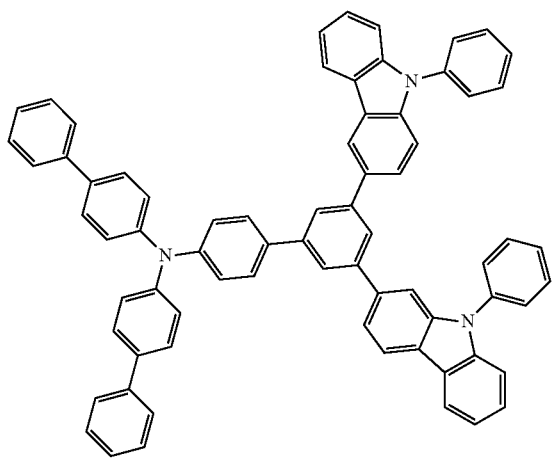
104
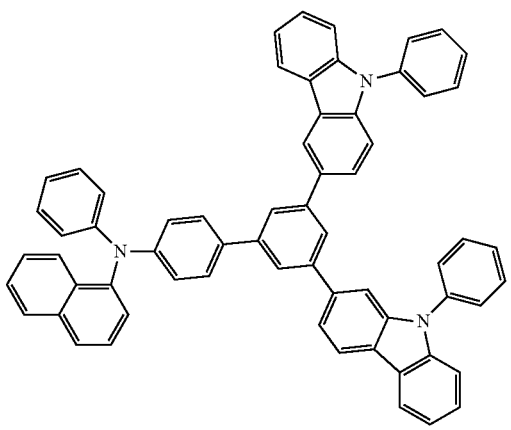
105
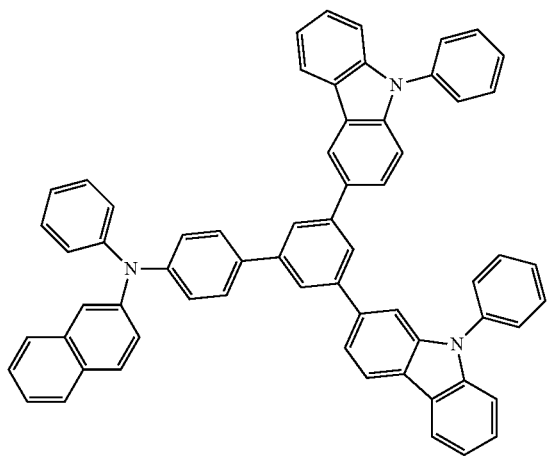
106
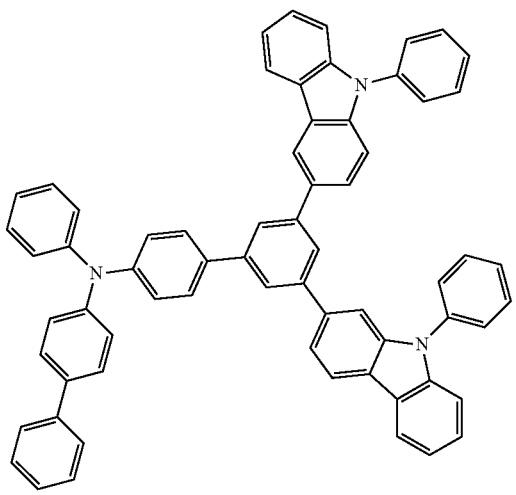

-continued
107
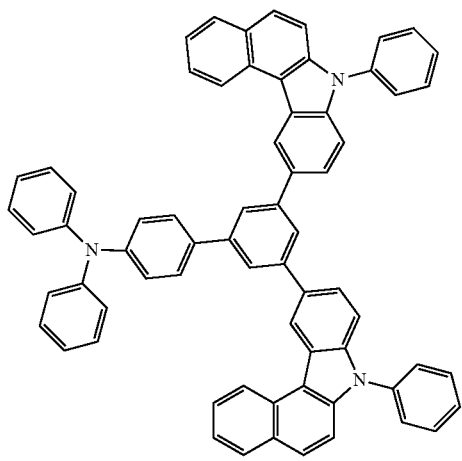
108
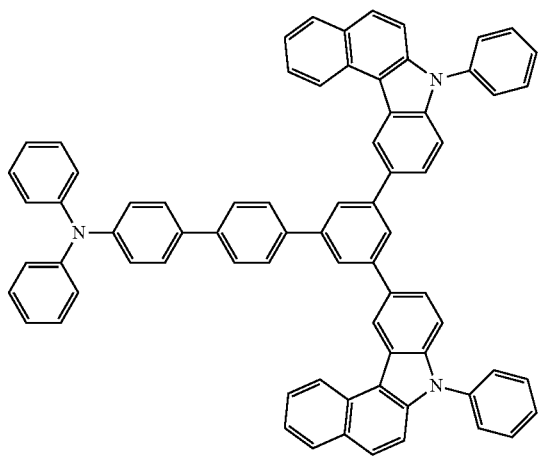
109
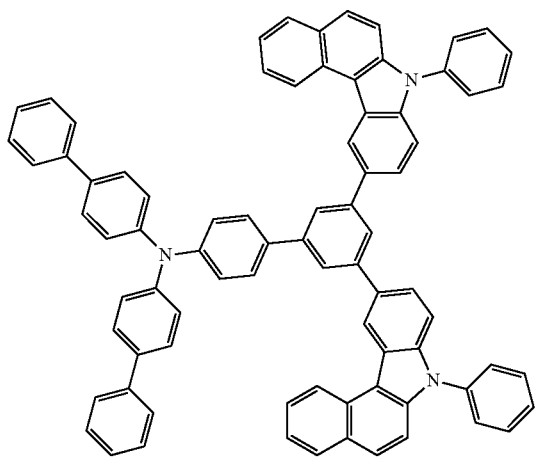
110
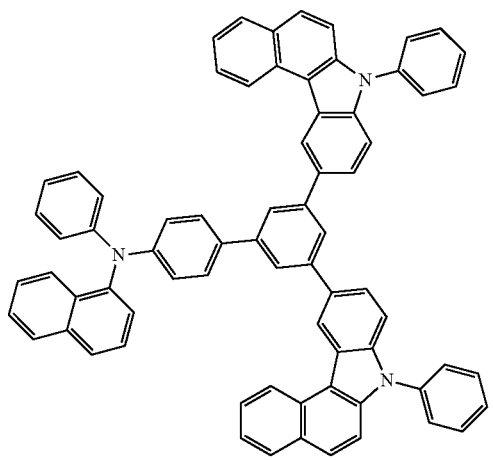
111
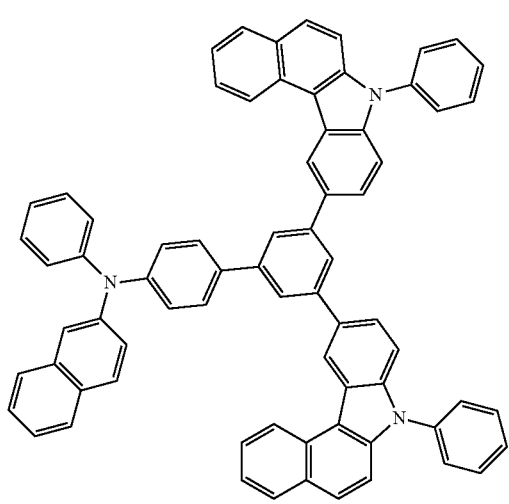
112
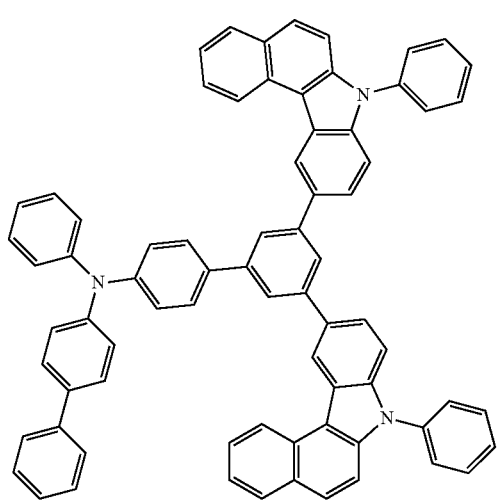

113
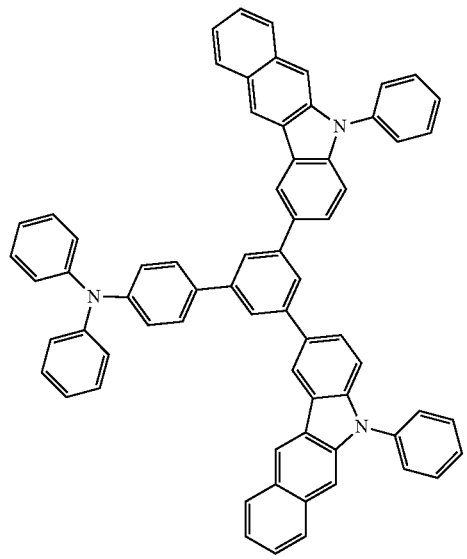
114
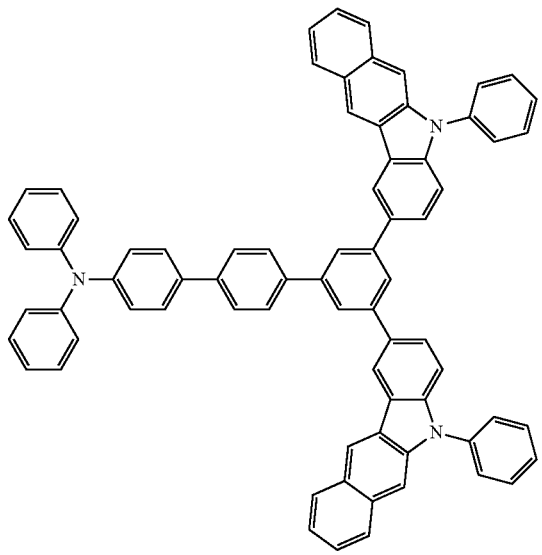
115
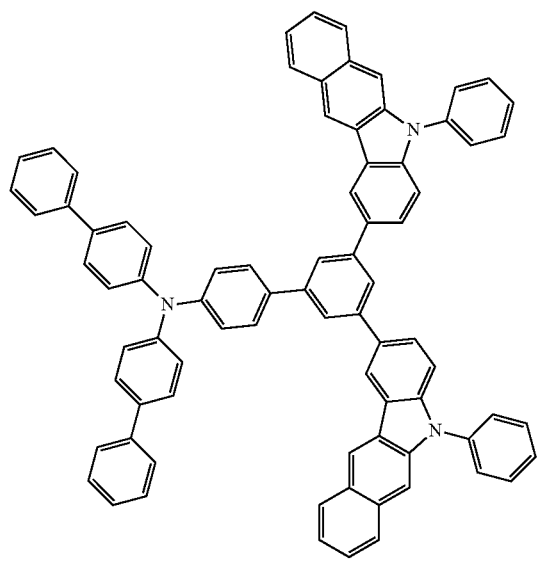
116
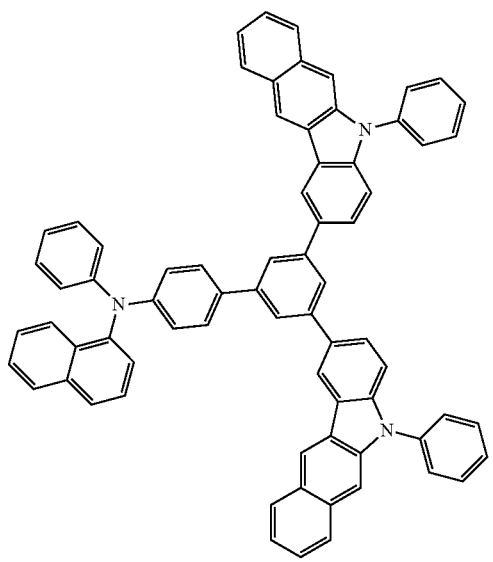

-continued
117
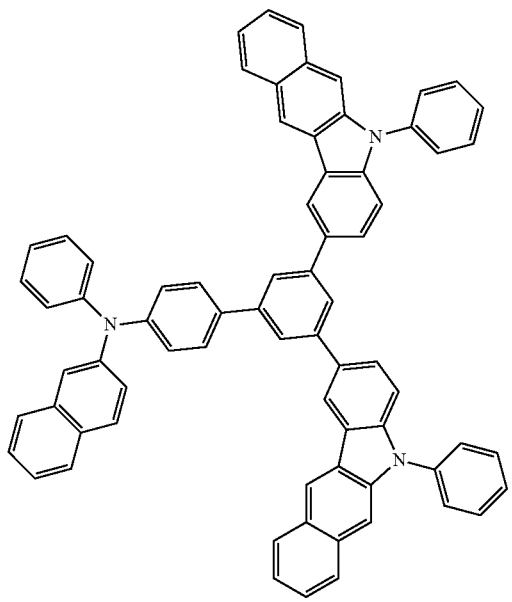
118
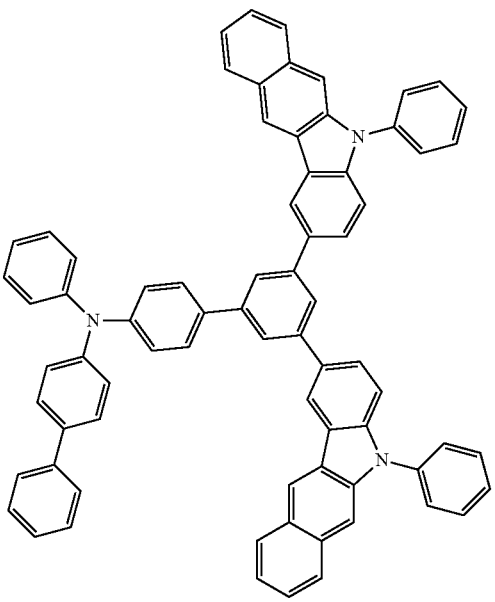
119
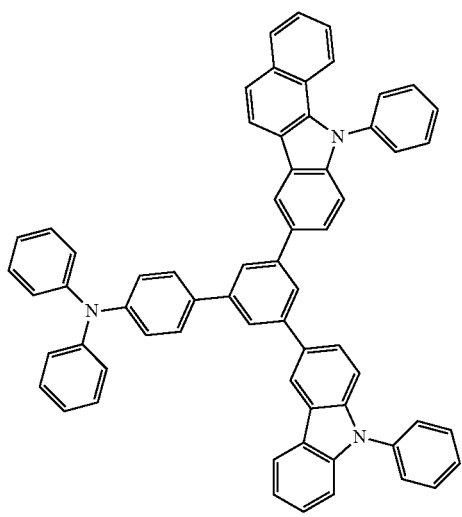
120
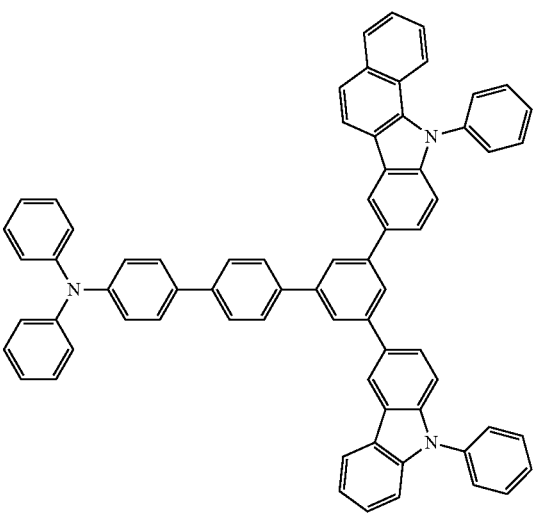
121
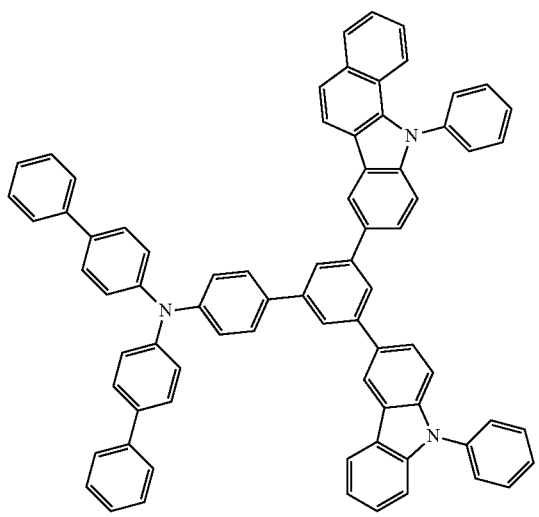
122
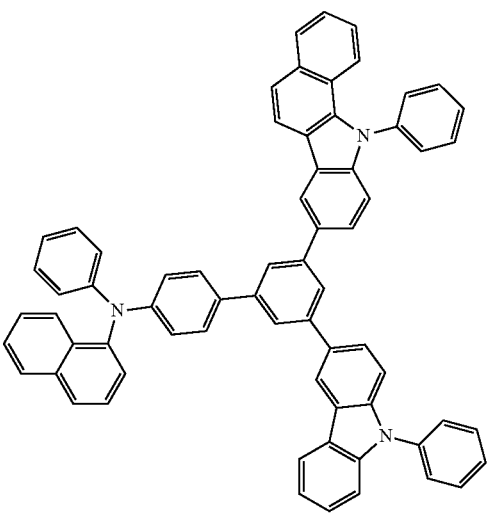

-continued
123
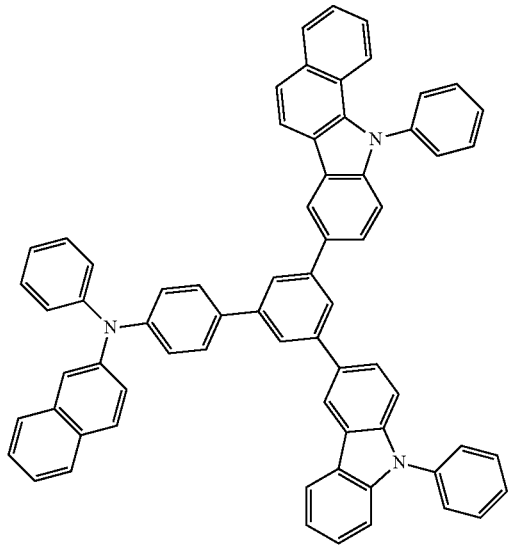
124
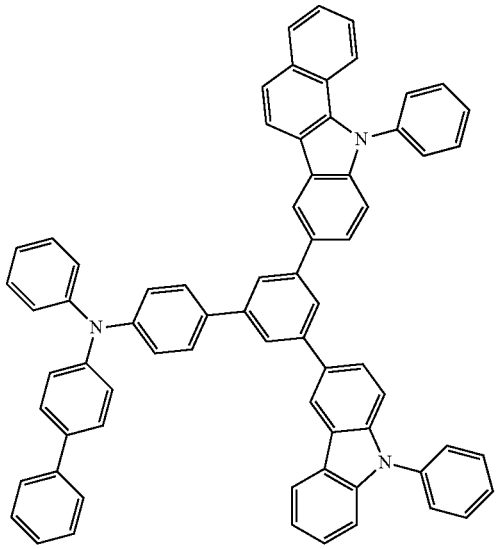
125
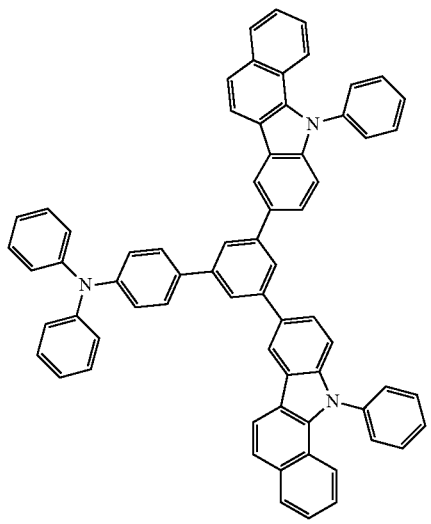
126
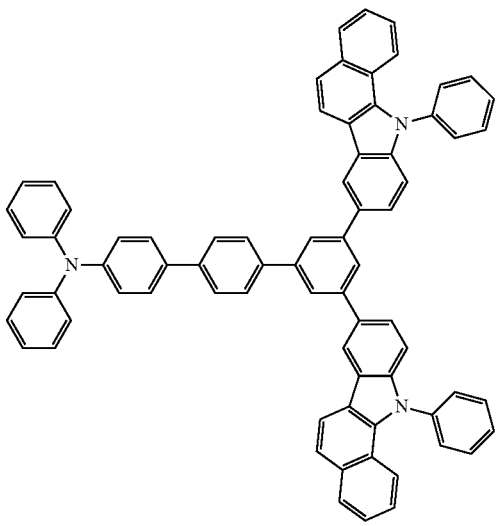
127
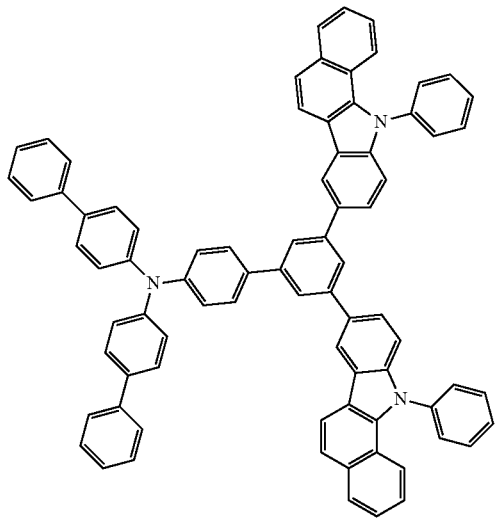
128
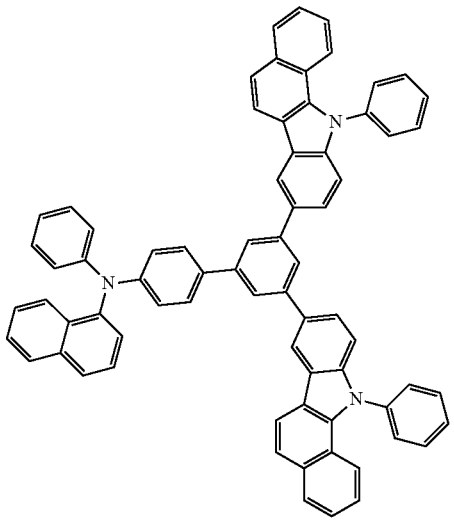

-continued
129
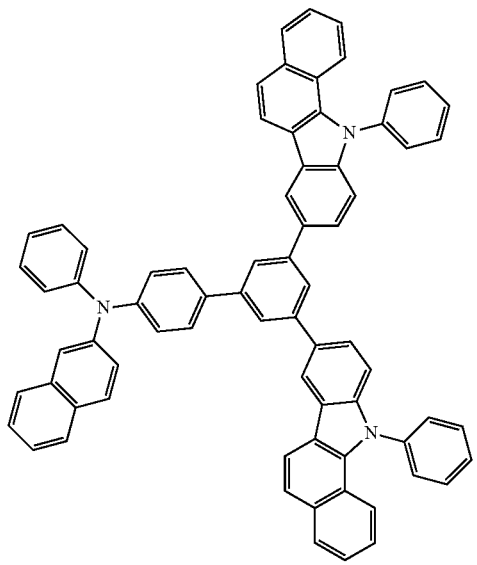
130
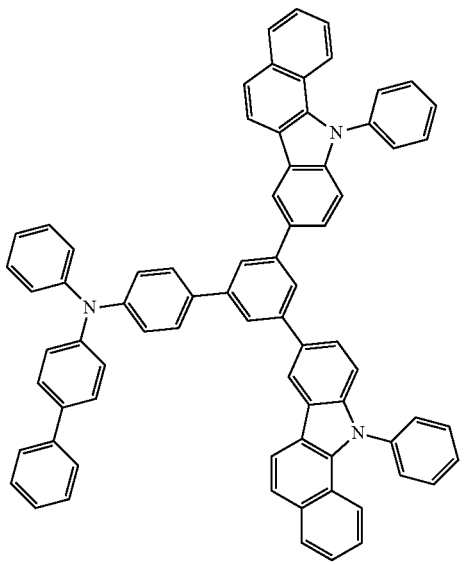
131
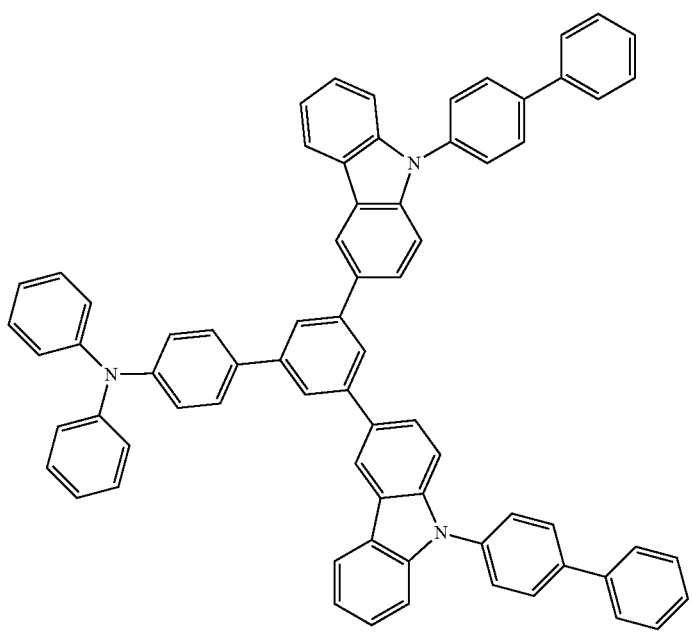

132
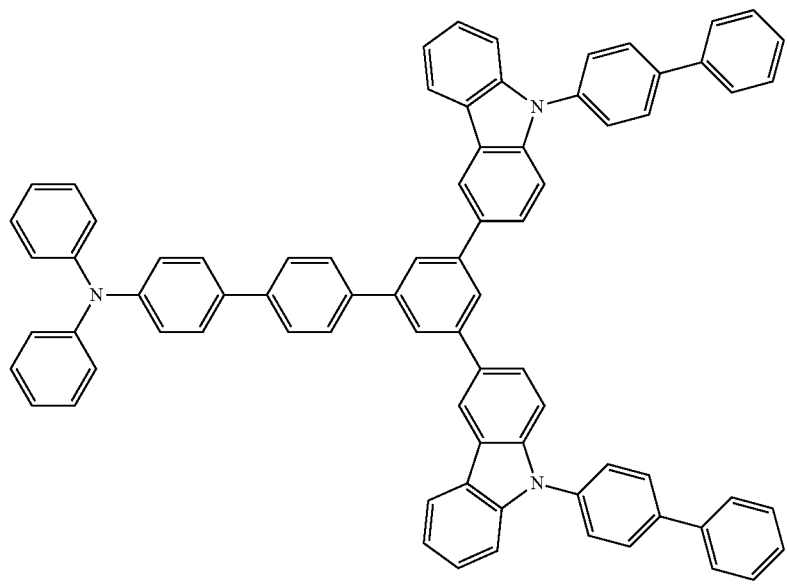
133
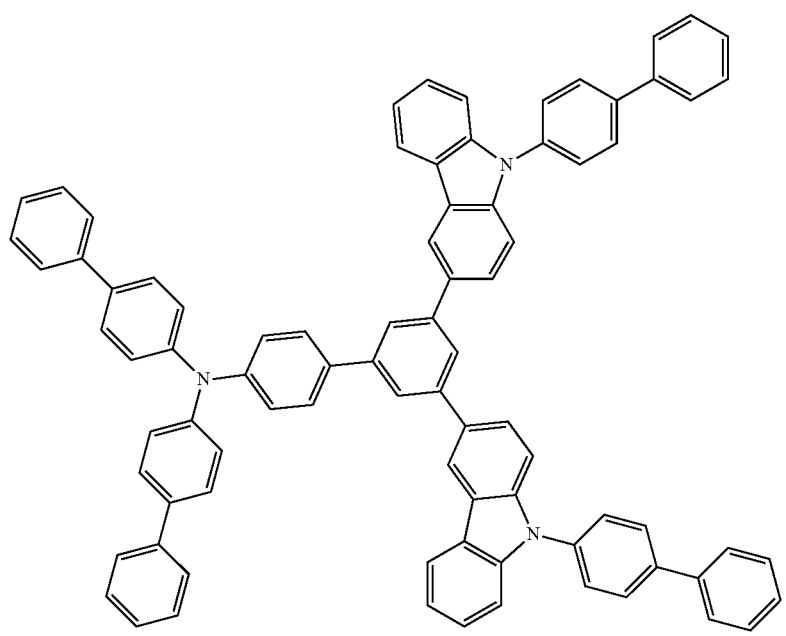
134 135
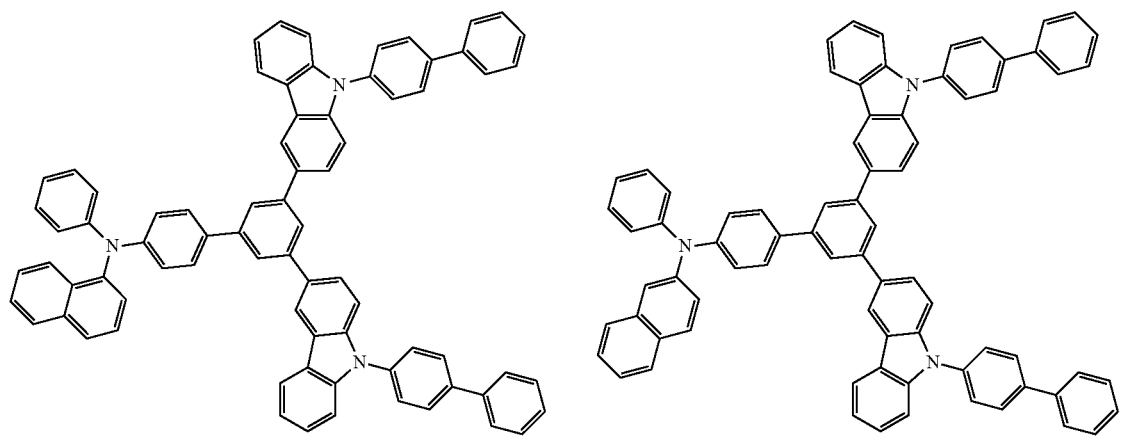

-continued
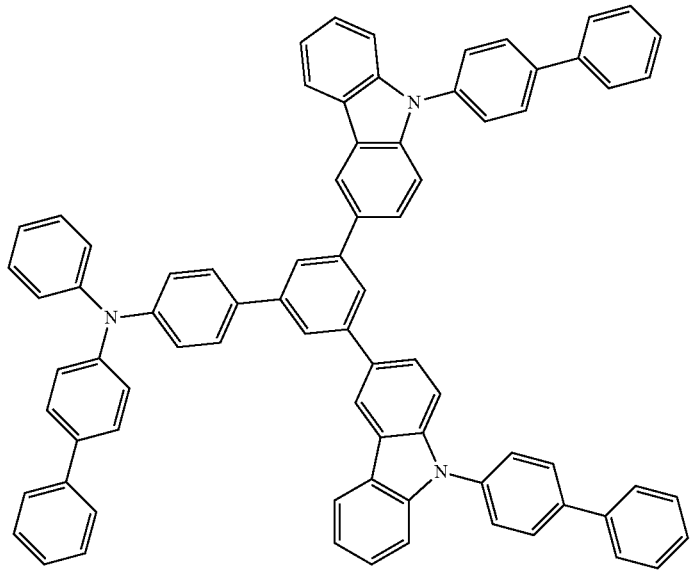
136
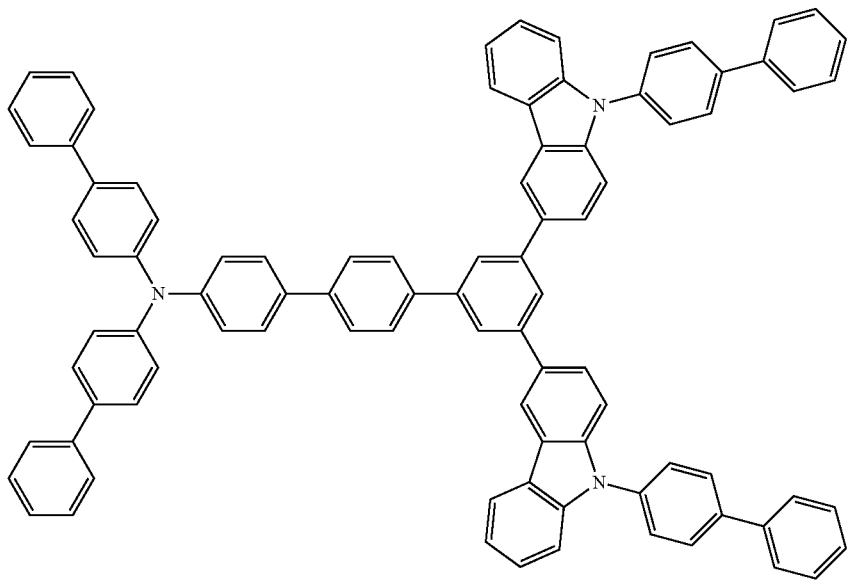
137

-continued
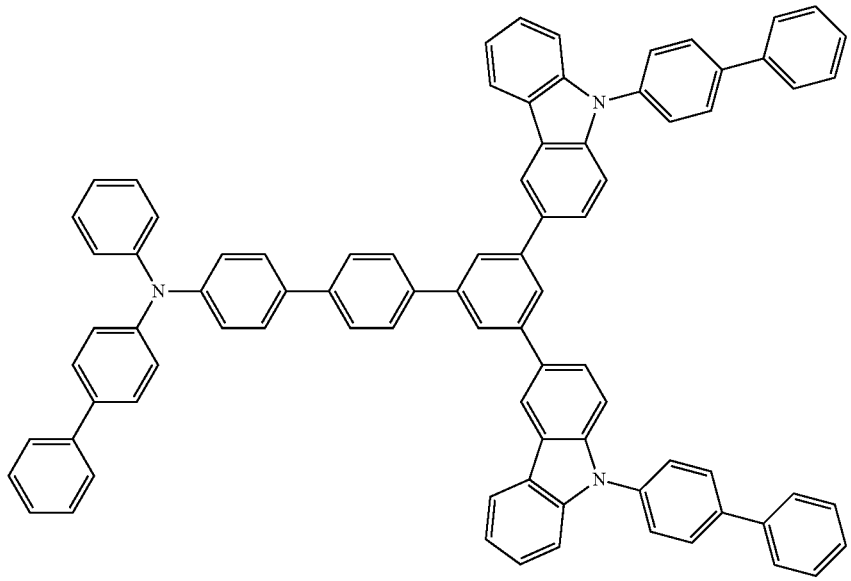
138
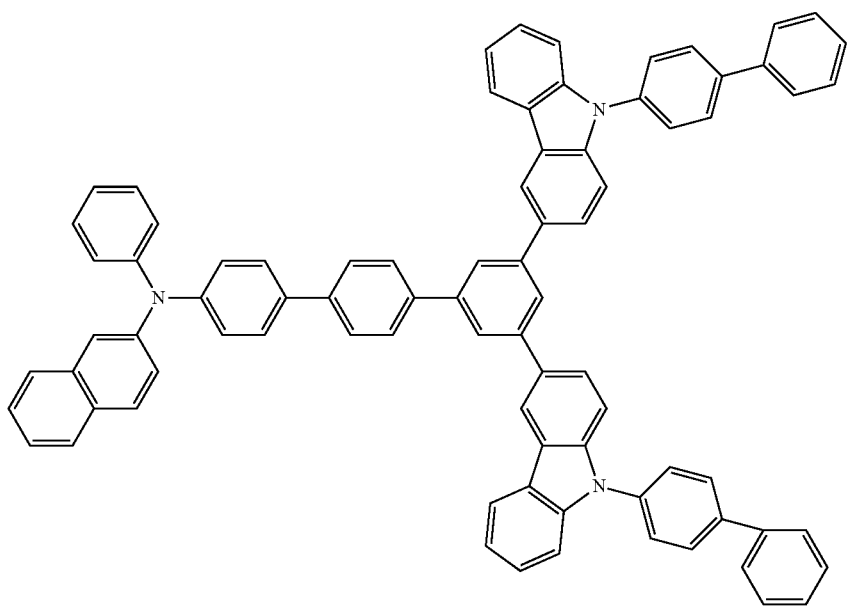
139

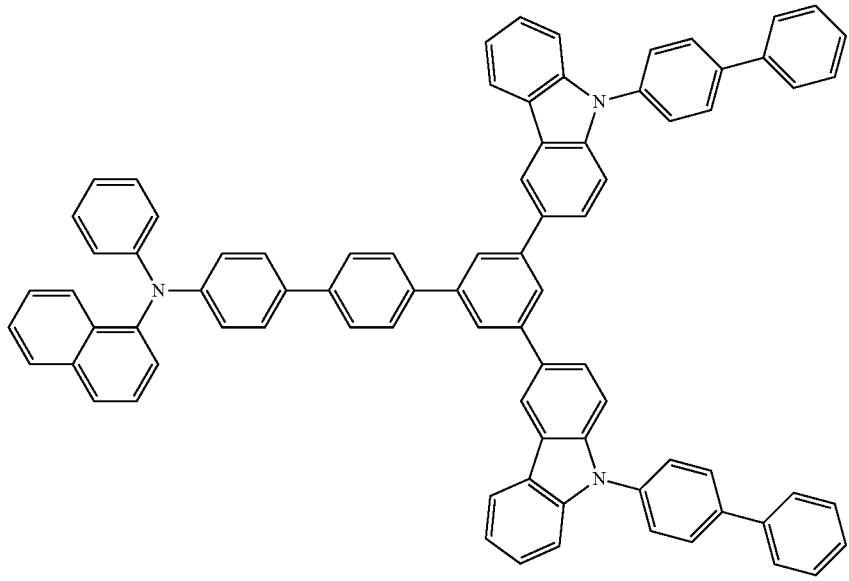
140
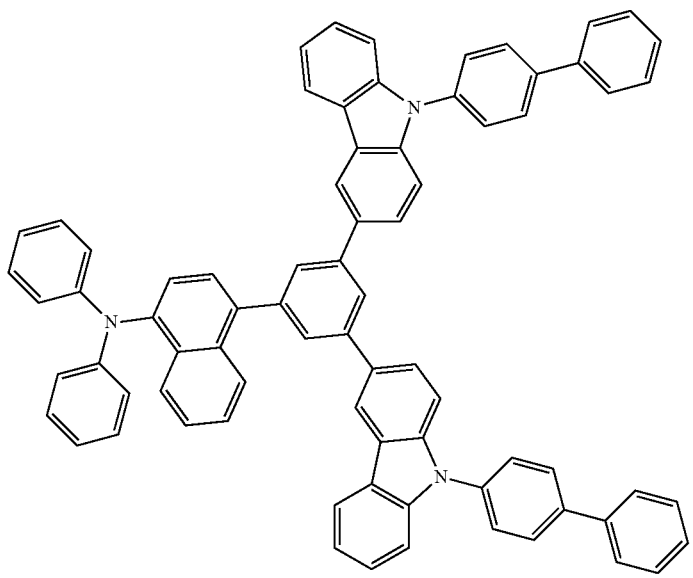
141

142
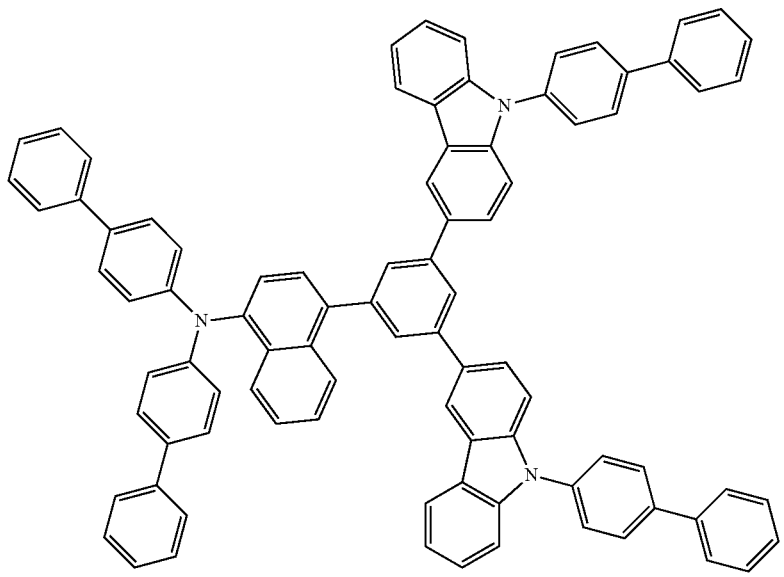
143 144
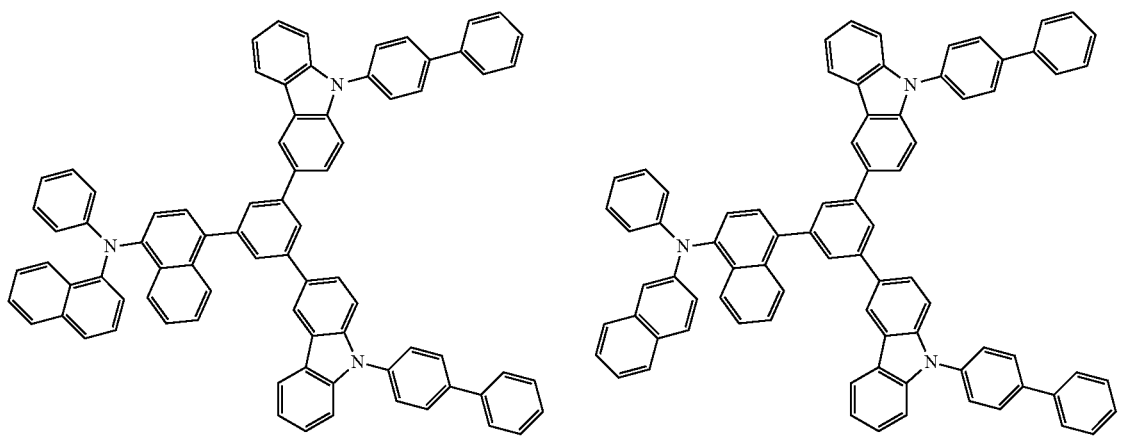
145 146
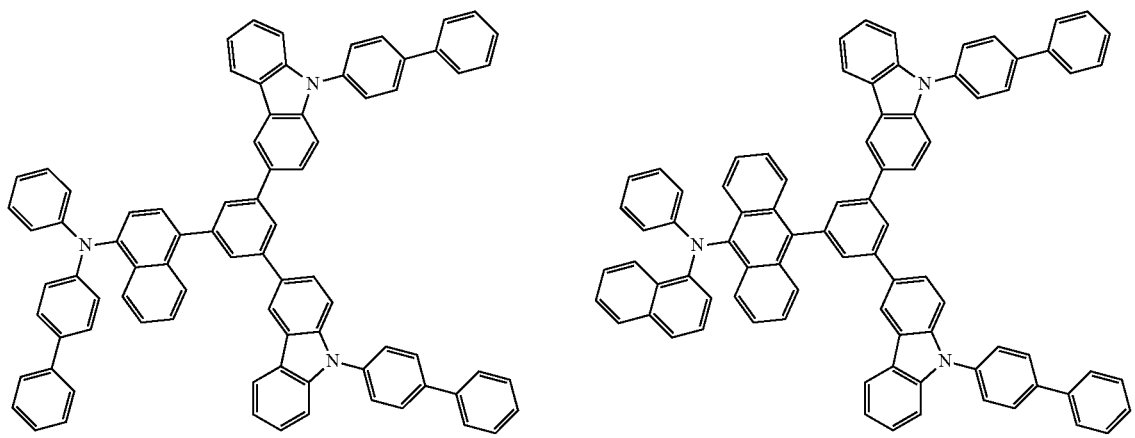

147
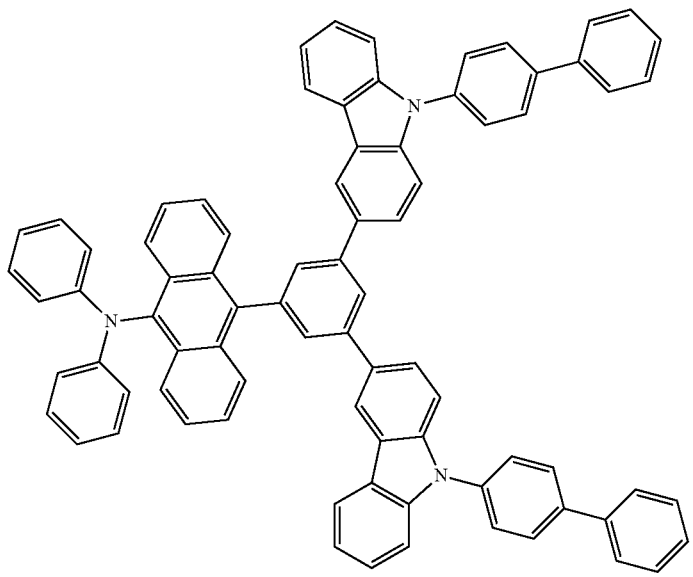
148
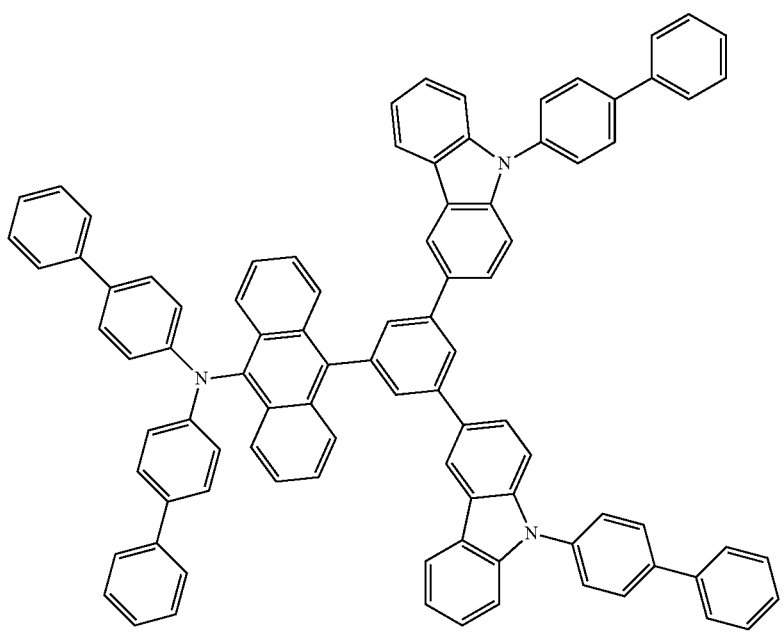
149      150
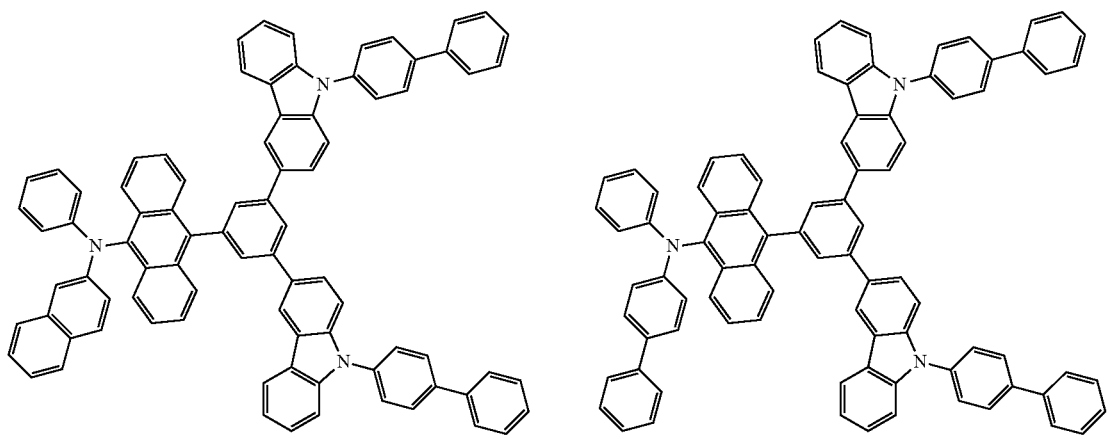

151
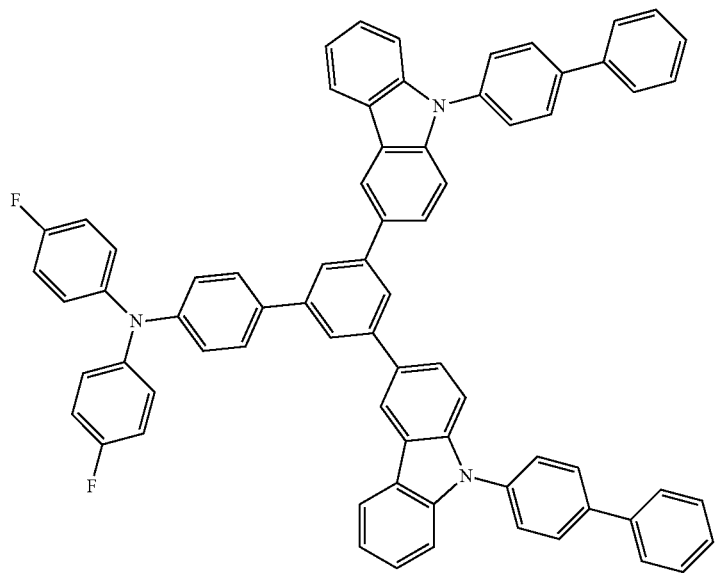
152
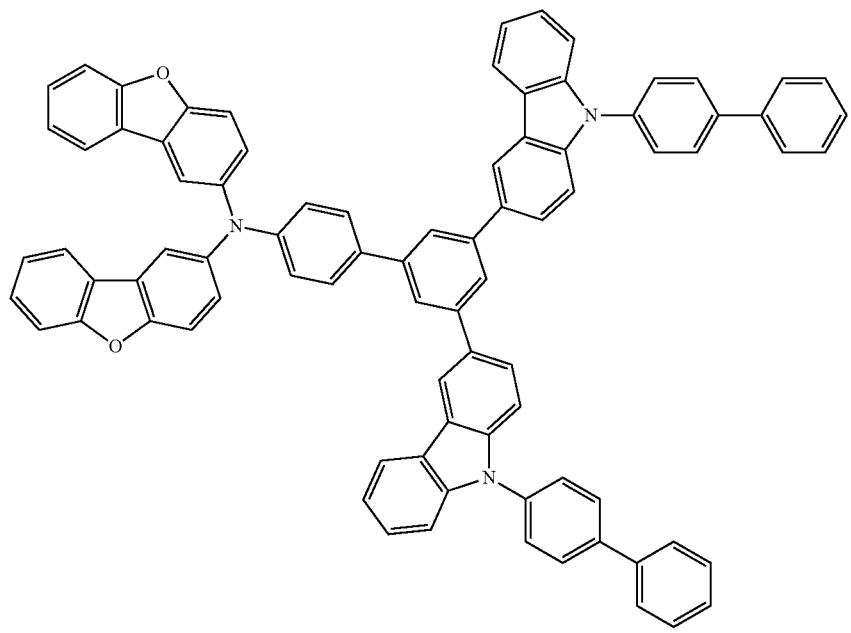

153
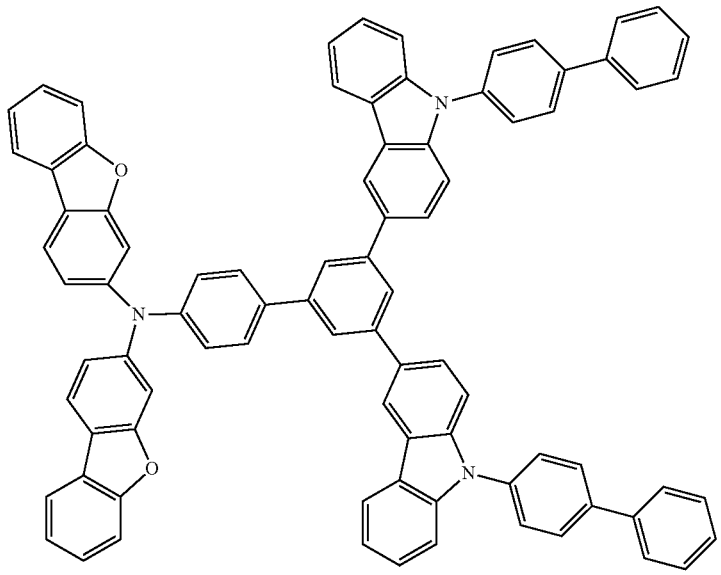
154
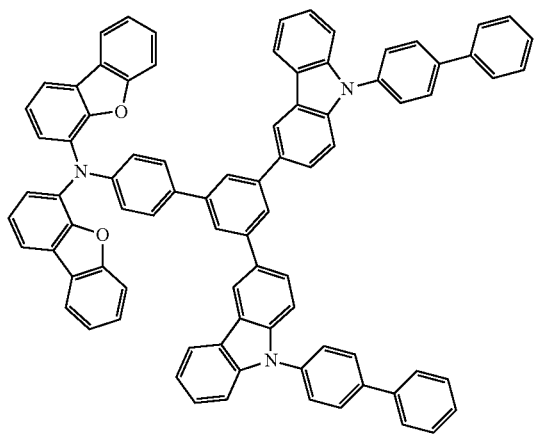
155
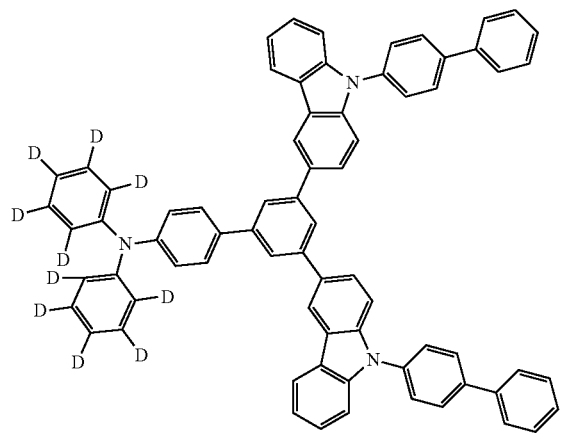

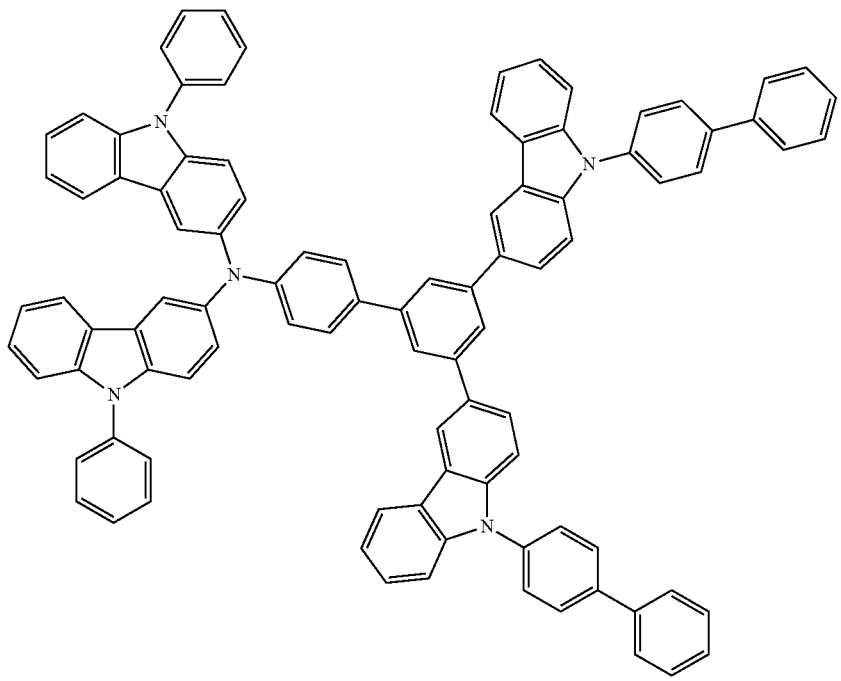
156
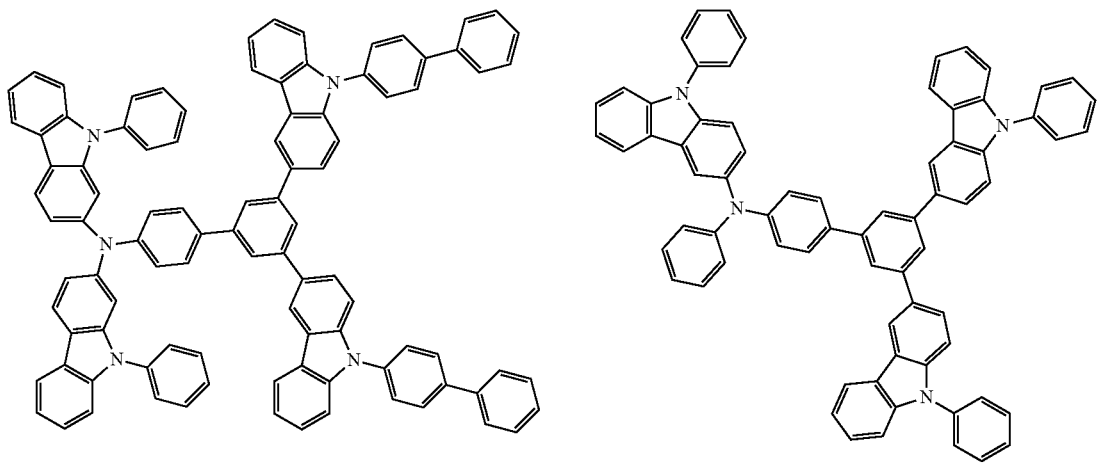
157
158
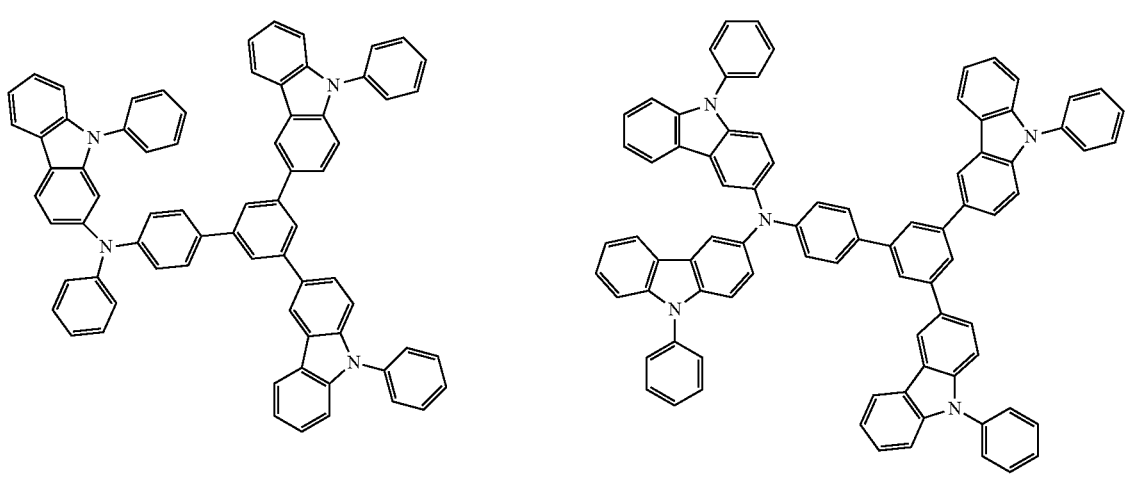
159
160

161
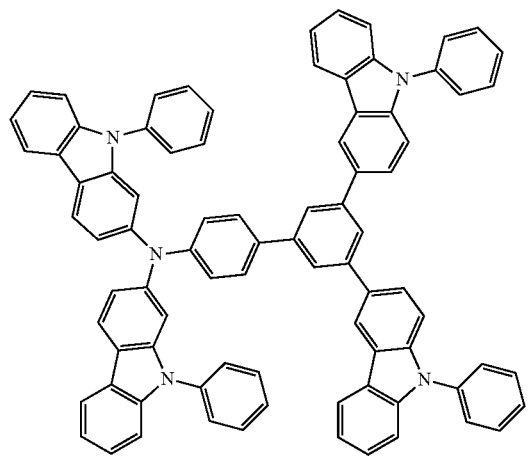
162
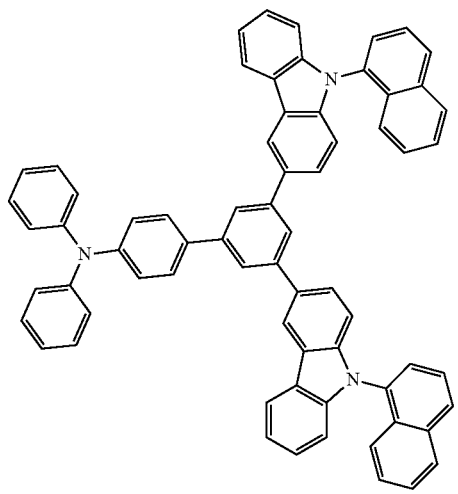
163
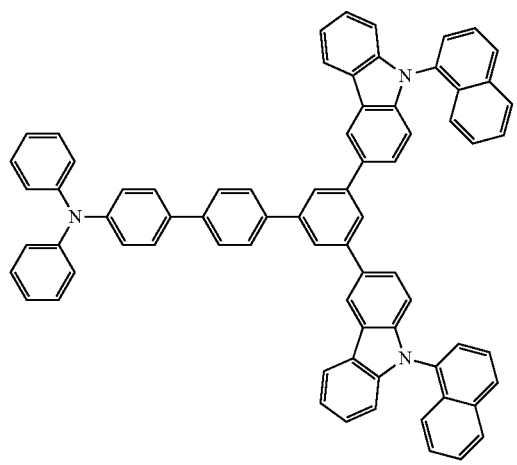
164
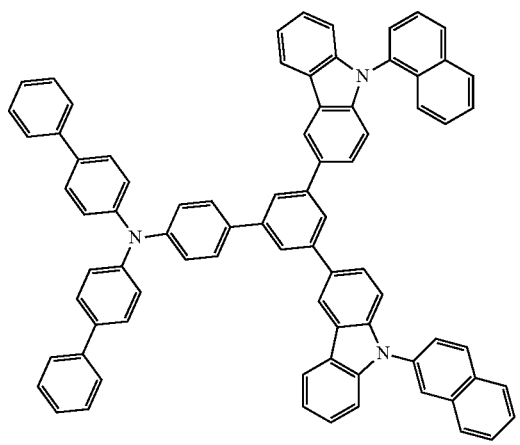
165
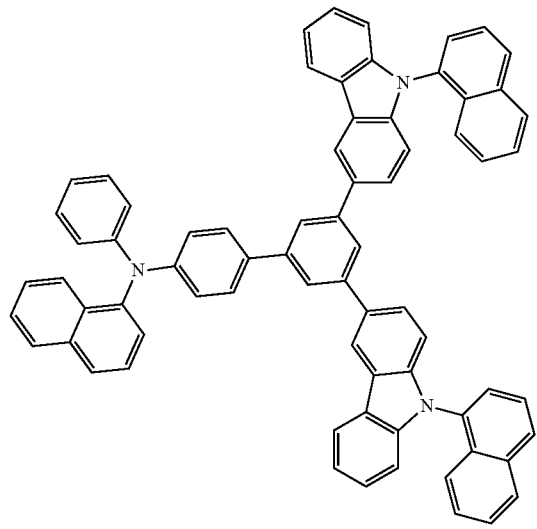
166
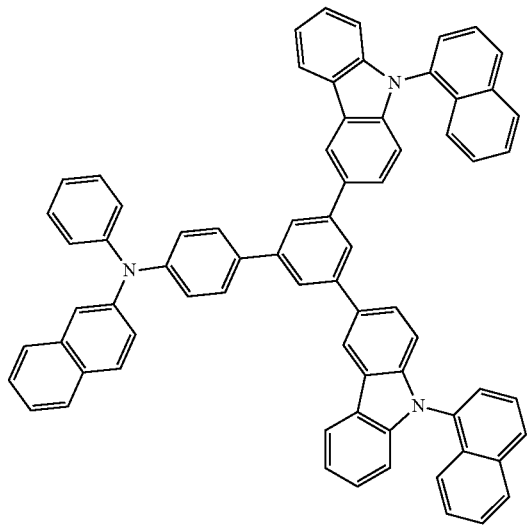

-continued
167
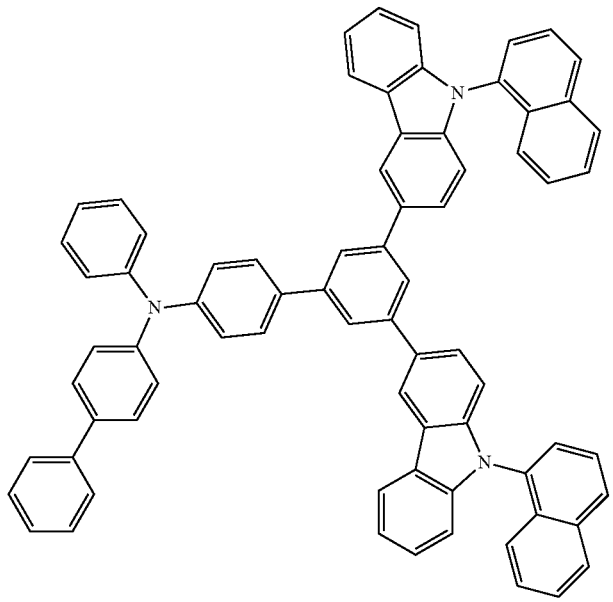
168
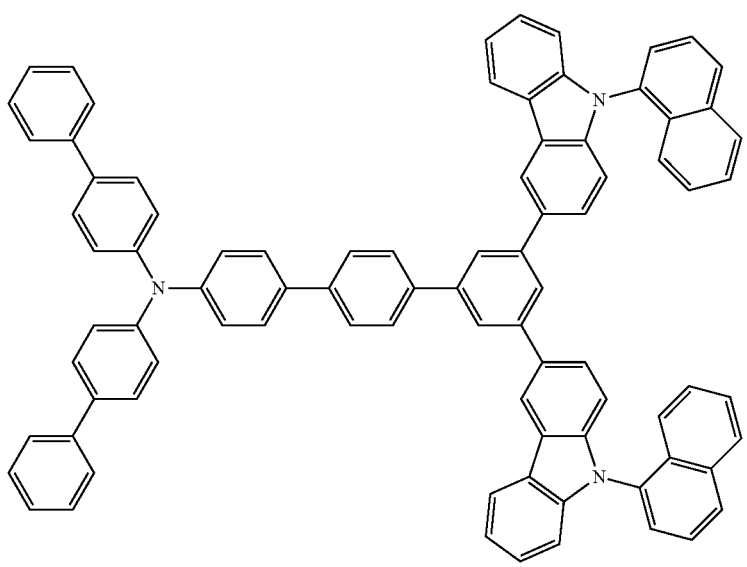

-continued
169
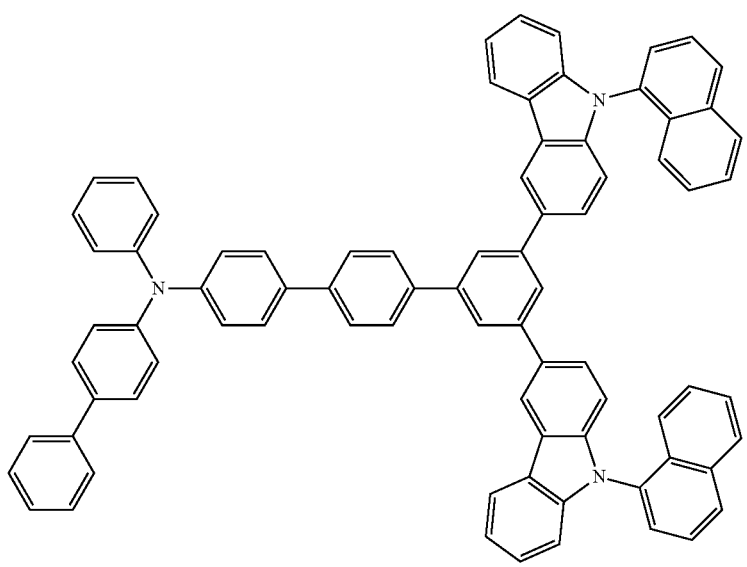
170
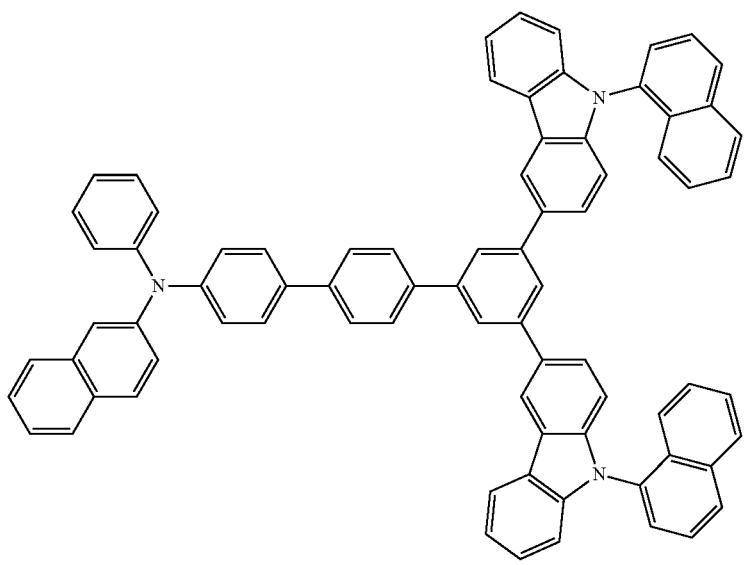

-continued
171
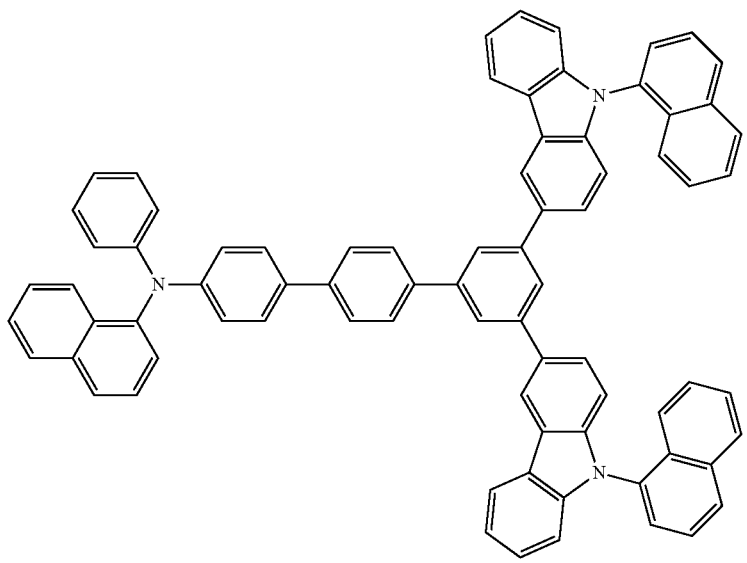
172
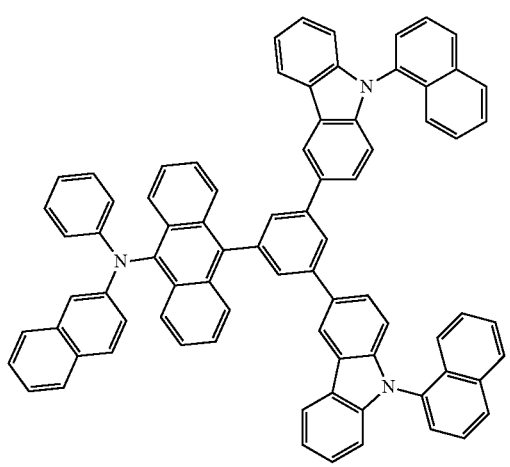
173
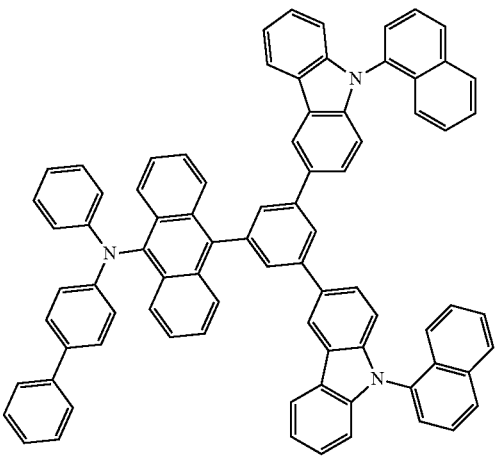
174
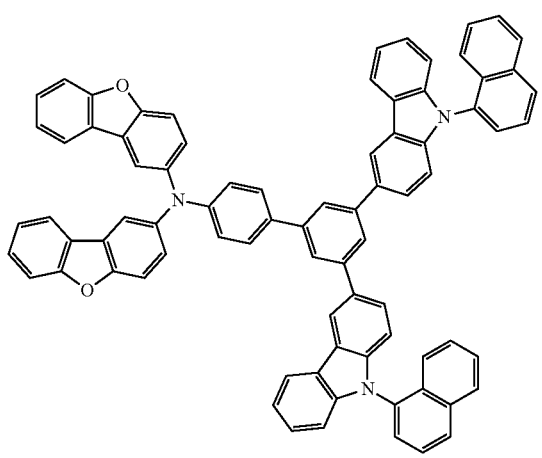
175
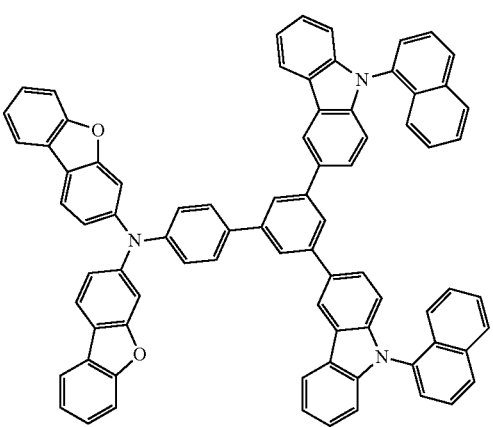

-continued
176
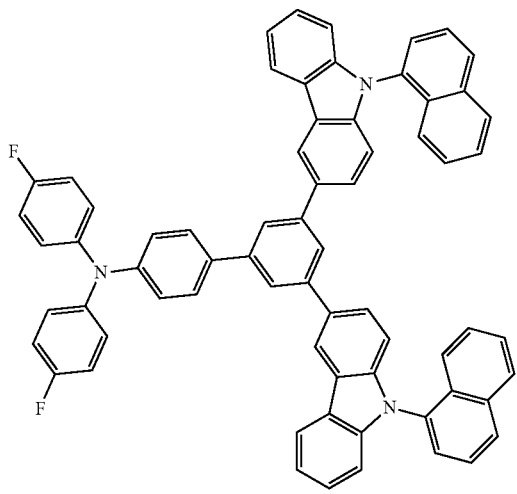
177
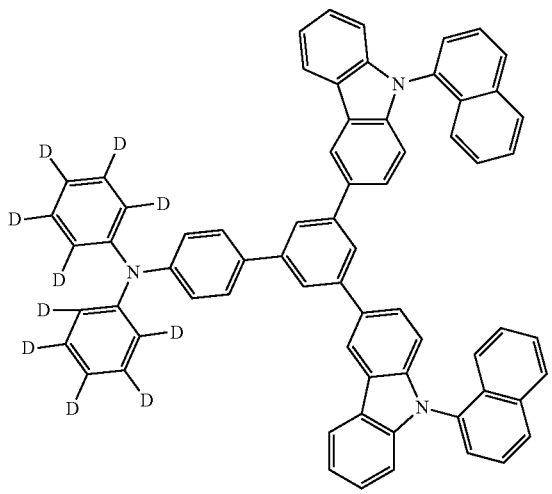
178
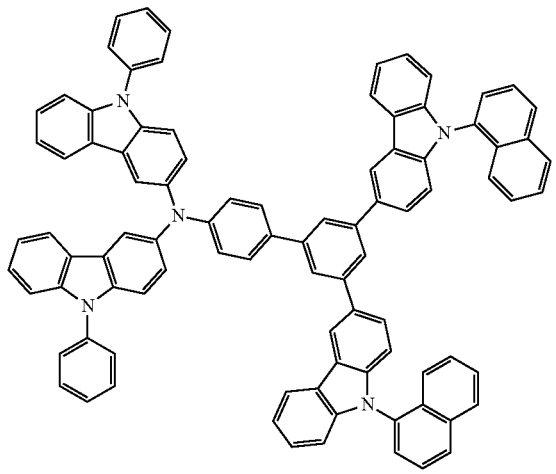
179
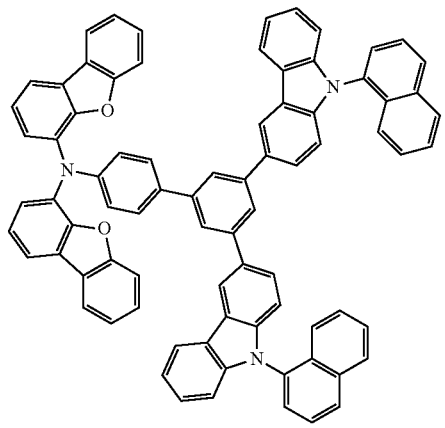
180
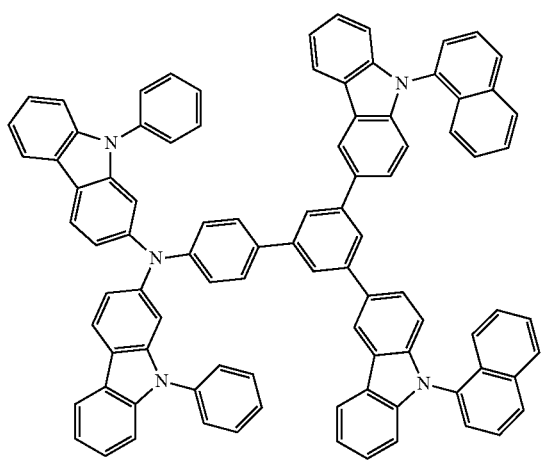
181
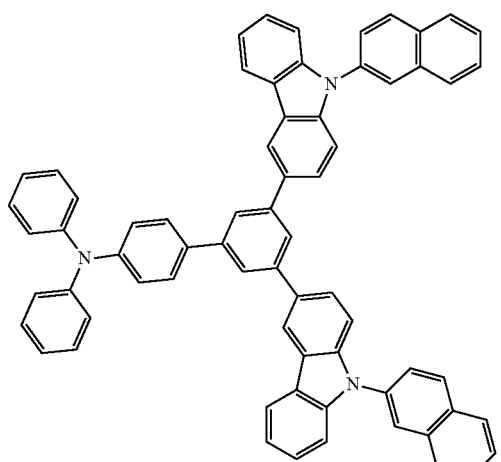

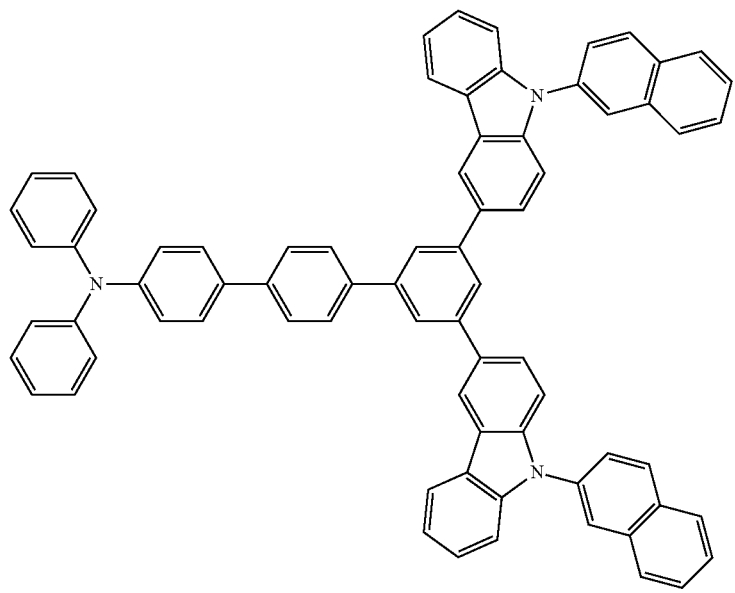
182
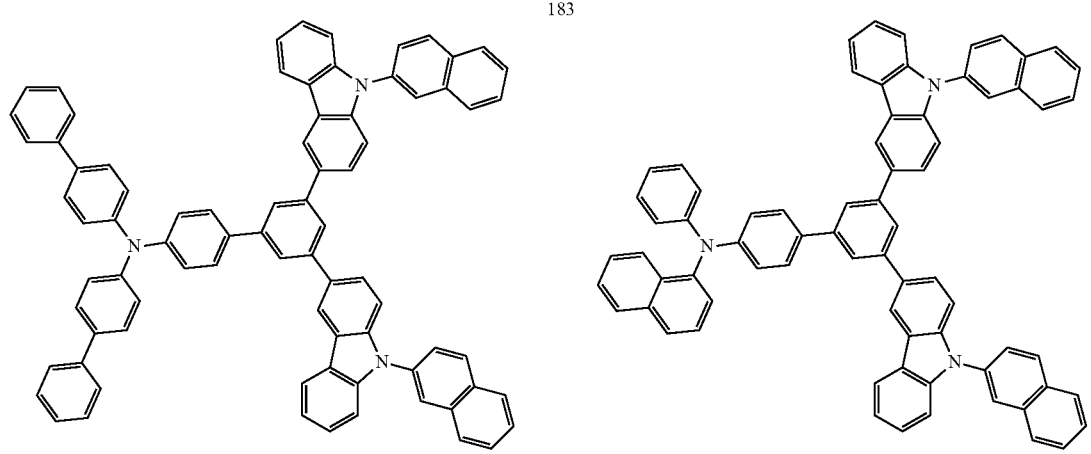
183　　　184
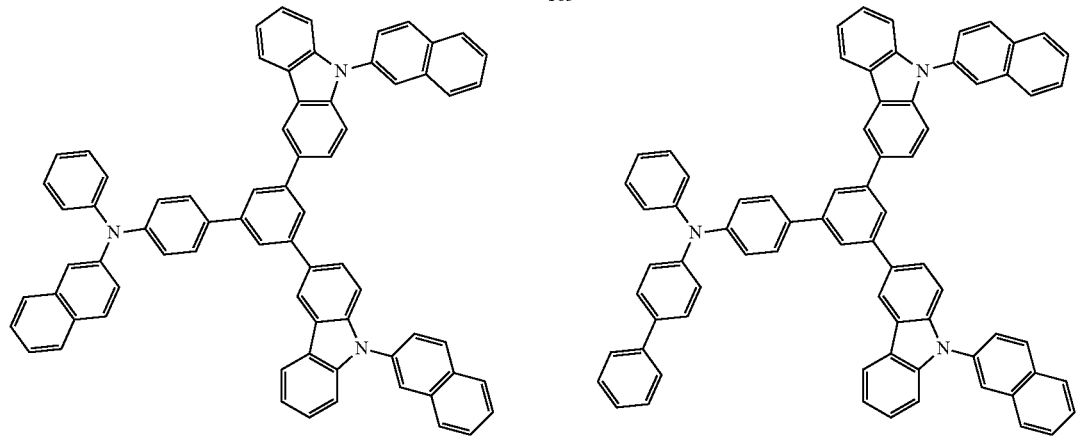
185　　　186

-continued
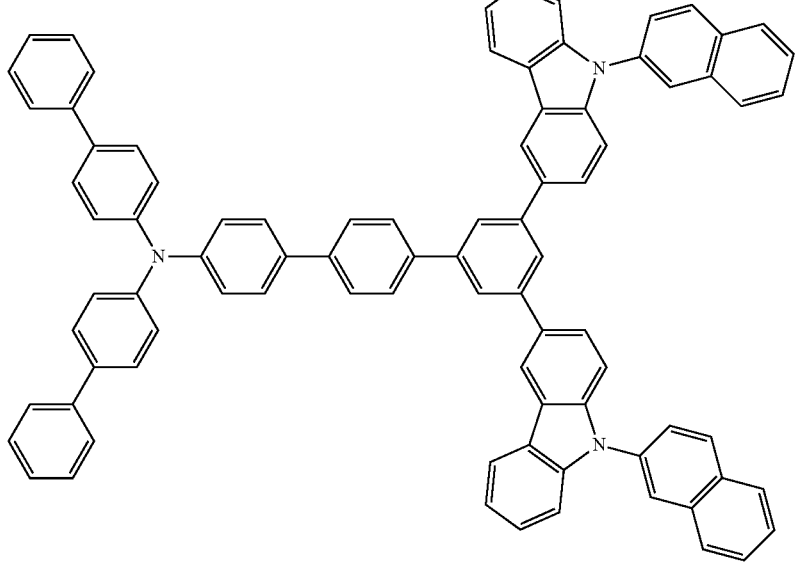
187
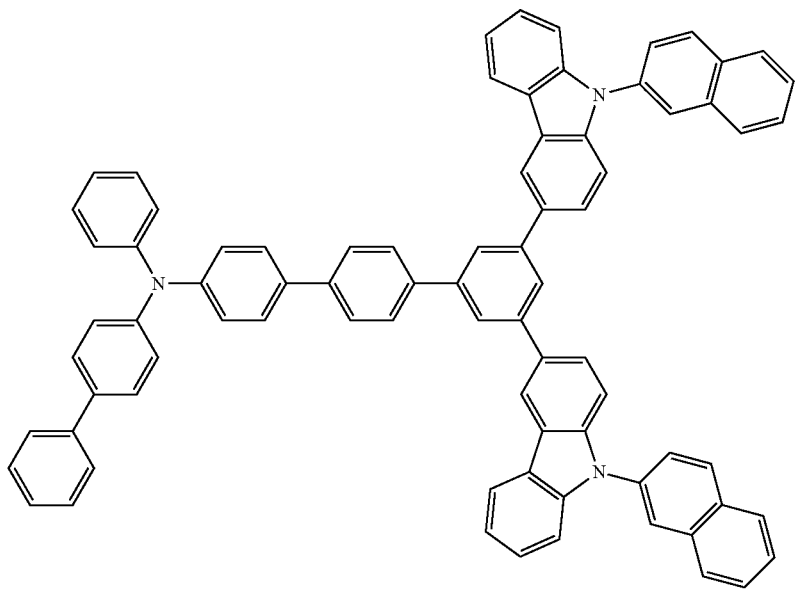
188

-continued
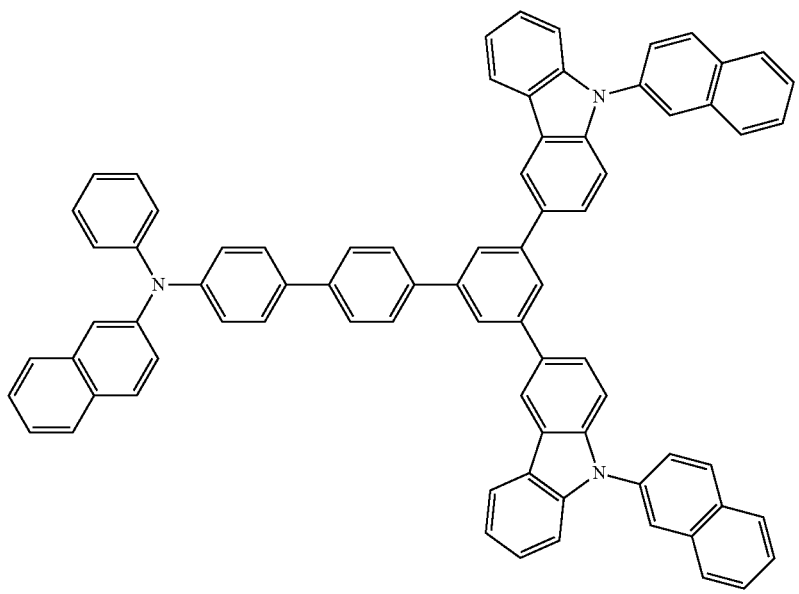
189
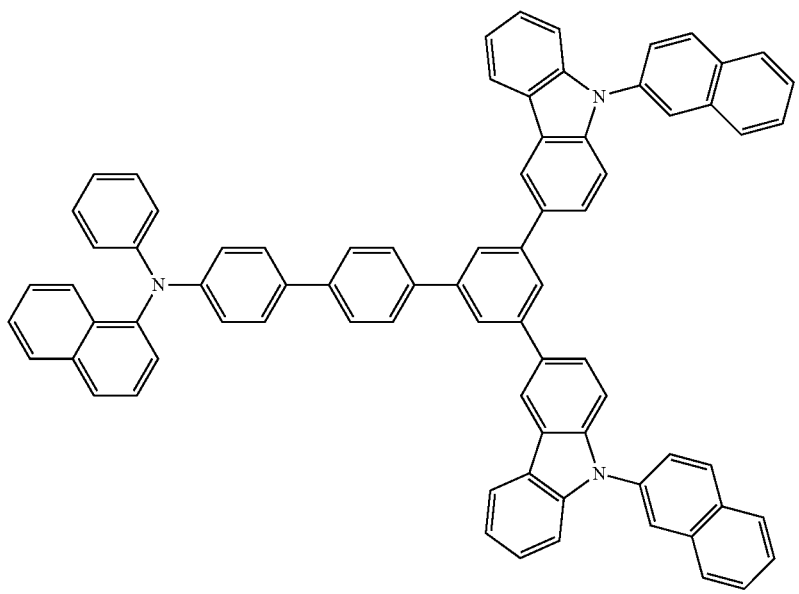
190
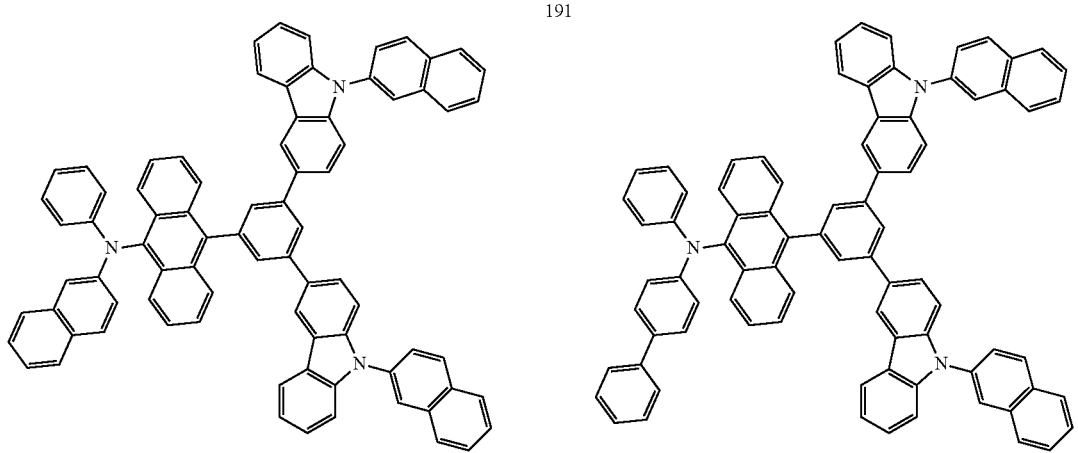
191 192

-continued
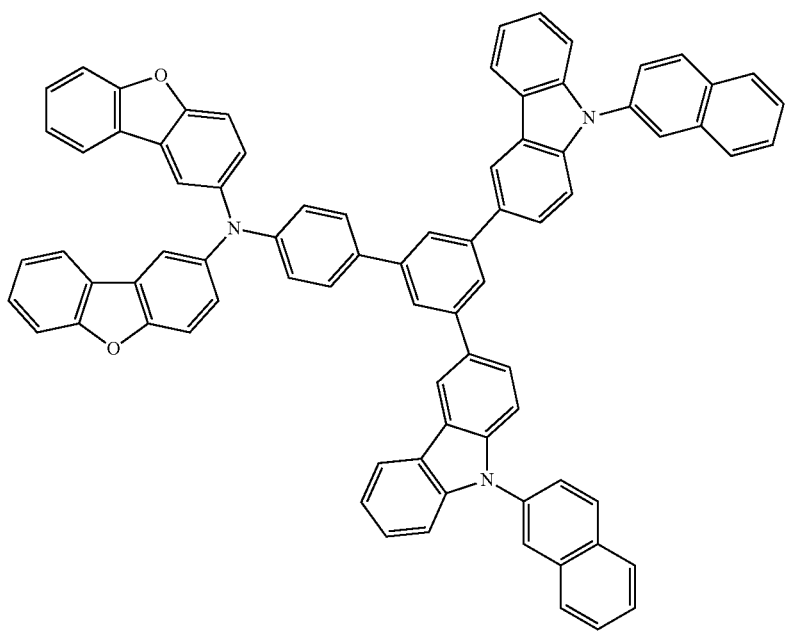
193
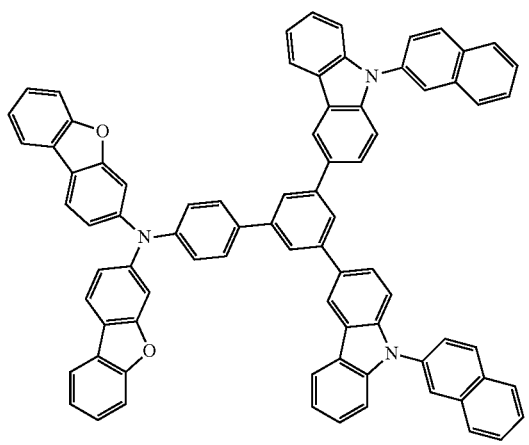
194
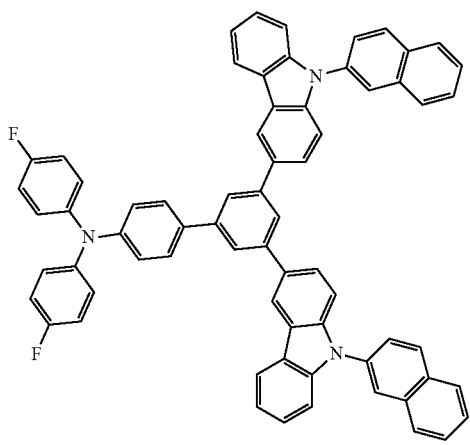
195
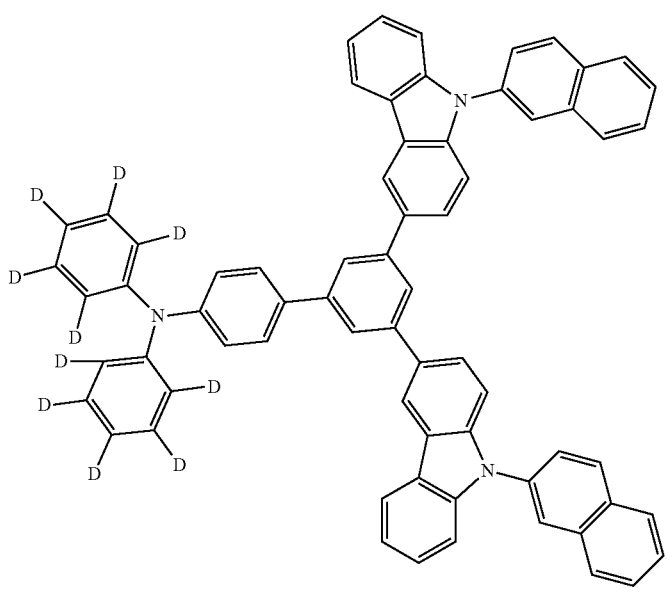
196

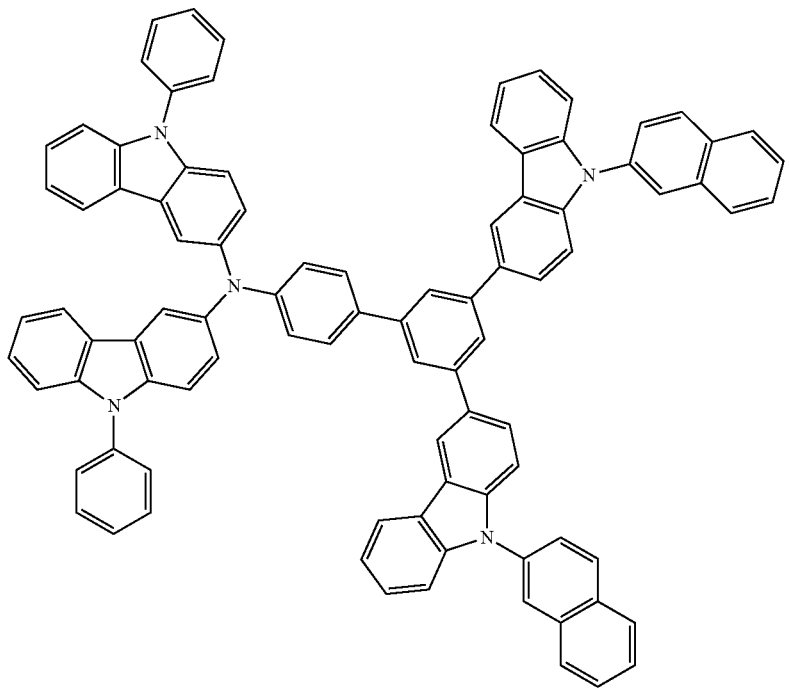

197

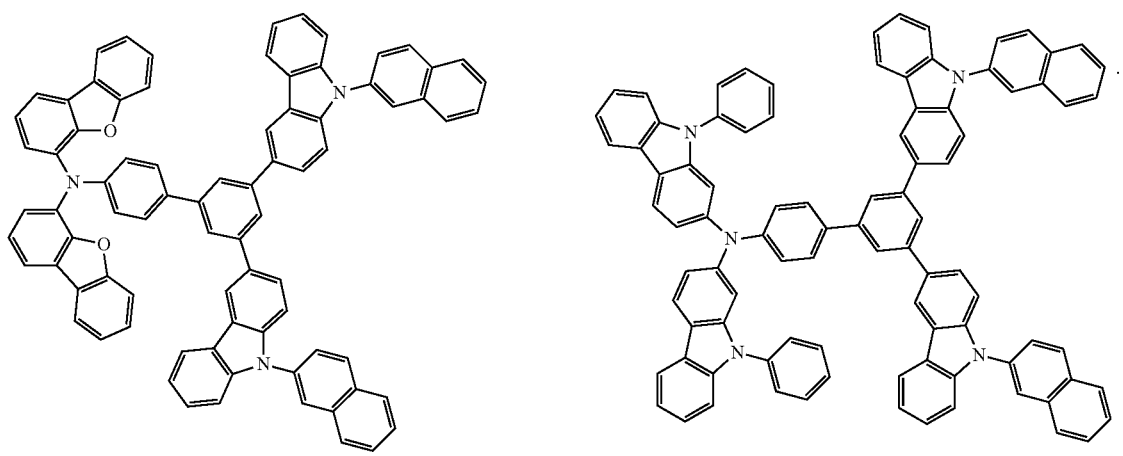

198  199

11. An organic light-emitting device, comprising:
a first electrode;
a second electrode facing the first electrode; and
an organic layer between the first electrode and the second electrode, the organic layer including an emission layer, wherein the organic layer includes the compound of claim 1.

12. The organic light-emitting device as claimed in claim 11, wherein the organic layer is formed by using wet process.

13. The organic light-emitting device as claimed in claim 11, wherein:
the first electrode is an anode,
the second electrode is a cathode,
and the organic layer further includes:
a hole transport region between the first electrode and the emission layer, the hole transport region including at least one selected from a hole injection layer, a hole transport layer, a buffer layer, and an electron blocking layer, and
an electron transport region between the emission layer and the second electrode, the electron transport region including at least one selected from a hole blocking layer, an electron transport layer, and an electron injection layer.

14. The organic light-emitting device as claimed in claim 13, wherein the hole transport region includes the compound.

15. The organic light-emitting device as claimed in claim 13, wherein:
the hole transport region includes the hole transport layer, and
the hole transport layer includes the compound.

16. The organic light-emitting device as claimed in claim 13, wherein the electron transport region comprises a metal complex.

17. The organic light-emitting device as claimed in claim 16, wherein the metal complex is a lithium (Li) complex.

18. The organic light-emitting device as claimed in claim 16, wherein the metal complex is lithium quinolate (LiQ).

19. The organic light-emitting device as claimed in claim 16, wherein the metal complex is Compound ET-D2 below:

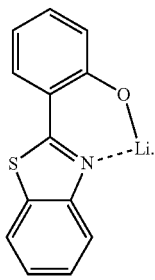

<ET-D2>

20. A flat display apparatus comprising:
a thin film transistor, the thin film transistor including a source electrode and a drain electrode; and
the organic light-emitting device as claimed in claim 11, wherein the first electrode of the organic light-emitting device is electrically connected to the source electrode or the drain electrode of the thin film transistor.

* * * * *